US008329988B2

(12) United States Patent
Frank et al.

(10) Patent No.: US 8,329,988 B2
(45) Date of Patent: *Dec. 11, 2012

(54) METHOD FOR INCREASING PATHOGEN RESISTANCE IN TRANSGENIC PLANTS

(75) Inventors: Markus Frank, Neustadt (DE); Patrick Schweizer, Ballenstedt (DE); Dimitar Douchkov, Gatersleben (DE)

(73) Assignee: BASF Plant Science GmbH (DE)

(*) Notice: Subject to any disclaimer, the term of this patent is extended or adjusted under 35 U.S.C. 154(b) by 518 days.

This patent is subject to a terminal disclaimer.

(21) Appl. No.: 12/444,927

(22) PCT Filed: Oct. 12, 2007

(86) PCT No.: PCT/EP2007/060857
§ 371 (c)(1),
(2), (4) Date: Apr. 9, 2009

(87) PCT Pub. No.: WO2008/043826
PCT Pub. Date: Apr. 17, 2008

(65) Prior Publication Data
US 2010/0071089 A1 Mar. 18, 2010

(30) Foreign Application Priority Data
Oct. 12, 2006 (EP) .................................... 06122217

(51) Int. Cl.
A01H 5/00 (2006.01)
A01H 5/10 (2006.01)
C12N 15/09 (2006.01)
C12N 15/82 (2006.01)

(52) U.S. Cl. ........ 800/279; 800/278; 800/298; 800/295; 435/320.1; 435/468; 435/418; 435/419; 536/23.6

(58) Field of Classification Search .................. None
See application file for complete search history.

(56) References Cited

U.S. PATENT DOCUMENTS

| 5,565,350 | A | 10/1996 | Kmiec |
| 7,456,335 | B2 | 11/2008 | Kogel et al. |
| 2004/0038212 | A1 | 2/2004 | Kurochkin et al. |
| 2006/0123505 | A1 | 6/2006 | Kikuchi et al. |
| 2008/0047033 | A1 | 2/2008 | Kogel et al. |
| 2009/0241215 | A1 | 9/2009 | Douchkov et al. |

FOREIGN PATENT DOCUMENTS

| CA | 2628505 A1 | 5/2007 |
| WO | WO-98/04586 A2 | 2/1998 |
| WO | WO-99/47552 A2 | 9/1999 |
| WO | WO-00/01722 A1 | 1/2000 |
| WO | WO-00/15815 A1 | 3/2000 |
| WO | WO-03/020939 A1 | 3/2003 |
| WO | WO-2004/009820 A1 | 1/2004 |
| WO | WO-2007/054441 A2 | 5/2007 |
| WO | WO-2007/054441 A2 | 5/2007 |

OTHER PUBLICATIONS

Fourgoux-Nicol et al. 1999, Plant Molecular Biology 40: 857-872.*
Guo et al. (PNAS (2004)101 : 9205-9210.*
Keskin et al. Protein Science (2004), 13:1043-1055.*
Azevedo, C., et al., "The U-box Protein Family in Plants", Trends in Plant Science, 2001, vol. 6, No. 8, pp. 354-358.
Amador, V., et al, "Gibberellins Signal Nuclear Import of PHOR1, a Photoperiod-Responsive Protein with Homology to *Drosophila* armadillo", Cell, 2001, vol. 106, pp. 343-354.
Gu, T., et al., "Binding of an Arm Repeat Protein to the Kinase Domain of the S-locus Receptor Kinase", Proc. Natl. Acad. Sci. USA, 1998, vol. 95, pp. 382-387.
Zeng, L.-R., et al., "*Spotted leaf11*, a Negative Regulator of Plant Cell Death and Defense, Encodes a U-Box/Armadillo Repeat Protein Endowed with E3 Ubiquitin Ligase Activity", The Plant cell, 2004, vol. 16, pp. 2795-2808.
González-Lamothe, R., et al., "The U-Box Protein CMPG1 Is Required for Efficient Activation of Defense Mechanisms Triggered by Multiple Resistance Genes in Tobacco and Tomato", The Plant Cell, 2006, vol. 18, pp. 1067-1083.
Coates, J.C., "Armadillo Repeat Proteins: Beyond the Animal Kingdom", Trends in Cell Biology, 2003, vol. 13, No. 9, pp. 463-471.
Yang, C.-W., et al., "The E3 Ubiquitin Ligase Activity of *Arabidopsis* PLANT U-Box17 and Its Functional Tobacco Homolog ACRE276 Are Required for Cell Death and Defense", The Plant Cell, 2006, vol. 18, pp. 1084-1098.
Zierold, U., et al., "Transciptome Analysis of *mlo*-mediated Resistance in the epidermis of Barley", Molecular Plant Pathology, 2005, vol. 6, No. 2, pp. 139-151.
Schweizer, P., et al., "Double-Stranded RNA Interferes with Gene Function at the Single-Cell Level in Cereals", The Plant Journal, 2000, vol. 24, No. 6, pp. 895-903.
"Predicted *Oryza sativa* (japonica cultivar-group), OJ1060_D03. 106 mRNA", NCBI Database, Accession No. XM_506432, Nov. 9, 2004.
"*Oryza sativa* (japonica cultivar-group), predicted mRNA", NCBI Database, Accession No. XM_463544, Nov. 9, 2004.
"*Oryza sativa* (japonica cultivar-group), mRNA", NCBI Database, Accession No. XM_479734.1, Nov. 9, 2004.

(Continued)

*Primary Examiner* — Medina A Ibrahim
(74) *Attorney, Agent, or Firm* — Connolly Bove Lodge & Hutz LLP

(57) ABSTRACT

The invention relates to a method of increasing the resistance to one or more penetrating pathogen(s) in a monocotyledonous or dicotyledonous plant or a part of a plant, for example in an organ, tissue, a cell or a part of a plant cell, for example in an organell, wherein a DNA sequence which codes for an armadillo repeat ARM1 protein and which mediates an increased pathogen resistance, preferably an increased resistance to fungal pathogens, is increased into, and expressed in, the plant or plant cell; or wherein an endogenous DNA sequence which codes for an armadillo repeat ARM1 protein and which mediates an increased pathogen resistance, preferably an increased resistance to fungal pathogens, is increased in the plant or plant cell in comparison with the original, or wild-type, plant, or wherein the endogenous gene sequence or preferably the 5'-untranslated region (5'UTR) is modified in comparison with the original sequence. The invention also relates to plants, to parts of a plant, for example an organ, tissue, a cell or a part of a plant cell, for example an organelle, which are obtained by the above methods, and to corresponding propagation material.

40 Claims, 44 Drawing Sheets

OTHER PUBLICATIONS

"*Oryza sativa* (japonica cultivar-group), genomic DNA, chromosome 1, BAC clone:B1065E10.", EMBL Database, Accession No. AP003561, May 7, 2001.

"*Nicotiana tabacum* arm repeat-containing protein mRNA, complete cds.", EMBL Database, Accession No. AY219234, Mar. 19, 2003.

"*Arabidopsis thaliana* unknown protein (At3g54850) mRNA, complete cds.", EMBL Database, Accession No. AY096530, May 7, 2002.

"*Arabidopsis thaliana* mRNA for arm repeat containing protein, complete cds, clone: RAFL22-04-A03.", EMBL Database, Accession No. AK175585, Sep. 9, 2004.

"*Arabidopsis thaliana* genomic DNA, chromosome 5, TAC clone:K8K14", EMBL Database, Accession No. AB007645, Oct. 31, 1997.

"*Arabidopsis thaliana* genomic DNA, chromosome 5, P1 clone:MDH9", EMBL Database, Accession No. AB016888, Aug. 24, 1998.

"*Arabidopsis thaliana* DNA chromosome 3, BAC clone T5N23", EMBL Database, Accession No. AL138650, Feb. 2, 2000.

"*Arabidopsis thaliana* DNA chromosome 3, BAC clone F28P10", EMBL Database, Accession No. AL049655, Apr. 20, 1999.

"*Arabidopsis thaliana* DNA chromosome 3, BAC clone F12A12", EMBL Database, Accession No. AL133314, Dec. 2, 1999.

"*Arabidopsis thaliana* clone 34582 mRNA, complete sequence", EMBL Database, Accession No. AY087360, Jun. 14, 2002.

"*Arabidopsis thaliana* chromosome III BAC T13O15 genomic sequence, complete sequence", EMBL Database, Accession No. AC010870, Sep. 26, 1999.

"*Arabidopsis thaliana* chromosome 2 cloneF21P24 map CIC06C07, complete sequence", EMBL Database, Accession No. AC004401, Mar. 16, 1998.

"*Arabidopsis thaliana* At5g67340 mRNA, complete cds.", EMBL Database, Accession No. BT020206, Nov. 14, 2004.

"*Arabidopsis thaliana* At4g16490 mRNA for unknown protein, complete cds, clone RAFL21-08-B04.", EMBL Database, Accession No. AK118730, Dec. 13, 2002.

"*Arabidopsis thaliana* At3g54790 mRNA for unknown protein, complete cds, clone: RAFL19-87-C08.", EMBL Database, Accession No. AK118613, Dec. 13, 2002.

"*Arabidopsis thaliana* AT3g01400/T13O15_4 mRNA, complete cds", EMBL Database, Accession No. AY125543, Jul. 25, 2002.

"*Arabidopsis thaliana* armadillo/beta-catenin repeat family protein / U-box domain-containing protein (AT3G54790) mRNA, complete cds." NCBI Database, Accession No. NM_115336, Apr. 30, 2008.

"*Arabidopsis thaliana* armadillo/beta-catenin repeat family protein / U-box domain-containing protein (AT2G23140) mRNA, complete cds.", NCBI Database, Accession No. NM_127878, Apr. 20, 2007.

Stone, et al., "A Breakdown of *Brassica* Self-Incompatibility in ARC1 Antisense Transgenic Plants", Science, vol. 286, (1999), pp. 1729-1731.

Altpeter, F., et al., "Stable Expression of a Defense-related Gene in Wheat Epidermis Under Transcriptional Control of a Novel Promoter Confers Pathogen Resistance", Plant Molecular Biology, vol. 57, (2005), pp. 271-283.

Douchkov, D., et al., "A High-Throughput Gene-Silencing System for the Functional Assessment of Defense-Related Genes in Barley Epidermal Cells", MPMI, vol. 18, No. 8, (2005), pp. 755-761.

Malnoy, M., et al., "Activation of the Pathogen-inducible *Gst1* Promoter of Potato After Elicitation by *Venturia inaequalis* and *Etwinia amylovora* in Transgenic Apple (*Malus x domestica*)", Transgenic Research, vol. 15, (2006), pp. 83-93.

Mudgil, Y., et al., "A Large Complement of the Predicted Arabidopsis ARM Repeat Proteins Are Members of the U-Box E3 Ubiquitin Ligase Family", Plant Physiology, vol. 134, (2004), pp. 59-66.

\* cited by examiner

Figure 1A

HvARM: (SEQ ID NO. 1):

atgcaaatggctctgctagcaaggctttctcttgcaagttctgaaggaagagagtctagtttgg
aagaaagacatgctggttctgatgaacaaacttcagaacaatcaacgaaggaagcatttcaagc
atctcattttgacagtgattcacaggttcgtctaggcagatcttcagttaatgataatcttcct
aatacccgtcagcttgacgaggagtgtgacatcaacgatgggatgatacgagttccaggtgata
ggacaaattatagtagtgatgcgtctggagaggttgctgaccgtgggctttctatctcttctgc
ccctcaaaggaaaatgtaatcctgccaagattgggtcatgtctgcatggagggaccatttgtt
cagcggcaaacatctgacaagggattcccgagaataatttcgtcgttatccatggatgcccggg
atgatttctctgccatcgagaatcaggtacgcgagctaatcaatgatttgggaagtgattccat
agaaggtcagagatcagcaacatcagagattcgccttctagctaagcacaacatggagaacagg
attgccattgctaattgtggggctataaacttgctggttggccttcttcattcacccgatgcca
aaatccaagaaaatgcagtgacagccctccttaatttgtcactcagtgatatcaataagattgc
catcgtgaatgcagatgctattgatcctctcatccatgtcctggaaacagggaaccctgaagct
aaagagaattcagcagctactttgttcagtctctcaattattgaagaaaacagagtgaggatag
ggcgatctggtgctgtaaagcctctcgtggacttgctgggaaatgggagcccacgaggaaagaa
agatgcggttactgcattgttaatttatccatacttcatgagaacaagggtcgaattgtgcaa
gctgatgcattgaagcacctagttgagcttatggaccctgctgctgaatggtcgataaagctg
tagctgtcttggcaaatcttgctacgataccagaaggaaggactgcgattgggcaggcgcgtgg
tattccggcccttgttgaagttgtcgaactgggttcagcgaaagcgaaggaaaatgctaccgcg
gcattgcttcagctatgcacaaacagcagcaggttttgcaacatagttcttcaagaggatgccg
tgccccctttagtcgcactgtcacagtcaggaacaccacgcgcaagagaaaaggcgcaggttct
cctcagctatttccgcagccaaagacatgggaactcgggaaggagatga HvARM including 5'UTR: (SEQ ID NO. 63)(Start ATG Pos. 481)

gaaagtgcatttccttgttgcttcccaggctgaccgaccagccacaccaacccaaaccaacgc
ggcaaaaccttggcccccgcctgtctagcgctgCCGCCGTGCCGTGCCGTGCCGTGCCT
CAGCGCCAGCGACCGCCGACGACTCAATCCCGTACCACGCCCCACCGCCGCCTCCCACGCCCCT
CGTGCCCATCGCCGATCCCGTTCCCCCTCACCGCAGCATCGCGCTCCCGCGTATCCGCCCCTTC
CGCAACCGTCGGCCATTGGTTTCTGAGAGCCTCAAGATTTGAGCACCACAGGCAACAGCCTCCT
ACATCCTGTGTCGGTACTTGGTAGGGTAATCTTCCCTGGACCCCGGGAGCTGACATGTATAGAG
AAGCTTGAACAGAGCATGTGAACCATCCTGAAATCTGATGCCATGTGAACCATCCTGGTCATGA
GGCCTCATCGATCAGTCTTTAGATATGCAAATGGCTCTGCTAGCAAGGCTTTCTCTTGCAAGTT
CTGAAGGAAGAGAGTCTAGTTTGGAAGAAAGACATGCTGGTTCTGATGAACAACTTCAGAACAA
TCAACGAAGGAAGCATTTCAAGCATCTCATTTTGCAGTGATTCACAGGTTCGTCTAGGCAGATC
TTCAGTTAATGATAATCTTCCTAATACCCGTCAGCTTGACGAGGAGTGTGACATCAAGATGGGA
TGATACGAGTTCCAGGTGATAGGACAAATTATAGTAGGATGCGTCTGGAGAGGTTGCTGACCGT
GGGCTTTCTATCTCTTCTGCCCCTCAAAGGGAAAATGTAATCCTGCCAGATTGGGTCATGTCTG
CATGGAGGGACCATTTGTTCAGCGGCAACATCTGACAAGGGATTCCCGAGAATAATTTCGTCGT
TATCCATGGATGCCCGGGATGATTTCTCTGCCATCGAGAATCAGGTACGCGAGTAATCAATGAT
TTGGGAAGTGATTCCATAGAAGGTCAGAGATCAGCACATCAGAGATTCGCCTTCTAGCTAAGCA
CAACATGGAGAACAGATTGCCATTGCTAATTGTGGGCTATAACTTGCTGGTTGGCCTTCTTCA
TTCACCCGATGCCAAAATCCAAGAAAATGCAGTGACAGCCCTCCTTAATTTGTCActCAGTGAT
ATCAATAAGATTGCCATCGTGAATGCAGATGCTATTGATCCTCTCATCATGTCCTGGAAACAGG
GAACCCTGAAGCTAAAGAGAATTCAGCAGTACTTTGTTCAGTCTCTCAATTATTGAAGAAAACA
GAGTGAGGATAGGGCGATCTGGTGCTGTAAAGCCTCTCGTGGACTTGCTGGGAATGGGAGCCCA
CGAGGAAAGAAAGATGCGGTTACTGCATTGTTAATTTATCCATACTTCATGAGAACAAGGGTCG
AATTGTGCAAGCTGATGCATTGAAGCACCTAGTTGAGCTTATGGACCCTGCTGCTGAATGGTCG
ATAAAGCTGTAGCTGTCTTGGCAAATCTTGCTACGATACAGAAGGAAGGACTGCGATTGGGCAG
GCGCGTGGTATTCCGGCCCTTGTTGAAGTTGTCGAACTGGGTTCAGCGAAAGGAAGGAAAATGC
TACCGCGGCATTGCTTCAGCTATGCACAAACAGCACAGGTTTTGCAACATAGTTCTTCAAGAGG
ATGCCGTGCCCCCTTTAGTCGCACTGTCACAGTCAGGAACACCACGCGCAAGAGAAAAGGCGCA
GGTTCTCCTCAGCTATTTCCGCAGCCAAAGACATGGGAACTCGGAAGGAGATGAGGACGATGGT
CCTACGATATATTTTCTAGTTACGTCGAGTATTTCCCTGAATTTCTCAGATGATAGTTATTGT
TGTTGACTGGCGCTGTGTACTGCTTATAGTCACTGTGAGATTGTGCCATCTTCTCAAGCTACTG
GTGGATTAGTTGCTGTGTTTGGACTGGTCGTTGTTGTTGTTGAGATGGTGTATTCTTCGGGTTT
ATATTTTTTTACATCTtGTCTATTGGTATCTAAAAAAAA

Figure 1B

HvARM 5'UTR: (SEQ ID NO. 64)

gaaagtgcatttccttgttgcttccccaggctgaccgaccagccaccaccaacccaaaccaacg
cggcaaaaccttggcccccgcctgtcctagcgctgCCGCCGTGCCGTGCCGTGCCGTGCCGTGC
CTCAGCGCCAGCGACCGCCGACGACTCAATCCCGTACCACGCCCCCACCGCCGCCTCCCACGCC
CCTCGTGCCCATCGCCGATCCCGTTCCCCCTCACCGCAGCATCGCGCTCCCGCGGTATCCGCCC
CTTCCGCAACCGTCGGCCATTGGTTTCTGAGAGCCTTCAAGATTTGAGCACCACAGGCAACAGC
CTCCTACATCCTGTGTCGGTACTTGGTAGGGTAATCTTCCCTGGACCCCGGGAGCTGACATGTA
TATGAGAAGCTTGAACAGAGCATGTGAACCATCCTGAAATCTGATGCACATGTGAACCATCCTG
GTCATGAGGCCTCATCGATCAGTCTTTAGATT

OS_1_XM_479734.1 (SEQ ID NO. 3):

atggaaaatttctccccgagaaccctgctcaatagtatcttgcgtatcactgtcttaacctccg
atggctctactgcaaggcccaagcccattcagaagtactgccaaaatgtgtgtgatatctcaag
cattgtgagccctctcatagaggatctatgtgagtctcctgaagagcaactcaatgaggtgtta
agggagcttggcactgctattaacagagcttcagggcttattgggaactggcaacagacaacca
gcaaaatatattttatatggcagattgaatcagtaatctcagatatccagggatgttctctaca
gctgtgccagcttgttaactctctattaccttctttgactggccgtgcatgcacatgtattgag
aaactccaagacataaattatgaaaacatgtttgatctggtaaaggagtcttcattggagctag
ttgagacggacacaacaagtcctgagaatctgtcgagactatctagttcattgagtttgtcaac
taacctggaattttacatggaagctgtttcccttgagaatctcagagcaagggcaatgcggagt
gagaaccgtgaagaaatggatctggctgacaagatgatcccctggtcaactatatgcatgacc
accttctgagggaaacacaactgcttagcatcaatggggtgcccattcctgcagattttgctg
cccgctgtccctagagctgatgtcagatcctgttattgtagcatctggtcagacatatgagcgg
gtttatatcaagttatggcttgatgagggttttactatctgcccgaagacacgccaaagacttg
gtcactccaatttaattccaattacaccgtgaaagctttgatagctaattggtgcgaatcaca
caacattaggcttcctgatcctatgaaatccttgaaattgaacttcccttggctgcgtctgct
ctccaggattcgagcaccacaggaagcagccctctacatcctactgtcgctgctaagggtaata
ttcctgggtccccggaagctgacctttatatgagaagcttgaatagagcatctcctccacacag
tgtagtccatcagaattctcatgcgcatgtgaaccgtgctggtcatgaagcctccattaagcaa
tcttcagaaaatgctaatggttctgcatcagatgtttcaaggttatctcttgcaggttctgaaa
caagagagtctagtctggaagaaagaaatgctggttctatcggtcaaacttcagaacagtcaat
tgaggaagcatttcaagcatctaatttggacaggattcacatgaccatgtgggtagttcttcg
gtgaatggtagccttccaaatagcggtcaacttgatgcagaatgtgacaatgggccaagcgaaa
ggacaaattacagtagtgatgcatctggagaagttacagatgggccttcagcatcttctgctcc
tcagagggagcatctaatcccttctagattggctgatgttcgtagtagaggccaatttgttcgg
cgaccatctgaaagggggtttccccagaataatatcttcctcatccatggatacacggagtgatc
tttccgccatcgagaatcaggtccgcaagttagttgatgatttaagaagtgattctgtagatgt
tcaaagatcagcgacatcagatatccgccttttagctaagcacaacatggagaacaggatcatc
attgcaaactgtggagctataaacttgctggttggtcttcttcattcgccagattccaaaaccc
aagagcatgccgtgacagcccttctgaatttgtcaatcaatgataataataagattgccattgc
aaatgctgatgctgttgaccccctcatccatgtccttgagactgggaaccctgaagccaaggag
aattcagcggctacattattcagtctctcggttattgaagaaaacaaagtgaggattggaagat
ccggtgccatcaaacctctcgtcgacctactaggaaatgggacccctcgaggaagaaagatgc
agctactgcattgttttaatttatccatattacatgaacaagcgcgtattgtgcaggctgac
gctgtgaagtacctagttgaacttatggaccctgctgctggaatggttgacaaagctgtggctg
ttttggcaaaccttgctaccataccagaagggaggacagcaattggtcaagcgcgtggtattcc
agcccttgttgaagttgttgaactcggttcagcaagggggaaggaaaatgcggctgcagcattg
cttcagctatgtacaaacagcagcagattttgcagtatagttcttcaagagggtgctgtgcctc
ctctagttgcattgtcacagtcaggcacgccacgggcaagagagaaggcacaggctcttctcag
ctactttcgcagccaaaggcacgggaattcagcaaggagatga Os_2_XM_463544 (SEQ ID NO. 5):

atggcgtttgtttgtggtggtggcaagtgatggattcagtgtcattgtcactactcgatagta
tttcaaatttccgggtgctgtcttcaagcaatgcctcgaaaacagagctagttaagaaatattg
ccaaacgatggatggcatccttgatcacttggaggtggccctaaacagagcttttcctcagatt
actccagatggtgaactaagtaaagttattcaggctgattcaattattgccaagatgcagatat
atgtattcgaattatgccaaattgtcaattctctcatgcagattgagtcaatgcatttggagga
tcttgaacacgatagctgtggaaaatttcagatgtcattagggaggcttccagggctttagca
ggggaagttatgccaaattcagaggaatttggaaagattcaaactactttgagcttatccacaa
atcaggagttgctgatggaatatgttgcacttgttaaggttaaaacaaaaggtaatcatgaaga
taacaaagaaatggatgatattaacgatattgttgaattagtcaaccatatgcttgacaaacat

Figure 1C gtggaagaaaagcaaacacgtagcattaatggagtgaccattcctgctgattttgttgtcctc
tttcccttgaactaatgtcggatccagtgattgtggcatctggtcaaacgtatgagcatgtttt
tatcagaaaatggtttgatctgggatacaacatttgtccaaagacacgccaaatattgggacac
accaaattgattcctaacttcactgtcaaacagttgattgaaaattggtgtgaggtacatggta
taatgctaccagatcctgttaaactcttgagtttgtgcttcctgtttccctcaacatcacaga
tggaagtgcaagtgcagacaagtctggatcaccagaacactgccaattggtagctgcattgcat
ccaaaagcacagtgcgcatcggatgatagtcatcattataatttgatacatgaaaactctgatt
cagatgatagagtgtcatcatttggagacacagatgattctgaacctgattctttaagattatc
aacagaaactactgcagcaaacaaatctctacttgatgaaaaaactgatcgttctgatggtctt
aagcaattgagagacaatggttttcaagtttctgatgaggaacagtatctcgaaggaatggta
aaagtcatatcagcagccatcatcaacttgaagttgatggagagaatgtcagggtacaagcatc
aagtgacatcaatgcatctgaagttatgcaagatgatccggtcaccacatgttcaaaggtatca
gataaccctcctagattgggtggtgttcgttctcgaaatcagccaaactggtggagacagtcta
ataaaactattcctaggatcggattgtcatcttcgacagattcaaaaccagatttttctggcaa
tgatgctaaagtgcgtaatcttatcgaggaactgaaaagtgattctgctgaggtccaaaggtca
gcaacaggagagctccgcattctttctagacacagcttggagaatagaattgccatcgcaaact
gcggagcaatcccccttcttggtgagtctacttcattctacagaccccagcacacaagaaaatgc
tgtgacaattctcctgaatttgtcattggatgacaataacaagattgccatagcaagtgctgag
gccattgagcctctcatcttcgttcttcaggtgggaaaccccgaagcgaaagccaactcagctg
caactttattcagcctctcagtcattgaagagaacaagatcaagattggacgttccggtgccat
cgaaccattagtagatttactgggagaaggtaccccgcaagggaagaaggatgcagctactgca
ctcttcaatctgtcgatatttcatgaacacaagacccgcattgttcaggctggggctgtcaacc
acctggtggagctgatggatccagctgctgggatggttgataaagctgttgctgttctggcaaa
ccttgcgactgtgcatgatggaaggaatgccattgctcaggcaggaggcatccgagtactggtt
gaggttgttgagctgggttctgcacgttcaaaggagaatgccgctgctgccctgctacaactct
gcacaaacagtaacaggttttgcaccctggttcttcaagaaggcgtcgtgccacctttggttgc
attgtcgcaatcaggcacagcccgtgcaagagagaaggctcaggttcttctaagctatttcgc
aaccagcgccacgtcagggttgggagagggcttagcttgctattagagttaaaacggaccacat
aa Os_3_AP003561 (SEQ ID NO. 7):

atggattcagtgtcattgtcactactcgatagtatttcaaatttccgggtgctgtcttcaagca
atgcctcgaaaacagagctagttaagaaatattgccaaacgatggatggcatccttgatcactt
ggaggtggccctaaacagagcttttcctcagattactccagatggtgaactaagtaaagtgctt
gaagaacttggcgctaccatcaatgaagcgactgagctagttggaggctggaatcaaatgatga
gcaagatttatttttgttattcaggctgattcaattattgccaagatgcagatatatgtattcga
attatgccaaattgtcaattctctcatgcagattgagtcaatgcatttggaggatcttgaacac
gatagctgtggaaaaatttcagatgtcattagggaggcttccagggctttagcaggggaagtta
tgccaaattcagaggaatttggaaagattcaaactactttgagcttatccacaaatcaggagtt
gctgatggaatatgttgcacttgttaaggttaaaacaaaaggtaatcatgaagataacaaagaa
atggatgatattaacgatattgttgaattagtcaaccatatgcttgacaaacatgtggaagaaa
agcaaacacgtagcattaatggagtgaccattcctgctgattttgttgtcctctttcccttga
actaatgtcggatccagtgattgtggcatctggtcaaacgtatgagcatgttttatcagaaaa
tggtttgatctgggatacaacatttgtccaaagacacgccaaatattgggacacaccaaattga
ttcctaacttcactgtcaaacagttgattgaaaattggtgtgaggtacatggtataatgctacc
agatcctgttaaactcttgagtttgtgcttccctgtttccctcaacatcacagatggaagtgca
agtgcagacaagtctggatcaccagaacactgccaattggtagctgcattgcatccaaaagcac
agtgcgcatcggatgatagtcatcattataatttgatacatgaaaactctgattcagatgatag
agtgtcatcatttggagacacagatgattctgaacctgattctttaagattatcaacagaaact
actgcagcaaacaaatctctacttgatgaaaaaactgatcgttctgatggtcttaagcaattga
gagacaatggttttcaagtttctgatgaggaacagtatctcgaaggaatggtaaaagtcatat
cagcagccatcatcaacttgaagttgatggagagaatgtcagggtacaagcatcaagtgacatc
aatgcatctgaagttatgcaagatgatccggtcaccacatgttcaaaggtatcagataaccctc
ctagattgggtggtgttcgttctcgaaatcagccaaactggtggagacagtctaataaaactat
tcctaggatcggattgtcatcttcgacagattcaaaaccagatttttctggcaatgatgctaaa
gtgcgtaatcttatcgaggaactgaaaagtgattctgctgaggtccaaaggtcagcaacaggag
agctccgcattctttctagacacagcttggagaatagaattgccatcgcaaactgcggagcaat
cccccttcttggtgagtctacttcattctacagaccccagcacacaagaaaatgctgtgacaatt
ctcctgaatttgtcattggatgacaataacaagattgccatagcaagtgctgaggccattgagc
ctctcatcttcgttcttcaggtgggaaaccccgaagcgaaagccaactcagctgcaactttatt
cagcctctcagtcattgaagagaacaagatcaagattggacgttccggtgccatcgaaccatta
gtagatttactgggagaaggtaccccgcaagggaagaaggatgcagctactgcactcttcaatc
tgtcgatatttcatgaacacaagacccgcattgttcaggctggggctgtcaaccacctggtgga

Figure 1D gctgatggatccagctgctgggatggttgataaagctgttgctgttctggcaaaccttgcgact
gtgcatgatggaaggaatgccattgctcaggcaggaggcatccgagtactggttgaggttgttg
agctgggttctgcacgttcaaaggagaatgccgctgctgccctgctacaactctgcacaaacag
taacaggttttgcaccctggttcttcaagaaggcgtcgtgccacctttggttgcattgtcgcaa
tcaggcacagcccgtgcaagagagaaggctcaggttcttctaagctatttcgcaaccagcgcc
acgtcagggttgggagagggtaa Os_4_XM_506432 (SEQ ID NO. 9):

atggtgtcgctagccggctcccagatccgtcgccggggcagagtccgtgcgcggcggcgcggt
cgcagcgccgcggcgcggggtactccatgcggaccatccggtcggcgctgctgcagccggactc
ctgcccgggctcgccgcatgtggcggccgcgtacgacgcggcgggggcggactcggacatggag
aacttgacggactccgtgattgatttccatctcagcgagctggcggccaccgcggggcccgcgc
accccgcggcggtggccaagtcgtcgtcggccaacgcggcggccacggagatgctcgagctctc
gcgggacttcagtgactactcgagcttcaactcggatatctccggcgagctcgagcggctcgcg
gcggcggcggcggcggtggtgacgcccagatccgacgcgccgcaggtgggccgtggatctga
tgagcttgagtcgatggatctgtccgtcgaggcggcgcgctggagcgcgtggagccgttcgt
gctggcgtgcgtgcgggcgctggggcccgacgccgcgccagacgcgcggcgcaccgcggcggcg
aggataaggctgctggcgaagcacaggtcggacatccgcgagctgatcggcgtgtccggcgcca
tcccggcgctggtgccgctgctgcggagcaccgacccggtggcgcaggagagcgcggtgacggc
gctgctcaacctctcgctcgaggagcggaaccggtcggccatcacggcggcgggggccatcaag
ccgctcgtgtacgcgctgcggacgggcaccgcgtcggccaagcagaacgccgcgtgcgcgctgc
tcagcctctcgggcatcgaggagaaccgcgccaccatcggcgcgtgcggcgccatccctcccct
cgtcgcgctgctctccgcgggctccaccgcgcggcaagaaggacgcgctcaccacgctctaccgg
ctctgctcggcgcgccggaacaaggagcgcgcggtcagcgccggcgccgtcgtgccgctcatcc
acctcgtcggcgagcgtggcagcgggacgtcggagaaggcaatggtggtcctcgccagcctcgc
gggcatcgtcgagggccgcgacgccgtggtggaggctggcgggataccggcgcttgtcgagacc
atcgaggacggcccggcgagggagagggagttcgccgtggtggcgctgctgcagctctgctccg
agtgcccccgcaaccgcgcgcttcttgtccgtgagggcgccatcccacgcttgtcgcgctctc
gcagtccggctctgcccgtgccaagcacaaggctgaaactttgcttgggtatctccgcgagcaa
cggcaaggaggtggtggctgcagggttgaacccgtggcagcttcgagcttggccaggtaa

NT_1_AY219234 (SEQ ID NO. 11):

atggagatatcattgttaaaagtgcttctcaacaatatctcctgttttcccatttatcatcaa
gtgatcacataagtggtgaactggttcgtagatattattgtaagattgaggatatactgaagct
tgtaaagccgattcttgacgccatcgttgatgttgaagctgcttctggtgagctgcttctgaaa
gcgtttgctgggctggctcaatgtgttgatgaactgagggagctattcgaaaccttggaaccgc
tgtgcagtaaagtttatttgtcctgcaagctgaaccattgattgggaaaattcgatcatgtag
cctggaaatacttgagcttcttaaatcttctcataaaagccttccagctgatgtaactttgaca
actctcgagctctatatactgaaaattaagtatgtagattatgaaatgatatcagtgacaatca
caaaggttattaaagctcaagtggaaggcttgggaaccagctcagatagctttgccaaaattgc
tgattgcctaagcttgaactcaaaccaagagctttgattgagcttgtggcccttgaaaaattg
aaagagaatgctgaacaagctgaaaagagtgaagttgttgaatatattgagcaaatgataactc
ttgtttctcatatgcacgattgctttgttactacaaaacagtcccagagttgtaccgctgtgcc
aatacctcctgatttttgctgtcctcttttcacttgagttgatgactgaccctgtaattgtcgct
tctggtcaaacctatgagagggcttttattaggagatggattgatcttggcctcactgtttgcc
ccaaaacacggcaaactctgggacatacaaatctcattcctaattacactgttaaggcactgat
cgcaaactggtgcgaaataaacaatgtaaagctgcctgatcccatgaagtctttgagcttgaac
cagccatctttgtcaccagactccacgcaatcttcaggttctccgagaaagagtttgatttcat
caactgtaagccaaagagaagaatcatctccatctcatcccgttcctcttcagaggaatcttt
acctggagttggtggtaatattcttgcttttgatgttgaaaggatgcgtattaagagtgaagac
cggatggcccactccggagagataagttcacatgtcatagtacattagtagctgatgaccagt
tccctctgggtcataatcgaacaacctcggcacctagcacgctttctaattcaaacttttcccc
ggtaattcctggtgatggaaacaagttgtcagaagattcttctgttgcttcagggggatgttggg
ttggattccaagcctgctgcttctgtccttccaaaggagccagaatttccatatacaccagaga
tgagacctcgtaatcaactgatctggcgcagaccaaccgagaggtttccaagaatagtttcttc
cgctacagttgaaagaagggctgatctttcagaagttgaggagcaagtaaaaaagttgattgag
gagttgaagagcacttcccttgatatgcagagaaatgctacagctgaactccggttacttgcca
agcataatatggataaccgtatggtaattgcaaattgtggcgctatcagctcgttggttaacct
acttcactcaaaagacatgaaagtacaggaagatgctgttactgcacttctcaacttgtcaatt
aatgacaacaacaagtgtgccattgcaaatgctgatgcaatcgaacctctgattcatgtcctcc
aaacagggagcgccgaggccaaagaaaattctgctgctactctttttagcctttccgtgatgga

Figure 1E ggaaaacaagatgaagattgggaggtctggagcaatcaaacctcttgttgatttactgggaaat
ggaactccaaggggcaagaaagatgcagcgacagctttatttaacttgtcaatacttcatgaga
acaagtctcgtataatacaggctggtgcggtaaagtatctcgtagagttgatggaccctgctac
tgggatggttgacaaggctgttgcagttttgtccaaccttgctaccattcccgagggacgagca
gaaatcggtcaggaaggagggattcctcttcttgttgaggttgttgagctgggctccgcaaggg
gtaaggagaatgcagcagctgctctcttgcaactatgcactaacagtagcaggttctgcaacat
ggttctccaggaaggagctgtacctccattagtggcattgtcacagtccggcaccccaagagca
agagaaaaggctcaacaactacttagctacttccgaaatcaacgccatggtaatgcaggaagag
gttga At_1_NM_127878 (SEQ ID NO. 13):

atggaagttcttctcagaagtatctcgtcgtttctaaatctgtcatcttctaaacatattgatt
tagacccgtttgagaagtactataagagagttgaagagttattgagagtgttgaagcctatagc
agatgttgttgttacctctgattttgttttgatgagaaacttggtaaagcatttgaagaattg
actcaggatgttgatcaatccattgatcttttcaggagttggcaagctttctctagtaaagtct
atttcgttcttcaaattgaatctttgctaccaaagatgcgggacaccattgtggatacttttca
gtttctcatgtcttctaagaaccatctacctgatgagctaagcccagcttctcttgagcaatgt
ctagagaagattaagcatcttagttatgaagaaatatcttctgtcattgacggtgctttgaggg
atcagagagatggtgttggacctagccctgagatcttggtgaaaattggagagaacactggtct
tagatcaaaccaggagattctgattgaagctgttgctctagagaggcagaaagagatggctgag
cagtctgagaataatgcagaagtcgagttccttgaccaactgattgttattgtaaaccgcatgc
atgaacgtcttcttctgatcaaacagactcagacttctagtgtcgccattcttccgacttctt
ttgccctctgtcacttgaagtaatgactgatccagtgattgtgtcatcaggacaaacatatgaa
aaggcgtttatcaagagatggattgatttgggtttaaaagtgtgtcccaagactcgacagaccc
tgactcacactactctaatacccaattacaccgtgaaggccttaatcgctaactggtgtgagac
aaacgatgtcaagctgcctgatcccaataaatcaacaagtttaaatgagctttctcctctttta
tcatgtacagactccattcctagcacgggtgctgatgtttctgctcgtaaagttagcaacaagt
cacatgattgggatgcttcttcaagtgaaaccggtaagcctcgttctcaagccgagcaactga
aagagaaggtgcttctccttcacgtcctgcttctgccttgggtgcttcttcaccgggtatatct
ggaaatggttacggtttggacgccaggaggggatcactaaatgattttgaagatagatcaaacg
attctcgagaactgaggacagatgcacctggtaggtcatctgtatcttcaactacacgaggctc
agtagaaaatggacaaacatctgagaaccaccatcataggtccccttctgctactagcactgtt
tccaatgaggagtttccaagggcagatgcgaatgagaattcagaagaatcagctcatgctacac
cttacagcagtgatgcttcaggagaaattagatcagggcctcttgctgcaaccacttcagcagc
tactcgccgagatttgtctgattttttccccaaaattcatggatagacgtacccgtggtcaattt
tggcgacgtccatcagagagactcggttcaaggattgtttcagcgccttcgaatgagacaagac
gtgatctttctgaggtcgaaactcaagttaagaagttggtggaggagttgaaaagcagctcatt
ggatactcagagacaagcaaccgcagaactaaggttgctagccaagcacaacatggataatcgg
atagtcattgggaactctggagcaatcgtcttattggtggaactactttactcaactgactcag
ctacacaggaaaacgctgttaccgcacttctcaacttatctatcaatgacaacaacaaaaaagc
aattgctgatgctggtgcaattgagccgctcattcacgtgcttgaaaatgggagctctgaagcc
aaggagaattcagctgctactctcttcagcctctctgtaatagaagaaaacaagattaagattg
gtcagtcgggtgcaatcgggcctcttgtagatcttctcggtaacggtaccccctcggggtaagaa
agacgctgctactgccttgtttaatctatcgatacatcaagaaaacaaggcgatgatcgtgcaa
tcaggtgctgtgagatatcttattgatctgatggacccagcagctgggatggtggataaagcag
ttgctgtttggcaaatctagctacaattccggaaggaagaaacgcgattggtcaagaaggcgg
aatccctcttcttgttgaagtcgttgagttgggttcagctagagggaaagaaaacgcagcagca
gctcttcttcaactttcaaccaacagtggtcggttctgcaacatggttcttcaagaaggcgccg
ttcctccactcgtcgctctctcacagtctggtactcctagagctagagaaaaggtacaaacttt
ataa At_2_AC004401 (SEQ ID NO. 15):

atgattttgcggttttggcgggaaaacattattttgcggttttggcggaaaatccatgattttg
cggttttgaaactcattcagatgtatcatccagatgatccatccaaatacttgttaaattataa
aaaacaaacatcatttttcatctgcatttggatgaatcatttggatgaaaacaaacaaggtct
gagtctgatttccaaaagagatataagaagggtggaaatggaagttcttctcagaa
gtatctcgtcgtttctaaatctgtcatcttctaaacatattgatttagacccgtttgagaagta
ctataagagagttgaagagttattgagagtgttgaagcctatagcagatgttgttgttacctct
gattttgttttgatgagaaacttggtaaagcatttgaagaattgactcaggatgttgatcaat
ccattgatcttttcaggagttggcaagctttctctagtaaagtctatttcgttcttcaaattga
atctttgctaccaaagatgcgggacaccattgtggatacttttcagtttctcatgtcttctaag

Figure 1F aaccatctacctgatgagctaagcccagcttctcttgagcaatgtctagagaagattaagcatc
ttagttatgaagaaatatcttctgtcattgacggtgctttgagggatcagagagatggtgttgg
acctagccctgagatcttggtgaaaattggagagaacactggtcttagatcaaaccaggagatt
ctgattgaagctgttgctctagagaggcagaaagagatggctgagcagtctgagaataatgcag
aagtcgagttccttgaccaactgattgttattgtaaaccgcatgcatgaacgtcttcttctgat
caaacagactcagacttctagtgtcgccattcttgccgacttcttttgccctctgtcacttgaa
gtaatgactgatccagtgattgtgtcatcaggacaaacatatgaaaaggcgtttatcaagagat
ggattgatttgggtttaaaagtgtgtcccaagactcgacagaccctgactcacactactctaat
acccaattacaccgtgaaggccttaatcgctaactggtgtgagacaaacgatgtcaagctgcct
gatcccaataaatcaacaagtttaaatgagctttctcctcttttatcatgtacagactccattc
ctagcacgggtgctgatgtttctgctcgtaaagttagcaacaagtcacatgattgggatgcttc
ttcaagtgaaaccggtaagccctcgttctcaagccgagcaactgaaagagaaggtgcttctcct
tcacgtcctgcttctgccttgggtgcttcttccgggtatatctggaaatggttacggtttgg
acgccaggagggatcactaaatgattttgaagatagatcaaacgattctcgagaactgaggac
agatgcacctggtaggtcatctgtatcttcaactacacgaggctcagtagaaatggacaaaca
tctgagaaccaccatcataggtccccttctgctactagcactgtttccaatgaggagtttccaa
gggcagatgcgaatgagaattcagaagaatcagctcatgctacaccttacagcagtgatgcttc
aggagaaattagatcagggcctcttgctgcaaccacttcagcagctactcgccgagatttgtct
gattttccccaaaattcatggatagacgtacccgtggtcaattttggcgacgtccatcagaga
gactcggttcaaggattgtttcagcgccttcgaatgagacaagacgtgatctttctgaggtcga
aactcaagttaagaagttggtggaggagttgaaaagcagctcattggatactcagagacaagca
accgcagaactaaggttgctagccaagcacaacatggataatcggatagtcattgggaactctg
gagcaatcgtcttattggtggaactactttactcaactgactcagctacacaggaaaacgctgt
taccgcacttctcaacttatctatcaatgacaacaacaaaaaagcaattgctgatgctggtgca
attgagccgctcattcacgtgcttgaaaatgggagctctgaagccaaggagaattcagctgcta
ctctcttcagcctctctgtaatagaagaaaacaagattaagattggtcagtcgggtgcaatcgg
gcctcttgtagatcttctcggtaacggtacccctcggggtaagaaagacgctgtactgccttg
tttaatctatcgatacatcaagaaaacaaggcgatgtcgtgcaatcaggtgctgtgagatatc
ttattgatctgatggacccagcagctgggatggtggataaagcagttgctgttttggcaaatct
agctacaattccggaaggaagaaacgcgattggtcaagaaggcggaatccctcttcttgttgaa
gtcgttgagttgggttcagctagagggaaagaaaacgcagcagcagctcttcttcaactttcaa
ccaacagtggtcggttctgcaacatggttcttcaagaaggcgccgttcctccactcgtcgctct
ctcacagtctggtactcctagagctagagaaaagaaaccaacggcatggaaacgctgggcgtgg
ctgatgatggatgatgatgatgatgatgttgatgatgcacagattctggtctctcagtgcc
tatttttatgttttgtcttgtga At_3_BT020206 (At5g67340) (SEQ ID NO. 17):

atgatggtacatatggaggtgtcttggttaagagttcttctagataacatctcctcctatctaa
gtttatcatctatggacgatttatcttcaaaccctgctcataagtactacaccagaggagaaga
tataggaaagcttatcaagcctgttcttgagaacctcattgactctgacgcggctcctagcgag
ttgcttaacaatggttttgaagaattagctcaatacgttgatgaacttagagaacagtttcaga
gttggcaacctctttcaactagaatctttatgttcttcgaattgaatcattagcatcaaagtt
acgagaatccagtttggaagtctttcagctcctcaaacactgcgaacaacatttgcctgctgac
ttgatctcaccttctttgaggagttgcattgaattggtgaagttagtgcaagagacgaaatat
cgtatactattgatcaagctctaaaagatcaaaagaaaggtgttggacctacttcagaggttct
ggtgaaaattgccgagagtactggtttaagatccaaccaggagattcttgttgaaggtgtggta
cttacaaacatgaaggaggatgctgagcttaccgataatgacaccgaagccgagtatctagacg
gattgatctctctaacaacacaaatgcatgagtaccttagcgacataaagcaggctcagttacg
ttgtccagtacgcgtaccttctgatttccgctgctctctatctcttgagcttatgactgatcca
gtcattgtagcatctggtcaaacattcgaacgggttttatccagaaatggatcgatatgggac
tcatggtttgtccaaagacaaggcaggctttatctcataccactttgacacctaatttcattgt
cagagctttctgcaagttggtgtgaaactaacaatgtctatcctcctgatccattggagttg
attcactcaagtgagccattccctcttcttgttgaatcagtgagagcttcatcatcagagaatg
gccattcagaatctttagatgcagaggaactgcgtcaggtctttagtaggtctgcttcggcgcc
aggcattgtctctgaagtggtttgcaaaaccaaaagaaacaacaatgctgctgcagatagatca
ctgacacggagtaataccccttggaaatttccagaagagaggcattggcgtcacccgggatca
tcccagcgaccgtaagagaaacaggaagcagttcaagtatcgaaaccgaggtgaagaaactcat
tgatgatctcaagagttcttcattggatacacagagagaggccacagctagaatcaggatacta
gcaagaaacagtacagacaatcgcattgtcattgcgcggtgcgaagcaatcccttcgttagtca
gtcttctttactcaacggatgagagaatccaagcagacgcagtgacttgcttactaaacttatc
catcaacgacaacaacaagtccctcatcgcggaaagtggagccatcgtaccgcttattcacgtt
ctcaaaacaggatacttagaagaagctaaagcaaactcagcagcaactctattcagcttgtcgg
tgatcgaagagtacaagacagagataggagaagcaggagctatagagccacttgttgacctctt

Figure 1G aggaagtggaagtctcagtggggaagaaagatgcagccacggctttattcaacctctcaatacac
catgagaacaaaacgaaagtaatcgaagctggagcagtgagatacttagttgaactgatggatc
ctgcttttgggatggtggagaaagctgtggtggtgctagcgaatcttgcaacggttagagaagg
aaagattgcgataggcgaagaaggaggaataccggtattggtggaagttgtggagttaggttca
gcaagaggcaaagagaatgcaactgcagcactattgcagctttgtacgcatagcccgaaattct
gcaacaatgtcataagagaaggagtgattccacctcttgtggcacttactaaatcaggaacagc
tagaggcaaagagaaggcacagaatcttctgaagtactttaaagcacacagacaaagcaatcag
aggagaggctga At_4_AB007645 (SEQ ID NO. 19):

atggaggtgtcttggttaagagttcttctagataacatctcctcctatctaagtttatcatcta
tggacgatttatcttcaaaccctgctcataagtactacaccagaggagaagatataggaaagct
tatcaagcctgttcttgagaacctcattgactctgacgcggctcctagcgagttgcttaacaat
ggttttgaagaattagctcaatacgttgatgaacttagagaacagtttcagagttggcaacctc
tttcaactagaatcttttatgttcttcgaattgaatcattagcatcaaagttacgagaatccag
tttggaagtctttcagctcctcaaacactgcgaacaacatttgcctgctgacttgatctcacct
tcttttgaggagtgcattgaattggtgaagttagtggcaagagacgaaatatcgtatactattg
atcaagctctaaaagatcaaaagaaaggtgttggacctacttcagaggttctggtgaaaattgc
cgagagtactggtttaagatccaaccaggagattcttgttgaaggtgtggtacttacaaacatg
aaggaggatgctgagcttaccgataatgacaccgaagccgagtatctagacggattgatctctc
taacaacacaaatgcatgagtaccttagcgacataaagcaggctcagttacgttgtccagtacg
cgtaccttctgatttccgctgctctctatctcttgagcttatgactgatccagtcattgtagca
tctggtcaaacattcgaacgggtttttatccagaaatggatcgatatgggactcatggtttgtc
caaagacaaggcaggctttatctcataccactttgacacctaatttcattgtcagagcttttct
tgcaagttggtgtgaaactaacaatgtctatcctcctgatccattggagttgattcactcaagt
gagccattccctcttcttgttaatcagtgagagcttcatcatcagagaatggccattcagaat
ctttagatgcagaggaactgcgtcaggtctttagtaggtctgcttcggcgccaggcattgtctc
tgaagtggtttgcaaaaccaaaagaaacaacaatgctgctgcagatagatcactgacacggagt
aatacccccttggaaattttccagaagagaggcattggcgtcaccccgggatcatcccagcgaccg
taagagaaacaggaagcagttcaagtatcgaaaccgaggtgaagaaactcattgatgatctcaa
gagttcttcattggatacacagagagaggccacagctagaatcaggatactagcaagaaacagt
acagacaatcgcattgtcattgcgcggtgcgaagcaatcccttcgttagtcagtcttctttact
caacggatgagagaatccaagcagacgcagtgacttgcttactaaacttatccatcaacgacaa
caacaagtccctcatcgcggaaagtggagccatcgtaccgcttattcacgttctcaaaacagga
tacttagaagaagctaaagcaaactcagcagcaactctattcagcttgtcggtgatcgaagagt
acaagacagagataggagaagcaggagctatagagccacttgttgacctcttaggaagtggaag
tctcagtggggaaagatgcagccacggctttattcaacctctcaatacaccatgagaacaaa
acgaaagtaatcgaagctggagcagtgagatacttagttgaactgatggatcctgcttttgga
tggtggagaaagctgtggtggtgctagcgaatcttgcaacggttagagaaggaaagattgcgat
aggcgaagaaggaggaataccggtattggtggaagttgtggagttaggttcagcaagaggcaaa
gagaatgcaactgcagcactattgcagctttgtacgcatagcccgaaattctgcaacaatgtca
taagagaaggagtgattccacctcttgtggcacttactaaatcaggaacagctagaggcaaaga
gaaggttctttttttgtttcctcttctttgtttggtaaatgtctcatga At_5_NM_115336 (At3g54790) (SEQ ID NO. 21):

atggatcctgttcctgttcgatgtcttcttaacagtatatctcggtatcttcatctggttgcgt
gccagactataagatttaatcctattcaaacatgtattggaaatatggttctcttgttgaagct
cttgaaaccgttgctcgatgaagttgttgattgcaagataccttctgatgactgtttatataaa
ggatgtgaagaccttgattctgttgttaaccaggctcgggagttcttagaggactggtcaccaa
agttgagcaagttgtttggtgtgtttcaatgcgaggttttgttgggaaaggtccagacttgttc
gttggagattagtcgcatacttcttcagttatcacagtcaagtccggttacttcaagcgtacaa
agtgttgagcgctgcgtgcaggagactgagagttttaagcaagagggacattaatggaactca
tggagaatgctttacggaatcagaaagatgatattacctcttrggataacaatcatctggaaag
cataattcaaatgcttggattgatatcaaaccaagatctcttaaaggaaagcattactgtggag
aaagagaggataagatcccaggccagtaagtcagaagaagatatggaacaaaccgaacagttga
tagaactcgtcttgtgcatccgtgaacacatgcttaaaactgagtttcttgaagtggctaaagg
tatctcgataccccgtatttccggtgtcctttgtcaacagaactcatgctggatccggtaata
gtagcttcaggacagacatttgacagaacatccattaagaaatggcttgataacgggttagctg
tttgtccaaggacgcggcaggtgctgactcatcaagaactcattcccaattacacggttaaggc
tatgatagcgagttggttggaggcaaacaggatcaaccttgctactaactcttgtcatcagtat
gatggtggtgatgcttcatccatggctaataatatgggttctcaagactttaaccgcaccgaga
gttttcgttttctttacggagcagcagtttaacctcaagatcatctcttgaaactggaaatgg

Figure 1H gtttgagaaactgaagattaacgtgtctgccagtttatgcggggaatctcaaagcaaggatctt
gaaatattcgagcttttgtctccggggcagtcttacactcacagcaggagtgaatcagtttgca
gtgttgtctcgtctgttgattatgtaccttcggtgacacatgagacagaaagtatactagggaa
tcaccaaagctccagtgagatgtctcccaagaaaaacttagaaagttcaaacaatgtaaatcat
gagcatagcgcagcaaagacttatgagtgttctgtacatgatttagatgattcaggaacaatga
cgacttcacataccataaaattggtagaagatcttaaaagcgggtctaacaaagtgaagactgc
tgctgcagctgaaatacgtcatctcaccattaacagcattgaaaatcgtgttcacatcgggcgt
tgtggtgctattactccactgctgtcacttttatactcagaagaaaagctaactcaagaacacg
cagtcacggctcttttgaatctttccatcagtgaactaaacaaagccatgattgtggaagtcgg
ggcgatagaaccgcttgttcatgttttgaacacaggaaatgacagagccaaagagaattcagca
gcatcattgttcagtctgtctgttctgcaggtcaacagagaacgaataggccagtctaacgcag
cgatacaagctctggtgaatcttcttggtaaaggaacatttagaggaaagaaagacgccgcctc
tgctttgttcaatctatcgattactcatgataacaaggcccgtatcgtgcaagctaaggcggtt
aagtaccttgtggagctgttagacccagatttagagatggttgataaagcagttgctcttcttg
caaatctttctgcagttggagaagggcgtcaagccatcgtgagggaaggtgggattccattact
tgttgaaactgttgacttaggatctcagagagggaaagagaatgcagcttctgtgctgcttcag
ttgtgtctgaacagtcccaagttttgcactctggtcttgcaagaaggcgccatacctccgcttg
ttgccttgtctcagtctggtacacagagagcaaaagagaaggcacagcaacttcttagccactt
ccgaaaccagagagatgcaaggatgaagaaaggtagatcatga At_6_AK118613 (SEQ ID NO. 23):

atggatcctgttcctgttcgatgtcttcttaacagtatatctcggtatcttcatctggttgcgt
gccagactataagatttaatcctattcaaacatgtattggaaatatggttctcttgttgaagct
cttgaaaccgttgctcgatgaagttgttgattgcaagatacctctgatgactgtgtttatataaa
ggacgtgaagaccttgattctgttgttaaccaggctcgggagttcttagaggactggtcaccaa
agttgagcaagttgtttggtgtgtttcaatgcgaggttttgttgggaaaggtccagacttgttc
gttggagattagtcgcatacttcttcagttatcacagtcaagtccggttacttcaagcgtacaa
agtgttgagcgctgcgtgcaggagactgagagttttaagcaagaggggacattaatggaactca
tggagaatgctttacggaatcagaaagatgatattacctctttggataacaatcatctggaaag
cataattcaaatgcttggattgatatcaaaccaagatctcttaaaggaaagcattactgtggag
aaagagaggataagatcccaggccagtaagtcagaagaagatatggaacaaaccgaacagttga
tagaactcgtcttgtgcatccgtgaacacatgcttaaaactgagtttcttgaagtggctaaagg
tatctcgatacccccgtatttccggtgtcctttgtcaacagaactcatgctggatccggtaata
gtagcttcaggacagacatttgacagaacatccattaagaaatggcttgataacgggttagctg
tttgtccaaggacgcggcaggtgctgactcatcaagaactcattcccaattacacggttaaggc
tatgatagcgagttggttggaggcaaacaggatcaaccttgctactaactcttgtcatcagtat
gatggtggtgatgcttcatccatggctaataatatgggttctcaagactttaaccgcaccgaga
gttttcgttttttctttacggagcagcagtttaacctcaagatcatctcttgaaactggaaatgg
gtttgagaaactgaagattaacgtgtctgccagtttatgcggggaatctcaaagcaaggatctt
gaaatattcgagcttttgtctccggggcagtcttacactcacagcaggagtgaatcagtttgca
gtgttgtctcgtctgttgattatgtaccttcggtgacacatgagacagaaagtatactagggaa
tcaccaaagctccagtgagatgtctcccaagaaaaacttagaaagttcaaacaatgtaaatcat
gagcatagcgcagcaaagacttatgagtgttctgtacatgatttagatgattcaggaacaatga
cgacttcacataccataaaattggtagaagatcttaaaagcgggtctaacaaagtgaagactgc
tgctgcagctgaaatacgtcatctcaccattaacagcattgaaaatcgtgttcacatcgggcgt
tgtggtgctattactccactgctgtcacttttatactcagaagaaaagctaactcaagaacacg
cagtcacggctcttttgaatctttccatcagtgaactaaacaaagccatgattgtggaagtcgg
ggcggtagaaccgcttgttcatgttttgaacacaggaaatgacagagccaaagagaattcagca
gcatcattgttcagtctgtctgttctgcaggtcaacagagaacgaataggccagtctaacgcag
cgatacaagctctggtgaatcttcttggtaaaggaacatttagaggaaagaaagacgccgcctc
tgctttgttcaatctatcgattactcatgataacaaggcccgtatcgtgcaagctaaggcggtt
aagtaccttgtggagctgttagacccagatttagagatggttgataaagcagttgctcttcttg
caaatctttctgcagttggagaagggcgtcaagccatcgtgagggaaggtgggattccattact
tgttgaaactgttgacttaggatctcagagagggaaagagaatgcagcttctgtgctgcttcag
ttgtgtctgaacagtcccaagttttgcactctggtcttgcaagaaggcgccatacctccgcttg
ttgccttgtctcagtctggtacacagagagcaaaagagaaggcacagcaacttcttagccactt
ccgaaaccagagagatgcaaggatgaagaaaggtagatcatga At_7_AL138650 (SEQ ID NO. 25):

atggttctcttgttgaagctcttgaaaccgttgctcgatgaagttgttgattgcaagatacctt
ctgatgactgtttatataaaggatgtgaagaccttgattctgttgttaaccaggctcgggagtt
cttagaggactggtcaccaaagttgagcaagttgtttggtgtgtttcaatgcgaggttttgttg

Figure 1I ggaaaggtccagacttgttcgttggagattagtcgcatacttcttcagttatcacagtcaagtc
cggttacttcaagcgtacaaagtgttgagcgctgcgtgcaggagactgagagttttaagcaaga
ggggacattaatggaactcatggagaatgctttacggaatcagaaagatgatattacctctttg
gataacaatcatctggaaagcataattcaaatgcttggattgatatcaaaccaagatctcttaa
aggaaagcattactgtggagaaagagaggataagatcccaggccagtaagtcagaagaagatat
ggaacaaaccgaacagttgatagaactcgtcttgtgcatccgtgaacacatgcttaaaactgag
tttcttgaagtggctaaaggtatctcgataccccgtatttccggtgtcctttgtcaacagaac
tcatgctggatccggtaatagtagcttcaggacagacatttgacagaacatccattaagaaatg
gcttgataacgggttagctgtttgtccaaggacgcggcaggtgctgactcatcaagaactcatt
cccaattacacggttaaggctatgatagcgagttggttggaggcaaacaggatcaaccttgcta
ctaactcttgtcatcagtatgatggtggtgatgcttcatccatggctaataatatgggttctca
agactttaaccgcaccgagagttttcgttttttcttacggagcagcagttaacctcaagatca
tctcttgaaactggaaatgggtttgagaaactgaagattaacgtgtctgccagtttatgcgggg
aatctcaaagcaaggatcttgaaatattcgagcttttgtctccggggcagtcttacactcacag
caggagtgaatcagtttgcagtgttgtctcgtctgttgattatgtaccttcggtgacacatgag
acagaaagtatactagggaatcaccaaagctccagtgagatgtctcccaagaaaaacttagaaa
gttcaaacaatgtaaatcatgagcatagcgcagcaaagacttatgagtgttctgtacatgattt
agatgattcaggaacaatgacgacttcacataccataaaattggtagaagatcttaaaagcggg
tctaacaaagtgaagactgctgctgcagctgaaatacgtcatctcaccattaacagcattgaaa
atcgtgttcacatcgggcgttgtggtgctattactccactgctgtcacttttatactcagaaga
aaagctaactcaagaacacgcagtcacggctcttttgaatcttttccatcagtgaactaaacaaa
gccatgattgtggaagtcggggcgatagaaccgcttgttcatgttttgaacacaggaaatgaca
gagccaaagagaattcagcagcatcattgttcagtctgtctgttctgcaggtcaacagagaacg
aataggccagtctaacgcagcgatacaagctctggtgaatcttcttggtaaaggaacatttaga
ggaaagaaagacgccgcctctgctttgttcaatctatcgattactcatgataacaaggcccgta
tcgtgcaagctaaggcggttaagtaccttgtggagctgttagacccagatttagagatggttga
taaagcagttgctcttcttgcaaatctttctgcagttggagaagggcgtcaagccatcgtgagg
gaaggtgggattccattacttgttgaaactgttgacttaggatctcagagagggaaagagaatg
cagcttctgtgctgcttcagttgtgtctgaacagtcccaagttttgcactctggtcttgcaaga
aggcgccatacctccgcttgttgccttgtctcagtctggtacacagagagcaaaagagaaggta
tatactatattcttcttctgcggttacacgaaaacacaccaagttcagtttcttattgatcgag
atatctga At_8_AL133314 (SEQ ID NO. 27):

atggaggaagagaaagcttctgctgcacagagcttaatcgatgtagttaacgagattgctgcga
tttctgattatcgtataacagtgaagaagctttgttataatctagcgaggagattaaagctgct
tgttcctatgtttgaggaaattagagaaagtaacgaaccgatcagcgaagatacgttgaagact
ttgatgaatttgaaggaagctatgtgttcagcgaaggattatctcaaattttgtagccaaggga
gcaagatttatctggtgatggagagggaacaagtgacaagtaaattgatggaggtgtctgttaa
gttagaacaatctttaagccagattccatatgaagaactcgatatatcggatgaagttagagaa
caggttgagctggttcttagtcagtttcggcgagctaaaggaagagtagatgtatcagatgatg
agctatatgaagatcttcagtcgctttgcaacaaaagtagtgatgtagatgcttatcagcctgt
gctagagcgggttgcgaagaagttacatttgatggagattcctgacctagctcaagaatcagtg
gctctgcatgaaatggttgcttcaagcggtggagatgttggtgaaaatattgaggagatggcaa
tggtattaaagatgattaaggattttgtgcagacggaggatgataatggcgaggagcagaaagt
aggagttaactctagaagcaatggacagacttctacggcagcgagtcagaagatacctgtgatt
cctgatgattttcgctgtccgatttcgctggaaatgatgagagatccagttattgtttcatcag
ggcagacatacgaacgcacatgtattgagaaatggatagaaggtggacactcgacatgtccaaa
aacacagcaggcgctaacaagcacaaccctcacaccaaactatgttctccgtagtctcatagct
cagtggtgcgaggccaacgatattgagcctccaaagcctccgagcagtttaagacccagaaaag
tatcgtccttctcatctcccgcagaagcgaacaagattgaagatcttatgtggagacttgcgta
cggaaacccgaggaccaacgatctgcagctgggaaatccgccttcttgcaaaacgaaatgca
gacaaccgcgtggccatagccgaagctggagccataccttctcgtaggtctcctctcaactc
ctgattctcgtattcaagaacattcggtaacagctcttctaaacctctccatatgtgagaacaa
caaaggagccattgtttcagctggagctattcctggtatagttcaagtgcttaagaaaggaagc
atggaggccagagagaatgcggcggctacacttttcagtctatcagtgatcgatgaaaataaag
tgactatcggtgccttaggagcaattccgccactcgttgtattacttaatgaaggtacacaaag
aggcaagaaagatgctgctactgcactctttaacctctgtatataccaaggaaacaaggaaaa
gctatacgtgcaggagtgattcccacgttgactagactcttgacagagcccggaagcggaatgg
tcgatgaggcactcgcgattttggcgattctctctagccaccccgaaggaaaagcaatcatagg
atcctctgatgcagtcccaagtttggttgagtttatcagaactggctcgcctagaaacagagaa
aacgcagctgctgttctagtccacctctgttctggagacccacaacatcttgtcgaagcgcaga
aactcggccttatgggtccattgatagatttagctggaaatgggacggatagagggaaacgaaa

Figure 1J agcagcgcagttgcttgaacgcatcagccgtctcgctgaacagcagaaggaaacggctgtgtca
caaccggaagaagaagctgaaccaacacatccagaatccaccacagaagctgcagatacttaa At_9_AC010870 (SEQ ID NO. 29):

atggagatggagaatcaccgccccggcagtttcacctacatgggccgcaaattcagcgatttaa
gtctcaacgatgactcctctgctttcagcgattgtaacagcgacagatccggcgaattccccac
tgcttcctccgagagccgtcgtctcctcctctcttgcgcctctgagaattccgatgatctcatc
aatcatctcgtgtcgcatcttgattcctcctattcgatcgatgagcagaagcaagctgctatgg
agatcaggctcttatccaagaacaaacctgagaatcggatcaaaatcgccaaggccggtgcgat
taagccgttgatttctctgatctcttcttcggatcttcagcttcaggagtatggtgtcactgca
atcttgaatctatctctctgcgacgagaacaaagagtcgattgcttcttccggtgcgattaagc
cgcttgtcagggctttgaaaatgggaacaccgactgctaaagagaacgctgcttgtgctctgct
ccgtctatcgcagatcgaggagaacaaagtcgccatcgggagatccggagcgattcctctgttg
gtgaaccttctagaaacaggcggattcagagcgaagaaggacgcgtcgacggctctgtactcgt
tgtgctcagctaaagagaacaaaatcagagccgtgcaatcgggaattatgaagccgcttgttga
attgatggcggatttcggatcaaacatggtggataaatcggcgtttgtgatgagtctgttaatg
tcggtgccggaatcgaaaccggcgattgtggaggaaggaggagttccggtgctggtggagatag
tagaggtgggaacacagagacagaaagagatggctgtgtcgatattgctacagctttgtgagga
gagtgttgtgtatagaacaatggtggctagagaaggagcgatacctccgctagtggctctgtcg
caggcaggaacaagtcgagctaagcaaaaggctgaggcgttgattgagcttctaaggcaaccaa
gatccattagtaatggtggtgctagatcatcgtcccaactctga At_10_AY125543 (At3g01400) (SEQ ID NO. 31):

atggagatggagaatcaccgccccggcagtttcacctacatgggccgcaaattcagcgatttaa
gtctcaacgatgactcctctgctttcagcgattgtaacagcgacagatccggcgaattccccac
tgcttcctccgagagccgtcgtctcctcctctcttgcgcctctgagaattccgatgatctcatc
aatcatctcgtgtcgcatcttgattcctcctattcgatcgatgagcagaagcaagctgctatgg
agatcaggctcttatccaagaacaaacctgagaatcggatcaaaatcgccaaggccggtgcgat
taagccgttgatttctctgatctcttcttcggatcttcagcttcaggagtatggtgtcactgca
atcttgaatctatctctctgcgacgagaacaaagagtcgattgcttcttccggtgcgattaagc
cgcttgtcagggctttgaaaatgggaacaccgactgctaaagagaacgctgcttgtgctctgct
ccgtctatcgcagatcgaggagaacaaagtcgccatcgggagatccggagcgattcctctgttg
gtgaaccttctagaaacaggcggattcagagcgaagaaggacgcgtcgacggctctgtactcgt
tgtgctcagctaaagagaacaaaatcagagccgtgcaatcgggaattatgaagccgcttgttga
attgatggcggatttcggatcaaacatggtggataaatcggcgtttgtgatgagtctgttaatg
tcggtgccggaatcgaaaccggcgattgtggaggaaggaggagttccggtgctggtggagatag
tagaggtgggaacacagagacagaaagagatggctgtgtcgatattgctacagctttgtgagga
gagtgttgtgtatagaacaatggtggctagagaaggagcgatacctccgctagtggctctgtcg
caggcaggaacaagtcgagctaagcaaaaggctgaggcgttgattgagcttctaaggcaactaa
gatccattagtaatggtggtgctagatcatcgtcccaactctga At_11_AY087360 (SEQ ID NO. 33):

atggagatggagaatcaccgccccggcagtttcacctacatgggccgcaaattcagcgatttaa
gtctcaacgatgactcctctgctttcagcgattgtaacagcgacagatccggcgaattccccac
tgcttcctccgagagccgtcgtctcctcctctcttgcgcctctgagaattccgatgatctcatc
aatcatctcgtgtcgcatcttgattcctcctattcgatcgatgagcagaagcaagctgctatgg
agatcaggctcttatccaagaacaaacctgagaatcggatcaaaatcgccaaggccggtgcgat
taagccgttgatttctctgatctcttcttcggatcttcagcttcaggagtatggtgtcactgcw
atcttgaatctatctctctgcgacgagaacaaagagtcgattgcttcttccggtgcgattaagc
cgcttgtcagggctttgaaaatgggaacaccgactgctaaagataacgctgcttgtgctctgct
ccgtctatcgcagatcgaggagaacaaagtcgccatcgggagatccggagcgattcctctgttg
gtgaaccttctagaaacaggcggattcagagcgaagaaggacgcgtcgacggctctgtactcgt
tgtgctcagctaaagagaacaaaatcagagccgtgcaatcgggaattatgaagccgcttgttga
attgatggcggatttcggatcaaacatggtggataaatcggcgtttgtgatgagtctgttaatg
tcggtgccggaatcgaaaccggcgattgtggaggaaggaggagttccggtgctggtggagatag
tagaggtgggaacacagagacagaaagagatggctgtgtcgatattgctacagctttgtgagga
gagtgttgtgtatagaacaatggtggctagagaaggagcgatacctccgctagtggctctgtcg
caggcaggaacaagtcgagctaagcaaaaggctgaggcgttgattgagcttctaaggcaaccaa
gatccattagtaatggtggtgctagatcatcgtcccaactctga At_12_AB016888 (SEQ ID NO. 35):

Figure 1K atggatacagatgaagaagccacaggagatgcagagaaccgtgatgaagaagttaccgcagaag
aaccgattcacgatgaggttgtggatgcggtggagattcatgaggaagaagtgaaagaagatga
tgatgattgtgaaggattggtgagcgatatcgtatcgattgtcgagtttttggatcagattaac
ggttatcgaagaacacaacaaaaagaatgttttaatctcgttagacgattgaagattcttattc
cattttttggatgagattcgaggttttgaatcaccaagttgcaagcattttttaaatcgtttgag
gaaagtgtttcttgctgccaagaaattattagaaacttgcagcaatggcagtaaaatctatatg
gcattggatggcgaaacaatgatgacgagatttcattcgatttacgaaagttgaatcgtgttc
ttgttaaagctccttttgatgaattaatgatttctggtgatgcgaaagacgagattgattcatt
gtgtaaacaactgaaaaaagcaaaagaagaacagatacacaagacatagagctagcagtagac
atgatggtggtattctcaaaaaccgatcctcgaaacgcagatagcgcgataatagagaggctag
cgaaaaagcttgagctacaaacaattgatgatttaaagacagaaactatagccatacaaagctt
aatccaagacaaaggaggtttgaacatagagactaaacaacatatcattgagcttcttaacaag
ttcaagaagcttcaaggtcttgaagctaccgacattctctaccaacccgtcatcaataaagcaa
tcaccaagtcaacgtctctaatattacctcatgagttttttgtgtcctataacactcgaaataat
gcttgacccggttatcatcgccactggacagacatatgagaaggagagtatacagaaatggttt
gacgcaggacataagacttgtcctaaaacaagacaggagttagatcatctctctcttgcaccta
acttcgctttaaagaacttgattatgcagtggtgtgagaagaacaatttcaagattccagagaa
agaagtaagtcctgactcacaaaatgagcagaaagatgaggtctcttttgctggtggaagcgtta
tcgtcaagccaactggaagaacaacgaagatcagtgaagcagatgcgtttgctagccagagaaa
atcccgagaaccgcgttttaatagcgaatgcaggagcgattcctttgttagttcaactcctttc
ttaccctgattcaggaatccaagaaaacgcggtaacgacattgttgaatctatctatcgacgag
gtcaacaagaaactcatttcaaatgaaggagctattccaaacattattgaaatccttgaaaatg
gaaacagagaggcaagagagaactctgctgcagctttgtttagtttatcgatgctcgatgagaa
caaagtaactatcggattatcgaatgggataccgcctttagtcgatttactacaacatgggaca
ttaagagggaagaaagatgctctcactgcactctttaacttgtctcttaactcagctaataaag
gaagagctatcgatgctggtattgttcaacctttgcttaaccttcttaaagataaaaacttagg
gatgatcgatgaagcgctttcgattctgttgctgcttgcatcacaccctgaaggacgtcaagcc
attggacaactctccttcattgaaacacttgtggaattcatcagacaaggcaccccgaaaaaca
aagagtgtgcgacctcggtgctgcttgaactaggctctaacaactcgtcttttatcctcgcagc
gcttcaattcggagtttatgaatatctggtagaaataaccacctctggaacaaacagagctcag
agaaaagcaaatgctcttatacaactcataagcaaatctgaacaaatttag At_13_AK175585 (SEQ ID NO. 37):

atggtcgatgtgatggatacagatgaagaagccacaggagatgcagagagccgtgatgaagaag
ttaccgcagaagaaccgattcacgatgaggttgtggatgcggtggagattcatgaggaagaagt
gaaagaagatgatgatgattgtgaaggattggtgagcgatatcgtatcgattgtcgagtttttg
gatcagattaacggttatcgaagaacacaacaaaaagaatgttttaatctcgttagacgattga
agattcttattccattttttggatgagattcgaggttttgaatcaccaagttgcaagcattttt
aaatcgtttgaggaaagtgtttcttgctgccaagaaattattagaaacttgcagcaatggcagt
aaaatctatatggcattggatggcgaaacaatgatgacgagatttcattcgatttacgaaagt
tgaatcgtgttcttgttaaagctccttttgatgaattaatgatttctggtgatgcgaaagacga
gattgattcattgtgtaaacaactgaaaaaagcaaaagaagaacagatacacaagacatagag
ctagcagtagacatgatggtggtattctcaaaaaccgatcctcgaaacgcagatagcgcgataa
tagagaggctagcgaaaaagcttgagctacaaacaattgatgatttaaagacagaaactatagc
catacaaagcttaatccaagacaaaggaggtttgaacatagagactaaacaacatatcattgag
cttcttaacaagttcaagaagcttcaaggtcttgaagctaccgacattctctaccaacccgtca
tcaataaagcaatcaccaagtcaacgtctctaatattacctcatgagttttttgtgtcctataac
actcggaataatgcttgacccggttatcatcgccactggacagacatatgagaaggagagtata
cagaaatggtttgacgcaggacataagacttgtcctaaaacaagacaggagttagatcatctct
ctcttgcacctaacttcgctttaaagaacttgattatgcagtggtgtgagaagaacaatttcaa
gattccagagaaagaagtaagtcctgactcacaaaatgagcagaaagatgaggtctcttttgctg
gtggaagcgttatcgtcaagccaactggaagaacaacgaagatcagtgaagcagatgcgtttgc
tagccagagaaatcccgagaaccgcgttttaatagcgaatgcaggagcgattcctttgttagt
tcaactcctttcttaccctgattcaggaatccaagaaaacgcggtaacgacattgttgaatcta
tctatcgacgaggtcaacaagaaactcatttcaaatgaaggagctattccaaacattattgaaa
tccttgaaaatggaaacagagaggcaagagagaactctgctgcagctttgtttagtttatcgat
gctcgatgagaacaaagtaactatcggattatcgaatgggataccgcctttagtcgatttacta
caacatgggacattaagagggaagaaagatgctctcactgcactctttaacttgtctcttaact
cagctaataaaggaagagctatcgatgctggtattgttcaacctttgcttaaccttcttaaaga
taaaaacttagggatgatcgatgaagcgctttcgattctgttgctgcttgcatcacaccctgaa
ggacgtcaagccattggacaactctccttcattgaaacacttgtggaattcatcagacaaggca
ccccgaaaaacaaagagtgtgcgacctcggtgctgcttgaactaggctctaacaactcgtcttt

Figure 1L tatcctcgcagcgcttcaattcggagtttatgaatatctggtagaaataaccacctctggaaca
aacagagctcagagaaaagcaaatgctcttatacaactcataagcaaatctgaacaaatttag At_14_AL049655 (SEQ ID NO. 39):

atgggattaacgaattgttgttcccacgaggagctaatgagtcgactcgttgactccgttaaag
aaatatcagggttttcatcttcaaggggttttattgggaagatccaaggcgatcttgttcgtag
gatcacgcttctcagccctttcttcgaggaattgattgacgtcaatgttgaattgaaaaggat
cagattacagggtttgaggctatgagaatcgctcttgattcaagtcttgacttttttcgatcgg
ttaatggaggaagcaagcttttttcagcttttcgatagagattctcttgtggagaagttccgtga
catgacagtggagatagaagcagcgttaagtcagattccttatgaagagattgaggtatcagag
gaagtcagagaacaggttcagcttctgcattttcagttcaagagagcaaaagaaagatgggagg
agtctgatctacagcttagccatgatctagctatggcagagaatgtgatggatcctgaccctat
aatcctcaaaagactttcacaagagctccaacttactaccattgatgagctgaagaaagaatcg
catgcgatacatgagtattttctttcatatgatggagatcctgatgactgtttcgagaggatgt
cttcacttcttaaaaacctggtagactttgtaacaatggaaagttcagaccctgatccatccac
tggcagcagaatcgtttcgagacatcgttctcctgttataccagagtattttcggtgtccgata
tcacttgaactgatgaaggatcctgttatcgtctccactggacagctgaattttttcgaccttgc
agacatatgaaagatcatcaattcagaagtggcttgatgctggtcataaaacatgtccgaaatc
tcaggagacacttttacatgctggattaaccctaattatgtgttaaagagtctcattgctttg
tggtgtgaaagcaacggcattgagctaccgcaaaatcaagggagctgtagaaccacaaaaatag
gaggaagcagctcttcagattgtgatcgaacatttgtccttttccttgttagagaaattggccaa
cggtactacagaacagcaaagagctgcagctggagaattaaggttactagccaagaggaacgtg
gataacagagtttgtatcgctgaggctggagccataccactccttgtagagcttctatcctcac
cagatcctcggactcaggaacattctgtgacagctcttctgaatctttccataaatgaagggaa
caaaggagccattgttgatgcaggagccataacggatatagtagaagtcctaaagaacggaagc
atggaagctagagagaacgctgctgcaaccctttttcagtttatctgttatagatgaaaacaaag
tggcaataggtgctgctggagctatccaagcacttataagcttgcttgaggaaggaacccgaag
aggcaaaaaagatgctgctacagcgattttcaacttatgcatataccaggggaacaaatcaagg
gcggttaaaggcggtattgttgaccctctgaccagattactgaaagatgcaggtggcggaatgg
tggatgaggctctggccatttttagcaattctttcaactaaccaagaagggaaaacagcgatagc
tgaagcagaatctatcccggttttggttgagattataaggacagggtcaccaaggaaccgggaa
aatgctgcagcaatactttggtatctatgtattgggaatatagaaaggctaaatgtagcaagag
aggttggtgcagatgtggccttgaaggaacttactgagaatggcactgatagagcaaagaggaa
agctgcgagcttgttggagcttattcagcaaaccgaaggtgttgcagtaactactgttccatga At_15_AY096530 (At3g54850) (SEQ ID NO. 41):

atgggattaacgaattgttgttcccacgaggagctaatgagtcgactcgttgactccgttaaag
aaatatcagggttttcatcttcaaggggttttattgggaagatccaaggcgatcttgttcgtag
gatcacgcttctcagccctttcttcgaggaattgattgacgtcaatgttgaattgaaaaggat
cagattacagggtttgaggctatgagaatcgctcttgattcaagtcttgacttttttcgatcgg
ttaatggaggaagcaagcttttttcagcttttcgatagagattctcttgtggagaagttccgtga
catgacagtggagatagaagcagcgttaagtcagattccttatgaagagattgaggtatcagag
gaagtcagagaacaggttcagcttctgcattttcagttcaagagagcaaaagaaagatgggagg
agtctgatctacagcttagccatgatctagctatggcagagaatgtgatggatcctgaccctat
aatcctcaaaagactttcacaagagctccaacttactaccattgatgagctgaagaaagaatcg
catgcgatacatgagtattttctttcatatgatggagatcctgatgactgtttcgagaggatgt
cttcacttcttaaaaacctggtagactttgtaacaatggaaagttcagaccctgatccatccac
tggcagcagaatcgtttcgagacatcgttctcctgttataccagagtattttcggtgtccgata
tcacttgaactgatgaaggatcctgttatcgtctccactggacagacatatgaaagatcatcaa
ttcagaagtggcttgatgctggtcataaaacatgtccgaaatctcaggagacacttttacatgc
tggattaaccctaattatgtgttaaagagtctcattgctttggtgtgaaagcaacggcatt
gagctaccgcaaaatcaagggagctgtagaaccacaaaaataggaggaagcagctcttcagatt
gtgatcgaacatttgtccttttccttgttagagaaattggccaacggtactacagaacagcaaag
agctgcagctggagaattaaggttactagccaagaggaacgtggataacagagtttgtatcgct
gaggctggagccataccactccttgtagagcttctatcctcaccagatcctcggactcaggaac
attctgtgacagctcttctgaatctttccataaatgaagggaacaaaggagccattgttgatgc
aggagccataacggatatagtagaagtcctaaagaacggaagcatggaagctagagagaacgct
gctgcaaccctttttcagtttatctgttatagatgaaaacaaagtggcaataggtgctgctgag
ctatccaagcacttataagcttgcttgaggaaggaacccgaagaggcaaaaaagatgctgctac
agcgattttcaacttatgcatataccaggggaacaaatcaagggcggttaaaggcggtattgtt
gaccctctgaccagattactgaaagatgcaggtggcggaatggtggatgaggctctggccattt
tagcaattctttcaactaaccaagaagggaaaacagcgatagctgaagcagaatctatcccggt

Figure 1M tttggttgagattataaggacagggtcaccaaggaaccgggaaaatgctgcagcaatactttgg
tatctatgtattgggaatatagaaaggctaaatgtagcaagagaggttggtgcagatgtggcct
tgaaggaacttactgagaatggcactgatagagcaaagaggaaagctgcgagcttgttggagct
tattcagcaaaccgaaggtgttgcagtaactactgttccatga At_16_AK118730 (At4g16490) (SEQ ID NO. 43):

atggtatcggtggaggaacctttatctcattccaattccactcgctttccgttaacaaccgatt
tctacggttcatcatcgccgtcggcggcgaggttacaccgtcaagctggccggtcgatgagaac
agtgagatctaacttctatcaaagcggagatcaatcttgctcattcgtcggctcaatcggcgat
aaatcagagtatgcgtcggagtttctctcggattccgtcatcgacatgagactcggcgagcttg
ctttgaaaaacagtaattctctcaattcaaacgcttcctcaatgaaagaggaagcgtttctcga
catttctcaggcgtttagtgattttccgcttgtagtagtgatatctccggcgagttacagcgt
cttgcttgcttgccgtcgccggaggctgatagaaatgagagcggcggagataacgaagcggagc
atgatccagagttagagagagagccttgtctagggtttctacagagagaaaacttctctacaga
gattatcgagtgtatttcgccggaagatctgcagccaactgtgaaactatgcatcgacggactt
cgttcctcttcggtggcgataaagcgatctgctgcggcgaagctacggctattggcgaagaatc
gagcggataatcgtgtgttgattggggaatctggagctattcaagctttgattccacttcttcg
ttgtaacgatccatggacgcaagagcgcgcagttacagctctgttaaacctctcgttacacgac
cagaacaaagctgtaatcgccgcaggaggagcgattaaatcactagtgtgggtactcaaaacgg
ggacggagacttcaaagcagaacgctgcatgtgctttgcttagtttggcgctattggaggagaa
caaaggctcaatcggagcttgcggtgctattccgccgctggtttctcttctgttgaacggatct
tgcaggggaaagaaggatgcgttgacggcgctctacaagctgtgtacgcttcagcaaaacaagg
agagagcggtcactgctggagcggtgaagccgttggtggaccttgtggctgaggaagggactgg
tatggcggagaaagctatggtggttctgagtagccttgcagcgatagatgatggcaaagaggct
attgtcgaggaaggagggatcgcagcgcttgttgaggccatcgaggatggatctgtgaaaggga
aagaatttgcgatcttgacgctgttgcagctttgttctgatagcgttagaaaccgtgggttgct
tgtgagggaaggcgcgattcctccgcttgtgggcctctctcagagcggctccgtcagtgttaga
gctaagcgcaaggcagaaagacttctggggtatcttcgggagccaaggaaggaggcaagttcat
caagcccatga

Figure 2A

HvArm (SEQ ID NO. 2):

mqmallarlslassegressleerhagsdeqtseqstkeafqashfdsdsqvrlgrssv
ndnlpntrqldeecdindgmirvpgdrtnyssdasgevadrglsissapqrenvilprl
ghvcmegpfvqrqtsdkgfpriisslsmdarddfsaienqvrelindlgsdsiegqrsa
tseirllakhnmenriaiancgainllvgllhspdakiqenavtallnlslsdinkiai
vnadaidplihvletgnpeakensaatlfslsiieenrvrigrsgavkplvdllgngsp
rgkkdavtalfnlsilhenkgrivqadalkhlvelmdpaagmvdkavavlanlatipeg
rtaigqargipalvevvelgsakakenataallqlctnssrfcnivlqedavpplvals
qsgtprarekaqvllsyfrsqrhgnsgrr*

OS_1_XM_479734.1 (SEQ ID NO. 4):

menfsprtllnsilritvltsdgstarpkpiqkycqnvcdissivspliedlcespeeq
lnevlrelgtainrasglignwqqttskiyfiwqiesvisdiqgcslqlcqlvnsllps
ltgractcieklqdinyenmfdlvkesslelvetdttspenlsrlssslslstnlefym
eavslenlraramrsenreemdladkmiplvnymhdhllretqllsingvpipadfccp
lslelmsdpvivasgqtyervyiklwldegfticpktrqrlghsnlipnytvkalianw
ceshnirlpdpmkslklnfplaasalqdssttgssplhptvaakgnipgspeadlymrs
lnraspphsvvhqnshahvnragheasikqssenangsasdvsrlslagsetresslee
rnagsigqtseqsieeafqasnldrdshdhvgsssvngslpnsgqldaecdngpsertn
yssdasgevtdgpsassapqrehlipsrladvrsrgqfvrrpsergfpriissssmdtr
sdlsaienqvrklvddlrsdsvdvqrsatsdirllakhnmenriiiancgainllvgll
hspdsktqehavtallnlsindnnkiaianadavdplihvletgnpeakensaatlfsl
svieenkvrigrsgaikplvdllgngtprgkkdaatalfnlsilhenkarivqadavky
lvelmdpaagmvdkavavlanlatipegrtaigqargipalvevvelgsargkenaaaa
llqlctnssrfcsivlqegavpplvalsqsgtprarekaqallsyfrsqrhgnsarr (SEQ ID NO. 6):

mafvcgggqvmdsvslslldsisnfrvlsssnasktelvkkycqtmdgildhlevalnr
afpqitpdgelskviqadsiiakmqiyvfelcqivnslmqiesmhledlehdscgkisd
vireasralagevmpnseefgkiqttlslstnqellmeyvalvkvktkgrhednkemdd
indivelvnhmldkhveekqtrsingvtipadfccplslelmsdpvivasgqtyehvfi
rkwfdlgynicpktrqilghtklipnftvkqlienwcevhgimlpdpvkllslcfpvsl
nitdgsasadksgspehcqlvaalhpkaqcasddshhynlihensdsddrvssfgdtdd
sepdslrlstettaanksllldektdrsdglkqlrdngfqvsdeeqylerngkshisshh
qlevdgenvrvqassdinasevmqddpvttcskvsdnpprlggvrsrnqpnwwrqsnkt
ipriglssstdskpdfsgndakvrnlieelksdsaevqrsatgelrilsrhslenriai
ancgaipflvsllhstdpstqenavtillnlslddnnkiaiasaeaieplifvlqvgnp
eakansaatlfslsvieenkikigrsgaieplvdllgegtpqgkkdaatalfnlsifhe
hktrivqagavnhlvelmdpaagmvdkavavlanlatvhdgrnaiaqaggirvlvevve
lgsarskenaaaallqlctnsrfctlvlqegvvpplvalsqsgtararekaqvllsyf
rnqrhvrvgrglslllelkrtt (SEQ ID NO. 8):

mdsvslslldsisnfrvlsssnasktelvkkycqtmdgildhlevalnrafpqitpdge
lskvleelgatineatelvggwnqmmskiyfviqadsiiakmqiyvfelcqivnslmqi
esmhledlehdscgkisdvireasralagevmpnseefgkiqttlslstnqellmeyva
lvkvktkgnhednkemddindivelvnhmldkhveekqtrsingvtipadfccplslel
msdpvivasgqtyehvfirkwfdlgynicpktrqilghtklipnftvkqlienwcevhg
imlpdpvkllslcfpvslnitdgsasadksgspehcqlvaalhpkaqcasddshhynli
hensdsddrvssfgdtddsepdslrlstettaanksllldektdrsdglkqlrdngfqvs
deeqylerngkshisshhqlevdgenvrvqassdinasevmqddpvttcskvsdnpprl

Figure 2B ggvrsrnqpnwwrqsnktipriglssstdskpdfsgndakvrnlieelksdsaevqrsa
tgelrilsrhslenriaiancgaipflvsllhstdpstqenavtillnlslddnnkiai
asaeaieplifvlqvgnpeakansaatlfslsvieenkikigrsgaieplvdllgegtp
qgkkdaatalfnlsifhehktrivqagavnhlvelmdpaagmvdkavavlanlatvhdg
rnaiaqaggirvlvevvelgsarskenaaaallqlctnsnrfctlvlqegvvpplvals
qsgtararekaqvllsyfrnqrhvrvgrg (SEQ ID NO. 10):

mvslagsqipspgqspcaaarsqrrgagysmrtirsallqpdscpgsphvaaaydaaga
dsdmenltdsvidfhlselaatagpahpaavakssanaaatemlelsrdfsdyssfns
disgelerlaaaaaavvtprsdapqvgavdlnelesmdlsveaaplervepfvlacvra
lgpdaapdarrtaaarirllakhrsdireligvsgaipalvpllrstdpvaqesavtal
lnlsleernrsaitaagaikplvyalrtgtasakqnaacallslsgieenratigacga
ipplvallsagstrgkkdalttlyrlcsarrnkeravsagavvplihlvgergsgtsek
amvvlaslagivegrdavveaggipalvetiedgparerefavvallqlcsecprnral
lvregaipplvalsqsgsarakhkaetllgylreqrqggggcrvepvaassslar (SEQ ID NO. 12):

meisllkvllnnniscfshlsssdhisgelvrryyckiedilklvkpildaivdveaasg
elllkafaglaqcvdelrelfetleplcskvyfvlqaepligkirscsleilellkssh
kslpadvtlttlelyilkikyvdyemisvtitkvikaqveglgtssdsfakiadclsln
snqellielvaleklkenaeqaeksevveyieqmitlvshmhdcfvttkqsqsctavpi
ppdfccplslelmtdpvivasgqtyerafirrwidlgltvcpktrqtlghtnlipnytv
kalianwceinnvklpdpmkslslnqpslspdstqssgsprkslisstvsqreesspsh
prssseeslpgvggnilafdvermriksedrmahsgeisshghstlvaddqfplghnrt
tsapstlsnsnfspvipgdgnklsedssvasgdvgldskpaasvlpkepefpytpemrp
rnqliwrrpterfprivssatverradlseveeqvkklieelkstsldmqrnataelrl
lakhnmdnrmviancgaisslvnllhskdmkvqedavtallnlsindnnkcaianadai
eplihvlqtgsaeakensaatlfslsvmeenkmkigrsgaikplvdllgngtprgkkda
atalfnlsilhenksriiqagavkylvelmdpatgmvdkavavlsnlatipegraeigq
eggipllvevvelgsargkenaaaallqlctnssrfcnmvlqegavpplvalsqsgtpr
arekaqqllsyfrnqrhgnagrg (SEQ ID NO. 14):

mevllrsissflnlsssskhidldpfekyykrveellrvlkpiadvvvtsdfvfdeklgk
afeeltqdvdqsidlfrswqafsskvyfvlqiesllpkmrdtivdtfqflmssknhlpd
elspasleqclekikhlsyeeissvidgalrdqrdgvgpspeilvkigentglrsnqei
lieavalerqkemaeqsennaevefldqlivivnrmherllllikqtqtssvailadffc
plslevmtdpvivssgqtyekafikrwidlglkvcpktrqtlthttlipnytvkalian
wcetndvklpdpnkstslnelspllsctdsipstgadvsarkvsnkshdwdasssetgk
psfssrateregaspsrpasalgasspgisgngygldarrgslndfedrsndsrelrtd
apgrssvssttrgsvengqtsenhhhrspsatstvsneefpradanenseesahatpys
sdasgeirsgplaattsaatrrdlsdfspkfmdrrtrgqfwrrpserlgsrivsapsne
trrdlsevetqvkklveelksssldtqrqataelrllakhnmdnrivignsgaivllve
llystdsatqenavtallnlsindnnkkaiadagaieplihvlengsseakensaatlf
slsvieenkikigqsgaigplvdllgngtprgkkdaatalfnlsihqenkamivqsgav
rylidlmdpaagmvdkavavlanlatipegrnaigqeggipllvevvelgsargkenaa
aallqlstnsgrfcnmvlqegavpplvalsqsgtprarekvqtl (SEQ ID NO. 16):

milrfwreniilrfwrkihdfavlkliqmyhpddpskyllnykkqtsfficiwmnhlde
kqtrsesdftvskrdirrvemevllrsissflnlsssskhidldpfekyykrveellrvl
kpiadvvvtsdfvfdeklgkafeeltqdvdqsidlfrswqafsskvyfvlqiesllpkm

Figure 2C rdtivdtfqflmssknhlpdelspasleqclekikhlsyeeissvidgalrdqrdgvgp
speilvkigentglrsnqeilieavalerqkemaeqsennaevefldqlivivnrmher
lllikqtqtssvailadffcplslevmtdpvivssgqtyekafikrwidlglkvcpktr
qtlthttlipnytvkalianwcetndvklpdpnkstslnelspllsctdsipstgadvs
arkvsnkshdwdasssetgkpsfssrateregaspsrpasalgasspgisgngygldar
rgslndfedrsndsrelrtdapgrssvssttrgsvengqtsenhhhrspsatstvsnee
fpradanenseesahatpyssdasgeirsgplaattsaatrrdlsdfspkfmdrrtrgq
fwrrpserlgsrivsapsnetrrdlsevetqvkklveelkssssldtqrqataelrllak
hnmdnrivignsgaivllvellystdsatqenavtallnlsindnnkkaiadagaiepl
ihvlengsseakensaatlfslsvieenkikigqsgaigplvdllgngtprgkkdaata
lfnlsihqenkamivqsgavrylidlmdpaagmvdkavavlanlatipegrnaigqegg
ipllvevvelgsargkenaaaallqlstnsgrfcnmvlqegavpplvalsqsgtprare
kkptawkrwawlmmddddddddvddaqilvsqclflcfvl (At5g67340) (SEQ ID NO. 18):

mmvhmevswlrvlldnissylslssmddlssnpahkyytrgedigklikpvlenlidsd
aapsellnngfeelaqyvdelreqfqswqplstrifyvlrieslasklresslevfqll
khceqhlpadlispsfeecielvklvardeisytidqalkdqkkgvgptsevlvkiaes
tglrsnqeilvegvvltnmkedaeltdndteaeyldglislttqmheylsdikqaqlrc
pvrvpsdfrcslslelmtdpvivasgqtfervfiqkwidmglmvcpktrqalshttltp
nfivraflaswcetnnvyppdplelihssepfpllvesvrassenghseslaeelrq
vfsrsasapgivsevvcktkrnnnaaadrsltrsntpwkfpeerhwrhpgiipatvret
gssssietevkkliddlkssssldtqreataririlarnstdnriviarceaipslvsll
ystderiqadavtcllnlsindnnksliaesgaivplihvlktgyleeakansaatlfs
lsvieeykteigeagaieplvdllgsgslsgkkdaatalfnlsihhenktkvieagavr
ylvelmdpafgmvekavvvlanlatvregkiaigeeggipvlvevvelgsargkenata
allqlcthspkfcnnviregvipplvaltksgtargkekaqnllkyfkahrqsnqrrg (SEQ ID NO. 20):

mevswlrvlldnissylslssmddlssnpahkyytrgedigklikpvlenlidsdaaps
ellnngfeelaqyvdelreqfqswqplstrifyvlrieslasklresslevfqllkhce
qhlpadlispsfeecielvklvardeisytidqalkdqkkgvgptsevlvkiaestglr
snqeilvegvvltnmkedaeltdndteaeyldglislttqmheylsdikqaqlrcpvrv
psdfrcslslelmtdpvivasgqtfervfiqkwidmglmvcpktrqalshttltpnfiv
raflaswcetnnvyppdplelihssepfpllvesvrasssenghseslaeelrqvfsr
sasapgivsevvcktkrnnnaaadrsltrsntpwkfpeerhwrhpgiipatvretgsss
sietevkkliddlkssssldtqreataririlarnstdnriviarceaipslvsllystd
eriqadavtcllnlsindnnksliaesgaivplihvlktgyleeakansaatlfslsvi
eeykteigeagaieplvdllgsgslsgkkdaatalfnlsihhenktkvieagavrylve
lmdpafgmvekavvvlanlatvregkiaigeeggipvlvevvelgsargkenataallq
lcthspkfcnnviregvipplvaltksgtargkekvlflfpllclvnvs (SEQ ID NO. 22):

mdpvpvrcllnsisrylhlvacqtirfnpiqtcignmvlllkllkplldevvdckipsd
dclykgcedldsvvnqarefledwspklsklfgvfqcevllgkvqtcsleisrillqls
qsspvtssvqsvercvqetesfkqegtlmelmenalrnqkdditsldnnhlesiiqmlg
lisnqdllkesitvekerirsqaskseedmeqteqlielvlcirehmlkteflevakgi
sippyfrcplstelmldpvivasgqtfdrtsikkwldnglavcprtrqvlthqelipny
tvkamiaswleanrinlatnschqydqgdassmannmgsqdfnrtesfrfslrssslts
rssletgngfeklkinvsaslcgesqskdleifellspgqsythsrsesvcsvvssvdy
vpsvthetesilgnhqsssemspkknlessnnvnhehsaaktyecsvhdlddsgtmtts
htiklvedlksgsnkvktaaaaeirhltinsienrvhigrcgaitpllsllyseekltq
ehavtallnlsiselnkamivevgaieplvhvlntgndrakensaaslfslsvlqvnre
rigqsnaaiqalvnllgkgtfrgkkdaasalfnlsithdnkarivqakavkylvellldp
dlemvdkavallanlsavgegrqaivreggipllvetvdlgsqrgkenaasvllqlcln
spkfctlvlqegaipplvalsqsgtqrakekaqqllshfrnqrdarmkkgrs

Figure 2D (SEQ ID NO. 24):

mdpvpvrcllnsisrylhlvacqtirfnpiqtcignmvlllkllkplldevvdckipsd
dclykgredldsvvnqarefledwspklsklfgvfqcevllgkvqtcsleisrillqls
qsspvtssvqsvercvqetesfkqegtlmelmenalrnqkdditsldnnhlesiiqmlg
lisnqdllkesitvekerirsqaskseedmeqteqlielvlcirehmlkteflevakgi
sippyfrcplstelmldpvivasgqtfdrtsikkwldnglavcprtrqvlthqelipny
tvkamiaswleanrinlatnschqydggdassmannmgsqdfnrtesfrfslrsssslts
rssletgngfeklkinvsaslcgesqskdleifellspgqsythsrsesvcsvvssvdy
vpsvthetesilgnhqsssemspkknlessnnvnhehsaaktyecsvhdlddsgtmtts
htiklvedlksgsnkvktaaaaeirhltinsienrvhigrcgaitpllsllyseekltq
ehavtallnlsiselnkamivevgaveplvhvlntgndrakensaaslfslsvlqvnre
rigqsnaaiqalvnllgkgtfrgkkdaasalfnlsithdnkarivqakavkylvelldp
dlemvdkavallanlsavgegrqaivreggipllvetvdlgsqrgkenaasvllqlcln
spkfctlvlqegaipplvalsqsgtqrakekaqqllshfrnqrdarmkkgrs (SEQ ID NO. 26):

mvlllkllkplldevvdckipsddclykgcedldsvvnqarefledwspklsklfgvfq
cevllgkvqtcsleisrillqlsqsspvtssvqsvercvqetesfkqegtlmelmenal
rnqkdditsldnnhlesiiqmlglisnqdllkesitvekerirsqaskseedmeqteql
ielvlcirehmlkteflevakgisippyfrcplstelmldpvivasgqtfdrtsikkwl
dnglavcprtrqvlthqelipnytvkamiaswleanrinlatnschqydggdassmann
mgsqdfnrtesfrfslrsssltsrssletgngfeklkinvsaslcgesqskdleifell
spgqsythsrsesvcsvvssvdyvpsvthetesilgnhqsssemspkknlessnnvnhe
hsaaktyecsvhdlddsgtmttshtiklvedlksgsnkvktaaaaeirhltinsienrv
higrcgaitpllsllyseekltqehavtallnlsiselnkamivevgaieplvhvlntg
ndrakensaaslfslsvlqvnrerigqsnaaiqalvnllgkgtfrgkkdaasalfnlsi
thdnkarivqakavkylvelldpdlemvdkavallanlsavgegrqaivreggipllve
tvdlgsqrgkenaasvllqlclnspkfctlvlqegaipplvalsqsgtqrakekvytif
ffcgytkthqvqflidrdi (SEQ ID NO. 28):

meeekasaaqslidvvneiaaisdyritvkklcynlarrlkllvpmfeeiresnepise
dtlktlmnlkeamcsakdylkfcsqgskiylvmereqvtsklmevsvkleqslsqipye
eldisdevreqvelvlsqfrrakgrvdvsddelyedlqslcnkssdvdayqpvlervak
klhlmeipdlaqesvalhemvassggdvgenieemamvlkmikdfvqteddngeeqkvg
vnsrsngqtstaasqkipvipddfrcpislemmrdpvivssgqtyertciekwiegghs
tcpktqqaltsttltpnyvlrsliaqwceandieppkppsslrprkvssfsspaeanki
edlmwrlaygnpedqrsaageirllakrnadnrvaiaeagaipllvgllstpdsriqeh
svtallnlsicennkgaivsagaipgivqvlkkgsmearenaaatlfslsvidenkvti
galgaipplvvllnegtqrgkkdaatalfnlciyqgnkgkairagviptltrlltepgs
gmvdealailailsshpegkaiigssdavpslvefirtgsprnrenaaavlvhlcsgdp
qhlveaqklglmgplidlagngtdrgkrkaaqllerisrlaeqqketavsqpeeeaept
hpestteaadt (SEQ ID NO. 30):

memenhrpgsftymgrkfsdlslnddssafsdcnsdrsgefptassesrrllllscasen
sddlinhlvshldssysideqkqaameirllsknkpenrikiakagaikplislisssd
lqlqeygvtailnlslcdenkesiassgaikplvralkmgtptakenaacallrlsqie
enkvaigrsgaipllvnlletggfrakkdastalyslcsakenkiravqsgimkplvel
madfgsnmvdksafvmsllmsvpeskpaiveeggvpvlveivegtqrqkemavsillq
lceesvvyrtmvaregaipplvalsqagtsrakqkaealiellrqprsisnggarsssq
l

Figure 2E (SEQ ID NO. 32):

memenhrpgsftymgrkfsdlslnddssafsdcnsdrsgefptassesrrlllscasen
sddlinhlvshldssysideqkqaameirllsknkpenrikiakagaikplislisssd
lqlqeygvtailnlslcdenkesiassgaikplvralkmgtptakenaacallrlsqie
enkvaigrsgaipllvnlletggfrakkdastalyslcsakenkiravqsgimkplvel
madfgsnmvdksafvmsllmsvpeskpaiveeggvpvlveivevgtqrqkemavsillq
lceesvvyrtmvaregaipplvalsqagtsrakqkaealiellrqlrsisnggarsssq
l (SEQ ID NO. 34):

memenhrpgsftymgrkfsdlslnddssafsdcnsdrsgefptassesrrlllscasen
sddlinhlvshldssysideqkqaameirllsknkpenrikiakagaikplislisssd
lqlqeygvtailnlslcdenkesiassgaikplvralkmgtptakdnaacallrlsqie
enkvaigrsgaipllvnlletggfrakkdastalyslcsakenkiravqsgimkplvel
madfgsnmvdksafvmsllmsvpeskpaiveeggvpvlveivevgtqrqkemavsillq
lceesvvyrtmvaregaipplvalsqagtsrakqkaealiellrqprsisnggarsssq
l (SEQ ID NO. 36):

mdtdeeatgdaenrdeevtaeepihdevvdaveiheeevkeddddceglvsdivsivef
ldqingyrrtqqkecfnlvrrlkilipfldeirgfespsckhflnrlrkvflaakklle
tcsngskiymaldgetmmtrfhsiyeklnrvlvkapfdelmisgdakdeidslckqlkk
akrrtdtqdielavdmmvvfsktdprnadsaiierlakklelqtiddlktetiaiqsli
qdkgglnietkqhiiellnkfkklqgleatdilyqpvinkaitkstslilpheflcpit
leimldpviiatgqtyekesiqkwfdaghktcpktrqeldhlslapnfalknlimqwce
knnfkipekevspdsqneqkdevsllvealsssqleeqrrsvkqmrllarenpenrvli
anagaipllvqllsypdsgiqenavttllnlsidevnkklisnegaipniieilengnr
earensaaalfslsmldenkvtiglsngipplvdllqhgtlrgkkdaltalfnlslnsa
nkgraidagivqpllnllkdknlgmidealsillllashpegrqaigqlsfietlvefi
rqgtpknkecatsvllelgsnnssfilaalqfgvyeylveittsgtnraqrkanaliql
iskseqi (SEQ ID NO. 38):

mvdvmdtdeeatgdaesrdeevtaeepihdevvdaveiheeevkeddddceglvsdivs
ivefldqingyrrtqqkecfnlvrrlkilipfldeirgfespsckhflnrlrkvflaak
klletcsngskiymaldgetmmtrfhsiyeklnrvlvkapfdelmisgdakdeidslck
qlkkakrrtdtqdielavdmmvvfsktdprnadsaiierlakklelqtiddlktetiai
qsliqdkgglnietkqhiiellnkfkklqgleatdilyqpvinkaitkstslilphefl
cpitlgimldpviiatgqtyekesiqkwfdaghktcpktrqeldhlslapnfalknlim
qwceknnfkipekevspdsqneqkdevsllvealsssqleeqrrsvkqmrllarenpen
rvlianagaipllvqllsypdsgiqenavttllnlsidevnkklisnegaipniieile
ngnrearensaaalfslsmldenkvtiglsngipplvdllqhgtlrgkkdaltalfnls
lnsankgraidagivqpllnllkdknlgmidealsillllashpegrqaigqlsfietl
vefirqgtpknkecatsvllelgsnnssfilaalqfgvyeylveittsgtnraqrkana
liqliskseqi (SEQ ID NO. 40):
mgltnccsheelmsrlvdsvkeisgfsssrgfigkiqgdlvrritllspffeelidvnv
elkkdqitgfeamrialdsslelfrsvnggsklfqlfdrdslvekfrdmtveieaalsq
ipyekievseevreqvqllhfqfkrakerweesdlqlshdlamaenvmdpdpiilkrls
qelqlttidelkkeshaiheyflsydgdpddcfermssllknlvdfvtmessdpdpstg
srivsrhrspvipeyfrcpislelmkdpvivstgqlnfstlqtyerssiqkwldaghkt
cpksqetllhagltpnyvlkslialwcesngielpqnqgscrttkiggsssssdcdrtfv
lslleklangtteqqraaagelrllakrnvdnrvciaeagaipllvellsspdprtqeh
svtallnlsinegnkgaivdagaitdivevlkngsmearenaaatlfslsvidenkvai

Figure 2F gaagaiqalislleegtrrgkkdaataifnlciyqgnksravkggivdpltrllkdagg
gmvdealailailstnqegktaiaeaesipvlveiirtgsprnrenaaailwylcigni
erlnvarevgadvalkeltengtdrakrkaaslleliqqtegvavttvp (SEQ ID NO. 42):

mgltnccsheelmsrlvdsvkeisgfsssrgfigkiqgdlvrritllspffeelidvnv
elkkdqitgfeamrialdsslelfrsvnggsklfqlfdrdslvekfrdmtveieaalsq
ipyekievseevreqvqllhfqfkrakerweesdlqlshdlamaenvmdpdpiilkrls
qelqlttidelkkeshaiheyflsydgdpddcfermssllknlvdfvtmessdpdpstg
srivsrhrspvipeyfrcpislelmkdpvivstgqtyerssiqkwldaghktcpksqet
llhagltpnyvlkslialwcesngielpqnqgscrttkiggssssdcdrtfvlsllekl
angtteqqraaagelrllakrnvdnrvciaeagaipllvellsspdprtqehsvtalln
lsinegnkgaivdagaitdivevlkngsmearenaaatlfslsvidenkvaigaagaiq
alislleegtrrgkkdaataifnlciyqgnksravkggivdpltrllkdagggmvdeal
ailailstnqegktaiaeaesipvlveiirtgsprnrenaaailwylcignierlnvar
evgadvalkeltengtdrakrkaaslleliqqtegvavttvp (SEQ ID NO. 44):

mvsveeplshsnstrfplttdfygssspsaarlhrqagrsmrtvrsnfyqsgdqscsfv
gsigdkseyaseflsdsvidmrlgelalknsnslnsnassmkeeafldisqafsdfsac
ssdisgelqrlaclpspeadrnesggdneaehdpelerepclgflqrenfsteiiecis
pedlqptvklcidglrsssvaikrsaaaklrllaknradnrvligesgaiqaliplllrc
ndpwtqeravtallnlslhdqnkaviaaggaikslvwvlktgtetskqnaacallslal
leenkgsigacgaipplvslllngscrgkkdaltalyklctlqqnkeravtagavkplv
dlvaeegtgmaekamvvlsslaaiddgkeaiveeggiaalveaiedgsvkgkefailtl
lqlcsdsvrnrgllvregaipplvglsqsgsvsvrakrkaerllgylreprkeasssp

Figure 3A

```
                                    1                                                   50
Translation of Armadillo ORF  (1)   --------------------------------------------------
AC010870                      (1)   --------------------------------------------------
AB007645                      (1)   --------------------------------------------------
AB016888                      (1)   -----------------------------------MDTDEEATGDAENRDE
AC004401                      (1)   MILRFWRENIILRFWRKIHDFAVLKLIQMYHPDDPSKYLLNYKKQTSFFI
AK118613                      (1)   --------------------------------------------------
AK118730                      (1)   --------------------------------------------------
AK175585                      (1)   ----------------MVDVMDTDEEATGDAESRDE--------------
AL049655                      (1)   --------------------------------------------------
AL133314                      (1)   --------------------------------------------------
AL138650                      (1)   --------------------------------------------------
AP003561                      (1)   --------------------------------------------------
AY087360                      (1)   --------------------------------------------------
AY096530                      (1)   --------------------------------------------------
AY125543                      (1)   --------------------------------------------------
AY219234                      (1)   --------------------------------------------------
BT020206                      (1)   --------------------------------------------------
NM_115336                     (1)   --------------------------------------------------
NM_127878                     (1)   --------------------------------------------------
XM_463544                     (1)   --------------------------------------------------
XM_479734.1                   (1)   --------------------------------------------------
XM_506432                     (1)   --------------------------------------------------
Consensus                     (1)   --------------------------------------------------
```

Figure 3B

```
                              51                                                  100
Translation of Armadillo ORF  (1)  ----------------------------------------------------
AC010870                      (1)  ----------------------------------------------------
AB007645                      (1)  ----------------------------------------------------
AB016888                     (17)  EVTAEEPIHDEVVDAVEIHEEEVKEDDDDCEGIVSDIVSIVEFLDQINGY
AC004401                     (51)  -----------------------MEVSWLRVLLDNISSYISLSSMDDLS
AK118613                      (1)  CIWMNHLDEKQTRSESDFTVSKRDIRRVEMEVLRSISSFINLSSKHID
AK118730                      (1)  --------------------------MDPVPVRCLLNSISRYLHLVACQTIR
AK175585                     (21)  EVTAEEPIHDEVVDAVEIHEEEVKEDDDDCEGIVSDIVSIVEFLDQINGY
AL049655                      (1)  ------------------------------MGLTNCCSHEELMSRLVDSVKEISGFSSS
AL133314                      (1)  -------------------------------MEEEKASAAQSLIDVVNEIAAISDY
AL138650                      (1)  ----------------------------------------------------
AP003561                      (1)  ------------------------------MDSVSLSLLDSISNFRVLSSSNASK
AY087360                      (1)  ----------------------------------------------------
AY096530                      (1)  -----------------------MGLTNCCSHEELMSRLVDSVKEISGFSSS
AY125543                      (1)  ----------------------------------------------------
AY219234                      (1)  ---------------------------MEISLLKVLLNNISCFSHLSSSDHIS
BT020206                      (1)  ------------------------MMVHMEVSWLRVLLDNISSYISLSSMDDLS
NM_115336                     (1)  -----------------------MDPVPVRCLLNSISRYLHLVACQTIR
NM_127878                     (1)  ---------------------------MEVLRSISSFINLSSKHID
XM_463544                     (1)  -------------------------MAFVCGGGQVMDSVSLSLLDSISNFRVLSSSNASK
XM_479734.1                   (1)  ----------------------------------------------------
XM_506432                     (1)  ----------------------------MENFSPRTLLNSILRITVLTSDGST
Consensus                    (51)                                    LL    I    L    L   S
```

Figure 3C

```
                                  101                                                              150
Translation of Armadillo ORF  (1)  ------------------------------------------------
              AC010870        (1)  ------------------------------------------------
              AB007645       (27)  SNPAHKYYTRGEDIGKLIKPVLENLIDSDAAPSELLNNGFEELAQYVDEL
              AB016888       (67)  RRTQQKECFNLVRRLKLLIPFLDEIRGFESPSCKHFLNRLRKVFLAAKKL
              AC004401     (101)  LDPFEKYYKRVEELLRVLKPIADVVTSDFVFDEKLGKAFEELTQDVDQS
              AK118613       (27)  FNPIQTCIGNMVLLIKPLLDEVDCKIPSDDCLYKPSDDCLYKGREDLDSVVNQA
              AK118730        (1)  ------------------------------------------------
              AK175585       (71)  RRTQQKECFNLVRRLKLLIPFLDEIRGFESPSCKHFLNRLRKVFLAAKKL
              AL049655       (30)  RGFIGKIQGDLVRRITLLSPFFEELIDVNVELKKDQITGFEAMRIALDSS
              AL133314       (26)  RITVKKLCYNLARRLKLVPMFEEIRESNEPISEDTLKTLMNLKEAMCSA
              AL138650        (1)  ---MVLLIKPLLDEVDCKIPSDDCLYKGCEDLDSVVNQA
              AP003561       (26)  TELVKKYCQTMDGILDHLEVALNRAFPQITPDGELSKVLEE-LGATINEA
              AY087360        (1)  ------------------------------------------------
              AY096530       (30)  RGFIGKIQGDLVRRITLLSPFFEELIDVNVELKKDQITGFEAMRIALDSS
              AY125543        (1)  ------------------------------------------------
              AY219234       (27)  GELVRRYYCKIEDILKVKPIIDATVDVEAASGELLLKAFAGLAQCVDEL
              BT020206       (31)  SNPAHKYYTRGEDIGKLIKPVLENLIDSDAAPSELLNNGFEELAQYVDEL
              NM_115336      (27)  FNPIQTCIGNMVLLIKPLLDEVDCKIPSDDCLYKGREDLDSVVNQA
              NM_127878      (22)  LDPFEKYYKRVEELLRVLKPIADVVTSDFVFDEKLGKAFEELTQDVDQS
              XM_463544      (36)  TELVKKYCQTMDGILDHLEVALNRAFPQITPDGELS-------------
              XM_479734.1    (26)  ARPKPIQKYCQNVCDISSIVSPLIEDLCESPEEQLNEVLRE-LGTAINRA
              XM_506432       (1)  ------------------------------------------------
              Consensus    (101)          K    L      LKLL P   D V              E    E L   V
```

Figure 3D

```
                              151                                                        200
Translation of Armadillo ORF   (1) ---------------------------------------------------------
                  AC010870     (1) ---------------------------------------------------------
                  AB007645    (77) REQFQSWQPLSTRIFYVLRIESLASKLRESSLEVFQLLKHCEQHLPADLI
                  AB016888   (117) LETCS--N--GSKIYMALDGETMMTRFHSIYEKLNRVLVKAPFDELMISG
                  AC004401   (151) IDLFRSWQAFSSKVYFVLQIESLLPKMRDTIVDTFQFLMSSKNHLPDELS
                  AK118613    (77) REFLEDWSPKLSKLFGVFQCEVLLGKVQTCSLEISRILQLSQSSPVTSS
                  AK118730     (1) ---------------------------------------------------------
                  AK175585   (121) LETCS--N--GSKIYMALDGETMMTRFHSIYEKLNRVLVKAPFDELMISG
                  AL049655    (80) LELFRSVNG-GSKLFQLFDRDSLVEKFRDMTVELEAALSQIPYEKIEVSE
                  AL133314    (76) KDYLKFCSQ-GSKIYLVMEREQVTSKIMEVSVKLEQSLSQIPYEELDISD
                  AL138650    (41) REFLEDWSPKLSKLFGVFQCEVLLGKVQTCSLEISRILQLSQSSPVTSS
                  AP003561    (75) TELVGGWNQMMSKIYFVIQADSILAKMQIYVFELCQIVNSLMQIES---
                  AY087360     (1) ---------------------------------------------------------
                  AY096530    (80) LELFRSVNG-GSKLFQLFDRDSLVEKFRDMTVELEAALSQIPYEKIEVSE
                  AY125543     (1) ---------------------------------------------------------
                  AY219234    (77) RELFETLEPLCSKVYFVLQAEPLIGKIRSCSLELLELLKSSHKSLPADVT
                  BT020206    (81) REQFQSWQPLSTRIFYVLRIESLASKLRESSLEVFQLLKHCEQHLPADLI
               NM_115336      (77) REFLEDWSPKLSKLFGVFQCEVLLGKVQTCSLEISRILQLSQSSPVTSS
               NM_127878      (72) IDLFRSWQAFSSKVYFVLQIESLLPQMRDTIVDTFQFLMSSKNHLPDELS
               XM_463544      (72) --K--------VIQADSILAKMQIYVFELCQIVNSLMQIES---
               XM_479734.1    (75) SGLIGNWQQTTSKIYFIWQIESVISDIQGCSLQLCQLVNSLLIPSLTGRA-
               XM_506432      (1) ---------------------------------------------------------
                 Consensus   (151)      E        SKIY V   ESLL  KM         LEI     IL
```

```
                                              251                                                                                300
Translation of Armadillo ORF    (1)   --------------------------------------------------
                   AC010870     (1)   --------------------------------------------------
                   AB007645   (170)   IAESTGLRSNQELVEGVVLTNMKEDAELTDND----TEAEYLDGLIS
                   AB016888   (213)   LAKKLELQTIDDLKTETIAQSLIQDKGGLNIETKQHIIELINKFKKLQG
                   AC004401   (244)   IGENTGLRSNQEILIEAVALEROKEMAEQSENN----AEVEFLDQLLV
                   AK118613   (172)   IIQMEGLISNQDLLKESITVEKERIRSQASKSE----EDMEQTEQLIE
                   AK118730     (1)   --------------------------------------------------
                   AK175585   (217)   LAKKIELQTIDDLKTETIAQSLIQDKGGLNIETKQHIIELINKFKKLQG
                   AL049655   (176)   LSQELQLTTIDELKKESHAIHEYFLSYDGDPDDCFERMSSLIKNLVDFVT
                   AL133314   (175)   VAKKIHLMEIPDLAQESVALHEMVASSGGDVGENIEEMAMVIKMIKDFVQ
                   AL138650   (136)   IIQMEGLISNQDLLKESITVEKERIRSQASKSE----EDMEQTEQLIE
                   AP003561   (159)   IQTTLSLSTNQELLMEYVALVKVKTKGNHEDN----KEMDDINDIVE
                   AY087360     (1)   --------------------------------------------------
                   AY096530   (176)   LSQELQLTTIDELKKESHAIHEYFLSYDGDPDDCFERMSSLIKNLVDFVT
                   AY125543     (1)   --------------------------------------------------
                   AY219234   (170)   IADCISINSNQELLIELVALEKLKENAEQAEKS----EVVEYIEQMIT
                   BT020206   (172)   IAESTGLRSNQEILIELVALEKLTNMKEDAELTDND----TEAEYLDGLIS
                   NM_115336   (172)   IIQMGLISNQDLLKESITVEKERIRSQASKSE----EDMEQTEQLIE
                   NM_127878   (165)   IGENTGLRSNQEILIEAVALEROKEMAEQSENN----AEVEFLDQLLV
                   XM_463544   (141)   IQTTISLSTNQELLMEYVALVKVKTKGNHEDN----KEMDDINDIVE
                   XM_479734.1 (163)   LSSSLSLSTNLEFYMEAVSLENLRARAMRSENR----EEMDLADKMIP
                   XM_506432     (1)   --------------------------------------------------
                   Consensus  (251)   I    L  L  SN EL    E VAL      K               ME     LI
```

Figure 3G

```
                              301                                                  350
Translation of Armadillo ORF   (1) --------------------------------------------------
                    AC010870   (1) --------------------------------------------------
                    AB007645 (214) ------LTTQMHEYL------SDIKQAQLRCPVRVPSDFRCSLSLELMTDPVI
                    AB016888 (263) ------LEATDILYQP------VINKAITKSTSLILPHEFLCPITLEIMLDPVI
                    AC004401 (288) ------IVNRMHERL------LLIKQTQTSS-VAILADFFCPLSLEVMTDPVI
                    AK118613 (216) ------LVLCIREHM------LKTEFLEVAKGISIPPYFRCPLSTELMLDPVI
                    AK118730   (1) --------------------------------------------MVSVEEPL
                    AK175585 (267) ------LEATDILYQP------VINKAITKSTSLILPHEFLCPTTIGIMLDPVI
                    AL049655 (226) ------MESSDPDPS------TGSRIVSRHRSPVIPEYFRCPISLELMKDPVI
                    AL133314 (225) ------TEDDNGEBQKVGVNSRSNGQTSTAASQKIPVIPDDFRCPISLEMRDPVI
                    AL138650 (180) ------LVLCIREHM------LKTEFLEVAKGISIPPYFRCPLSTEIMLDPVI
                    AP003561 (202) ------LVNHMLDKH------VEEKQTRSINGVTIPADFCCPLSLELMSDPVI
                    AY087360   (1) --------------------------------------------------
                    AY096530 (226) ------MESSDPDPS------TGSRIVSRHRSPVIPEYFRCPISLELMKDPVI
                    AY125543   (1) --------------------------------------------------
                    AY219234 (214) ------LVSHMHDCF------VTTKQSQSCTAVPIPPDFCCPLSLELMTDPVI
                    BT020206 (218) ------LTTQMHEYL------SDIKQAQLRCPVRVPSDFRCSLSLELMTDPVI
                    NM_115336 (216) ------LVLCIREHM------LKTEFLEVAKGISIPPYFRCPLSTELMLDPVI
                    NM_127878 (209) ------IVNRMHERL------LLIKQTQTSS-VAILADFFCPLSLEVMTDPVI
                    XM_463544 (184) ------LVNHMLDKH------VEEKQTRSINGVTIPADFCCPLSLELMSDPVI
                    XM_479734.1 (207) ------LVNYMHDHL------LRETQLLSINGVPIPADFCCPLSLELMSDPVI
                    XM_506432   (1) --------------------------------------------MVSLAGSQI
                   Consensus (301)       L  M E            L     K     V  IP DF CPLSLELM DPVI
```

Figure 3H

```
                              351                                                              400
Translation of Armadillo ORF   (1) ------------------------------------------------
               AC010870        (1) ------------------------------------------------
               AB007645      (255) VASGQT------------------------FERVFIQKWIDMGLMVCPKTRQALSHTTLTPNFIVRA
               AB016888      (305) IATGQT------------------------YEKESIQKWFDAGHKTCPKTRQEIDHLSIAPNFALKN
               AC004401      (328) VSSGQT------------------------YEKAFIKRWIDLGLKVCPKTRQTLTHTTLIPNYTVKA
               AK118613      (257) VASGQT------------------------FDRTSIKKWLDNGLAVCPRTRQVLTHQELIPNYTVKA
               AK118730        (9) SHSNSI------------------------RFPLITDFYGSSSPSAARLHRQAGRSMRTVRSNFYQS
               AK175585      (309) IATGQT------------------------YEKESIQKWFDAGHKTCPKTRQEIDHLSIAPNFALKN
               AL049655      (267) VSTGQLNFSTLQTYERSSIQKWIDAGHKTCPKSQETLLHAGITPNYVLKS
               AL133314      (275) VSSGQT------------------------YERTCIEKWIEGGHSTCPKTQQALTSTTITPNYVLRS
               AL138650      (221) VASGQT------------------------FDRTSIKKWLDNGLAVCPRTRQVLTHQELIPNYTVKA
               AP003561      (243) VASGQT------------------------YEHVFTRKWFDLGYNIGPKTRQILGHTKLIPNFTVKQ
               AY087360        (1) ------------------------------------------------
               AY096530      (267) VSTGQT------------------------YERSSIQKWIDAGHKTCPKSQETLLHAGITPNYVLKS
               AY125543        (1) ------------------------------------------------
               AY219234      (255) VASGQT------------------------YERAFIRRWIDLGLITVCPKTRQTLGHTNIIPNYTVKA
               BT020206      (259) VASGQT------------------------FERVFIQKWIDMGLMVCPKTRQALSHTTLTPNFIVRA
               NM_115336     (257) VASGQT------------------------FDRTSIKKWLDNGLAVCPRTRQVLTHQELIPNYTVKA
               NM_127878     (249) VSSGQT------------------------YEKAFIKRWIDLGLKVCPKTRQTLTHTTLIPNYTVKA
               XM_463544     (225) VASGQT------------------------YEHVFTRKWFDLGYNICPKTRQILGHTKLIPNFTVKQ
               XM_479734.1   (248) VASGQT------------------------YERVYIKLWIDEGFTICPKTRQLGHSNLIPNYTVKA
               XM_506432      (10) PSPGQS------------------------PCAAARSQRRGAGYSMRTIRSALLQPDSCPGSPHVAA
               Consensus     (351) VASGQT                            YER   I KWID G  VCPKTRQ L H   L PNY VKA
```

Figure 3I

```
                                401                                                           450
Translation of Armadillo ORF  (1)  ------------------------------------------------------------
                   AC010870   (1)  ------------------------------------------------------------
                   AB007645 (298)  FLASWCETNNVYPPDPLELIHSSEPFPLLVESVRASSSEN---------------------
                   AB016888 (348)  LIMQWCEKNNFKIPE---------------------------------------------
                   AC004401 (371)  LIANWCETNDVKLPDPNKSTSLNELSPLLSCTDSIPSTGADVSARKVSNK----------
                   AK118613 (300)  MIASWLEANRINLATNSCHQYDGGDASSMANNMGSQDFNR--------------------
                   AK118730  (52)  GDQSCSFVGSIGDKSEYASEFLSDSVIDMRLGELALKNSN--------------------
                   AK175585 (352)  LIMQWCEKNNFKIPE---------------------------------------------
                   AL049655 (317)  LIALWCESNGIELP----------------------------------------------
                   AL133314 (318)  LIAQWCEANDIEPPKP--------------------------------------------
                   AL138650 (264)  MIASWLEANRINLATNSCHQYDGGDASSMANNMGSQDFNR--------------------
                   AP003561 (286)  LIENWCEVHGIMLPDPVKLLSLCFPVSLNITDGSASADKS-------------------G
                   AY087360   (1)  ------------------------------------------------------------
                   AY096530 (310)  LIALWCESNGIELP----------------------------------------------
                   AY125543   (1)  ------------------------------QNQG--------------------------
                   AY219234 (298)  LIANWCEINNVKLPDPMKSLSLNQPSLSPDSTQSSGSPRK--------------------
                   BT020206 (302)  FLASWCETNNVYPPDPLELIHSSEPFPLLVESVRASSSEN---------------------
                   NM_115336 (300) MIASWLEANRINLATNSCHQYDGGDASSMANNMGSQDFNR--------------------
                   NM_127878 (292) LIANWCETNDVKLPDPNKSTSLNELSPLLSCTDSIPSTGADVSARKVSNK----------
                   XM_463544 (268) LIENWCEVHGIMLPDPVKLLSLCFPVSLNITDGSASADKS-------------------G
                   XM_479734.1 (291) LIANWCESHNIRLPDPMKSLKLNFPLAASALQDSSTTGSSPLHPTVAAKG----------
                   XM_506432  (53) AYDAAGADSDMENLTDSVIDFHLSELAATAGPAHPAAVAK--------------------
                   Consensus (401) LIA WCE N I LP
```

Figure 3J

```
                        451                                                    500
Translation of Armadillo ORF  (1)  ------------------------------------------------- 
AC010870                 (1)  ------------------------------------------------- 
AB007645               (338)  ------------------------------------------------- 
AB016888               (363)  ------------------------------------------------- 
AC004401               (421)  S----HDWDASSETGKPSFSSRATEREGASPSRPASALGASSPGISGN 
AK118613               (340)  -------TESFRFSLR---SSSLTSRSSLETGNG 
AK118730                (92)  ------------------------------------------------- 
AK175585               (367)  ------------------------------------------------- 
AL049655               (335)  ------------------------------------------------- 
AL133314               (334)  ------------------------------------------------- 
AL138650               (304)  ----------TESFRFSLRS----SSLTSRSSLETGNG 
AP003561               (327)  S----PEHCQLVAALHPKAQCASDDSHHYNLIHENSDSDDRVSSFGDTD 
AY087360                 (1)  ------------------------------------------------- 
AY096530               (328)  ------------------------------------------------- 
AY125543                 (1)  ------------------------------------------------- 
AY219234               (338)  ---------SLISSTVSQREESSPSHPRSSSEESLPGVGGN 
BT020206               (342)  ------------------------------------------------- 
NM_115336              (340)  ----------TESFRFSLRS----SSLTSRSSLETGNG 
NM_127878              (342)  S----HDWDASSETGKPSFSSRATEREGASPSRPASALGASSPGISGN 
XM_463544              (309)  S----PEHCQLVAALHPKAQCASDDSHHYNLIHENSDSDDRVSSFGDTD 
XM_479734.1            (341)  NIPGSPEADLYMRSLNRASPPHSVVHQNSHAHVNRAGHEASIKQSSENAN 
XM_506432               (93)  ------------------------------------------------- 
Consensus              (451)  ------------------------------------------------- 
```

Figure 3K

```
                                  501                                                            550
Translation of Armadillo ORF  (1)  MQMALLARLSLASSEGRESSLEERHAGSD------------EQTSEQSTKEAFQ
                   AC010870   (1)  --------------------------------------------------------ME
                   AB007645 (338)  -------------------------------------------------------GHS
                   AB016888 (363)  ----------------------------------------------------------
                   AC044401 (466)  GYGLDARRGSLNDFEDRSNDSRELRTDAPGRSSVSSTTRGSVENGQTSEN---------
                   AK118613 (364)  FEKLKINVSASLCGESQSKDLEIFELLSPG-------------------------QSY
                   AK118730  (92)  ---SLNSNAS------------------------------------------------SMK
                   AK175585 (367)  ----------------------------------------------------------
                   AL049655 (335)  ----------------------------------------------------------
                   AL133314 (334)  ----------------------------------------------------------
                   AL138650 (328)  FEKLKINVSASLCGESQSKDLEIFELLSPG-------------------------QSY
                   AP003561 (372)  DSEPDSLRLSTETTAANKSLLDEKTDRSDG-------------LKQLRDNGFQVSDE
                   AY087360   (1)  --------------------------------------------------------ME
                   AY096530 (328)  ----------------------------------------------------------
                   AY125543   (1)  --------------------------------------------------------ME
                   AY219234 (370)  ILAFDVERMRIKSEDRMAHSGEISSHGHS---------------TLVADDQFPLGHN
                   BT020206 (342)  -------------------------------------------------------GHS
                   NM_115336 (364) FEKLKINVSASLCGESQSKDLEIFELLSPG-------------------------QSY
                   NM_127878 (387) GYGLDARRGSLNDFEDRSNDSRELRTDAPGRSSVSSTTRGSVENGQTSEN---------
                   XM_463544 (354) DSEPDSLRLSTETTAANKSLLDEKTDRSDG-------------LKQLRDNGFQVSDE
                   XM_479734.1 (391) GSASDVSRLSLAGSETRESSLEERNAGSI---------------GQTSEQSIEEAFQ
                   XM_506432  (93) ---SSS-----------------------------------------------ANAA
                   Consensus (501) ----------------------------------------------------------
```

Figure 3L

```
                              551                                                           600
Translation of Armadillo ORF  (43) ASHFDSDSQVRLGRSSVNDNLPNTRQLDEECDINDGMIRVPGDRTNYSSD
AC010870                       (3) MENHRPGSFTYMGRKFSDLSLNDDSSAFSDCNSDR---------------
AB007645                     (341) ESLDAEELRQVFSRSASAPGIVSEVVCKTKRNNN---------------
AB016888                     (363) -----------------KEVSPDSQNEQK--------------------
AC004401                     (516) HHHRSPSATSTVSNEEFPRADANENSEESAHATP------------YSSD
AK118613                     (397) THSRSESVCSVVSSVDYVPSVTHETESILGNHQS---------------
AK118730                     (102) BEAFLDISQAFSDFSACSSDISGELQRLACLPSPE--------------
AK175585                     (367) -----------------KEVSPDSQNEQK--------------------
AL049655                     (335) --------SCRTTKIGGSSS--S--------------------------
AL133314                     (334) --------P-SSLRPRKVSSFS---------------------------
AL138650                     (361) THSRSESVCSVVSSVDYVPSVTHETESILGNHQS---------------
AP003561                     (416) EQYLERNGKSHISSHHQLEVDGENVRVQASSDIN---------------
AY087360                       (3) MENHRPGSFTYMGRKFSDLSLNDDSSAFSDCNSDR---------------
AY096530                     (328) --------SCRTTKIGGSSS-----------------------------
AY125543                       (3) MENHRPGSFTYMGRKFSDLSLNDDSSAFSDCNSDR---------------
AY219234                     (412) RTTSAPSTLSNSNFSPVIPGDGNKLSEDSSVASG---------------
BT020206                     (345) ESLDAEELRQVFSRSASAPGIVSEVVCKTKRNNN---------------
NM_115336                    (397) THSRSESVCSVVSSVDYVPSVTHETESILGNHQS---------------
NM_127878                    (437) HHHRSPSATSTVSNEEFPRADANENSEESAHATP------------YSSD
XM_463544                    (398) EQYLERNGKSHISSHHQLEVDGENVRVQASSDIN---------------
XM_479734.1                  (433) ASNLDRDSHDHVGSSSVNGSLPNSGQLDAECDNG----PSERTNYSSD
XM_506432                    (100) ATEMLELSRDFSDYSSFNSDISGELERLAAAAAA---------------
Consensus                    (551)                  S V           I  E  S
```

Figure 3M

```
                                    601                                                            650
Translation of Armadillo ORF  (93) ASGEVADRGLSISSAPQRENVI---LPRLGHVCMEGPFVQRQTSDKGFPR
               AC010870       (38) ----SGE--FPTASSESRR-------------------------------L
               AB007645      (375) ---AAADRSLTRSNTPWKFP-----------------------EERHWRHPG
               AB016888      (375) --------------------------------------------------
               AC004401     (554) ASGEIRSGPLAATTSAATRRDLSDFSPKFMDRRTRGQFWRRP-SERLGSR
               AK118613     (431) ---SSEMSPKKNLESSNN------------------------VNHEHSAAK
               AK118730     (137) ADRNESGGDNEAEHDPELER----------------------EPCLGFLQR
               AK175585     (379) --------------------------------------------------
               AL049655     (348) --------------------------------------------------
               AL133314     (347) ----S---------------------------------------------
               AL138650     (395) ----SSEMSPKKNLESSNN------------------------VNHEHSAAK
               AP003561     (450) AS-EVMQDDPVTTCSKVSDN------PPRLGGVRSRNQPNWWRQSNKTIPR
               AY087360      (38) ----SGE--FPTASSESRR-------------------------------L
               AY096530     (340) --------------------------------------------------
               AY125543      (38) ----S---------------------------------------------
               AY2192234    (446) -D-VGLDSKPAASVLPKEPE------FPYTPEMRPRNQLIWRR-PTERFPR
               BT020206     (379) ---AAADRSLTRSNTPWKFP-----------------------EERHWRHPG
               NM_115336    (431) ----SSEMSPKKNLESSNN------------------------VNHEHSAAK
               NM_127878    (475) ASGEIRSGPLAATTSAATRRDLSDFSPKFMDRRTRGQFWRRP-SERLGSR
               XM_463544    (432) -ASEVMQDDPVTTCSKVSDN------PPRLGGVRSRNQPNWWRQSNKTIPR
               XM_479734.1  (477) ASGEVTDG-PSASSAPQREHLI----PSRLADVRSRGQFVRRP-SERGFPR
               XM_506432    (134) ---VVTPRSDAPQVGAVDLN------------------------EL
               Consensus    (601)                     T                             R
```

Figure 3N

```
                          651                                                        700
Translation of Armadillo ORF (140) IISSLSMDARDDFSAIENQVRELINDLGSDSIEGQRSATSEIRLLAKHNM
              AC010870    (52)  LLSCASE------NSDDLINHLVSHLDSSYSIDEQKQAAMEIRLLSKNKP
              AB007645   (401)  IIPATVRETGSS-SSIETEVKKLIDDIKSSLDTQREATARIRLLARNST
              AB016888   (375)  ------------DEVSLLVEALSSQLEEQRRSVKQMRLLARENP
              AC004401   (603)  IVSAPSNETRRDLSEVETQVKKLVEELKSSSLDTQRQATAELRLLAKHNM
              AK118613   (455)  TYECSVHDLDDSGTMTTSHTIKLVEDLKSGSNKVKTAAAAEIRHLTINSI
              AK118730   (166)  ENFSTEIIECISPEDLQPTVKLCIDGLRSSSVAIKRSAAAKLRLLAKNRA
              AL175585   (379)  ------------DEVSLLVEALSSSQIEEQRRSVKQMRLLARENP
              AL049655   (348)  ------------DCDRTFVLSLLEKLANGTTEQQRAAAGEIRLLAKRNV
              AL133314   (348)  ------------PAEANKIEDLMWRLAYGNPEDQRSAAGEIRLLAKRNA
              AL138650   (419)  TYECSVHDLDDSGTMTTSHTIKIVEDLKSGSNKVKTAAAAEIRHLTINSI
              AP003561   (494)  IGLSSSTDSKPDFSGNDAKVRNLIEELKSDSAEVQRSATGELRLLSRHSL
              AY003360    (52)  LLSCASE------NSDDLINHLVSHLDSSYSIDEKQAAMEIRLLSKNKP
              AY087360   (341)  ------------DCDRTFVLSLLEKLANGTTEQQRAAAGEIRLLAKRNV
              AY096530    (52)  LLSCASE------NSDDLINHLVSHLDSSYSIDEQKQAAMEIRLLSKNKP
              AY125543   (488)  IVSSATVERRADLSEVEEQVKKLIEELKSTSLDMQRNATAELRLLAKHNM
              AY219234   (405)  IIPATVRETGSS-SSIETEVKKLIDDLKSSSLDTQREATARIRLLARNST
              BT020206   (455)  TYECSVHDLDDSGTMTTSHTIKLVEDLKSGSNKVKTAAAAEIRHLTINSI
              NM_115336  (524)  IVSAPSNETRRDLSEVETQVKKLIEELKSSSLDTQRQATAELRLLAKHNM
              NM_127878  (476)  IGLSSSTDSKPDFSGNDAKVRNLIEELKSDSAEVQRSATGELRLLSRHSL
              XM_463544  (522)  IISSSMDTRSDLSAIENQVRKLVDDLRSDSVDVQRSATSDIRLLAKHNM
              XM_479734.1 (153) ESMDLSVEAAPLERVEPFVLACVRALGPDAAPDARRTAAAPIRLLAKHRS
              XM_506432  (651)  I   S   D   S   E   V   IVEDLKS  SLD  QRSAAAEIRLLAK   M
              Consensus
```

Figure 30

```
                              701                                                                        750
Translation of Armadillo ORF  (190) ENRIAIANCGAINLLVGLLHSPDAKIQENAVTALLNLSLSDINKIAIVNA
                   AC010870   ( 96) ENRIKIAKAGAIKPLISLISSSDLQLQEYGVTAILNLSLCDENKESIASS
                   AB007645   (450) DNRIVIARCEAIPSIVSLLYSTDERIQADAVTCLLNLSINDNNKSLIAES
                   AB016888   (408) ENRVLIANAGAIPLLVQLLSYPDSGIQENAVTTLLNLSIDEVNKKLISNE
                   AC004401   (653) DNRIVIGNSGAIVLLVELLYSTDSATQENAVTALLNLSINLSIKAMIVEV
                   AK118613   (505) ENRVHIGRCGAITPLISLLYSEEKLIQEHAVTALLNLSISELNKAMIVEV
                   AK118730   (216) DNRVLIGESGAIQALIPLLRCNDPWTQERAVTALLNLSLHDQNKAVIAAG
                   AK175585   (412) ENRVLIANAGAIPLLVQLLSYPDSGIQENAVTTLLNLSIDEVNKKLISNE
                   AL049655   (385) DNRVCIAEAGAIPLLVELLSSPDPRTQEHSVTALLNLSINEGNKGAIVDA
                   AL133314   (385) DNRVAIAEAGAIPLLVGLLSTPDSRIQEHSVTALLNLSICENNKGAIVSA
                   AL138650   (469) ENRVHIGRCGAITPLISLLYSEEKLIQENAVTILNLSIDDNNKIAIASA
                   AP003561   (544) ENRIAIANCGAIPFLVSLLHSTDPSTQENAVTALLNLSLCDENKESIASS
                   AY087360   ( 96) ENRIKIAKAGAIKPLISLISSSDLQLQEYGVTAILNLSLCDENKESIASS
                   AY096530   (378) DNRVCIAEAGAIKPLIVELLSSPDPRTQEHSVTALLNLSINEGNKGAIVDA
                   AY125543   ( 96) ENRIKIAKAGAIKPLISLISSSDLQLQEYGVTAILNLSLCDENKESIASS
                   AY219234   (538) DNRMVIANCGAISSIVNLIHSKDMKVQEDAVTALLNLSINDNNKCAIANA
                   BT020206   (454) DNRIVIARCEAIPSIVSLNYSTDERIQADAVTCLLNLSINDNNKSLIAES
                   NM_115336  (505) ENRVHIGRCGAITPLISLLYSEEKLIQEHAVTALLNLSISELNKAMIVEV
                   NM_127878  (574) DNRIVIGNSGAIVLLVELLYSTDSATQENAVTALLNLSINDNNKKAIADA
                   XM_463544  (526) ENRIAIANCGAIPFLVSLIHSTDPSTQENAVTILLNLSLDDNNKIAIASA
                   XM_479734.1 (572) ENRIIANCGAINLLVGLIHSPDDAKIQENAVTALLNLSINDNNKIAIANA
                   XM_506432  (203) DIRELIGVSGAIPALVPLLRSTDPVAQESAVTALLNLSLEERNRSAITAA
                   Consensus  (701) ENRI  IA  AGAI    LV  LLYS  D  TQE  AVTALLNLSI   D  NK AIA  A
```

Figure 3P

```
                          751                                                                    800
Translation of Armadillo ORF (240) DAIDPLIHVLETG-NPEAKENSAATLFSLSIEENRVRIGRS-GAVKPLV
                    AC010870 (146) GAIKPLVRALKMG-TPTAKENAACALLRLSQIEENKVAIGRS-GAIPLLV
                    AB007645 (500) GAIVPLIHVLKTGYLEEAKANSAATLFSLSVIEEYKTEIGEA-GAIEPIV
                    AB016888 (458) GAIPNIIEILENG-NREARENSAAALFSLSMLDENKVTIGLS-NGIPPLV
                    AC004401 (703) GAIEPLVHVLENG-SSEAKENSAATLFSLSVIEENKIKIGQS-GAIGPLV
                    AK118613 (555) GAVEPLVHVLNTG-NDRAKENSAASLFSLSVLQVNRERIGQSNAATQALV
                    AK118730 (266) GAIKSLVWVLKTG-TETSKQNAACALLSLALLEENKGSIGAC-GAIPPLV
                    AK175585 (462) GAIPNIIEILENG-NREARENSAAALFSLSMLDENKVTIGLS-NGIPPLV
                    AL049655 (435) GAITDIVEVLKNG-SMEARENAAATLFSLSVIDENKVAIGAA-GAIQALI
                    AL133314 (435) GAIPGIVQVLKKG-SMEARENAAATLFSLSVIDENKVTIGAL-GAIQPLV
                    AL138650 (519) GAIEPLIHVLNTG-NDRAKENSAASLFSLSVIEENKIKIGRS-GAIEPLV
                    AP003561 (594) EAIEPLFVLQVG-NPEAKANSAATLFSLSVIEENKVAIGRS-GAIPLLV
                    AY087360 (146) GAIKPLVRALKMG-TPTAKDNAACALLRLSQIEENKVAIGAA-GAIQALI
                    AY096530 (428) GAITDIVEVLKNG-SMEARENAAATLFSLSVIDENKVAIGAA-GAIQALI
                    AY125543 (146) GAIKPLVRALKMG-TPTAKENAACALLRLSQIEENKVAIGRS-GAIPLLV
                    AY219234 (588) DAIEPLIHVLQTG-SAFAKENSAATLFSLSVMEENKMKIGRS-GAIKPLV
                    BT020206 (504) GAIVPLIHVLKTGYLEEAKANSAATLFSLSVIEEYKTEIGEA-GAIEPIV
                    NM_115336 (555) GAIEPLVHVLNTG-NDRAKENSAASLFSLSVLQVNRERIGQSNAAIQALV
                    NM_127878 (624) GAIEPLIHVLENG-SSEAKENSAATLFSLSVIEENKIKIGQS-GAIGPLV
                    XM_463544 (576) EAIEPLIFVLQVG-NPEAKANSAATLFSLSVIEENKIKIGRS-GAIEPLV
                    XM_479734.1 (622) DAMDPLIHVLETG-NPEAKENSAATLFSLSVIEENKVRIGRS-GAIKPLV
                    XM_506432 (253) GAIKPLVVALRTG-TASAKQNAACALLSLSGIEENRATIGAC-GAIPPLV
                   Consensus (751) GAI PLIHVL  G S EAKENSAATLFSLSVIEENKV IG S GAI PLV
```

Figure 3Q

```
                                   801                                                                850
Translation of Armadillo ORF (288) DLLGNGSPRGKKDAVTALFNLSILHENKGRIVQADALKHLVELM-DPAAG
                    AC010870 (194) NLLETGGFRAKKDASTALYSLCSAKENKIRAVQSGIMKPLVELMADFGSN
                    AB007645 (549) DLLGSGSLSGKKDAATALFNLSIHHENKTKVIEAGAVRYLVELM-DPAFG
                    AB016888 (506) DLLQHGTLRGKKDALTALFNLTALFNLSIHQENKAMIVQSGAVRYLIDLM-DPAAG
                    AC004401 (751) DLLGNGTPRGKKDAASALFNLSIHQENKAMIVQSGAVRYLIDLM-DPAAG
                    AK118613 (604) NLLGKGTFRGKKDALTALYKLCTLQQNKERAVTAGAVKPLVDLVAREGTG
                    AK118730 (314) SILLNGSCRGKKDALTALFNLSINSANKGRAIDAGIVQPLINLIKDKNLG
                    AK175585 (510) DLLQHGTLRGKKDALTALFNLSINSANKGRAIDAGIVQPLINLIKDKNLG
                    AL049655 (483) SLLEEGTRRGKKDAATAIFNLSITHDNKARIVQSRAVKGGIVDPLITRLIKDAGGG
                    AL133314 (483) VLLNEGTQRGKKDAATALFNLCIYQGNKGKAIRAGVLPTITRLITEPGSG
                    AL138650 (568) NLLGKGTFRGKKDAASALFNLSITHDNKARIVQAKAVKYLVELI-DPDLE
                    AP003561 (642) DLLGEGTPQGKKDAATALFNLSIFHEHKTRIVQAGAVNHLVELM-DPAAG
                    AY087360 (194) NLLETGGFRAKKDASTALYSLCSAKENKIRAVQSGIMKPLVELMADFGSN
                    AY096530 (476) SLLEEGTRRGKKDAATAIFNLCIYQGNKSRAVKGGIVDPLTRLIKDAGGG
                    AY125543 (194) NLLETGGFRAKKDASTALYSLCSAKENKIRAVQSGIMKPLVELMADFGSN
                    AY2192334 (636) DLLGNGTPRGKKDAATALFNLSILHENKSRTIQAGAVRYLVELM-DPATG
                    BT020206 (553) DLLGSGSLSGKKDAATALFNLSIHHENKTKVIEAGAVRYLVELI-DPDLE
                    NM_115336 (604) NLLGKGTFRGKKDAASALFNLSITHDNKARIVQAKAVKYLVELI-DPDLE
                    NM_127878 (672) DLLGNGTPRGKKDAATALFNLSIHQENKAMIVQSGAVRYLIDLM-DPAAG
                    XM_463544 (624) DLLGEGTPQGKKDAATALFNLSIFHEHKTRIVQAGAVNHIVELM-DPAAG
                    XM_479734.1 (670) DLLGNGTPRGKKDAATALFNLSILHENKERAVQADAVKYLVELM-DPAAG
                    XM_506432 (301) ALLSAGSTRGKKDALITLYRLCSARRNKERAVSAGAVPLIHLVGERGSG
                    Consensus (801)  DLLG GT RGKKDAATALFNLSI  ENK RIVQAGAVKYLIVELM DPAAG
```

Figure 3R

| | | 851 | | 900 |
|---|---|---|---|---|
| Translation of Armadillo ORF | (337) | MVDKAVAVLANLATIPEGRTAIGQARGIPALVEVELGSAKAKENATAAL |
| AC010870 | (244) | MVDKSAFVMSLLMSVPESKPAIVEEGGVPVLVE VEVGTQRQKEMAVSIL |
| AB007645 | (598) | MVEKAVVVLANLATVREGKIAIGEEGIPVLVEVVELGSARGKENATAAL |
| AB016888 | (556) | MIDEALSILLLLASHPEGRQAIGQLSFIETLVEFIRQCTPKNKECATSVL |
| AC004401 | (800) | MVDKAVAVLANLATIPEGRNAIGQEGGIPLLVEVVELGSARGKENAAAAL |
| AK118613 | (653) | MVDKAVAILANLSAVGEGRQAIVREGGIPLLVETVDLGSQRGKENAASVL |
| AK118730 | (364) | MAEKAMVVLSSLAAIDDGKEAIVEEGGIAAALVEAIEDGSVKGKEFAILTL |
| AK175585 | (560) | MIDEALSILLLLAIISTNQEGKTAIAEAESIPVLVEIIRTGSPRNKECATSVL |
| AL049655 | (533) | MVDEALALALIAIISSHPEGKAIIGSSDAVPSLVEFIRTGSPRNRENAAAIL |
| AL133314 | (533) | MVDEALALALIAIISSHPEGRQAIVREGGIPLLVEVVELGSARSKENAASVL |
| AL138650 | (617) | MVDKAVAILANLATVHDGRNAIAQAGGIRVLVEIVEEGGVPVLVEIVEVGTQRQKEMAVSIL |
| AP003561 | (691) | MVDKSAFVMSLLMSVPESKPAIVEEGGVPVLVEIVEVIRTGSPRNRENAAAIL |
| AY087360 | (244) | MVDEALAIAIIISTNQEGKTAIAEAESIPVIVEIPVLVEIVEVIRTGSPRNRENAAAIL |
| AY096530 | (526) | MVDKSAFVMSLLMSVPESKPAIVEEGGVPVLVEIVEVIRTGSPRNRENAAAIL |
| AY125543 | (244) | MVDKAVAVLSNLATIPEGRAEIGQEGEGIPVLVEVVELGSARGKENATAAL |
| AY219234 | (685) | MVEKAVVVLANLATVREGKIAIGEEGIPVLVEVVELGSARGKENAAAAL |
| BT020206 | (602) | MVDKAVAVLANLSAVGEGRQAIVREGGIPLLVETVDLGSQRGKENAAASVL |
| NM_115336 | (653) | MVDKAVAVLANLATIPEGRNAIGQEGGIPLLVEVVELGSARGKENAAAAL |
| NM_127878 | (721) | MVDKAVAILANLATIPEGRNAIAQAGGIRVLVEVVELGSARSKENAAAAL |
| XM_463544 | (673) | MVDKAVAVLANLATIPEGRTAIGQARGIPALVEVVELGSARGKENAAAAL |
| XM_479734.1 | (719) | MVDKAVAVLANLATIPEGRDAVVEAGGIPAIVETIEDGPAREFAVVAL |
| XM_506432 | (351) | TSEKAMVVLASLAGIVEGRDAVVEAGGIPAIVETIEDGPAREFAVVAL |
| Consensus | (851) | MVDKAVAVLANLATVPEGR AIG EGGIPVLVEVELGS RGKENAAAVL |

Figure 3S

```
                              901                                                              950
Translation of Armadillo ORF  (387) LQLCTNSSRFCNIVLQEDAVPPLVALSQSG--TPRAREKAQVLLSYFRSQ
                   AC010870   (294) LQLCEESVVYRTMVAREGAIPPLVALSQAG--TSRAKQKAEALIELRQP
                   AB007645   (648) LQLCTHSPKFCNNVIREGVIPPLVALTKSG--TARGKEKVLFLFPLLCLV
                   AB016888   (606) LELGSNNSSFILAALQFGVYEYLVEITTSG--TNRAQRKANALIQLISKS
                   AC004401   (850) LQLSTNSGRFCNMVLQEGAVPPLVALSQSG--TPRAREKKPTAWKRWAWL
                   AK118613   (703) LQLCLNSPKFCTLVLQEGAIPPLVALSQSG--TQRAKEKAQQLISHFRNQ
                   AK118730   (414) LQLCSDSVRNRGLLVREGAIPPLVGLSQSGSVSVRAKRKAERLLGYLREP
                   AK175585   (610) LELGSNNSSFILAALQFGVYEYLVEITTSG--TNRAQRKANALIQLISKS
                   AL049655   (583) WYLCIGNIERLNVAREVGADVALKELTENG--TDRAKRKAASLLELLQQT
                   AL133314   (583) VHLCSGDPQHLVEAQKLGLMGPLTDLAGNG--TDRGKRKAAQLIERLSRL
                   AL138650   (667) LQLCTNSNRFCTLVLQEGAIPPLVALSQSG--TQRAKEKVYTLFFFCGYT
                   AP003561   (741) LQLCEESVVYRTMVAREGAIPPLVALSQAG--IARAREKAQVLLSYFRNQ
                   AY003361   (294) LQLCEESVVYRTMVAREGAIPPLVALSQAG--TSRAKQKAEALIELRQP
                   AY096530   (576) WYLCIGNIERLNVAREVGADVALKELTENG--IDRAKRKAASLLELLQQT
                   AY125543   (294) LQLCEESVVYRTMVAREGAIPPLVALSQAG--TSRAKQKAEALIELRQL
                   AY219234   (735) LQLCTNSSRFCNNVIREGVIPPLVALSQSG--TPRAREKAQQLLSYFRNQ
                   BT020206   (652) LQLCTHSPKFCNNVIREGVIPPLVALTKSG--TARGKEKAQNLLKYFKAH
                   NM_115336  (703) LQLCLNSPKFCTLVLQEGAVPPLVALSQSG--IQRAKEKAQQLLSHFRNQ
                   NM_127878  (771) LQLSTNSGRFCNMVLQEGAVPPLVALSQSG--TPRAREKVQTL------
                   XM_463544  (723) LQLCTNSNRFCSIVLQEGAVPPLVALSQSG--LARAREKAQVLLSYFRNQ
                   XM_479734.1 (769) LQLCTNSSRFCNIVLQEGAIPPLVALSQSG--TPRAREKAQALLSYFRSQ
                   XM_506432  (401) LQLCSECPRNRALLVREGAIPPLVALSQSG--SARAKHKAETLLGYLREQ
                   Consensus  (901) LQLCTNS RFC LVLQEGATPPLVALSQSG   T RAKEKAQ LL   LR
```

Figure 3T

```
                                      951                                           980
Translation of Armadillo ORF    (435) RHGNSGRR----------------------------
                     AC010870   (342) RSISNGGARSSSQL----------------------
                     AB007645   (696) NVS---------------------------------
                     AB016888   (654) EQI---------------------------------
                     AC004401   (898) MMDDDDDDVDDAQILVSQCLFLCFVL----------
                     AK118613   (751) RDARMKKGRS--------------------------
                     AK118730   (464) RKEASSSSP---------------------------
                     AK175585   (658) EQI---------------------------------
                     AL049655   (631) EGVAVTTVP---------------------------
                     AL133314   (631) AEQQKETAVSQPEEEAEPTHPESTTEAADT
                     AL138650   (715) KTHQVQFLIDRDI-----------------------
                     AP003561   (789) RHVRVGRG----------------------------
                     AY087360   (342) RSISNGGARSSSQL----------------------
                     AY096530   (624) EGVAVTTVP---------------------------
                     AY125543   (342) RSISNGGARSSSQL----------------------
                     AY2l9234   (783) RHGNAGRG----------------------------
                     BT020206   (700) RQSNQRRG----------------------------
                     NM_115336  (751) RDARMKKGRS--------------------------
                     NM_127878  (812) ------------------------------------
                     XM_463544  (771) RHVRVGRGLSLLLELKRTT-----------------
                   XM_479734.1  (817) RHGNSARR----------------------------
                     XM_506432  (449) RQGGGGCRVEPVAASSLAR-----------------
                     Consensus  (951) R
```

Figure 5A (page 1 of 2):

Consensus sequence 1 (Seq ID NO.: 60):
(yellow identical amino acids)

RXLXXXXXXXRXXXIXXXXAIXXLXXLXXXXXXXQXXXVTXXLNLSXXXXXNXXXIXXXAIXXXXXXXLXXGXXX
XXXXNXAXXLXXLXXXXXXIGXXXXXXXLXXLLXXGXXXXXKKDAXXXXXLXXXXXXKXXXXXXXXX
XLXXLXXXXXXXXXXXXXLXXXXXXXXXXLVEXXXXGXXXXFEXAXXLXXLXXXXXXX
XXXXXXXXXXXLXXXXXGXXXXRXXXKXX

Consensus sequence 2 (Seq ID NO.: 61):
(yellow and blue identical amino acids)

RLLAKXXXENRIXIAXXGAIXXLVXLLXSXDXXTQEXAVTALLNLSIXDXNKXAIAXAGAIXPLXXVLXXGXXXEAK
ENSAATLFSLSVIEENKXXIGXSXGAIXPLVDLLGXGTXRGKKDAATALFNLSIXXENKXRXVQAGAVXXLVELMXD
PXXGMVDKAVAVLANLATXPEGRXAIXXEGGIPXLVEXVELGSXRXKENAAAXLLQLCXNSXXFCXXVLQEGAXPP
LVALSQSGXXTXRAKEKAX

Consensus sequence 3 (Seq ID NO.: 62):
(yellow, blue, green identical amino acids and alternative AS)

Figure 5B

```
RLLAKXXMENRIXIAXAGAIXXLVXLLYSXDXXTQEXAVTALLNLSIXDXNKXAIAXAGAI
 I  SR   LD  V G S      L  IHT E       G   I   LE R SS  S  V
            I  M                        S                   G
            V

XPLIHVLXXGXSXEAKENSAATLFSLSVIEENKVXIGXSXGAIXPLVDLLGXGTXRGKKDA
    IVYI     T  SRD A  S        AMLD  R I   A AGV  I      S   A
                                   LM
                                   I

ATALFNLSIXXENKXRIVQAGAVKYLVELMXDPAAGMVDKAVAVLANLATVPEGRXAIGX
 SS IY    L  D   KVI  S  MRH ID  V E GS    IE SMSLMS  SS I D K  VA
                      G    I  L  L         L  I

EGGIPVLVEVVELGSXRGKENAAAVLLQLCTNSXRFCXLVLQEGAIPPLVALSQSGXXTXR
 AV L   I IDV T KAR       S I V    S  KY  ILV    V  IG IT A   S
                                       M I        M       A
                                       V

AKEKAQ
 GR   N
```

Figure 6 - A

ARM1 (rnr5) cDNA sequence (starting from the putative transcription start):
(Start ATG at position 481)

```
gaaagtgcatttccttgttgcttccccaggctgaccgaccagccaccaccaacccaaaccaacgcggcaa
aaccttggcccccgcctgtcctagcgctgCCGCCGTGCCGTGCCGTGCCGTGCCGTGCCTCAGCGCCAGC
GACCGCCGACGACTCAATCCCGTACCACGCCCCCACCGCCGCCTCCCACGCCCCTCGTGCCCATCGCCGA
TCCCGTTCCCCCTCACCGCAGCATCGCGCTCCCGCGGTATCCGCCCCTTCCGCAACCGTCGGCCATTGGT
TTCTGAGAGCCTTCAAGATTTGAGCACCACAGGCAACAGCCTCCTACATCCTGTGTCGGTACTTGGTAGG
GTAATCTTCCCTGGACCCCGGGAGCTGACATGTATATGAGAAGCTTGAACAGAGCATGTGAACCATCCTG
AAATCTGATGCACATGTGAACCATCCTGGTCATGAGGCCTCATCGATCAGTCTTTAGATTATGCAAATGG
CTCTGCTAGCAAGGCTTTCTCTTGCAAGTTCTGAAGGAAGAGAGTCTAGTTTGGAAGAAAGACATGCTGG
TTCTGATGAACAAACTTCAGAACAATCAACGAAGGAAGCATTTCAAGCATCTCATTTTGACAGTGATTCA
CAGGTTCGTCTAGGCAGATCTTCAGTTAATGATAATCTTCCTAATACCCGTCAGCTTGACGAGGAGTGTG
ACATCAACGATGGGATGATACGAGTTCCAGGTGATAGGACAAATTATAGTAGTGATGCGTCTGGAGAGGT
TGCTGACCGTGGGCTTTCTATCTCTTCTGCCCCTCAAAGGGAAAATGTAATCCTGCCAAGATTGGGTCAT
GTCTGCATGGAGGGACCATTTGTTCAGCGGCAAACATCTGACAAGGGATTCCCGAGAATAATTTCGTCGT
TATCCATGGATGCCCGGGATGATTTCTCTGCCATCGAGAATCAGGTACGCGAGCTAATCAATGATTTGGG
AAGTGATTCCATAGAAGGTCAGAGATCAGCAACATCAGAGATTCGCCTTCTAGCTAAGCACAACATGGAG
AACAGGATTGCCATTGCTAATTGTGGGGCTATAAACTTGCTGGTTGGCCTTCTTCATTCACCCGATGCCA
AAATCCAAGAAAATGCAGTGACAGCCCTCCTTAATTTGTCAcTCAGTGATATCAATAAGATTGCCATCGT
GAATGCAGATGCTATTGATCCTCTCATCCATGTCCTGGAAACAGGGAACCCTGAAGCTAAAGAGAATTCA
GCAGCTACTTTGTTCAGTCTCTCAATTATTGAAGAAAACAGAGTGAGGATAGGGCGATCTGGTGCTGTAA
AGCCTCTCGTGGACTTGCTGGGAAATGGGAGCCCACGAGGAAAGAAAGATGCGGTTACTGCATTGTTTAA
TTTATCCATACTTCATGAGAACAAGGGTCGAATTGTGCAAGCTGATGCATTGAAGCACCTAGTTGAGCTT
ATGGACCCTGCTGCTGGAATGGTCGATAAAGCTGTAGCTGTCTTGGCAAATCTTGCTACGATACCAGAAG
GAAGGACTGCGATTGGGCAGGCGCGTGGTATTCCGGCCCTTGTTGAAGTTGTCGAACTGGGTTCAGCGAA
AGCGAAGGAAAATGCTACCGCGGCATTGCTTCAGCTATGCACAAACAGCAGCAGGTTTTGCAACATAGTT
CTTCAAGAGGATGCCGTGCCCCCTTTAGTCGCACTGTCACAGTCAGGAACACCACGCGCAAGAGAAAAGG
CGCAGGTTCTCCTCAGCTATTTCCGCAGCCAAAGACATGGGAACTCGGGAAGGAGATGAGGACGATGGTC
CTACGATATATTTTTCTAGTGTACGTCGAGTATTTCCCTGAATTTCTCAGATGATAGTTATTGTTGTTGA
CTGGCGCTGTGTACTGCTTATAGTCACTGTGAGATTGTGCTCATCTTCTCAAGCTACTGGTGGATTAGTT
GCTGTGTTTGTGACTGGTCGTTGTTGTTGTTGAGATGGTGTATTCTTCGGGTTTATATTTTTTTACATCT
tGTCTATTGGTATCTAAAAAAAA
```

Figure 6 - B

ARM1 (rnr5) 5' UTR sequence:

gaaagtgcatttccttgttgcttccccaggctgaccgaccagccaccaccaacccaaaccaacgcggcaa
aaccttggcccccgcctgtcctagcgctgCCGCCGTGCCGTGCCGTGCCGTGCCGTGCCTCAGCGCCAGC
GACCGCCGACGACTCAATCCCGTACCACGCCCCCACCGCCGCCTCCCACGCCCCTCGTGCCCATCGCCGA
TCCCGTTCCCCCTCACCGCAGCATCGCGCTCCCGCGGTATCCGCCCCTTCCGCAACCGTCGGCCATTGGT
TTCTGAGAGCCTTCAAGATTTGAGCACCACAGGCAACAGCCTCCTACATCCTGTGTCGGTACTTGGTAGG
GTAATCTTCCCTGGACCCCGGGAGCTGACATGTATATGAGAAGCTTGAACAGAGCATGTGAACCATCCTG
AAATCTGATGCACATGTGAACCATCCTGGTCATGAGGCCTCATCGATCAGTCTTTAGATT

US 8,329,988 B2

METHOD FOR INCREASING PATHOGEN RESISTANCE IN TRANSGENIC PLANTS

RELATED APPLICATIONS

This application is a national stage application (under 35 U.S.C. §371) of PCT/EP2007/060857, filed Oct. 12, 2007, which claims benefit of European application 06122217.0, filed Oct. 12, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_Listing__13987__00100. The size of the text file is 351 KB, and the text file was created on Nov. 29, 2011.

The present invention relates to a method of increasing the pathogen resistance in transgenic plants and/or plant cells, where a DNA sequence which codes for a *Hordeum vulgare* armadillo repeat (HvARM) polynucleotide or a functional equivalent thereof is introduced into, and expressed in, the plant or plant cell. The present invention also relates to the use of nucleic acids which code for such a protein for the generation of transgenic plants or plant cells with an increased pathogen resistance. The present invention furthermore relates to nucleic acid sequences which code for such a protein which mediates an increased pathogen resistance in plants. The invention furthermore relates to homologous sequences (ARM1) thereof, and to their use in a method for obtaining a pathogen resistance in plants, and to nucleic acid constructs, expression cassettes and vectors which comprise these sequences and which are suitable for mediating a fungal resistance in plants. The invention furthermore relates to transgenic organisms transformed with these expression cassettes or vectors, in particular to plants, to cultures, parts or transgenic propagation material derived therefrom.

Plant diseases which are caused by various pathogens such as, for example viruses, bacteria and fungi, can lead to, considerable yield losses in crop plant cultivation, which firstly has economic consequences, but, secondly, also endangers the safety of human nutrition. Since the last century, chemical fungicides have been employed for controlling fungal diseases. While the use of these substances has succeeded in reducing the extent of plant diseases, it cannot be ruled out even now that these compounds have a harmful effect on humans, animals and the environment. If the consumption of conventional plant protection agents is to be reduced to a minimum in the long term, it is therefore important to study the natural pathogen defense of various plants against different causative organisms, and to exploit them in a targeted manner for the generation of pathogen-resistant plants by means of recombinant manipulation, for example by the introduction of external resistance genes or by the manipulation of the endogenous gene expression in the plants.

There are only few approaches which confer a resistance to pathogens, mainly fungal pathogens, to plants. This shortcoming can partly be attributed to the complexity of the biological systems in question. Another fact which stands in the way of obtaining resistances to pathogens is that little is known about the interactions between pathogen and plant. The large number of different pathogens, the infection mechanisms developed by these organisms and the defense mechanisms developed by the plant families, genera and species interact with one another in many different ways.

Fungal pathogens have developed essentially two infection strategies. Some fungi enter into the host tissue via the stomata (for example rusts, *Septoria* species, *Fusarium* species) and penetrate the mesophyll tissue, while others penetrate via the cuticles into the epidermal cells underneath (for example *Blumeria* species).

The infections caused by the fungal pathogens lead to the activation of the plant's defense mechanisms in the infected plants. Thus, it has been possible to demonstrate that defense reactions against epidermis-penetrating fungi frequently start with the formation of a penetration resistance (formation of papillae, strengthening of the cell wall with callose as the main constituent) underneath the fungal penetration hypha (Elliott et al. Mol Plant Microbe Interact. 15: 1069-77; 2002).

In some cases, however, the plant's defense mechanisms only confer an insufficient protection mechanism against the attack by pathogens.

The formation of a penetration resistance to pathogens whose infection mechanism comprises a penetration of the epidermal cells or of the mesophyll cells is of great importance both for monocotyledonous and for dicotyledonous plants. In contrast to described mlo-mediated resistance, it can probably make possible the development of a broad-spectrum resistance against obligatory biotrophic, hemi-biotrophic and necrotrophic fungi.

Until now, the strategy for generating fungus-resistant plants has frequently involved the crossing-in of quantitative resistance traits (resistance QTLs). However, the disadvantage of this procedure is that undesirable traits are frequently also crossed in. Moreover, the breeding methods required are very complicated and time-consuming.

The present invention was therefore based on the object of providing a method for generating a resistance of plants to penetrating pathogens.

BRIEF DESCRIPTION OF THE FIGURES

FIG. 1 provides nucleic acid sequences of ARM1 from barley, rice, and *Arabidopsis thaliana*.

FIG. 2 provides polypeptide sequences of ARM1 from barley, rice, and *Arabidopsis thaliana*.

FIG. 3 shows a sequence alignment from ARM1 protein sequences from barley, rice and *Arabidopsis thaliana*. The following amino acid sequences are depicted: the Armadillo ORF (SEQ ID NO: 2), AC010870 (SEQ ID NO: 30), AB007645 (SEQ ID NO: 20), AB016888 (SEQ ID NO: 36), AC004401 (SEQ ID NO: 16), AK118613 (SEQ ID NO: 24), AK118730 (SEQ ID NO: 44), AK175585 (SEQ ID NO: 38), AL049655 (SEQ ID NO: 40), AL133314 (SEQ ID NO: 28), AL138650 (SEQ ID NO: 26), AP003561 (SEQ ID NO: 8), AY087360 (SEQ ID NO: 34), AY096530 (SEQ ID NO: 42), AY125543 (SEQ ID NO: 32), AY219234 (SEQ ID NO: 12), BT020206 (SEQ ID NO: 18), NM__115336 (SEQ ID NO: 22), NM__127878 (SEQ ID NO: 14), XM__463544 (SEQ ID NO: 6), XM__479734.1 (SEQ ID NO: 4), and XM__506432 (SEQ ID NO: 10).

FIG. 5 shows consensus sequences of the sequence alignment from ARM1 protein sequences from barley, rice, and *Arabidopsis thaliana*.

FIG. 6A shows the nucleic acid sequence of ARM1 (rnr5) cDNA (starting from the putative transcription start (start ATG at position 481) (SEQ ID NO: 72) and FIG. 6B shows the ARM1 (rnr5) the 5'-UTR region (SEQ ID NO: 64).

DETAILED DESCRIPTION OF THE INVENTION

Figure 4:
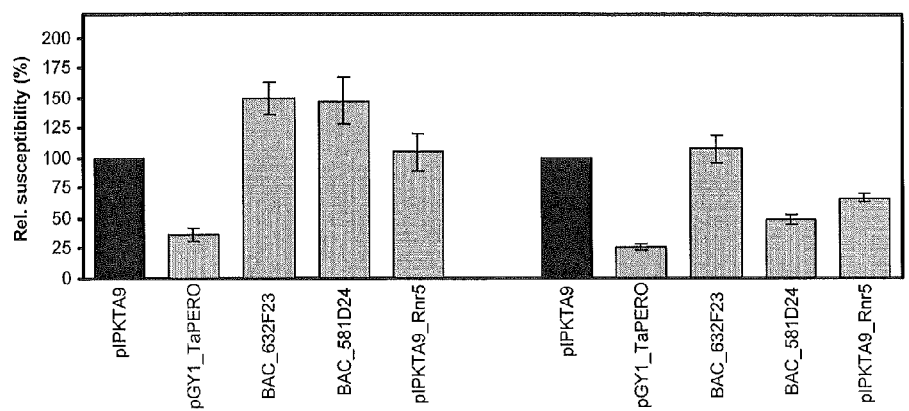
FIG. 4 illustrates increasing the mildew resistance of wheat by introducing and expressing ARM repeat sequences.

The object is achieved by the embodiments characterized in the claims.

The invention therefore relates to a method of increasing the resistance to one or more penetrating pathogens in a monocotyledonous or dicotyledonous plant, or a part of a plant, for example in an organ, tissue, a cell or a part of a plant cell, for example in an organelle, which comprises introducing into, and expressing in, the plant or plant cell a DNA sequence which codes for an armadillo repeat ARM1 protein and which mediates an increased pathogen resistance, preferably an increased resistance to fungal pathogens.

In a further embodiment, the invention relates to a method of increasing the resistance to one or more penetrating pathogen(s) in a monocotyledonous or dicotyledonous plant, or a part of a plant, for example in an organ, a tissue, a cell or a part of a plant cell, for example in an organelle, in which method an endogenous DNA sequence which codes for an armadillo repeat ARM1 protein and which mediates an increased pathogen resistance, preferably an increased resistance to fungal pathogen, is increased in the plant, plant part or plant cell in comparison with the original or wild-type plant, or a part thereof, or in which method the endogenous gene sequence or preferably the 5'-untranslated region (5'UTR) is modified in comparison with the original sequence.

Originally, it has been found in the context of a TIGS (=Transient Induced Gene Silencing) analysis in barley by the method of Schweizer et al. (2001) that a dsRNAi-mediated silencing of a gene coding for an armadillo repeat reduces the susceptibility of the plant to the fungal pathogen *Blumeria graminis*, and that the gene could therefore play a role in mediating the pathogen resistance of plants.

However, it must be noted in this context that, owing to the high number of conserved residues and the homology between the individual armadillo repeat ARM1 polypeptides and their functional equivalents, it is possible to suppress the expression of further homologous polypeptides and/or their functional equivalents of the same organism using a single dsRNA sequence which has been generated starting from a specific armadillo repeat ARM1 protein sequence of an organism.

Surprisingly, however, it has now been found that the introduction of the gene from barley, or its expression or overexpression in plants other than barley, preferably monocotyledonous plants, in particular wheat, is also capable of bringing about an increased resistance.

In the method according to the invention, it is preferred to obtain a race-unspecific resistance. Thus, for example, it is possible to achieve, by the method according to the invention, a broad-range resistance to obligatory-biotrophic and/or hemibiotrophic and/or necrotrophic fungi of plants, in particular against mesophyll- and/or epidermis-penetrating pathogens.

The armadillo repeat motif has originally been discovered in the *Drosophila melanogaster* armadillo segment polarity gene. It codes for a beta-catenin, which plays an important role in cell-to-cell adhesion and in cell differentiation. Armadillo (Arm) repeat proteins comprise copies arranged in tandem of a degenerate sequence of approximately 42 amino acids, which sequence codes for a three-dimensional structure for mediating protein-protein interactions (Azevedo et al., Trends Plant Sci. 6, 354 (2001)). Most of these proteins are involved in the intracellular signal transduction or in the regulation of gene expression within the context of cellular developmental processes. In contrast to animals, only two plant armadillo repeat proteins have been functionally characterized: the first gene is PHOR1 (photoperiod-responsive 1) from potato, for which a role in gibberellic acid signal transduction has been demonstrated (Amador V., Cell 106 (3), 343 (2001)). The second armadillo repeat protein is ARC1 (armadillo-repeat containing protein 1) from oilseed rape, which interacts with the receptor kinase SRK1 (Gu et al., Proc. Natl. Acad. Sci. USA 95, 382 (1998)). Thus, it plays an important role in regulating the self-incompatibility of oilseed rape. Transgenic plants in which the expression of ARC1 is reduced by silencing show a reduced self-incompatibility. Interestingly, ARC1 belongs to the U-box-containing subclass of the armadillo repeat proteins, which includes 18 genes in *Arabidopsis* (Azevedo et al., Trends Plant Sci. 6, 354 (2001)). The U-box is a motif consisting of approximately 70 amino acid residues. Besides the HECT and the RING finger proteins, they probably form a third class of ubiquitin E3 ligases, whose primary function is to determine the substrate specificity of the ubiquitination machinery (Hatakeyama et al., J. Biol. Chem. 76, 33111 (2001)).

Genes with high homology to HvArm probably mediate similar functions. Preferably, the genes or the used nucleic acids or the expressed proteins have 40% or more identity, preferably 50%, 60%, 70%, 80%, 85%, 90%, 95%, 97%, 98%, 99% or more identity, in comparison with the respective sequence of HvARM (SEQ ID No.: 1 or SEQ ID No.: 63 [cDNA sequence with UTR] or the protein sequence SEQ ID No.: 2). The genes with the highest homologies to HvArm from rice (Acc. No.: XM_479734.1, XM_463544, AP003561, or XM_506432), tobacco (AY219234) and *Arabidopsis* (Acc.-No. NM_127878, AC004401, BT020206, AB007645, NM_115336, AK118613, AL138650, AL133314, AC010870, AY125543, AY087360, AB016888, AK175585, AL049655, AY096530 and AK118730) therefore probably exert similar functions in the plant as HvARM. Hereinbelow, the homologous sequences are referred to by the term "Armadillo Repeat ARM 1" or "ARM1". In contrast, HvARM or HvARM1 refer to such a sequence from barley etc.

In the description, the term of the "sequence(s) according to the invention" is used for simplification reasons, and refers, depending on the context, to the nucleic acid and/or amino acid sequences disclosed herein. The skilled worker will know from the context what they refer to.

Recently, Spl11, a further plant armadillo repeat protein, has been described in maize, for which protein a regulation of the plant cell death response in connection with the abiotic stress response has been detected. The loss of function of the corresponding gene leads to what is known as a lesion-mimic phenotype, which adversely affects the agronomic performance of the plant (Zeng L. R., Plant Cell. 16 (10), 2795 (2004)). Interestingly, the sequence homology of Spl11 to HvARM is only 23.4% at the amino acid level. Without wishing to be bound by theory, not only the different functions, but also the weak sequence homology, suggests that HvARM and Spl11 belong to different subclasses of armadillo repeat proteins.

As a consequence, it was surprising that the introduction and the expression of HvArm sequences according to the invention leads to an increased resistance of wheat to powdery mildew of wheat. In a preferred embodiment, the polypeptide according to the invention, which is encoded by a sequence according to the invention, does not contain a U-box in the 5'-UTR.

In a further embodiment, the invention therefore relates to a method of generating a plant with an increased resistance to one or more plant pathogens, preferably with a broad-spectrum resistance, in particular to fungal pathogens, for example from the classes Ascomycetes, Basidiomycetes, Chytridiomycetes or Oomycetes, preferably of mildews of the family Erysiphaceae, and especially preferably of the genus *Blumeria*, by introducing and expressing a sequence according to the invention, which codes for a protein comprising at least one armadillo repeat. Preferably, the protein comprises two, especially preferably more than two, armadillo repeats.

In a further embodiment, the protein-encoding cDNA (or the mRNA including the UTR sequence(s)) comprises essentially no U-box, i.e. either no U-box or no functional U-box.

The nucleic acid sequence according to the invention, i.e. the nucleic acid sequence which codes for an armadillo repeat ARM1 protein and which mediates an increased pathogen resistance, preferably an increased resistance to fungal pathogens, and which is, in the methods according to the invention, introduced into, and expressed in, the plant or plant cell or a part thereof, or the endogenous DNA sequence according to the invention, which is increased in the plant or plant cell in comparison with the original or wild-type plant or its part, or where the endogenous gene sequence or preferably the 5'-untranslated region (5'UTR) is modified in comparison with this original sequence, is selected from the group consisting of (a) nucleic acid molecule which codes for at least one polypeptide comprising the sequence shown in SEQ ID No.: 2, 4, 6, 8, 10, 12, 14, 16, 18, 20, 22, 24, 26, 28, 30, 32, 34, 36, 38, 40, 42, 44, 60, 61 or 62;
(b) nucleic acid molecule which comprises at least one polynucleotide of the sequence shown in SEQ ID No.: 1, 3, 5, 7, 9, 11, 13, 15, 17, 19, 21, 23, 25, 27, 29, 31, 33, 35, 37, 39, 41, 43 or 63;
(c) nucleic acid molecule which codes for a polypeptide whose sequences has at least 50%, preferably at least 60%, 70%, 80%, 85%, 90%, 95%, 97%, 98% or 99%, identity with the sequences SEQ ID No.: 2;
(d) nucleic acid molecule according to (a) to (c) which codes for a fragment or an epitope of the sequences as shown in SEQ. ID No.: 2, 4, 6, 8, 10, 12, 14, 16, 18, 20, 22, 24, 26, 28, 30, 32, 34, 36, 38, 40, 42, 44, 60, 61 or 62;
(e) nucleic acid molecule which codes for a polypeptide which is recognized by a monoclonal antibody directed against a polypeptide which is encoded by the nucleic acid molecules as shown in (a) to (c);
(f) nucleic acid molecule which hybridizes under stringent conditions with a nucleic acid molecule as shown in (a) to (c); and
(g) nucleic acid molecule which can be isolated from a DNA library using a nucleic acid molecule as shown in (a) to (c) or their part-fragments of at least 15 nt, preferably 20 nt, 30 nt, 50 nt, 100 nt, 200 nt or 500 nt, as probe under stringent hybridization conditions; or comprises a complementary sequence thereof.

In the method according to the invention, it is particularly the resistance to mesophyll and/or epidermal cell penetrating pathogens which is preferably increased.

In one embodiment, the resistance is obtained by introducing, and expressing, a nucleic acid sequence according to the invention, for example the nucleic acid sequence of an ARM1 from rice (Acc. No.: XM_479734.1, XM_463544, AP003561, or XM_506432), tobacco (AY219234) and *Arabidopsis* (Acc.-No. NM_127878, AC004401, BT020206, AB007645, NM_115336, AK118613, AL138650, AL133314, AC010870, AY125543, AY087360, AB016888, AK175585, AL049655, AY096530 and AK118730).

On the other hand, it is also possible to increase the endogenous expression or activity of one of these sequences by methods known to the skilled worker, for example by mutating a UTR region, preferably the 5'-UTR, a promoter region, a genomically coding region for the active center, for binding sites, for localization signals, for domains, clusters and the like, such as, for example, of coding regions for coiled coil, HEAT, FBOX, LRR, IBIB, C2, WD40, beach, U-box or UND domains. The activity can be increased in accordance with the invention by mutations which affect the secondary, tertiary or quaternary structure of the protein.

Mutations can be inserted for example by an EMS mutagenesis. Domains can be identified by suitable computer programs such as, for example, SMART or InterPRO, for example as described in Andersen P., The Journal of Biol. Chemistry, 279, 38, 40053, 2004 or Y. Mudgil, Plant Physiology, 134, 59, 2004, and literature cited therein. The suitable mutants can then be identified for example by tilling (for example as described by Henikoff et al., Plant Physiol. 135 (2) 630 (2004)).

In another embodiment, the introduction and expression of a sequence according to the invention into a plant, or increasing or modifying or mutating an endogenous sequence according to the invention, if appropriate of one or both untranslated regions, in a plant is combined with increasing the polypeptide quantity, activity or function of other resistance factors, preferably of a Bax inhibitor 1 protein (BI-1), preferably of the Bax inhibitor 1 protein from *Hordeum vulgare* (GenBank Acc.-No.: AJ290421), from, *Nicotiana tabacum* (GenBank Acc.-No.: AF390556), rice (GenBank Acc.-No.: AB025926), *Arabidopsis* (GenBank Acc.-No.: AB025927) or tobacco and oilseed rape (GenBank Acc.-No.: AF390555, Bolduc N et al. (2003) Planta 216, 377 (2003)) or of ROR2 (for example from barley (GenBank Acc.-No.: AY246906), SnAP34 (for example from barley (GenBank Acc.-No.: AY247208) and/or of the lumenal binding protein BiP for example from rice (GenBank Acc.-No. AF006825). An increase can be achieved for example by mutagenesis or overexpression of a transgene, inter alia.

In a further embodiment, the lowering of the protein quantity, or activity or function of the proteins RacB (for example from barley (GenBank Acc.-No.: AJ344223)), CSL1 (for example from *Arabidopsis* (GenBank Acc.-No.: NM116593), HvNaOX (for example from barley (GenBank Acc.-No.: AJ251717), MLO (for example from barley (GenBank Acc.-No. Z283834) is combined with the methods according to the invention.

The activity or function of MLO, BI-1 and/or NaOX can be reduced or inhibited analogously to what has been described for MLO in WO 98/04586; WO 00/01722; WO 99/47552 and the further publications mentioned hereinbelow, whose content is herewith specifically and expressly incorporated by reference, in particular in order to describe the activity and inhibition of MLO. The description of the abovementioned publications describes processes, methods and especially preferred embodiments for lessening or inhibiting the activity or function of MLO; the examples indicate specifically how this can be realized.

The reduction of the activity or function, if appropriate of the expression of BI-1 is described in detail in WO 2003/020939, which is herewith specifically and expressly incorporated into the present description. The description of the abovementioned publication describes processes and methods for lessening or inhibiting the activity or function of BI-1; the examples indicate specifically how this can be realized. The reduction or inhibition of the activity or function of BI-1 is especially preferably carried out in accordance with the embodiments especially preferred in WO 2003/020939 and the examples and in the organisms shown therein as being especially preferred, in particular in a plant, for example constitutively, or a part thereof, for example in a tissue, but especially at least in the epidermis or in a considerable part of the epidermal cells. The reduction of the activity or function, if appropriate of the expression, of BI-1 is described extensively in WO 2003/020939. The skilled worker finds in WO 2003/020939 the sequences which code for BI-1 proteins and can also identify BI-1 with the method provided in WO 2003/020939.

The reduction of the activity or function, if appropriate of the expression, of NaOX is described extensively in WO 2004/09820 (PCT/EP/03/07589), which is herewith specifically and expressly incorporated into the present description. The description of the abovementioned publication describes processes and methods for lessening or inhibiting the activity or function of NaOX, and the examples indicate specifically how this can be realized. The reduction or inhibition of the activity or function of NaOX is especially preferably carried out in accordance with the embodiments especially preferred in WO 2004/09820 (PCT/EP/03/07589) and the examples and in the organisms shown therein as being especially preferred, in particular in a plant, for example constitutively, or a part thereof, for example in a tissue, but especially advantageously at least in the epidermis or in a considerable part of the epidermal cells. The skilled worker finds in WO 2004/09820 (PCT/EP/03107589) the sequences which code for NaOX proteins and can also identify NaOX with the method provided in WO 2004/09820 (PCT/EP/03/07589).

The terms "to lessen", "to reduce" or "to repress" or their substantives are used synonymously in the present text.

In a further embodiment, the increase in the polypeptide quantity, activity or function of a Bax inhibitor 1 protein from *Hordeum vulgare* (GenBank Acc.-No.: AJ290421), from *Nicotiana tabacum* (GenBank Acc.-No.: AF390556), rice (GenBank Acc.-No.: AB025926), *Arabidopsis* (GenBank Acc.-No.: AB025927) or tobacco and oilseed rape (GenBank Acc.-No.: AF390555, Bolduc N et al. (2003) Planta 216, 377 (2003)) or of ROR2 (for example from barley (GenBank Acc.-No.: AY246906), SnAP34 (for example from barley (GenBank Acc.-No.: AY247208) and/or of the lumenal binding protein BiP for example from rice (GenBank Acc.-No. AF006825) is effected in combination with the reduction in the protein quantity or activity or function of the proteins RacB (for example from barley (GenBank Acc.-No.: AJ344223), CSL1 (for example from *Arabidopsis* (GenBank Acc.-No.: NM116593), HvNaOX (for example from barley (GenBank Acc.-No.: AJ251717), and/or MLO (for example from barley (GenBank Acc.-No. Z83834). As a consequence, in one embodiment, at least one of the abovementioned genes which are suitable for overexpression or increased activity is activated or overexpressed and/or at least one of the abovementioned genes which is suitable for reduction is reduced.

An increase in the expression can be obtained as described herein. An increase in the expression or function is understood as meaning herein both the activation or enhancement of the expression or function of the endogenous protein, including a de novo expression, and an increase or enhancement by expression of a transgenic protein or factor.

For the purposes of the invention, "organism" means "non-human organisms" as long as the term relates to a viable multi-celled organism.

For the purposes of the invention, "plants" means all dicotyledonous or monocotyledonous plants. Preferred are plants which can be subsumed under the class of the Liliatae (Monocotyledoneae or monocotyledonous plants). The term includes the mature plants, seeds, shoots and seedlings, and parts, propagation material, plant organs, tissue, protoplasts, callus and other cultures, for example cell cultures derived from the above, and all other types of associations of plant cells which give functional or structural units. Mature plants means plants at any developmental stage beyond the seedling stage. Seedling means a young, immature plant in an early developmental stage.

Dicotyledonous plants are also preferred. The term includes the mature plants, seeds, shoots and seedlings, and parts, propagation material, plant organs, tissue, protoplasts, callus and other cultures, for example cell cultures derived from the above, and all other types of associations of plant cells which give functional or structural units. Mature plants means plants at any developmental stage beyond the seedling stage. Seedling means a young, immature plant in an early developmental stage.

"Plant" also comprises annual and perennial dicotyledonous or monocotyledonous plants and includes by way of example, but not by limitation, those of the genera *Bromus, Asparagus, Pennisetum, Lolium, Oryza, Zea, Avena, Hordeum, Secale, Triticum, Sorghum* and *Saccharum*.

In a preferred embodiment, the method according to the invention is applied to monocotyledonous plants, for example from the family Poaceae, especially preferably to the genera *Oryza, Zea, Avena, Hordeum, Secale, Triticum, Sorghum* and *Saccharum*, very especially preferably to agriculturally important plants such as, for example, *Hordeum vulgare* (barley), *Triticum aestivum* (wheat), *Triticum aestivum* subsp. *spelta* (spelt), *Triticale, Avena sativa* (oats), *Secale cereale* (rye), *Sorghum bicolor* (sorghum), *Zea mays* (maize), *Saccharum officinarum* (sugarcane) or *Oryza sativa* (rice).

"Epidermal tissue" or epidermis means the external tissue layers of the plants. It can be single layered or multiple layered; and there is epidermis-"enriched" gene expression, such as, for example, Cer3, which can act as marker; (Hannoufa, A., Plant J. 10 (3), 459 (1996)).

By "epidermis", the skilled worker preferably means the predominant dermal tissue of primary aerial plant parts, such as of the shoots, the leaves, flowers, fruits and seeds. The epidermal cells excrete a water-repellent layer, the cuticle, towards the outside. The roots are surrounded by the rhizodermis, which resembles the epidermis in many ways, but also differs substantially therefrom. The epidermis develops from the outermost layer of the apical meristem. The origin of the rhizodermis, in contrast, is less clear. Phylogenetically speaking, it can be assigned either to the calyptra or to the primary bark, depending on the species. A large number of functions can be ascribed to the epidermis: it protects the plant from dehydration and regulates the transpiration rate. It protects the plant from a wide range of chemical and physical external factors and against feeding animals and attack by parasites. It is involved in the gas exchange, in the secretion of certain metabolites and in the absorption of water. It contains receptors for light and mechanical stimuli. It therefore acts as signal transformer between the environment and the plant. In accordance with the various functions, the epidermis comprises a number of differently differentiated cells. Other aspects are species having specific variants and different organization of the epidermides in the individual parts of a plant. Essentially, it consists of three categories of cells: the "actual" epidermal cells, the cells of the stomata and of the trichomes (Greek: trichoma, hair), which are epidermal appendages with different shapes, structures and functions.

The "actual", i.e. the least specialized epidermal cells, account for most of the bulk of the cells of the epidermal tissue. In top view, they appear either polygonal (slab or plate shaped) or elongated. The walls between them are often wavy or sinuate. It is not known what induces this shape during development; existing hypotheses only offer unsatisfactory explanations herefor. Elongated epidermal cells can be found in organs or parts of organs that are elongated themselves, thus, for example, in stems, petioles, leaf veins and on the leaves of most monocots. The upper surface and undersurface of laminae can be covered in epidermides with different structures, it being possible for the shape of the cells, the wall thickness and the distribution and number of specialized cells (stomata and/or trichomes) per unit area to vary. A high degree of variation is also found within individual families, for example in the Crassulaceae. In most cases, the epidermis consists of a single layer, though multi-layered water-storing epidermides have been found among species from a plurality of families (Moraceae: most *Ficus* species; Piperaceae: *Peperonia*, Begoniaceae, Malvaceae and the like). Epidermal cells secrete a cuticle to the outside which covers all epidermal surfaces as an uninterrupted film. It may either be smooth or structured by bulges, rods, folds and furrows. However, the folding of the cuticle, which can be observed when viewing the surface, is not always caused by the formation of cuticular rods. Indeed, there are cases where cuticular folding is merely the expression of the underlying bulges of the cell wall. Epidermal appendages of various form, structure and function are referred to as trichomes and, in the present context, likewise come under the term "epidermis". They occur in the form of protective hairs, supportive hairs and gland hairs in the form of scales, different papillae and, in the case of roots, as absorbent hairs. They are formed exclusively by epidermal cells. Frequently, a trichome is formed by only one such cell, however, occasionally, more than one cell is involved in its formation.

The term "epidermis" likewise comprises papillae. Papillae are bulges of the epidermal surface. The textbook example thereof is the papillae on flower surfaces of the pansy (*Viola tricolor*) and the leaf surfaces of many species from tropical rainforests. They impart a velvet-like consistency to the surface. Some epidermal cells can form water stores. A typical example is the water vesicles at the surfaces of many *Mesembryanthemum* species and other succulents. In some plants, for example in the case of campanula (*Campanula persicifolia*), the outer walls of the epidermis are thickened like a lens.

The main biomass of all tissues is the parenchyma. The parenchymatic tissues include the mesophyll which, in leaves, can be differentiated into palisade parenchyma and spongy parenchyma. Accordingly the skilled worker understands, by mesophyll, a parenchymatic tissue. Parenchymatic cells are always alive, in most cases isodiametric, rarely elongated. The pith of the shoots, the storage tissues of the fruits, seeds, the root and other underground organs are also to be considered as parenchymas, as is the mesophyll. "Mesophyll tissue" means the foliar tissue between the epidermal layers, and consists of palisade tissue, spongy tissue and the vascular bundles of the leaf.

In the leaves of most ferns and phanerogams, especially in the case of the dicots and many monocots, the mesophyll is subdivided into palisade parenchymas and spongy parenchymas. A "typical" leaf is of dorsiventral organization. In most cases, the palisade parenchyma is at the upper surface of the leaf immediately underneath the epidermis. The spongy parenchyma fills the underlying space. It is interspersed by a voluminous intercellular system whose gas space is in direct contact with the external space via the stomata.

The palisade parenchyma consists of elongated cylindrical cells. In some species, the cells are irregular, occasionally bifurcate (Y-shaped: arm palisade parenchyma). Such variants are found in ferns, conifers and a few angiosperms (for example in some *Ranunculaceae* and *Caprifoliaceae* species [example: elder]). Besides the widest-spread organization form which has just been described, the following variants have been found:

palisade parenchyma at the abaxial leaf surface. Particularly conspicuously in scaly leaves. For example arbor vitae (*thuja*), and in the leaves of wild garlic (*Allium ursinum*).

Palisade parenchyma at both leaf surfaces (adaxial and abaxial surface) is frequently found in plants of dry habitats (xerophytes). Example: prickly lettuce (*Lactuca serriola*).

Ring-shaped closed palisade parenchyma is found by way of example in cylindrically organized leaves and in needles of conifers.

The variability of the cells of the spongy parenchyma, and the organization of the spongy parenchyma itself, are even more varied than that of the palisade parenchyma. It is most frequently referred to as aerenchyma since it comprises a multiplicity of interconnected intercellular spaces.

The mesophyll may comprise what is known as the assimilation tissue, but the terms mesophyll and assimilation tissue are not to be used synonymously. There are chloroplast-free leaves whose organization differs only to a minor extent from comparable green leaves. As a consequence, they comprise mesophyll, but assimilation does not take place; conversely, assimilation also takes place in, for example, sections of the shoot. Further aids for characterizing epidermis and mesophyll can be found by the skilled worker for example in v. Guttenberg, H.: Lehrbuch der Allgemeinen Botanik [Textbook of general botany], Berlin: Akademie-Verlag 1955 (5th Ed.), Haberlandt, G.: Physiologische Pflanzenanatomie [Physiological plant anatomy]. Leipzig: W. Engelmann 1924 (6th Ed.); Troll, W.: Morphologie der Pflanzen [Plant morphology]. Volume 1: Vegetationsorgane [Vegetation organs]. Berlin: Gebr. Borntraeger, 1937; Troll, W.: Praktische. Einführung in die Pflanzenmorphologie [Practical introduction to plant morphology]. Jena: Veb G. Thieme Verlag 1954/1957; Troll, W., Höhn, K.: Allgemeine Botanik [General botany]. Stuttgart: F. Enke Verlag, 1973 (4th Ed.)

As a consequence, epidermis or epidermal cells can be characterized in histological or biochemical, including molecular-biochemical, terms. In one embodiment, the epidermis is characterized in biochemical terms. In one embodiment, the epidermis can be characterized by the activity of one or more of the following promoters:

WIR5 (=GstA1), acc. X56012, Dudler & Schweizer, unpublished.
GLP4, acc. AJ310534; Wei, Y., Plant Molecular Biology 36, 101 (1998).
GLP2a, acc. AJ237942, Schweizer, P., Plant J 20, 541 (1999).
Prx7, acc. AJ003141, Kristensen B K, Molecular Plant Pathology, 2(6), 311 (2001).
GerA, acc. AF250933; Wu S., Plant Phys Biochem 38, 685 (2000).
OsROC1, acc. AP004656
RTBV, acc. AAV62708, AAV62707; Klöti, A, 1999, PMB 40, 249 (1999).
Cer3; Hannoufa, A., Plant J. 10 (3), 459 (1996).

In another embodiment, the epidermis is characterized in that only some of the promoters are active, for example 2, 3, 5 or 7 or more, but at least one of the abovementioned promoters is active. In one embodiment, the epidermis is characterized in that all the abovementioned promoters are active in the tissue or the cell.

As a consequence, mesophyll or mesophyll cells can be characterized in biochemical, including molecular-biological, or histological terms. In one embodiment, the mesophyll is characterized in biochemical terms. In one embodiment, the mesophyll can be characterized by the activity of one or more of the following promoters:

PPCZm1 (=PEPC); Kausch, A. P., Plant Mol. Biol. 45, 1 (2001).
OsrbcS, Kyozuka J. et al., Plant Phys. 102 (3) 991 (1993).
OsPPDK, acc. AC099041.
TaGF-2.8, acc. M63223; Schweizer, P., Plant J. 20, 541 (1999).
TaFBPase, acc. X53957.
TaWIS1, acc. AF467542; US 200220115849.
HvBIS1, acc. AF467539; US 200220115849.
ZmMIS1, acc. AF467514; US 200220115849.
HvPR1a, acc. X74939; Bryngelsson et al., Mol. Plant Microbe Interact. 7 (2), 267 (1994).
HvPR1b, acc. X74940; Bryngelsson et al. Mol. Plant Microbe Interact. 7 (2), 267 (1994).
HvB1,3gluc; acc. AF479647.
HvPrx8, acc. AJ276227; Kristensen B. K., Molecular Plant Pathology 2 (6), 311 (2001).
HvPAL, acc. X97313; Wei, Y.; Plant Molecular Biology 36, 101 (1998).

In another embodiment, the mesophyll is characterized in that only some of the promoters are active, for example 2, 3, 5 or 7 or more, but at least one of the abovementioned promoters is active. In one embodiment, the mesophyll is characterized in that all the abovementioned promoters are active in the tissue or the cell.

In one embodiment, all of the abovementioned promoters are active in the epidermis of a plant which is used or generated in accordance with the invention or of a plant according to the invention in the epidermis and in the mesophyll. In one embodiment, only some of the abovementioned promoters are active, for example 2, 5, 7 or more, but at least one of the promoters enumerated above is in each case active.

"Nucleic acids" means biopolymers of nucleotides which are linked with one another via phosphodiester bonds (polynucleotides, polynucleic acids). Depending on the type of sugar in the nucleotides (ribose or deoxyribose), one distinguishes the two classes of the ribonucleic acids (RNA) and the deoxyribonucleic acids (DNA).

The term "crop" means all plant parts obtained by growing plants agriculturally and collected within the harvesting process.

"Resistance" means the preventing, the repressing, the reducing or the weakening of disease symptoms of a plant as the result of infection by a pathogen. The symptoms can be manifold, but preferably comprise those which directly or indirectly lead to an adverse effect on the quality of the plant, on the quantity of the yield, on the suitability for use as feed or foodstuff, or else which make sowing, growing, harvesting or processing of the crop more difficult.

In a preferred embodiment, the following disease symptoms are weakened, reduced or prevented: formation of pustules and hymenia on the surfaces of the affected tissues, maceration of the tissues, spreading necroses of the tissue, accumulation of mycotoxins, for example from *Fusarium graminearum* or *F. culmorum*, penetration of the epidermis and/or the mesophyll, etc.

An "increased pathogen resistance" means that the defense mechanisms of a certain plant or in a part of a plant, for example in an organ, a tissue, a cell or an organelle, have an increased resistance to one or more pathogens as the result of using the method according to the invention in comparison with a suitable control, for example the wildtype of the plant ("control plant", "original plant"), to which the method according to the invention has not been applied, under otherwise identical conditions (such as, for example, climatic conditions, growing conditions, type of pathogen and the like). Preferably, at least the epidermis and/or mesophyll tissue in a plant, or the organs which have an epidermis and/or mesophyll tissue, have an increased resistance to the pathogens. For example, the resistance in the leaves is increased.

In one embodiment, the resistance in lemma, palea and/or glume (anther primordium) is increased.

The increased resistance preferably manifests itself in a reduced manifestation of the disease symptoms, where disease symptoms—in addition to the abovementioned adverse effects—also comprise for example the penetration efficiency of a pathogen into the plant or the plant cell, or the proliferation efficiency of the pathogen in or on the same. In this context, the disease symptoms are preferably reduced by at least 10% or at least 20%, especially preferably by at least 40% or 60%, very especially preferably by at least 70% or 80%, most preferably by at least 90% or 95% in comparison with the control plant.

In this context, the increased resistance preferably manifests itself in a reduced manifestation of the disease symptoms, where the term disease symptoms—in addition to the abovementioned adverse effects—also comprises for example the penetration efficiency of a pathogen into the plant or the plant cell, or the proliferation efficiency in or on the same. Modifications in the cell wall structure, for example, may constitute a principal mechanism of pathogen resistance, as demonstrated for example in Jacobs A. K. et al., Plant Cell 15 (11), 2503 (2003).

For the purposes of the invention, "pathogen" means organisms whose interactions with a plant lead to the above-described disease symptoms; in particular, pathogens means organisms from the kingdom Fungi. Preferably, pathogen is understood as meaning a pathogen which penetrates epidermis or mesophyll cells, especially preferably pathogens which penetrate plants via stomata and subsequently penetrate mesophyll cells. Organisms which are preferably mentioned in this context are those from the phyla Ascomycota and Basidiomycota. Especially preferred in this context are the families Blumeriaceae, Pucciniaceae, Mycosphaerellaceae and Hypocreaceae.

Especially preferred are organisms of these families which belong to the genera *Blumeria, Puccinia, Fusarium* or *Mycosphaerella*.

Very especially preferred are the species *Blumeria graminis, Puccinia triticina, Puccinia striiformis, Mycosphaerella graminicola, Stagonospora nodorum, Fusarium graminearum, Fusarium culmorum, Fusarium avenaceum, Fusarium poae* and *Microdochium nivale*.

However, it is to be assumed that the methods according to the invention also bring about a resistance to further pathogens.

Especially preferred are Ascomycota such as, for example, *Fusarium oxysporum* (fusarium wilt on tomato), *Septoria nodorum* and *Septoria tritici* (glume blotch on wheat), Basidiomycetes such as, for example, *Puccinia graminis* (stem rust on wheat, barley, rye, oats), *Puccinia recondita* (leaf rust on wheat), *Puccinia disperse* (leaf rust on rye), *Puccinia hordei* (leaf rust on barley), *Puccinia coronata* (crown rust on oats).

In one embodiment, the method according to the invention leads to a resistance
  in barley to the pathogens:
    *Puccinia graminis* f.sp. *hordei* (barley stem rust), *Blumeria graminis* f.sp. *hordei* (powdery mildew of barley), and/or
  in wheat to the pathogens:
    *Blumeria graminis* f.sp. *tritici* (powdery mildew of wheat), *Fusarium graminearum, Fusarium avenaceum, Fusarium culmorum, Puccinia graminis* f.sp. *tritici,*

*Puccinia recondite* f.sp. *tritici*, *Puccinia striiformis*, *Septoria nodorum*, *Septoria tritici*, *Septoria avenae* or *Puccinia graminis* f.sp. *tritici* (wheat stem rust), and/or in maize to the pathogens:

*Fusarium moniliforme* var. *subglutinans*, *Puccinia sorghi* or *Puccinia polysora*, and/or in sorghum to the pathogens:

*Puccinia purpurea*, *Fusarium moniliforme*, *Fusarium graminearurri* or *Fusarium oxysporum*, and/or in soybean to the pathogens

*Phakopsora pachyrhizi* and *Phakopsora meibomiae*.

In a preferred embodiment, the term "nucleic acid (molecule)" as used in the present context additionally comprises the untranslated sequence at the 3' and at the 5' terminus of the coding gene region: at least 500, preferably 200, especially preferably 100 nucleotides of the sequence upstream of the 5' terminus of the coding region and at least 100, preferably 50, especially preferably 20 nucleotides of the sequence downstream of the 3' terminus of the coding gene region.

Moreover, nucleic acid sequences which are especially preferred in the present invention are isolated nucleic acid sequences. An "isolated" nucleic acid molecule is separated from other nucleic acid molecules which are present in the natural origin of the nucleic acid. An "isolated" nucleic acid preferably contains no sequences which naturally flank the nucleic acid in the genomic DNA of the organism from which the nucleic acid originates (for example sequences which are located at the 5' and 3' termini of the nucleic acid; however, this does not affect the abovementioned embodiments comprising 5'- and 3'-UTR regions). In different embodiments, the isolated molecule may comprise for example less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid originates. All the nucleic acid molecules mentioned here may be for example RNA, DNA or cDNA.

The nucleic acid molecules according to the invention can be isolated using standard techniques of molecular biology and the sequence information provided herein. Using comparative algorithms as they can be found for example on the NCBI homepage under ncbi.nlm.nih.gov, it is possible to identify for example a homologous sequence, or homologous, conserved sequence regions, at the DNA or amino acid level. Essential portions of this sequence or the entire homologous sequence can be used as hybridization probe using standard hybridization techniques (such as, for example, described in Sambrook et al., see above) for isolating further nucleic acid sequences which are useful in the method from other organisms by screening cDNA libraries and/or genomic libraries.

Moreover, a nucleic acid molecule according to the invention or a part thereof can be isolated by means of polymerase chain reaction, where oligonucleotide primers based on the sequences specified herein or parts thereof are used (for example, it is possible to isolate a nucleic acid molecule comprising the complete sequence or part thereof by means of polymerase chain reaction using oligonucleotide primers which have been generated on the basis of the very same sequence). For example, mRNA can be isolated from cells (for example by the guanidinium thiocyanate extraction method by Chirgwin et al., Biochemistry 18, 5294 (1979)) and cDNA prepared therefrom by means of reverse transcriptase (for example Moloney MLV reverse transcriptase, obtainable from Gibco/BRL, Bethesda, Md. or AMV reverse transcriptase, available from Seikagaku Amerika, Inc., St. Petersburg, Fla.). Synthetic oligonucleotide primers for the amplification by means of polymerase chain reaction can be generated on the basis of the sequences disclosed herein. A nucleic acid according to the invention can be amplified using cDNA or, alternatively, genomic DNA as template and suitable oligonucleotide primers by means of standard PCR amplification techniques. The nucleic acid amplified thus can be cloned into a suitable vector and characterized by means of DNA sequence analysis. Oligonucleotides which correspond to a nucleotide sequence coding for a protein according to the invention can be prepared by synthetic standard methods, for example using an automated DNA synthesizer.

The term "DNA fragment" as used in the present context is understood as meaning portions of the DNA which code for a protein according to the invention when this biological activity consists in mediating an increase in the pathogen resistance (preferably the resistance to fungal pathogens).

The term "fragments of the protein" as used in the present context refers to portions of the protein whose biological activity consists in mediating an increase in the pathogen resistance (preferably the resistance to fungal pathogens) in plants.

"Armadillo repeat Arm1 polypeptide" or "armadillo repeat ARM1 protein" or "Arm" or "Arm1" and their modifications means, for the purposes of the invention, a protein with one or more armadillo repeats.

In an especially preferred embodiment, the invention relates to an armadillo repeat ARM1 polypeptide which has the activity shown in the examples. In one embodiment, an armadillo repeat ARM1 protein is understood as meaning a protein with a homology to one of the amino acid sequences shown in SEQ ID No.: 2, 4, 6, 8, 10, 12, 14, 16, 18, 20, 22, 24, 26, 28, 30, 32, 34, 36, 38, 42, 44, 60, 61 or 62 or in the figures, for example an armadillo repeat ARM1 polypeptide from barley (HvARM) according to SEQ ID No.: 2 and/or from rice (*Oryza sativa*) according to SEQ ID No.: 4, 6, 8 and/or 10, and/or from tobacco (*Nicotiana tabacum*) according to SEQ ID No.: 12 and/or from *A. thaliana* according to SEQ. ID No.: 14, 16, 18, 20, 22, 24, 26, 28, 30, 32, 34, 36, 38, 42 and/or 44, or according to one of the consensus sequences according to SEQ ID No.: 60, 61 or 62, or a functional fragment thereof. In one embodiment, the invention relates to functional equivalents of the abovementioned polypeptide sequences.

"Polypeptide quantity" means for example the number of molecules, or moles, of armadillo repeat ARM1 polypeptide molecules in an organism, a tissue, a cell or a cell compartment. "Increasing" the polypeptide quantity means the molar increase in the number of the respective polypeptides in an organism, a tissue, a cell or a cell compartment—for example by one of the methods described hereinbelow—in comparison with a suitable control, for example the wildtype (control plant) of the same genus and species to which this method has not been applied, under otherwise identical conditions (such as, for example, culture conditions, age of the plants and the like). The increase in this context amounts to at least 5%, preferably at least 10% or at least 20%, especially preferably at least 40% or 60%, very especially preferably at least 70% or 80%, most preferably at least 90%, 95% or 99%, in particular 100%, particularly preferably more than 100%, preferably more than 150%, 200% or 300%.

Homology between two nucleic acid sequences is understood as meaning the identity of the nucleic acid sequence over in each case the entire sequence length, which is calculated by comparison with the aid of the program algorithm GAP (Wisconsin Package Version 10.0, University of Wisconsin, Genetics Computer Group (GCG), Madison, USA; Altschul et al., Nucleic Acids Res. 25, 3389 (1997)), setting the following parameters:

| | |
|---|---|
| Gap weight: 50 | Length weight: 3 |
| Average match: 10 | Average mismatch: 0 |

For example, a sequence which has at least 80% homology with the sequence SEQ ID NO: 1 at the nucleic acid level is understood as meaning a sequence which, upon comparison with the sequence SEQ ID NO 1 by the above program algorithm with the above parameter set, has at least 80% homology.

Homology between two polypeptides is understood as meaning the identity of the amino acid sequence over in each case the entire sequence length which is calculated by comparison with the aid of the program algorithm GAP (Wisconsin Package Version 10.0, University of Wisconsin, Genetics Computer Group (GCG), Madison, USA), setting the following parameters:

| | |
|---|---|
| Gap weight: 8 | Length weight: 2 |
| Average match: 2.912 | Average mismatch: −2.003 |

For example, a sequence which has at least 80% homology at the polypeptide level with the sequence SEQ ID NO: 2 is understood as meaning a sequence which, upon comparison with the sequence SEQ ID NO 2 by the above program algorithm with the above parameter set, has at least 80% homology.

"Armadillo repeat" is understood as meaning a sequence which comprises copies, arranged in tandem, of a degenerate sequence of approximately 42 amino acids, which sequence codes for a three-dimensional structure for mediating protein-protein interactions (Azevedo et al. Trends Plant Sci. 6, 354 (2001)). For example, the polypeptide which is employed in the method according to the invention, or the polypeptide according to the invention, has an activity which is involved in the intracellular signal transduction or in the regulation of the gene expression in the context of the cellular developmental processes.

The armadillo repeat ARM1 protein is encoded for example by a nucleic add molecule comprising a nucleic acid molecule selected from the group consisting of
(a) nucleic acid molecule which codes for at least one polypeptide comprising the sequence shown in SEQ ID No.: 2, 4, 6, 8, 10, 12, 14, 16, 18, 20, 22, 24, 26, 28, 30, 32, 34, 36, 38, 42, 44, 60, 61 or 62;
(b) nucleic acid molecule which comprises at least one polynucleotide of the sequence shown in SEQ ID No: 1, 3, 5, 7, 9, 11, 13, 15, 17, 19, 21, 23, 25, 27, 29, 31, 33, 35, 37, 39, 41, 43 or 63;
(c) nucleic acid molecule which codes for a polypeptide whose sequence has 40%, 50%, 60%, 70%, 80%, 90%, 95%, 97%, 98%, 99% or more identity with the sequences SEQ ID No: 2, 4, 6, 8, 10, 12, 14, 16, 18, 20, 22, 24, 26, 28, 30, 32, 34, 36, 38, 42, 44, 60, 61 or 62;
(d) nucleic acid molecule according to (a) to (c) which codes for a functional fragment or an epitope of the sequences as shown in SEQ. ID No.: 2, 4, 6, 8, 10, 12, 14, 16, 18, 20, 22, 24, 26, 28, 30, 32, 34, 36, 38, 42, 44, 60, 61 or 62;
(e) nucleic acid molecule which codes for a polypeptide which is recognized by a monoclonal antibody directed against a polypeptide which is encoded by the nucleic acid molecules as shown in (a) to (c);
(f) nucleic acid molecule which hybridizes under stringent conditions with a nucleic acid molecule as shown in (a) to (c) or their part-fragments consisting of at least 15 nucleotides (nt), preferably 20 nt, 30 nt, 50 nt, 100 nt, 200 nt or 500 nt;
(g) nucleic acid molecule which can be isolated from a DNA library using a nucleic acid molecule as shown in (a) to (c) or their part-fragments of at least 15 nt, preferably 20 nt, 30 nt, 50 nt, 100 nt, 200 nt or 500 nt, as probe under stringent hybridization conditions;
or comprises a complementary sequence thereof, or constitutes a functional equivalent thereof.

In a preferred embodiment, the sequence which codes for the polypeptide according to the invention does not comprise a U box in the 5'-UTR.

In accordance with the invention, the activity of the above-mentioned polypeptides is introduced into, and expressed in, a plant or a part of a plant, preferably in/into the epidermal cells and/or mesophyll cells of a plant, as illustrated hereinabove, or the expression of the endogenous polypeptide is increased analogously.

In one embodiment, the activity of ARM1 is increased in lemma, palea and/or glume.

Within the context of the invention, "introduction" or "to introduce" comprises all methods which are suitable for directly or indirectly introducing, into a plant or a cell, compartment, tissue, organ or seed, a nucleic acid sequence according to the invention, or generating it therein. The introduction may lead to a transient or to a stable presence of a nucleic acid sequence according to the invention.

"Introduction" or "to introduce" comprises, for example, methods such as transfection, transduction or transformation.

The introduction of an expression cassette according to the invention into an organism or cells, tissue, organs, parts or seeds thereof (preferably into plants or plant cells, tissue, organs, parts or seeds) can advantageously be carried out using vectors which comprise the expression cassettes. The expression cassette can be introduced into the vector (for example a plasmid) via a suitable restriction cleavage site. The plasmid obtained is first introduced into *E. coli* cells. Correctly transformed *E. coli* cells are selected, cultured, and the recombinant plasmid is obtained using methods with which the skilled worker is familiar. Restriction analysis and sequencing may be used for verifying the cloning step.

The vectors may take the form of, for example, plasmids, cosmids, phages, viruses or else agrobacteria. In an advantageous embodiment, the expression cassette is introduced by means of plasmid vectors. Preferred vectors are those which make possible a stable integration of the expression cassette into the host genome.

"Epitope" is understood as meaning the regions of an antigen which determine the specificity of the antibodies (the antigenic determinant). Accordingly, an epitope is the portion of an antigen which actually comes into contact with the antibody.

Such antigenic determinants are those regions of an antigen to which the T-cell receptors react and, as a consequence, produce antibodies which specifically bind the antigenic determinant/epitope of an antigen. Accordingly, antigens, or their epitopes, are capable of inducing the immune response of an organism with the consequence of the formation of specific antibodies which are directed against the epitope. Epitopes consist for example of linear sequences of amino acids in the primary structure of proteins, or of complex secondary or tertiary protein structures. A hapten is understood as meaning an epitope which is dissociated from the context of the antigen environment. Although haptens have by definition an antibody directed against them, haptens are, under certain circumstances, not capable of inducing an immune response in an organism, for example after an injection. To this end, haptens are coupled with carrier molecules. An example which may be mentioned is dinitrophenol (DNP), which, after coupling to BSA (bovine serum albumin), has been used for generating antibodies which are directed against DNP. (Bohn, A., König, W., Immunology 47 (2), 297 (1982)).

Haptens are therefore in particular substances (frequently low-molecular weight substances or small substances) which, while they themselves do not trigger immune response, will indeed trigger such a response when coupled to a large molecular carrier.

The antibodies generated thus also include those which can bind to the hapten alone.

In one embodiment, the present invention relates to an antibody against a polypeptide characterized herein, in particular to a monoclonal antibody which binds a polypeptide which comprises an AA sequence or consists thereof, as shown in the sequences shown in SEQ ID No.: 2, 4, 6, 8, 10, 12, 14, 16, 18, 20, 22, 24, 26, 28, 30, 32, 34, 36, 38, 40, 42, 44, 60, 61 or 62.

Antibodies within the scope of the present invention can be used for identifying and isolating polypeptides disclosed in accordance with the invention from organisms, preferably plants, especially preferably monocotyledonous plants, or further preferably dicotyledonous plants. The antibodies can either be monoclonal, polyclonal or synthetic in nature or else consist of antibody fragments such as Fab, Fv or scFv fragments, which are formed by proteolytic degradation. "Single chain" Fv (scFv) fragments are single-chain fragments which, linked via a flexible linker sequence, only comprise the variable regions of the heavy and light antibody chains. Such scFv fragments can also be produced as recombinant antibody derivatives. A presentation of such antibody fragments on the surface of filamentous phages makes possible the direct selection, from combinatory phage libraries, of scFv molecules which bind with high affinity.

Monoclonal antibodies can be obtained in accordance with the method described by Köhler and Milstein (Nature 256 (1975), 495).

"Functional equivalents" of an armadillo repeat ARM1 protein preferably means those polypeptides which have at least 40% homology with the polypeptides described by the sequences SEQ ID No: 2, 4, 6, 8, 10, 12, 14, 16, 18, 20, 22, 24, 26, 28, 30, 32, 34, 36, 38, 42, 44, 60, 61 or 62 and which have essentially the same properties or function. Preferably, the homology amounts to 50%, 60%, 70%, 80%, 90%, especially preferably 95%, 97%, 98%, 99% or more.

The functional equivalence can be determined for example by comparing the phenotypes of test organisms after expression of the polypeptides in question, under the most identical conditions possible.

"Essentially identical properties" of a functional equivalent means above all imparting a pathogen-resistant phenotype or imparting or increasing the pathogen resistance to at least one pathogen when increasing the polypeptide quantity, activity or function of said functional armadillo repeat ARM1 protein equivalent in a plant, organ, tissue, part or cells, in particular in epidermal or mesophyll cells of same, preferably measured by the penetration efficiency of a pathogen as shown in the examples.

"Analogous conditions" means that all basic conditions such as, for example, culture or growth conditions, assay conditions (such as buffers, temperature, substrates, pathogen concentration and the like) between the experiments to be compared are kept identical and that the set-ups only differ by the sequence of the armadillo repeat ARM1 polypeptides to be compared, by their source organism and, if appropriate, by the pathogen.

"Functional equivalents" also means natural or artificial mutation variants of the armadillo repeat ARM1 polypeptides as shown in SEQ ID No.: 2, 4, 6, 8, 10, 12, 14, 16, 18, 20, 22, 24, 26, 28, 30, 32, 34, 36, 38, 42, 44, 60, 61 or 62 and homologous polypeptides from other monocotyledonous and dicotyledonous plants which furthermore have essentially identical properties. Preferred are homologous polypeptides from preferred plants described herein. The sequences from other plants, which sequences are homologous to the armadillo repeat ARM1 protein sequences disclosed within the scope of the present invention, can be found readily for example by database search or by screening gene libraries using the armadillo repeat ARM1 protein sequences as search sequence or probe.

Functional equivalents can also be derived for example from one of the polypeptides according to the invention as shown in SEQ ID No: 2, 4, 6, 8, 10, 12, 14, 16, 18, 20, 22, 24, 26, 28, 30, 32, 34, 36, 38, 42, 44, 60, 61 or 62 by substitution, insertion or deletion and can have at least 40%, 50%, 60%, preferably at least 80%, by preference at least 90%, especially preferably at least 95%, very especially preferably at least 98% homology with these polypeptides and are distinguished by essentially identical functional properties to the polypeptides as shown in SEQ ID No: 2, 4, 6, 8, 10, 12, 14, 16, 18, 20, 22, 24, 26, 28, 30, 32, 34, 36, 38, 42, 44, 60, 61 or 62

Functional equivalents are also those nucleic acid molecules which are derived from the nucleic acid sequences according to the invention as shown in SEQ ID No: 1, 3, 5, 7, 9, 11, 13, 15, 17, 19, 21, 23, 25, 27, 29, 31, 33, 35, 37, 39, 41 or 43 by substitution, insertion or deletion and have at least 40%, 50%, 60%, preferably 80%, by preference at least 90%, especially preferably at least 95%, very especially preferably at least 98% homology with one of the polynucleotides according to the invention as shown in SEQ ID No: 1, 3, 5, 7, 9, 11, 13, 15, 17, 19, 21, 23, 25, 27, 29, 31, 33, 35, 37, 39, 41 or 43 and code for polypeptides with essentially identical functional properties to polypeptides as shown in SEQ ID No: 2, 4, 6, 8, 10, 12, 14, 16, 18, 20, 22, 24, 26, 28, 30, 32, 34, 36, 38, 42, 44, 60, 61 or 62.

Examples of the functional equivalents of the armadillo repeat ARM1 proteins as shown in SEQ ID No: 2, 4, 6, 8, 10, 12, 14, 16, 18, 20, 22, 24, 26, 28, 30, 32, 34, 36, 38, 42, 44, 60, 61 or 62 which are to be increased in the method according to the invention can be found by homology comparisons from databases, by way of example from organisms whose genomic sequence is known.

Screening cDNA libraries or genomic libraries of other organisms, preferably of the plant species mentioned further below, which are suitable as transformation hosts, using the nucleic acid sequences described in SEQ ID No: 1, 3, 5, 7, 9, 11, 13, 15, 17, 19, 21, 23, 25, 27, 29, 31, 33, 35, 37, 39, 41 or 43 or parts of the same as probe is also a method known to the skilled worker for identifying homologs in other species. In this context, the probes derived from the nucleic acid sequence as shown in SEQ ID No: 1, 3, 5, 7, 9, 11, 13, 15, 17, 19, 21, 23, 25, 27, 29, 31, 33, 35, 37, 39, 41 or 43 have a length of at least 20 bp, preferably at least 50 bp, especially preferably at least 100 bp, very especially preferably at least 200 bp, most preferably at least 400 bp. The probe can also be one or more kilobases in length, for example 1 kb, 1.5 kb or 3 kb. A DNA strand which is complementary to the sequences described in SEQ ID No: 1, 3, 5, 7, 9, 11, 13, 15, 17, 19, 21, 23, 25, 27, 29, 31, 33, 35, 37, 39, 41 or 43 or a fragment of same strand with a length of between 20 bp and several kilobases may also be employed for screening the libraries.

In the method according to the invention, those DNA molecules which hybridize under standard conditions with the nucleic acid molecules described by SEQ ID No: 1, 3, 5, 7, 9, 11, 13, 15, 17, 19, 21, 23, 25, 27, 29, 31, 33, 35, 37, 39, 41, 43 or 63 and which code for armadillo repeat ARM1 proteins, with the nucleic acid molecules which are complementary to the above or with parts of the above and which, as complete sequences, code for polypeptides which essentially have identical properties, preferred functional properties, to the polypeptides described in SEQ ID No: 2, 4, 6, 8, 10, 12, 14, 16, 18, 20, 22, 24, 26, 28, 30, 32, 34, 36, 38, 42, 44, 60, 61 or 62 may also be used.

"Standard hybridization conditions" is to be understood in the broad sense and means, depending on the application, stringent or else less stringent hybridization conditions. Such hybridization conditions are described, inter alia, in Sambrook J, Fritsch E F, Maniatis T et al., in Molecular Cloning (A Laboratory Manual), 2nd edition, Cold Spring Harbor Laboratory Press, 1989, pages 9.31-9.57) or in Current Protocols in Molecular Biology, John Wiley & Sons, N.Y. (1989), 6.3.1-6.3.6.

The skilled worker, based on his technical knowledge, would choose hybridization conditions which allow him to differentiate between specific and unspecific hybridizations.

For example, the conditions during the wash step can be selected from among low-stringency conditions (with approximately 2×SSC at 50° C.) and high-stringency conditions (with approximately 0.2×SSC at 50° C., preferably at 65° C.) (20×SSC: 0.3M sodium citrate, 3M NaCl, pH 7.0). Moreover, the temperature during the wash step can be raised from low-stringency conditions at room temperature, approximately 22° C., to higher-stringency conditions at approximately 65° C. The two parameters, salt concentration and temperature, can be varied simultaneously or else singly, keeping in each case the other parameter constant. During the hybridization, it is also possible to employ denaturant agents such as, for example, formamide or SDS. In the presence of 50% formamide, the hybridization is preferably carried out at 42° C. Some examples of preferred conditions for hybridization and wash step are detailed hereinbelow:

(1) Hybridization conditions can be selected for example among the following conditions:
   a) 4×SSC at 65° C.,
   b) 6×SSC at 45° C.,
   c) 6×SSC, 100 µg/ml denatured fragmented fish sperm DNA at 68° C.,
   d) 6×SSC, 0.5% SDS, 100 µg/ml denatured salmon sperm DNA at 68° C.,
   e) 6×SSC, 0.5% SDS, 100 µg/ml denatured fragmented salmon sperm DNA, 50% formamide at 42° C.,
   f) 50% formamide, 4×SSC at 42° C.,
   g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
   h) 2× or 4×SSC at 50° C. (low-stringency condition),
   i) 30 to 40% formamide, 2× or 4×SSC at 42° C. (low-stringency condition), or
   j) 500 mN sodium phosphate buffer pH 7.2, 7% SDS (g/V), 1 mM EDTA, 10 µg/ml single stranded DNA, 0.5% BSA (g/V) (Church and Gilbert, Proc. Natl. Acad. Sci. U.S.A. 81:1991 (1984))

(2) Wash steps can be selected for example among the following conditions:
   a) 0.015 M NaCl/0.0015 M sodium citrate/0.1% SDS at 50° C.,
   b) 0.1×SSC at 65° C.,
   c) 0.1×SSC, 0.5% SDS at 68° C.,
   d) 0.1×SSC, 0.5% SDS, 50% formamide at 42° C.,
   e) 0.2×SSC, 0.1% SDS at 42° C., or
   f) 2×SSC at 65° C. (low-stringency condition).

In one embodiment, the hybridization conditions are selected as follows:

A hybridization buffer comprising formamide, NaCl and PEG 6000 is chosen. The presence of formamide in the hybridization buffer destabilizes double-strand nucleic acid molecules, whereby the hybridization temperature can be lowered to 42° C. without thereby reducing the stringency. The use of salt in the hybridization buffer increases the renaturation rate of a duplex DNA, in other words the hybridization effciency. Although PEG increases the viscosity of the solution, which has a negative effect on the renaturation rates, the presence of the polymer in the solution increases the concentration of the probe in the remaining medium, which increases the hybridization rate. The composition of the buffer is

| Hybridization buffer |
| --- |
| 250 mM sodium phosphate buffer pH 7.2 |
| 1 mM EDTA |
| 7% SDS (g/v) |
| 250 mM NaCl |
| 10 µg/ml ssDNA |
| 5% polyethylene glycol (PEG) 6000 |
| 40% formamide |

The hybridizations are carried out for approximately 12 hours at 42° C., for example overnight. The filters are then washed 3× with 2×SSC+0.1% SDS for in each case approximately 10 minutes.

"Gene expression" and "expression" are to be understood as being synonymous and mean the realization of the information which is stored in a nucleic acid molecule.

The "modification" according to the invention of nucleotide sequences or amino acid sequences preferably comprises mutating them, or mutations. For the purposes of the present invention, "mutations" means the modification of the nucleic acid sequence of a gene variant in a plasmid or in the genome of an organism. Mutations can be generated for example as the consequence of errors during replication, or by mutagens. The spontaneous mutation rate in the cell genome of organisms is very low; however, the skilled person in the art knows a multiplicity of biological, chemical or physical mutagens and methods of mutating nucleotide sequences in a random or targeted manner, and therefore ultimately potentially also for modifying the amino acid sequences which they encode.

Mutations comprise substitutions, additions, deletions of one or more nucleic acid residues. Substitutions are understood as meaning the exchange of individual nucleic acid bases, where one distinguishes between transitions (substitution of a purine base for a purine base, and of a pyrimidine base for a pyrimidine base) and transversions (substitution of a purine base for a pyrimidine base, or vice versa).

Addition or insertion is understood as meaning the incorporation of additional nucleic acid residues in the DNA, which may result in reading-frame shifts. In the case of such reading frame shifts, one distinguishes between in-frame insertions/additions and out-of-frame insertions. In the case of the in-frame insertions/additions, the reading frame is retained, and a polypeptide which is lengthened by the number of the amino acids encoded by the inserted nucleic acids is formed. In the case of out-of-frame insertions/additions, the original reading frame is lost, and the formation of a complete and functional polypeptide is in many cases no longer possible, which of course depends on the site of the mutation.

Deletions describe the loss of one or more base pairs, which likewise leads to in-frame or out-of-frame reading-frame shifts and the consequences which this entails with regard to the formation of an intact protein.

The skilled worker is familiar with the mutagenic agents (mutagens) which can be used for generating random or targeted mutations and both the methods and techniques which may be employed. Such methods and mutagens are described for example in van Harten A. M. ("Mutation breeding: theory and practical applications", Cambridge University Press, Cambridge, UK (1998)), Friedberg E., Walker G., Siede W. ("DNA Repair and Mutagenesis", Blackwell Publishing (1995)), or Sankaranarayanan K., Gentile J. M., Ferguson L. R. ("Protocols in Mutagenesis", Elsevier Health Sciences (2000)).

Customary methods and processes of molecular biology such as, for example, the in-vitro mutagenesis kit, "LA PCR in vitro Mutagenesis Kit" (Takara Shuzo, Kyoto), or PCR mutageneses using suitable primers, may be employed for introducing targeted mutations.

As already mentioned above, a multiplicity of chemical, physical and biological mutagens exists.

Those mentioned hereinbelow are given by way of example, but not by limitation.

Chemical mutagens may be divided according to their mechanism of action. Thus, there are base analogs (for example 5-bromouracil, 2-aminopurine), mono- and bifunctional alkylating agents (for example monofunctional agents such as ethyl methyl sulfonate, dimethyl sulfate, or bifunctional agents such as dichloroethyl sulfite, mitomycin, nitrosoguanidine-dialkyl nitrosamine, N-nitrosoguanidine derivatives) or intercalating substances (for example acridine, ethidium bromide).

Examples of physical mutagens are ionizing radiations. Ionizing radiations are electromagnetic waves or corpuscular radiation which are capable of ionizing molecules, i.e. of removing electrons from them. The ions which remain are in most cases highly reactive so that they, in the event that they are formed in live tissue, are capable of inflicting great damage for example to the DNA and thereby inducing mutations (at low intensity). Examples of ionizing radiations are gamma radiation (photon energy of approximately one mega electron volt MeV), X-ray radiation (photon energy of several or many kilo electron volt keV) or else ultraviolet light (UV light, photon energy of over 3.1 eV). UV light causes the formation of dimers between bases, thymidine dimers are most common, and these give rise to mutations.

To the traditional generation of mutants by treating the seeds with mutagenizing agents such as, for example, ethyl methyl sulfonate (EMS) (Birchler J. A., Schwartz D., Biochem. Genet. 17 (11-12), 1173 (1979); Hoffmann G. R., Mutat. Res. 75 (1), 63 (1980)) or ionizing radiation there has now been added the use of biological mutagens, for example transposons (for example Tn5, Tn903, Tn916, Tn1000, Balcells et al., 1991, May B. P. et al., Proc. Natl. Acad. Sci USA. 100 (20), 11541 (2003)) or molecular-biological methods such as the mutagenesis by T-DNA insertion (Feldman K. A., Plant J. 1, 71 (1991), Koncz et al., Plant Mol. Biol. 20 (5), 963 (1992)).

To generate mutated gene variants, it is preferred to use chemical or biological mutagens. Among the chemical agents, it is especially preferred to generate mutants by using EMS (ethyl methyl sulfonate) mutagenesis. Among the generation of mutants using biological mutagens, the T-DNA mutagenesis or the transposon mutagenesis may be mentioned by preference.

Thus, for example, it is also possible to employ those polypeptides in the method according to the invention which are obtained as the result of a mutation of a nucleotide sequence coding for a polypeptide according to the invention, for example according to SEQ ID No: 2, 4, 6, 8, 10, 12, 14, 16, 18, 20, 22, 24, 26, 28, 30, 32, 34, 36, 38, 42, 44, 60, 61 or 62.

The term "transgenic" means for example with regard to a nucleic acid sequence, an expression cassette or a vector comprising said nucleic acid sequence or an organism transformed with said nucleic acid sequence, expression cassette or vector, all those constructs or organisms which are the result of recombinant methods and in which either (a) the armadillo repeat ARM1 protein nucleic acid sequence or
(b) a genetic control sequence, for example a promoter, which is operably linked with the armadillo repeat ARM 1 protein nucleic acid sequence, or
(c) (a) and (b)

are not located in their natural genetic environment or have been modified by recombinant methods, it being possible for the modification to be, for example, a substitution, addition, deletion, or insertion of one or more nucleotide residue(s). Natural genetic environment means the natural chromosomal locus in the organism of origin, or the presence in a genomic library. In the case of a genomic library, the natural genetic environment of the nucleic acid sequence is preferably retained at least in part. The environment flanks the nucleic acid sequence at least on one side and has a sequence length of at least 50 bp, preferably at least 500 bp, especially preferably at least 1000 bp, very especially preferably at least 5000 bp. A naturally occurring expression cassette—for example the naturally occurring combination of the armadillo repeat ARM 1 protein promoter with the corresponding armadillo repeat ARM 1 protein gene—becomes a transgenic expression cassette when the latter is modified by means of non-natural, synthetic ("artificial") methods such as, for example, mutagenization. Suitable methods have been described (U.S. Pat. No. 5,565,350; WO 00/15815).

The increase according to the invention of the pathogen resistance can also be obtained by manipulating the expression of the plant's own protein, i.e. the endogenous protein, which corresponds to the protein according to the invention, or of an endogenous nucleotide sequence, which constitutes a sequence according to the invention, and which may also comprise the 5'- and/or 3'-UTR region. It is, then, an endogenous nucleotide or peptide sequence which mediates an increase of the pathogen resistance and which preferably features one or more armadillo repeat sequences, or it is an amino acid sequence according to the invention which codes for such a protein. This manipulation can be achieved by any modification of the sequence, preferably a mutation, but also for example by a modification of the promoter DNA sequence of the protein-encoding gene. Such a modification, which results in a modified, preferably increased, expression rate of the endogenous gene according to the invention can be effected by means of deletion or insertion of DNA sequences. As a rule, a modification of the 5'-UTR region in total and/or of the promoter sequence of endogenous genes according to the invention will lead to a modification of the expressed amount of the gene and/or the function of the expressed gene or gene product, and therefore preferably also to a modification of the activity which can be detected in the cell or in the plants. The modification of the 5'-UTR region in total and/or of the promoter sequence of the endogenous gene according to the invention may also lead to a modification of the amount of, and/or the function of, a protein according to the invention in the cell.

Another possibility of increasing the activity and the content of the endogenous protein according to the invention is to up-regulate transcription factors which are involved in the transcription of the corresponding endogenous gene, for example by means of overexpression. The means for overexpressing transcription factors are known to the skilled worker and are also disclosed for proteins according to the invention within the context of the present invention.

Moreover, an increased expression of the endogenous gene according to the invention can be achieved by a regulator protein, which is not present in the untransformed organism, interacting with the promoter of these genes. Such a regulator may take the form of a chimeric protein which consists of a DNA binding domain and a transcription activator domain, as described for example in WO 96/06166.

The generation of a transformed organism (or of a transformed cell) requires the introduction of the relevant DNA molecules into the relevant host cell, and subsequently the formation of the corresponding RNAs and proteins as the result of gene expression.

A multiplicity of methods (Keown et al., Methods in Enzymology 185, 527(1990)) is available for this procedure, which is referred to as transformation (or transduction or transfection). Thus, the DNA or RNA can be introduced for example directly by means of microinjection or by bombardment with DNA-coated microparticles. Also, it is possible to chemically permeabilize the cell, for example using polyethylene glycol, so that the DNA can reach the cell by diffusion. The DNA can also be introduced into the cell by means of protoplast fusion with other DNA-comprising units such as minicells, cells, lysosomes or liposomes. A further suitable method of introducing DNA is electroporation, where the cells are reversibly permeabilized by means of an electrical pulse. Such methods have been described (for example in Bilang et al., Gene 100, 247 (1991); Scheid et al., Mol. Gen. Genet. 228, 104 (1991); Guerche et al., Plant Science 52, 111 (1987); Neuhause et al., Theor. Appl. Genet. 75, 30 (1987); Klein et al., Nature 327, 70(1987); Howell et al., Science 208, 1265 (1980); Horsch et al., Science 227, 1229 (1985); DeBlock et al., Plant Physiology 91, 694 (1989); "Methods for Plant Molecular Biology" (Weissbach and Weissbach, eds.) Academic Press Inc. (1988); and "Methods in Plant Molecular Biology" (Schuler and Zielinski, eds.) Academic Press Inc. (1989)).

In plants, the above-described methods for the transformation and regeneration of plants from plant tissue or plant cells are exploited for the purposes of transient or stable transformation. Suitable methods are mainly protoplast transformation by means of polyethylene-glycol-induced DNA uptake, the biolistic method with the gene gun, known as the particle bombardment method, electroporation, the incubation of dry embryos in DNA-comprising solution, and microinjection.

Besides these "direct" transformation techniques, transformation can also be effected by bacterial infection by means of *Agrobacterium tumefaciens* or *Agrobacterium rhizogenes*. The methods are described for example in Horsch et al. Science 225, 1229 (1985).

If agrobacteria are used, the expression cassette is to be integrated into specific plasmids, which may either be a shuttle or intermediate vector or a binary vector. If a Ti or Ri plasmid is used for the transformation, at least the right border, but in most cases both the right and the left border, of the Ti or Ri plasmid T-DNA as flanking region is linked with the expression cassette to be introduced.

It is preferred to use binary vectors. Binary vectors are capable of replicating both in *E. coli* and in *agrobacterium*. As a rule, they comprise a selection marker gene and a linker or polylinker flanked by the right and left T-DNA border sequence. They can be transformed directly into *agrobacterium* (Holsters et al., Mol. Gen. Genet. 163, 181 (1978)). The selection marker gene, for example the nptII gene, which mediates resistance to kanamycin, permits transformed agrobacteria to be selected. The agrobacterium which, in the present case, acts as the host organism should already comprise a helper Ti plasmid with the vir region, which is required for transferring the T-DNA to the plant cell. An *agrobacterium* thus transformed can be used for transforming plant cells. The use of T-DNA for the transformation of plant cells has been studied and described in great detail (EP 120 516; Hoekema, in "The Binary Plant Vector System", Offsetdrukkerij Kanters B.V., Alblasserdam, Chapter V; An et al. EMBO J. 4, 277 (1985)). Various binary vectors are known and in some cases commercially available, such as, for example, pBI101.2 or pBIN19 (Clontech Laboratories, Inc. USA).

In the event that DNA or RNA is injected or electroporated into plant cells, the plasmid used need not meet particular requirements. Simple plasmids such as those from the pUC series may be used. If intact plants are to be regenerated from the transformed cells, it is necessary for an additional selection marker gene to be located on the plasmid.

Stably transformed cells, i.e. those which comprise the introduced DNA integrated into the DNA of the host cell, can be distinguished from untransformed cells when a selection marker is constituent of the introduced DNA (McCormick et al, Plant Cell Reports 5, 81 (1986)). For example, any gene which is capable of mediating a resistance to antibiotics or herbicides (such as kanamycin, G 418, bleomycin, hygromycin or phosphinothricin) may act as a marker. Transformed cells which express such a marker gene are capable of surviving in the presence of concentrations of a suitable antibiotic or herbicide which destroy an untransformed wildtype. Examples include the bar gene, which mediates resistance to the herbicide phosphinothricin (Rathore et al., Plant Mol. Biol. 21 (5), 871 (1993)), the nptII gene, which mediates resistance to kanamycin, the hpt gene, which mediates resistance to hygromycin, or the EPSP gene, which mediates resistance to the herbicide glyphosate. The resulting plants can be bred and hybridized in the customary manner. Two or more generations should be cultivated in order to ensure that the genomic integration is stable and hereditary.

The above mentioned methods are described for example in Jones et al. ("Techniques for Gene Transfer", in "Transgenic Plants", Vol. 1, Engineering and Utilization, edited by Kung S. D. and Wu R., Academic Press, p. 128-143 (1993), and in Potrykus, Annu. Rev. Plant Physiol. Plant Molec. Biol. 42, 205 (1991)). It is preferred to clone the construct to be expressed into a vector which is suitable for transforming *agrobacterium tumefaciens*, for example into pBin 19 (Bevan et al., Nucl. Acids Res. 12, 8711 (1984)).

When a transformed plant cell has been generated, an intact plant can be obtained using methods known to the skilled worker. An example of a starting material used here are callus cultures. The formation of shoot and root from this as yet undifferentiated cell biomass can be induced in a known manner. The plantlets obtained can be planted out and bred.

A person skilled in the art also knows methods for regenerating plant parts and intact plants from plant cells. For example, methods described by Fennell et al., Plant Cell Rep, 11, 567 (1992); Stoeger et al., Plant Cell Rep. 14, 273 (1995); Jahne et al., Theor. Appl. Genet. 89, 525 (1994), are used for this purpose.

The present invention furthermore relates to a recombinant nucleic acid molecule comprising the following elements in 5'-3' orientation:
  regulatory sequences of a promoter which is active in plant cells,
  a DNA sequence according to the invention in operative linkage therewith,
  if appropriate, regulatory sequences which, in the plant cell, may act as transcription, termination and/or polyadenylation signals in operable linkage therewith.

In said expression constructs/expression cassettes, a nucleic acid molecule whose expression (transcription and, if appropriate, translation) generates an "armadillo repeat ARM1 protein compound" is preferably in operable linkage with at least one genetic control element (for example a promoter) which ensures expression in plants. If the expression construct is to be introduced directly into the plant and the "armadillo repeat ARM1 protein compound" generated therein in planta, then plant-specific genetic control elements (for example promoters) are preferred. However, the "armadillo repeat ARM1 protein compound" can also be generated in other organisms or in vitro and then introduced into the plant. In this context, preference is given to all prokaryotic or eukaryotic genetic control elements (for example promoters) which permit the expression in the plant selected in each case for the production.

The terms "operatively linked (therewith)" or "functionally linked (therewith)" are understood as meaning for example the sequential arrangements of a promoter with the nucleic acid sequence to be expressed (for example an "armadillo repeat ARM1 protein compound") and, if appropriate, further regulatory elements such as, for example, a terminator in such a way that each of the regulatory (or regulation) elements is capable of fulfilling its function upon the transgenic expression of the nucleic acid sequence, depending on the arrangement of the nucleic acid sequences to give sense or antisense RNA. A direct linkage in the chemical meaning of the word is not required here. Genetic control sequences such as, for example, enhancer sequences, may also exert their function, on the target sequence from positions at a certain distance, or even from other DNA molecules. Preferred arrangements are those in which the nucleic acid sequence to be expressed recombinantly is positioned after the sequence which acts as the promoter, so that the two sequences are bonded covalently with one another. In this context, it is preferred that the distance between the promoter sequence and the nucleic acid sequence to be expressed recombinantly is less than 200 base pairs, especially preferably less than 100 base pairs, very especially preferably less than 50 base pairs.

The generation of a functional linkage and the generation of an expression cassette can be carried out by means of customary recombination and cloning techniques as described for example in Maniatis T., Fritsch E. F. and Sambrook J., "Molecular Cloning: A Laboratory Manual", Cold Spring Harbor Laboratory, Cold Spring Harbor (N.Y.) (1989), in Silhavy T. J., Berman M. L. and Enquist L. W. "Experiments with Gene Fusions", Cold Spring Harbor Laboratory, Cold Spring Harbor (N.Y.) (1984), in Ausubel F. M. et al., "Current Protocols in Molecular Biology", Greene Publishing Assoc. and Wiley Interscience (1987) and in Gelvin et al., in "Plant Molecular Biology Manual" (1990). However, it is also possible to position, between the two sequences, further sequences which exert for example the function of a linker with specific restriction enzyme cleavage sites, or of a signal peptide. The insertion of sequences may also lead to the expression of fusion proteins. It is preferred that the expression cassette, consisting of a linkage of promoter and nucleic acid sequence to be expressed, can be present in vector-integrated form and inserted into a plant genome by, for example, transformation.

The method according to the invention can advantageously be combined with other methods which bring about a pathogen resistance (for example against insects, fungi, bacteria, nematodes and the like), stress resistance or another improvement of the plant characteristics. Examples are mentioned inter alia in Dunwell J. M., J. Exp. Bot. 51, (Spec No) 487 (2000).

In a preferred embodiment, the function of an armadillo repeat ARM1 protein in a plant is generated or increased in combination with an increase in the activity of a Bax inhibitor-1 protein. This can be done for example by expressing a nucleic acid sequence coding for a Bax inhibitor-1 protein, for example in the mesophyll tissue and/or in the root tissue.

The Bax inhibitor-1 proteins from *Hordeum vulgare* or *Nicotiana tabacum* are especially preferred in the method according to the invention.

The invention furthermore relates to nucleic acid molecules which comprise nucleic acid molecules coding for armadillo repeat ARM1 proteins from barley according to the polynucleotides SEQ. ID No.: 1, and the nucleic acid sequences which are complementary thereto, and the sequences which are derived due to the degeneracy of the genetic code, and the nucleic acid molecules which code for functional equivalents of the polypeptides as shown in SEQ. ID No.: 1, where the nucleic acid molecules do not consist of SEQ ID No: 3, 5, 7, 9, 11, 13, 15, 17, 19, 21, 23, 25, 27, 29, 31, 33, 35, 37, 39, 41 or 43.

The invention furthermore relates to the armadillo repeat ARM1 protein from barley according to SEQ. ID No.: 2 or one which comprises these sequences, and functional equivalents thereof, which do not correspond to one of the sequences of SEQ ID No.: 4, 6, 8, 10, 12, 14, 16, 18, 20, 22, 24, 26, 28, 30, 32, 34, 36, 38, 42 or 44.

The invention furthermore relates to transgenic expression cassettes comprising one of the nucleic acid sequences according to the invention. In the transgenic expression cassettes according to the invention, the nucleic acid sequence coding for the armadillo repeat ARM1 proteins from barley, wheat and maize is linked with at least one genetic control element as defined above in such a manner that the expression (transcription and, if appropriate, translation) can be effected in any organism, preferably in monocotyledonous plants. Genetic control elements which are suitable for this purpose are described above. The transgenic expression cassettes may also comprise further functional elements as defined above.

Such expression cassettes comprise for example a nucleic acid sequence according to the invention, for example a nucleic acid sequence which is essentially identical to a nucleic acid molecule as shown in SEQ ID No.: 1, 3, 5, 7, 9, 11, 13, 15, 17, 19, 21, 23, 25, 27, 29, 31, 33, 35, 37, 39, 41 or 43 or a fragment thereof according to the invention, where said nucleic acid sequence is preferably in sense orientation or in antisense orientation relative to a promoter and can therefore lead to the expression of sense or antisense RNA, said promoter being a promoter which is active in plants, preferably a promoter which can be induced by pathogen attack. Also comprised according to the invention are transgenic vectors which encompass said transgenic expression cassettes.

Plant-specific promoters means in principle any promoter which is capable of controlling the expression of genes, in particular foreign genes, in plants or plant parts, plant cells, plant tissues, plant cultures. Here, the expression can be for example constitutional, inducible or development-dependent.

The following are preferred:

a) Constitutive Promoters

"Constitutive" promoter means those promoters which ensure expression in numerous, preferably all, tissues over a relatively large period of plant development, preferably at all times during plant development. In particular, a plant promoter or a promoter derived from a plant virus is preferably used. The promoter of the 35S transcript of the CaMV cauliflower mosaic virus (Franck et al. Cell 21, 285 (1980); Odell et al. Nature 313, 810 (1985); Shewmaker et al. Virology 140, 281 (1985); Gardner et al. Plant Mol Biol 6, 221 (1986)) or the 19S CaMV Promoter (U.S. Pat. No. 5,352,606; WO 84/02913; Benfey et al. EMBO J. 8, 2195-2202 (1989)) is particularly preferred. A further suitable constitutive promoter is the rubisco small subunit (SSU) promoter (U.S. Pat. No. 4,962,028), the promoter of agrobacterium nopaline synthase, the TR double promoter, the *agrobacterium* OCS (octopine synthase) promoter, the ubiquitin promoter (Holtorf S et al. Plant Mol Biol 29, 637 (1995)), the ubiquitin 1 promoter (Christensen et al. Plant Mol Biol 18, 675 (1992); Bruce et al. Proc Natl Acad Sci USA 86, 9692 (1989)), the Smas promoter, the cinnamyl-alcohol dehydrogenase promoter (U.S. Pat. No. 5,683,439), the promoters of vacuolar ATPase subunits or the promoter of a proline-rich protein from wheat (WO 91/13991), and further promoters of genes whose constitutive expression in plants is known to the skilled worker. Especially preferred as constitutive promoter is the promoter of nitrilase-1 (nit1) gene from *A. thaliana* (GenBank Acc.-No.: Y07648.2, Nukleotide 2456-4340, Hillebrand et al. Gene 170, 197 (1996)).

b) Tissue-Specific Promoters

One embodiment employs promoters with specificities for the anthers, ovaries, flowers, leaves, stems, roots and seeds.

Seed-specific promoters are, for example, the promoter of phaseolin (U.S. Pat. No. 5,504,200; Bustos et al. Plant Cell 1(9), 839 (1989)), of the 2S albumin gene (Joseffson et al. J Biol Chem 262, 12196 (1987)), of legumin (Shirsat et al. Mol Gen Genet 215(2), 326 (1989)), of the USP (unknown seed protein; Bäumlein et al. Mol Gen Genet 225(3), 459 (1991)), of the napin gene (U.S. Pat. No. 5,608,152; Stalberg et al. L Planta 199, 515 (1996)), of the gene coding for the sucrose binding protein (WO 00/26388) or the legumin B4 promoter (LeB4; Bäumlein et al. Mol Gen Genet 225, 121 (1991); Bäumlein et al. Plant Journal 2(2), 233 (1992); Fiedler et al. Biotechnology (NY) 13(10), 1090 (1995)), the oleosin promoter from *arabidopsis* (WO 98/45461), the Bce4 promoter from *Brassica* (WO 91/13980). Further suitable seed-specific promoters are those of the genes coding for the high molecular weight glutenin (HMWG), gliadin, branching enzyme, ADP glucose pyrophosphatase (AGPase) or starch synthase. Further preferred promoters are those allowing seed-specific expression in monocotyledons such as maize, barley, wheat, rye, rice etc. It is possible and advantageous to employ the promoter of the lpt2 or lpt1 gene (WO 95/15389, WO 95/23230) or the promoters described in WO 99/16890 (promoters of the hordein gene, of the glutelin gene, of the oryzin gene, of the prolamin gene, of the gliadin gene, of the zein gene, of the kasirin gene or of the secalin gene).

Tuber-, storage root- or root-specific promoters are, for example, the patatin class I promoter (B33) or the promoter of the potato cathepsin D inhibitor.

Leaf-specific promoters are, for example, the promoter of the cytosolic FBPase from potato (WO 97/05900), the SSU promoter (small subunit) of the rubisco (ribulose-1,5-bisphosphate carboxylase) or the ST-LSI promoter from potato (Stockhaus et al. EMBO J. 8, 2445 (1989)). Epidermis-specific promoters are, for example the promoter of the OXLP gene ("oxalate oxidase like protein"; Wei et al. Plant Mol. Biol. 36, 101 (1998)) and a promoter consisting of the GSTA1 promoter and the WIR1a intron (WO 2005/035766) and the GLP4 promoter (WO 2006/12888=PCT/EP 2006/062747).

Examples of other tissue-specific promoters are: flower-specific promoters, for example the phytoene synthase promoter (WO 92/16635) or the promoter of the Prr gene (WO 98/22593) and anther-specific promoters, for example the 5126 promoter (U.S. Pat. Nos. 5,689,049, 5,689,051), the glob-I promoter and the γ-zein promoter.

c) Chemically Inducible Promoters

The expression cassettes may also comprise a chemically inducible promoter (review article: Gatz et al. Annu. Rev. Plant Physiol Plant Mol Biol 48, 89 (1997)) through which expression of the exogenous gene in the plant can be controlled at a particular point in time. Promoters of this type, such as, for example, the PRP1 promoter (Ward et al. Plant Mol Biol 22, 361 (1993)), a salicylic acid-inducible promoter (WO 95/19443), a benzenesulfonamide-inducible promoter (EP 0 388 186), a tetracycline-inducible promoter (Gatz et al. Plant J 2, 397 (1992)), an abscisic acid-inducible promoter (EP 0 335 528) and an ethanol- or cyclohexanone-inducible promoter (WO 93/21334) can likewise be used.

d) Stress- or Pathogen-Inducible Promoters

Very especially advantageous is the use of pathogen-inducible promoters which make possible an expression only when required (i.e. in the case of attack by pathogens).

In one embodiment, the method according to the invention therefore uses promoters which are active in plants which are pathogen-inducible promoters.

Pathogen-inducible promoters comprise the promoters of genes which are induced as a result of pathogen attack, such as, for example, genes of PR proteins, SAR proteins, β-1,3-glucanase, chitinase etc. (for example Redolfi et al. Neth J Plant Pathol 89, 245 (1983); Uknes, et al. Plant Cell 4, 645 (1992); Van Loon Plant Mol Viral 4, 111 (1985); Marineau et al. Plant Mol Bid 9, 335 (1987); Matton et al. Molecular Plant-Microbe Interactions 2, 325 (1987); Somssich et al. Proc Natl Acad Sci USA 83, 2427 (1986); Somssich et al. Mol Gen Genetics 2, 93 (1988); Chen et al. Plant J 10, 955 (1996); Zhang and Sing Proc Natl Acad Sci USA 91, 2507 (1994); Warner, et al. Plant J 3, 191 (1993); Siebertz et al. Plant Cell 1, 961 (1989))

Also comprised are wounding-inducible promoters such as that of the pinII gene (Ryan Ann Rev Phytopath 28, 425 (1990); Duan et al. Nat Biotech 14, 494 (1996)), of the wun1 and wun2 gene (U.S. Pat. No. 5,428,148), of the win1 and win2 gene (Stanford et al. Mol Gen Genet 215, 200 (1989)), of the systemin gene (McGurl et al. Science 225, 1570 (1992)), of the WIP1 gene (Rohmeier et al. Plant Mol Biol 22, 783 (1993); Eckelkamp et al. FEBS Letters 323, 73 (1993)), of the MPI gene (Corderok et al. Plant J 6(2), 141 (1994)) and the like.

A source of further pathogen-inducible promoters is the PR gene family. A series of elements in these promoters have proved advantageous. Thus, the nucleotide region of nucleotide −364 to nucleotide −288 in the promoter of PR-2d mediates salicylate specificity (Buchel et al. (1996) Plant Mol Biol 30, 493). The sequence 5'-TCATCTTCTT-3' (SEQ ID NO: 65) occurs repeatedly in the promoter of the barley β-1,3-glucanase and in more than 30 other stress-induced genes. In tobacco, this region binds a nuclear protein whose abundance is increased by salicylate. The PR-1 promoters from tobacco and *Arabidopsis* (EP-A 0 332 104, WO 98/03536) are also suitable as pathogen-inducible promoters. Preferred, since particularly specifically induced by pathogens, are the "acidic PR-5"-(aPR5) promoters from barley (Schweizer et al. Plant Physiol 114, 79 (1997)) and wheat (Rebmann et al. Plant Mol Biol 16, 329 (1991)). aPR5 proteins accumulate within approximately 4 to 6 hours after attack by pathogens and only show very little background expression (WO 99/66057). One approach for obtaining an increased pathogen-induced specificity is the generation of synthetic promoters from combinations of known pathogen-responsive elements (Rushton et al. Plant Cell 14, 749 (2002); WO 00/01830; WO 99/66057). Other pathogen-inducible promoters from different species are known to the skilled worker (EP-A 1 165 794; EP-A 1 062 356; EP-A 1 041 148; EP-A 1 032 684).

Further pathogen-inducible promoters comprise the Flachs Fis1 promoter (WO 96/34949), the Vst1 promoter (Schubert et al. Plant Mol Biol 34, 417 (1997)) and the tobacco EAS4 sesquiterpene cyclase promoter (U.S. Pat. No. 6,100,451).

Other preferred promoters are those which are induced by biotic or abiotic stress, such as, for example, the pathogen-inducible promoter of the PRP1 gene (or gst1 promoter), for example from potato (WO 96128561; Ward et al. Plant Mol Biol 22, 361 (1993)), the heat-inducible hsp70 or hsp80 promoter from tomato (U.S. Pat. No. 5,187,267), the chill-inducible alpha-amylase promoter from potato (WO 96/12814), the light-inducible PPDK promoter or the wounding-inducible pinII promoter (EP-A 0 375 091).

e) Mesophyll-Tissue-Specific Promoters

Mesophyll tissue means the leaf tissue, between the epidermis layers, consisting of the palisade mesophyll, the spongy mesophyll and the vascular bundles.

In one embodiment, the method according to the invention employs mesophyll-tissue-specific promoters such as, for example, the promoter of the wheat germin 9f-3.8 gene (GenBank Acc.-No.: M63224) or the barley GerA promoter (WO 02/057412). Said promoters are particularly advantageous since they are both mesophyll-tissue-specific and pathogen-inducible. Also suitable is the mesophyll-tissue-specific *Arabidopsis* CAB-2 promoter (GenBank Acc.-No.: X15222), and the *Zea mays* PPCZm1 promoter (GenBank Acc.-No.: X63869) or homologs thereof. Mesophyll-tissue-specific means that the transcription of a gene is limited to as few as possible plant tissues which comprise the mesophyll tissue as the result of the specific interaction of cis elements present in the promoter sequence and transcription factors binding to these elements; preferably, it means a transcription which is limited to the mesophyll tissue.

Further mesophyll-specific promoters are PPCZm1 (=PEPC; Kausch, Plant Mol. Biol. 45, 1 (2001)); OsrbcS (Kyozuka et al., Plant Phys. 102, 991-(1993)); OsPPDK, acc. AC099041; TaGF-2.8, acc. M63223 (Schweizer, Plant J. 20, 541 (1999)); TaFBPase, acc. X53957; TaWIS1, acc. AF467542 (US 20021115849); HvBIS1, acc. AF467539 (US 2002/115849); ZmMIS1, acc. AF467514 (US 2002/115849); HvPR1a, acc. X74939 (Bryngelsson et al., Molecular Plant-Microbe Interactions 7 (2), 267 (1994); HvPR1b, acc. X74940 (Bryngelsson et al., Molecular Plant-Microbe Interactions 7 (2), 267 (1994)); HvB1,3gluc; acc. AF479647; HvPrx8, acc. AJ276227 (Kristensen et al., Molecular Plant Pathology 2 (6), 311(2001)); and HvPAL, acc. X97313 (Wei, Plant Molecular Biology 36, 101 (1998)).

f) Epidermis-Specific Promoters

"Epidermal tissue" or epidermis means the outer tissue layers of the plants. The epidermis can be monolayer to multilayer; there is an epidermis-"enriched" gene expression, such as, for example, of Cer3, which may act as marker (Hannoufa, Plant J. 10 (3), 459 (1996)).

By "epidermis", the skilled worker preferably understands the prevailing epiderm of primary aerial plant parts, for example of the shoots, the leaves, the flowers, the fruits and the seeds.

Epidermis-specific promoters are, for example, WIR5 (=GstA1), acc. X56012 (Dudler & Schweizer, unpublished); GLP4, acc. AJ310534 (Wei, Plant Molecular Biology 36, 101 (1998)); GLP2a, acc. AJ237942 (Schweizer, Plant J. 20, 541 (1999).); Prx7, acc. AJ003141 (Kristensen, Molecular Plant Pathology 2 (6), 311(2001)); GerA, acc. AF250933 (Wu, Plant Phys. Biochem. 38, 685 (2000)); OsROC1, acc. AP004656; RTBV, acc. AAV62708, AAV62707 (Klöti, PMB 40, 249 (1999)) and Cer3 (Hannoufa, Plant J. 10 (3), 459 (1996)).

g) Development-Dependent Promoters

Examples of further suitable promoters are fruit ripening-specific promoters such as, for example, the fruit ripening-specific promoter from tomato (WO 94/21794, EP 409 625). Development-dependent promoters include some of the tissue-specific promoters because the development of individual tissues naturally takes place in a development-dependent manner.

Constitutive, and leaf- and/or stem-specific, pathogen-inducible, root-specific, mesophyll-tissue-specific promoters are particularly preferred, with constitutive, pathogen-inducible, mesophyll-tissue-specific and root-specific promoters being most preferred.

A further possibility is for further promoters which make expression possible in further plant tissues or in other organisms such as, for example, *E. coli* bacteria to be operably linked to the nucleic acid sequence to be expressed. All the promoters described above are in principle suitable as plant promoters.

Other promoters which are suitable for expression in plants are described (Rogers et al. Meth in Enzymol 153, 253 (1987); Schardl et al. Gene 61, 1 (1987); Berger et al. Proc Natl Acad Sci USA 86, 8402 (1989)).

Moreover, the average person skilled in the art is capable of isolating further suitable promoters by means of routine methods. Thus, the person skilled in the art can identify for example further epidermis-specific regulatory nucleic acid elements, with the aid of customary methods of molecular biology, for example with hybridization experiments or with DNA-protein binding studies. Here, a first step involves, for example, the isolation of the desired tissue from the desired organism from which the regulatory sequences are to be isolated, wherefrom the total poly(A)+RNA is isolated and a cDNA library is established. In a second step, those clones from the first library whose corresponding poly(A)+RNA molecules only accumulate in the desired tissue are identified by means of hybridization with the aid of cDNA clones which are based on poly(A)+RNA molecules from another tissue. Then, promoters with tissue-specific regulatory elements are isolated with the aid of these cDNAs thus identified. Moreover, a person skilled in the art has available further PCR-based methods for the isolation of suitable tissue-specific promoters.

The nucleic acid sequences present in the expression cassettes or vectors of the invention may be operably linked to further genetic control sequences besides a promoter. The term genetic control sequences has a wide meaning and means all sequences which have an influence on the coming into existence or the function of the recombinant nucleic acid molecule of the invention. For example, genetic control sequences modify transcription and translation in prokaryotic or eukaryotic organisms. The expression cassettes of the invention preferably comprise a promoter with an abovementioned specificity 5'-upstream from the particular nucleic acid sequence which is to be expressed transgenically, and a terminator sequence as additional genetic control sequence 3'-downstream, and if appropriate further conventional regulatory elements, in each case operably linked to the nucleic acid sequence to be expressed transgenically.

Genetic control sequences also comprise further promoters, promoter elements or minimal promoters capable of modifying the expression-controlling properties. It is thus possible for example through genetic control sequences for tissue-specific expression to take place additionally dependent on particular stress factors. Corresponding elements are described for example for water stress, abscisic acid (Lam E and Chua N H, J Biol Chem 1991; 266(26): 17131) and heat stress (Schoffl F et al., Molecular & General Genetics 217(2-3): 246, 1989).

It is possible in principle for all natural promoters with their regulatory sequences like those mentioned above to be used for the method of the invention. It is additionally possible also for synthetic promoters to be used advantageously.

Genetic control sequences further comprise also the 5'-untranslated regions (5'-UTR), introns or noncoding 3' region of genes such as, for example, the actin-1 intron, or the Adh1-S introns 1, 2 and 6 (generally: The Maize Handbook, Chapter 116, Freeling and Walbot, Eds., Springer, N.Y. (1994)). It has been shown that these may play a significant function in the regulation of gene expression. It has thus been shown that 5'-untranslated sequences are capable of enhancing transient expression of heterologous genes. An example of a translation enhancer which may be mentioned is the 5' leader sequence from the tobacco mosaic virus (Gallie et al. Nucl Acids Res 15, 8693 (1987)) and the like. They may in addition promote tissue specificity (Rouster J et al. Plant J 15, 435 (1998)). Especially preferred is the natural 5'-UTR of the HvArm gene, in particular that with the sequence of SEQ ID No.: 64 or a sequence with at least 50%, 60%, 70%, 80%, 90%, 95%, 97% or in particular 99% or more identity thereto.

The recombinant nucleic acid molecule according to the invention may advantageously comprise one or more so-called enhancer sequences in operable linkage with the promoter, which make increased transgenic expression of the nucleic acid sequence possible. Additional advantageous sequences such as further regulatory elements or terminators can also be inserted at the 3' end of the nucleic acid sequences to be expressed recombinantly. The nucleic acid sequences to be expressed recombinantly may be present in one or more copies in the gene construct.

Polyadenylation signals suitable as control sequences are plant polyadenylation signals, preferably those which correspond essentially to T-DNA polyadenylation signals from *Agrobacterium tumefaciens*, in particular to gene 3 of the T-DNA (octopine synthase) of the Ti plasmid pTiACHS (Gielen et al. (1984) EMBO J 3:835) or functional equivalents thereof. Examples of particularly suitable terminator sequences are the OCS (octopine synthase) terminator and the NOS (nopaline synthase) terminator.

Control sequences additionally mean those which make homologous recombination or insertion into the genome of a host organism possible or allow deletion from the genome. In homologous recombination, for example, the natural promoter of a particular gene can be specifically replaced by a promoter with specificity for the embryonal epidermis and/or the flower.

A recombinant nucleic acid molecule and a vector derived from it may comprise further functional elements. The term functional element has a wide meaning and means all elements which have an influence on the production, replication or function of the nucleic acid molecules, the vectors or the transgenic organisms of the invention. Non-restrictive examples which may be mentioned are:

a) Selection markers which confer a resistance to a metabolism inhibitor such as 2-deoxyglucose 6-phosphate (WO 98/45456), antibiotics or biocides, preferably herbicides, for example kanamycin, G 418, bleomycin, hygromycin or phosphinotricin and the like. Especially preferred selection markers are those which confer a resistance to herbicides. Examples which may be mentioned are: DNA sequences which code for phosphinothricin acetyltransferases (PAT), which inactivate glutamine synthase inhibitors (bar and pat gene), 5-enolpyruvylshikimate-3-phosphate synthase (EPSP synthase genes) which confer resistance to Glyphosat® (N-(phosphonomethyl)glycine), the gox gene, which codes for the Glyphosat®-degrading enzyme (glyphosate oxidoreductase), the deh gene (coding for a dehalogenase which inactivates dalapon), and bxn genes which code for bromoxynil-degrading nitrilase enzymes, the aasa gene, which confers a resistance to the antibiotic spectinomycin, the streptomycin phosphotransferase (SPT) gene, which makes possible a resistance to streptomycin, the neomycin phosphotransferase (NPTII) gene, which confers a resistance to kanamycin or geneticidin, the hygromycin phosphotransferase (HPT) gene, which mediates a resistance to hygromycin, the acetolactate synthase gene (ALS), which mediates a resistance to sulfonylurea herbicides (for example mutated ALS variants with, for example, the S4 and/or Hra mutation), and the acetolactate synthase gene (ALS), which mediates a resistance to imidazolinone herbicides.

b) Reporter genes which code for easily quantifiable proteins and ensure via an intrinsic color or enzymic activity an assessment of the transformation efficiency or of the location or timing of expression. Very particular preference is given in this connection to reporter proteins (Schenborn E. and Groskreutz D. Mol Biotechnol. 1999; 13(1):29) such as the green fluorescence protein (GFP) (Sheen et al. (1995) Plant Journal 8(5):777; Haselhoff et al. (1997) Proc Natl Acad Sci USA 94(6):2122; Reichel et al. (1996) Proc Natl Acad Sci USA 93(12):5888; Tian et al. (1997) Plant Cell Rep 16:267; WO 97/41228; Chui et al. (1996) Curr Biol 6:325; Leffel et al. (1997) Biotechniques. 23(5):912-8), the chloramphenicoltransferase, a luciferase (Ow et al. (1986) Science 234:856; Millar et al. (1992) Plant Mol Biol Rep 10:324), the aequorin gene (Prasher et al. (1985) Biochem Biophys Res Commun 126(3):1259), the β-galactosidase, R-locus gene (codes for a protein which regulates the production of anthocyanin pigments (red coloration) in plant tissue and thus makes possible the direct analysis of the promoter activity without the addition of additional adjuvants or chromogenic substrates; Dellaporta et al., In: Chromosome Structure and Function: Impact of New Concepts, 18th Stadler Genetics Symposium, 11:263, (1988), with β-glucuronidase being very especially preferred (Jefferson et al., EMBO J. 1987, 6, 3901).

c) Origins of replication which ensure replication of the expression cassettes or vectors of the invention in, for example, *E. coli*. Examples which may be mentioned are ORI (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

d) Elements which are necessary for agrobacterium-mediated plant transformation, such as, for example, the right or left border of the T-DNA or the vir region.

To select successfully transformed cells, it is generally required additionally to introduce a selection marker which confers to the successfully transformed cells a resistance to a biocide (for example a herbicide), a metabolism inhibitor such as 2-deoxyglucose 6-phosphate (WO 98/45456) or an antibiotic. The selection marker permits the selection of the transformed cells from untransformed cells (McCormick et al. (1986) Plant Cell Reports 5:81).

The present invention furthermore relates to transgenic plant cells and to transgenic plants which comprise a nucleic acid sequence according to the invention or a recombinant nucleic acid molecule according to the invention, and to parts of the plants, transgenic crops and transgenic propagation material of these plants, such as protoplasts, plant cells, calli, seeds, tubers, cuttings, and to the transgenic progeny of this plant.

The invention furthermore relates to plants which, as the result of natural processes or artificial induction, comprise one or more mutations in a nucleic acid molecule which comprises the nucleic acid sequence as shown in SEQ ID No.: 1, 3, 5, 7, 9, 11, 13, 15, 17, 19, 21, 23, 25, 27, 29, 31, 33, 35, 37, 39, 41 or 43, where said mutation brings about an increase of the activity, function or polypeptide quantity of one of the polypeptide encoded by the nucleic acid molecules as shown in SEQ ID No.: 1, 3, 5, 7, 9, 11, 13, 15, 17, 19, 21, 23, 25, 27, 29, 31, 33, 35, 37, 39, 41 or 43. For example a mutation generated, and identified, by tilling.

Preferred in this context are monocotyledonous plants, in particular those which belong to the family Poaceae, very especially preferred plants are selected from the plant genera *Hordeum*, *Avena*, *Secale*, *Triticum*, *Sorghum*, *Zea*, *Saccharum* and *Oryza*, very especially preferred are plants selected among the genera *Hordeum vulgare* (barley), *Triticum aestivum* (wheat), *Triticum aestivum* subsp. *spelta* (spelt), *Triticale*, *Avena sativa* (oats), *Secale cereale* (rye), *Sorghum bicolor* (sorghum), *Zea mays* (maize), *Saccharum officinarum* (sugarcane) and *Oryza saliva* (rice).

As a consequence, one embodiment of the invention relates to a plant, in particular to a monocotyledonous plant, comprising a nucleic acid sequence according to the invention which comprises a mutation which brings about, in the plants or parts thereof, an increase of the activity of one of the proteins encoded by the nucleic acid molecules of the invention. For example, the mutation concerns one or more amino acid residues which is identified in the consensus sequence in the figures as being conserved or highly conserved.

Consequently, the invention also relates to transgenic plants transformed with at least a) a nucleic acid sequence which comprises the nucleic acid molecules as shown in SEQ ID No.: 1, 3, 5, 7, 9, 11, 13, 15, 17, 19, 21, 23, 25, 27, 29, 31, 33, 35, 37, 39, 41 or 43, the nucleic acid sequences which are complementary thereto, or the nucleic acid molecules which code for functional equivalents of the polypeptides as shown in SEQ ID No.: 2, 4, 6, 8, 10, 12, 14, 16, 18, 20, 22, 24, 26, 28, 30, 32, 34, 36, 38, 40, 42, 44, 60, 61 or 62;

b) a transgenic expression cassette which comprises one of the nucleic acid sequences according to the invention, or a vector according to the invention, and cells, cell cultures, tissue, parts—such as for example leaves, roots and the like or propagation material in the case of plant organisms—derived from such organisms.

In one embodiment, the plant according to the invention, or the plant used according to the invention, is other than *Arabidopsis thaliana*.

Host organisms or starting organisms which are preferred as "transgenic organisms" are especially plants as defined above. In one embodiment, the transgenic organism is a mature plant, seed, shoot and seedling, and parts, propagation material and cultures derived therefrom, for example cell cultures. "Mature plant" means plants at any developmental stage beyond the seedling stage. "Seedling" means a young immature plant in an early developmental stage. Plants which are particularly preferred as host organisms are plants to which the method according to the invention for obtaining a pathogen resistance in accordance with the abovementioned criteria can be applied. In one embodiment, the plant is a monocotyledonous plant such as, for example, wheat, oats, sorghum/millet, barley, rye, maize, rice, buckwheat, sorghum, triticale, spelt or sugarcane, in particular selected among the genera *Hordeum vulgare* (barley), *Triticum aestivum* (wheat), *Triticum aestivum* subsp *spelta* (spelt), *Triticale*, *Avena sativa* (oats), *Secale cereale* (rye), *Sorghum bicolor* (sorghum), *Zea mays* (maize), *Saccharum officinarum* (sugarcane) and *Oryza sativa* (rice).

The transgenic organisms can be generated with the above-described methods for the transformation or transfection of organisms.

The invention furthermore relates to the transgenic plants described according to the invention which additionally have an increased Bax inhibitor 1 activity; preferred are plants with an increased Bax inhibitor 1 activity in mesophyll cells or root cells; especially preferred are transgenic plants which belong the Poaceae family and which have an increased Bax inhibitor 1 activity in mesophyll cells or root cells; most preferred are transgenic plants selected from the plant genera *Hordeum*, *Avena*, *Secale*, *Triticum*, *Sorghum*, *Zea*, *Saccharum* and *Oryza*; the most preferred plant species are *Hordeum vulgare* (barley), *Triticum aestivum* (wheat), *Triticum aestivum* subsp *spelta* (spelt), *Triticale*, *Avena sativa* (oats), *Secale cereale* (rye), *Sorghum bicolor* (sorghum), *Zea mays* (maize), *Saccharum officinarum* (sugarcane) and *Oryza sativa* (rice).

The invention furthermore relates to the use of the transgenic organisms according to the invention and of the cells, cell cultures, parts—such as, for example, roots, leaves and the like in the case of transgenic plant organisms—, and transgenic propagation material such as seeds or fruits for the preparation of foodstuffs or feeding stuffs, pharmaceuticals or fine chemicals.

In one embodiment, the invention furthermore relates to a method for the recombinant preparation of pharmaceuticals or fine chemicals in host organisms, where a host organism or a part thereof is transformed with one of the above-described nucleic acid molecule expression cassettes, and this expression cassette comprises one or more structural genes which code for the desired fine chemical or which catalyze the biosynthesis of desired fine chemical, the transformed host organism is cultured, and the desired fine chemical is isolated from the culture medium. This method can be applied to fine chemicals such as enzymes, vitamins, amino acids, sugars, fatty acids, natural and synthetic flavors, aromas and colorants. The production of tocopherols and tocotrienols and of carotenoids is especially preferred. The culturing of the transformed host organisms, and the isolation from the host organisms or from the culture medium, are carried out by methods known to the skilled worker. The production of pharmaceuticals such as, for example, antibodies or vaccines, is described in Hood E. E., Jilka J. M., Curr Opin Biotechnol. 10 (4), 382 (1999).; Ma J. K., Vine N. D., Curr. Top. Microbiol. Immunol. 236, 275 (1999).

According to the invention, the expression of a structural gene can, of course, also be effected, or influenced, independently of the embodiment of the method according to the invention or the use of the subject matter according to the invention.

The examples which follow are embodiments of the invention, and they are not intended to limit the scope of the invention as contained in the remainder of the description, the figures and the claims.

Figure 3E:
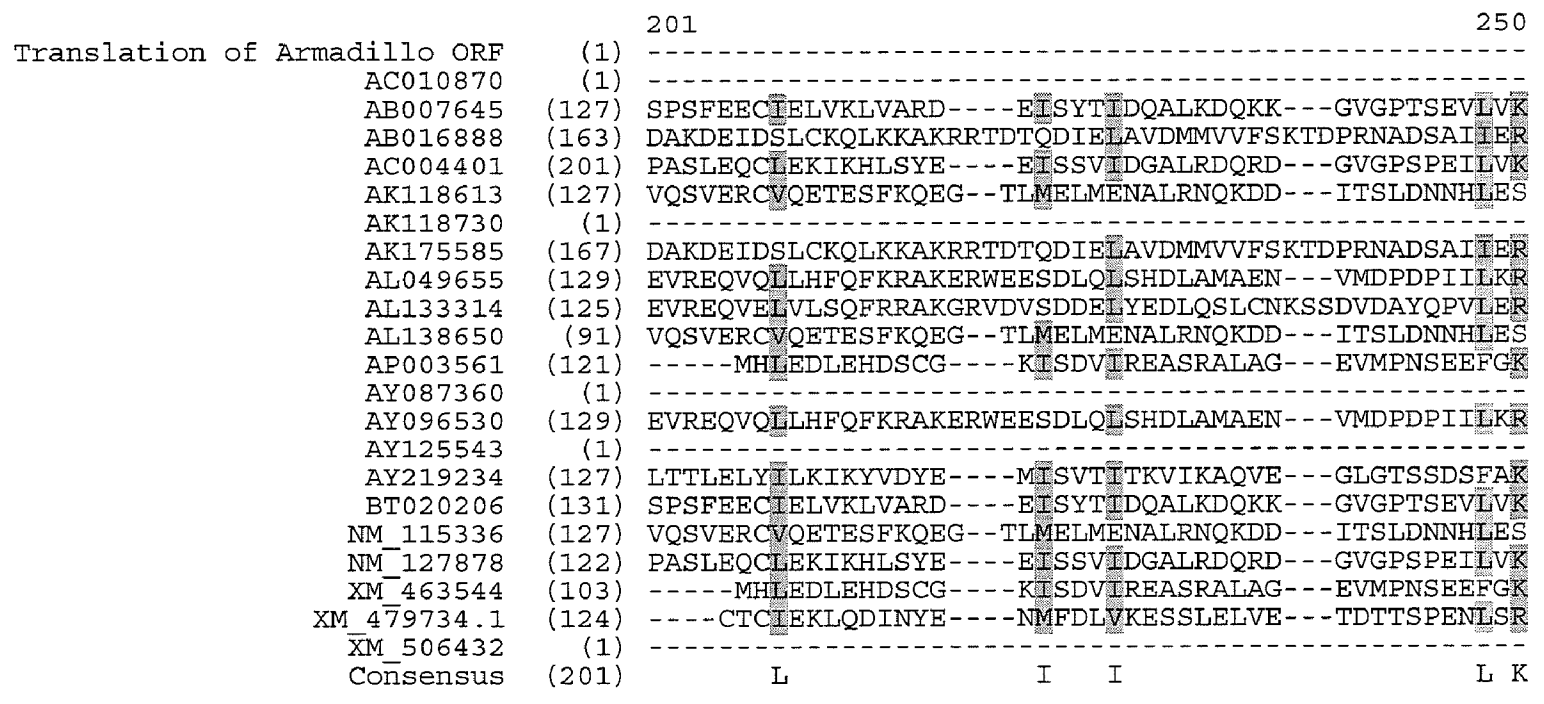

Sequences:
1. SEQ ID No.:1 and 2: HvArm
2. SEQ ID No.: 3 and 4: OS_1_XM_479734.1
3. SEQ ID No.: 5 and 6 Os_2_XM_463544
4. SEQ ID No.: 7 and 8 Os_3_AP003561
5. SEQ ID No.:9 and 10 Os_4_XM_506432
6. SEQ ID No.:11 and 12 NT_1_AY219234
7. SEQ ID No.: 13 and 14 At_1_NM_127878
8. SEQ ID No.: 15 and 16 At_2_AC004401
9. SEQ ID No.: 17 and 18 At_3_BT020206
10. SEQ ID No.:19 and 20 At_4_AB007645
11. SEQ ID No.: 21 and 22 At_5_NM_115336 (At3g54790)
12. SEQ ID No.:23 and 24 At_6_AK118613
13. SEQ ID No.: 25 and 26 At_7_AL138650
14. SEQ ID No.: 27 and 28 At_8_AL133314
15. SEQ ID No.: 29 and 30 At_9_AC010870
16. SEQ ID No.: 31 and 32 At_10_AY125543 (At3g01400)
17. SEQ ID No.:33 and 34 At_11_AY087360
18. SEQ ID No.: 35 and 36 At_12_AB016888
19. SEQ ID No.: 37 and 38 At_13_AK175585
20. SEQ ID No.: 39 and 40 At_14_AL049655
21. SEQ ID No.: 41 and 42 At_15_AY096530 (At3g54850)
22. SEQ ID No.:43 and 44 At_16_AK118730 (At4g16490)
23. SEQ ID No.: 45 to 59: primer
24. SEQ ID No.: 60, 61, 62: consensus sequences of the polynucleotide SEQ ID No. from 1 to 22.
25. SEQ ID No.: 63: 5'UTR in combination with the sequence of HvArm
26. SEQ ID No.: 64: 5'UTR of HvArm The figures show:
FIG. 1: nucleic acid sequences of ARM1 from barley, rice and *Arabidopsis thaliana*.
FIG. 2: polypeptide sequences of ARM1 from barley, rice and *Arabidopsis thaliana*.
FIG. 3: sequence alignment from ARM1 protein sequences polypeptides from barley, rice and *Arabidopsis thaliana*.
FIG. 4: increasing the mildew resistance of wheat by introducing and expressing ARM repeat sequences
FIG. 5: consensus sequences of the sequence alignment from ARM1 protein sequences polypeptides from barley, rice and *Arabidopsis thaliana*.
FIG. 6: nucleic acid sequence of barley ARM1 including the 5'-UTR region

EXAMPLES

General Methods

The chemical synthesis of oligonucleotides can take place for example in a known manner by the phosphoamidite method (Voet, Voet, 2nd edition, Wiley Press New York, page 896-897). The cloning steps carried out for the purposes of the present invention, such as, for example, restriction cleavages, agarose gel electrophoresis, purification of DNA fragments, transfer of nucleic acids to nitrocellulose and nylon membranes, linkage of DNA fragments, transformation of *E. coli* cells, culturing of bacteria, replication of phages and sequence analysis of recombinant DNA are carried out as described in Sambrook et al. (1989) Cold Spring Harbour Laboratory Press; ISBN 0-87969-309-6. The sequencing of recombinant DNA molecules takes place using a laser fluorescence DNA sequencer from the company MWG-Licor by the method of Sanger (Sanger et al., Proc Natl Acad Sci USA 74:5463 (1977)).

Example 1

Plants, Pathogens and Inoculation

The barley variety Golden Promise is from Patrick Schweizer, Institut für Pflanzengenetik und Kulturpflanzenforschung Gatersleben. The variety Pallas and the backcrossed line BCIngrid-mlo5 was provided by Lisa Munk, Department of Plant Pathology, Royal Veterinary and Agricultural University, Copenhagen, Denmark. Its preparation is described (Kølster P et al., Crop Sci 26: 903 (1986)).

The wheat variety kanzler is also from Patrick Schweizer, Institut für Pflanzengenetik und Kulturpflanzenforschung Gatersleben.

Unless otherwise described, the wheat or barley seed which has been pregerminated for 12 to 36 hours in the dark on moist filter paper is placed in batches of 5 grains along the edge of a square pot (8×8 cm) in Fruhstorfer soil type P, covered with soil and watered regularly with tapwater. All plants are grown in controlled-environment cabinets or chambers at from 16 to 18° C. for 5 to 8 days, at a relative atmospheric humidity of from 50 to 60% and in a 16 hr light/8 hr dark photoperiod with 3000 and 5000 lux, respectively (50 and 60 μmols-$^1$m-$^2$ photon flux density, respectively) and employed in the experiments in the seedling stage. In the case of experiments where primary leaves are treated, the latter are fully developed.

Before the plants are subjected to the transient transfection experiments, they are grown in controlled-environment cabinets or chambers at a daytime temperature of 24° C., nighttime temperature of 20° C., relative atmospheric humidity of 50 to 60% and a 16 hr light/8 hour dark photoperiod with 30 000 lux.

Powdery mildew of barley *Blumeria graminis* (DC) Speer f.sp. *hordei* Em. Marchal der Rasse A6 (Wiberg A, Hereditas 77: 89 (1974)) (BghA6) is used to inoculate barley plants. The mildew was provided by the Institut für Biometrie, JLU Gießen. The inoculum is maintained in controlled-environment cabinets under conditions which are identical to those which have been described above for the plants by transferring the conidia from infected plant material to 7-day-old barley plants cv. Golden Promise which have been raised at regular intervals, at a density of 100 conidia/mm$^2$.

Powdery mildew *Blumeria graminis* (DC) Speer f. sp. *tritici* is used to inoculate wheat plants. This mildew was isolated from field-grown plants. The propagation of the inoculum takes place in controlled-environment cabinets under the same conditions as have been described above for the barley and wheat plants, by transferring the conidia from infected plant material to regularly grown 7-day-old plants at a density of 100 conidia/mm$^2$.

Example 2

RNA Extraction

Total RNA is extracted from 8 to 10 primary leaf segments (5 cm in length) by means of "RNA extraction buffer" (AGS, Heidelberg, Germany).

To this end, central primary leaf segments 5 cm in length are harvested and homogenized in liquid nitrogen using a pestle and mortar. The homogenate is stored at −70° C. until the RNA is extracted.

Total RNA is extracted from the frozen leaf material with the aid of an RNA extraction kit (AGS, Heidelberg). To this end, 200 mg of the frozen leaf material is covered with 1.7 ml of RNA extraction buffer (AGS) in a microcentrifuge tube (2 ml) and immediately subjected to thorough mixing. After the addition of 200 µl of chloroform, the mixture is again mixed thoroughly and shaken for 45 minutes at room temperature on an orbital shaker at 200 rpm. Thereafter, the mixture is centrifuged for 15 minutes at 20 000 g and 4° C. in order to separate the phases, the (aqueous) top phase is transferred into a fresh microcentrifuge tube, and the bottom phase is discarded. The aqueous phase is again purified with 900 µl of chloroform by homogenizing 3 times for 10 seconds and recentrifuging (see above) and removing the top phase. To precipitate the RNA, 850 µl of 2-propanol are then added, the mixture is homogenized and placed on ice for 30 to 60 minutes. Thereafter, the mixture is centrifruged for 20 minutes (see above), the supernatant is carefully decanted off, 2 ml of 70% strength ethanol (−20° C.) are added, using a pipette, and the batch is mixed and again centrifuged for 10 minutes. The supernatant is then again decanted off and the pellet is carefully freed from residual fluid, using a pipette, and then dried in a stream of pure air on a sterile workbench. Thereafter, the RNA is dissolved in 50 µl of DEPC water on ice, and the batch is mixed and centrifuged for 5 minutes (see above). 40 µl of the supernatant are transferred into a fresh microcentrifuge tube as RNA solution and stored at −70° C.

The RNA concentration is determined photometrically. To this end, the RNA solution is diluted 1:99 (v/v) with distilled water and the absorbance (Photometer DU 7400, Beckman) is measured at 260 nm ($E_{260\,nm}=1$ at 40 µg RNA/ml). In accordance with the calculated RNA contents, the concentrations of the RNA solutions are subsequently standardized with DEPC water to 1 µg/µl and verified in an agarose gel.

To verify the RNA concentrations in a horizontal agarose gel (1% agarose in 1×MOPS buffer with 0.2 µg/ml ethidium bromide), 1 µl of RNA solution is treated with 1 µl of 10×MOPS, 1 µl of color marker and 7 µl of DEPC water, separated according to size at a voltage of 120 V in the gel in 1×MOPS running buffer in the course of 1.5 hours and photographed under UV light. Any differences in concentration of the RNA extracts are standardized with DEPC water, and the standardization is again verified in the gel.

Example 3

Cloning the Barley HvARM cDNA Sequence

The cDNA fragments required for isolating the armadillo cDNA, and for cloning and sequencing it, were obtained by means of RT-PCR using the GeneRacer Kit (from Invitrogen Life Technologies). To this end, total RNA from barley epidermis was used as the template. The RNA was isolated 12 h and 24 h post-infection from epidermal cells of barley Ingrid+ Bgt.

The HvARM cDNA sequence was extended by means of the RACE technology using the "GeneRacer Kit" (INVITROGENE Life Technologies). To this end, 4000 ng of total mRNA, 1 µl of 10×CIP buffer, 10 units RNAse inhibitor, 10 units CIP ("calf intestinal phosphatase") and DEPC-treated water up to a total volume of 10 µl were treated for 1 h at 50° C. To precipitate the RNA, a further 90 µl of DEPC water and 100 µl of phenol:chloroform were added and the mixture was mixed thoroughly for approximately 30 seconds. After 5 min centrifugation at 20 000 g, the top phase was treated with 2 µl 10 mg/ml mussel glycogen, 10 µl 3 M sodium acetate (pH 5.2) in a fresh microreaction vessel. 220 µl of 95% ethanol were added and the mixture was incubated on ice. Thereafter, the RNA was precipitated by centrifugation for 20 min at 20.000 g and 4° C. The supernatant was discarded, 500 µl of 75% ethanol were added, and the mixture was vortexed briefly and centrifuged for 2 min (20 000 g). Again, the supernatant was discarded, and the precipitate was dried in the air for 2 min at room temperature and subsequently suspended in 6 µl of DEPC water. mRNA CAP structures were removed by adding 1 µl of 10×TAP buffer, 10 units RNAsin and 1 unit TAP ("tobacco acid pyrophosphatase"). The mixture was incubated for 1 h at 37° C. and subsequently cooled on ice. Again, the RNA was precipitated—as described above—and transferred to a reaction vessel containing 0.25 µg of GeneRacer oligonucleotide primer. The oligonucleotide primer was resuspended in the RNA solution, and the mixture was incubated for 5 min at 70° C. and then cooled on ice. 1 µl of 10× ligase buffer, 10 mM ATP, 1 unit RNAsin and 5 units T4 RNA ligase were added, and the reaction mixture was incubated for 1 h at 37° C. Again, the RNA was precipitated—as described above—and resuspended in 7 µl of DEPC water. 10 pmol of GeneRacer oligo-dT primer and 2 µl of each dNTP solution (25 mM) were added to the RNA, and the mixture was heated for 10 min at 70° C. and again cooled on ice. Thereafter, a mix consisting of 2 µl 10×RT buffer, 4 µl of 25 mM MgCl$_2$, 2 µl of 0.1 M DTT, 5 U (1 µl) SuperscriptIII transcriptase (200 U/µl) and 1 µl of RNAse Out (40 U/µl) were added, and the reaction solution was incubated for 50 min at 50° C. and subsequently inactivated for 5 min at 85° C. After incubation for 20 min at 37° C. with 1 µl of RNAse H (2 U/µl), the first-strand cDNA thus prepared was stored at −20° C.

The following primers were used for the RT-PCR:

```
GeneRacer oligo-dT primer
(from Invitrogen Life Technologies):
                                    (Seq ID No.: 45)
GCTGTCAACGATACGCTACGTAACGGCATGACAGTG (T)18
```

In each case 4000 ng of total-RNA, 10 mM dNTPs, 50 µM GeneRacer oligo-dT primer (from Invitrogen Life Technologies), 1 µl RNase inhibitor and 1 µl of enzyme mix in 1×RT buffer (GeneRacer kit Invitrogen) were employed for the reaction (volume 20 µl).

The reaction was incubated for 50 minutes at 50° C.

The following primers were used for amplifying the 5' cDNA ends:

```
MWG 1:
5'GCAGACATGACCCAATCTTGGCAGG 3'       (Seq ID No.: 46)

GR 5' primer (Invitrogen):
5'cgactggagcacgaggacactga 5'          (Seq ID No.: 47)

MWG 2:
5'CCACGGTCAGCAACCTCTCCAGACG 3'        (Seq ID No.: 48)

GeneRacer 5' nested primer (Invitrogen):.
5'ggacactgacatggactgaaggagta 3'       (Seq ID No.: 49)

MWG 3:
5'cagatgatagttattgttgttgactgg 3'      (Seq ID No.: 50)

GR 3' primer (Invitrogen):
5'GCTGTCAACGATACGCTACGTAACG 3'        (Seq ID No.: 51)
```

-continued

MWG 4:
5'ctcatcttctcaagctactggtgg 3'    (Seq ID No.: 52)

GeneRacer 3' nested primer (Invitrogen):
5'CGCTACGTAACGGCATGACAGTG 3'    (Seq ID No.: 53)

The reaction mixture (total volume 50 µl) was composed as follows:
4 µl MWG1 (10 pmol/µL)
4.5 µl 5' Gene Racer (10 pmol/µL)
5 µl 10× buffer Roche
1.5 µl 10 mM dNTPs
1 µl cDNA
1 µl Tag (Roche)
33 µl H$_2$O The following temperature program was used (GeneAmp PCR system 9700; Applied Biosystems):

| | |
|---|---|
| 5 cycles | Denaturation for 2 min at 94° C. |
| | 30 sec at 94° C. (denaturation) |
| | 2 min at 72° C. (extension) |
| 5 cycles | 30 sec at 94° C. (denaturation) |
| | 2 min at 70° C. (extension) |
| 30 cycles | 30 sec at 94° C. (denaturation) |
| | 30 sec at 65° C. (annealing) |
| | 2 min at 68° C. (extension) |
| | 7 min at 68° C. final extension |
| | Cooling at 4° C. until further use |

The PCR gave no product. On this basis, a "nested" RACE with MWG2, the armadillo-specific oligonucleotide primer and the "GeneRacer nested 5' primer" was carried out:

| | |
|---|---|
| 30 cycles | Denaturation for 2 min at 94° C. |
| | 30 sec at 94° C. (denaturation) |
| | 30 sec at 65° C. (annealing) |
| | 2 min at 68° C. (extension) |
| | 7 min at 68° C. final extension |
| | 4° C. cooling until further use |

The PCR gave a product of approximately 8.50 bp. The PCR product obtained was isolated using a 1% strength agarose gel, extracted from the gel, cloned into pCR4-Topo (from Invitrogen Life Technologies) by means of T-overhang ligation and sequenced. This means that the sequence shown in SEQ ID No: is identical to the barley armadillo sequence.

The following primers were used to amplify the HvArm full-length sequence:

MWG 29:
5'atatgcaaatggctctgctag 3'    (Seq ID No.: 54)

MWG 30:
5'TATCATCTCCTTCCCGAGTTC 3'    (Seq ID No.: 55)

The reaction mixture (total volume 50 µl) was composed as follows:
4 µl MWG29 (10 pmol/µL)
4 µl MWG30 (10 pmol/µL)
5 µl 10×Pfu Ultra buffer (Stratagene)
1.5 µl 10 mM dNTPs
1 µl cDNA
1 µl Pfu Ultra (Stratagene)
33 µl H$_2$O The following temperature program was used (GeneAmp PCR system 9700; Applied Biosystems):

| | |
|---|---|
| 5 cycles | Denaturation for 2 min at 94° C. |
| | 30 sec at 94° C. (denaturation) |
| | 30 sec at 55° C. (annealing) |
| | 1.5 min at 72° C. (extension) |
| | 7 min at 72° C. final extension |
| | Cooling at 4° C. until further use |

The PCR gave a product of 1326 bp. The PCR product obtained was isolated using a 1% strength agarose gel, extracted from the gel, cloned into pCR4-Topo (from Invitrogen Life Technologies) by means of T-overhang ligation and sequenced. This means that the sequence shown in SEQ ID No: is identical to the barley armadillo sequence.

Example 4

Cloning the HvARM Genomic Full-Length Sequence

1) BAC Screening for Identifying the Clone Which Comprises the Sequence According to the Invention.

DNA pools from a barley BAC library (Yu et al., TAG 101,1093 (2000)) were used for identifying the gene coding for the sequence according to the invention in barley. BAC clones which carry the sequence according to the invention were identified by means of PCR using the primers 5' TAA TGA TAA TCT TCC TAA TAC CCG TCA G (SEQ ID NO: 66) and 5' CCT TTG AGG GGC AGA AGA GAT AG (SEQ ID NO: 67). In this context, two overlapping BAC clones Nos. 705A01 and 581D24 which comprised the identical HvARM gene were identified.

Identified individual clones were subcloned in two steps for the gene and promoter identification. First the BAC DNA of an individual clone was isolated by means of Qiagen column (Maxi-Kit; Qiagen; isolation according to the manufacture's protocol). 5-10 kbp fragments were generated from this BAC DNA by means of shearing (Hydroshear: Genomic Solutions), and the resulting ends were filled up with Klenow to give smooth ends (reaction following the manufacture's protocol). Fragment length selection was performed via an 0.8% strength agarose gel in 0.5% TBE. The suitable fragment length range was excised from the gel, and the DNA was eluted from the agarose gel with the aid of the Qiagen Gel Extraction kit (elution following the manufacture's protocol). The eluted 5-10 kbp fragments are ligated into an EcoRV-linearized pBluescript II SK(–) vector with smooth dephosphoryiated ends (restriction and dephosphorylation as specified by the manufacturer) and transformed chemical-thermally into highly competent E. coli cells. Thereafter, the transformants are arranged randomly with the aid of a picking robot (Qpick, Genetix) and transferred into microtiter plates containing LB medium.

PCR was used to select the subfragment which carries the gene of interest, and the length of the potential 5'-upstream region was maximized. The subfragment selected was again sheared into 1-2 kbp fragments, ligated, and transformed, and the clones were stored in microliter plates (see above). Among the picked clones, 96 colonies were selected at random and sequenced using the TempliPhi protocol as specified in the manufacturer's protocol. The sequences were assembled. The sequence information obtained was exploited for annotating the coding exons in comparison with known sequences from other organisms in order to determine the sequence according to the invention and its potential promoters.

PCR:

The PCR method was chosen for detecting the sought-after DNA sequence owing to its high sensitivity. The analysis was carried out in a reaction volume of 20 µl. The reaction mixture consisted of 10 mM Tris-HCl, pH 9.0; 50 mM KCl; 0.1% Triton X-100, 0.2 mM dNTP; 2 mM MgCl2, 0.6 µM of each oligonucleotide and Taq polymerase (concentration in the reaction mixture: ~1U µl$^{-1}$). A 10 ng of BAC pool DNA or 2 µl of bacterial culture (for colony PCR) was used for each reaction mixture. Existing cDNA sequences acted as the basis for deriving the oligonucleotides 5' CAG CCA CCA CCA ACC CAA AC (SEQ ID NO: 68) and 5' GCC CAC GGT CAG CAA CCT CTC C (SEQ ID NO: 69).

The BAC DNA to be amplified and the primers were initially introduced into the reaction vessel and then mixed with the PCR mixture. To kill and disrupt the bacteria in a colony PCR, the contents of the vessel were heated for 5 min at 95° C. before the PCR reaction mixture was added. An initial step of 5 min at 95° C. was used for denaturing the double-stranded DNA. The touch-down PCR reaction was performed in the intervals 30 sec 95° C.; 30 sec temperature T and 60 sec 72° C. for the first 10 cycles, with T in the first cycle being 60° C. and being lowered in each cycle by 0.5° C. Further 30 cycles were performed at the intervals 30 sec 95° C.; 30 sec 55° C. and 60 sec 72° C. The reaction was incubated for 5 min at 72° C. for the final chain elongation before being cooled to a temperature of 20° C. and being held constant. The analysis of the PCR experiments was carried out using 2.5% strength agarose gels in 0.5×TBE buffer, because a short reaction product of 1831 bp was expected.

2) Cloning the Genomic Full-Length Sequence

A 3.0 Kbp fragment which contained the HvARM full-length sequence was isolated by the using the primer pairs 5' ACC GAC TAG TCA CCA CCA ACC CAA ACC (SEQ ID NO: 70) (comprising an SpeI site) and 5' GCA GGG CCC AGC GCC AGT CAA CAA CAA TAA C (SEQ ID NO: 71) (comprising an ApaI cleavage site) and BAC 705A01 as template.

The PCR reaction was carried out under the following conditions:

Reaction buffer—20 mM Tris-HCl (pH 8,8 at 25° C.), 10 mM (NH$_4$)$_2$SO$_{4, 10}$ mM KCl, 1% (v/v) Triton X-10, 0.1 mg/ml BSA, 1 mM MgSO4, dNTPs at 0.2 mM each, 1 µM of each primer, 2.5 U Pfu proofreading DNA polymerase (Fermentas, Burlington, Canada).

The temperature program was: 94° for 2 min; then 5 cycles at 94°, 30 sec at 50° C., from where the temperature was increased by 2° C. in each cycle (touchup) to 60° C.; thereafter 30 cycles at 94° C. for 30 sec, 60° C. for 30 sec, 72° C. for 6 min; finally an extension reaction of 7 min at 72° C. The 3.0 Kbp PCR amplican was digested with ApaI and SpeI, and the DNA was eluted from an agarose gel and cloned into ApaI/SpeI-digested pIPKTA9 vector to perform the transient overexpression.

Example 5

Cloning of the *Arabidopsis thaliana* AtARM (At2g23140) Full-Length cDNA Sequence The following primers were used for amplifying the AtArm full length sequence:

MWG 31:
(Seq ID No.: 56)
5'cccgggatgattttgcggttttggcgg 3'

MWG 32:
(Seq ID No.: 57)
5'CCCGGGTCACAAGACAAAACATAAAAATAGG 3'

MWG 32b:
(Seq ID No.: 58)
5'gactcacactactctaatacc 3'

MWG 33:
(Seq ID No.: 59)
5'GACATCGTTTGTCTCACACC 3'

The mixture (total volume 50 µl) was composed as follows (owing to its size of 2775 bp, the gene was divided into two portions for the PCR):

4 µl MWG31 (10 pmol/µL)
4 µl MWG34 (10 pmol/µL)
5 µl 10×Pfu Ultra buffer (Stratagene)
1.5 µl 10 mM dNTPs
1 µl cDNA
1 µl Pfu Ultra (Stratagene)
33 µl H$_2$O
and
4 µl MWG32 (10 pmol/µL)
4 µl MWG33 (10 pmol/µL)
5 µl 10×Pfu Ultra buffer (Stratagene)
1,5 µl 10 mM dNTPs
1 µl cDNA
1 µl Pfu Ultra (Stratagene)
33 µl H$_2$O respectively.

The following temperature program was used (GeneAmp PCR System 9700; Applied Biosystems):

| | 2 min denaturation at 94° C. |
|---|---|
| 30 cycles of | 30 sec at 94° C. (denaturation) |
| | 30 sec at 59° C. (annealing) |
| | 1.5 min at 72° C. (extension) |
| | 7 min at 72° C. final extension |
| | 4° C. cooling until further use |

The PCR gives a product of 1143 bp and 1705 bp, respectively. The PCR product obtained is isolated via a 1% strength agarose gel, extracted from the gel and, by means of T-overhang ligation, cloned into pCR4-Topo (from Invitrogen Life Technologies) and sequenced. The sequence shown in SEQ ID No: is therefore identical to the *Arabidopsis thaliana* armadillo sequence.

In order to assemble the gene, the 1705 bp PCR product is cloned into pUC18. Thereafter, AtArm 1143 bp is cloned into pUC18-AtArm 1705 bp.

Example 6

Transient Expression in Barley and Wheat by Means of Particle Bombardment

1) The following construct mixture was introduced into wheat leaves by means of biolistic transformation using a "gene gun" (Bio-Rad, model PDS-1000/He, Hepta adapter) using the method of Douchkov et al., Mol. Plant-Microbe Interact. 18, 755 (2005):

| Plasmid | Batch 1 (μg/shot) | Batch 2 (μg/shot) | Batch 3 (μg/shot) | Batch 4 (μg/shot) | Batch 5 (μg/shot) |
|---|---|---|---|---|---|
| pUbiGUS (Reporter gene construct) | 7 | 7 | 7 | 7 | 7 |
| pIPKTA9 (empty overexpression vector) | 7 | — | — | — | — |
| pIPKTA9_Rnr5 (overexpression construct) | — | — | — | — | 7 |
| pIPKTA9_TaPERO (positive control) | — | 7 | — | — | — |
| BAC 632F23 (control BAC (empty)) | — | — | 14 | — | — |
| BAC 581D24 (Rnr5) | — | — | — | 14 | — |

Vectors and controls used:
pUbiGUS - GUS overexpression reporter gene construct (Schweizer et al., Molecular Plant-Microbe Interactions 12 (8), 647 (1999)).
pIPKTA9 - empty vector control (Zimmermann et al., Plant Physiology 142, 181 (2006)),
pIPKTA9_ARM40F - pIPKTA9 have based HvARM overexpression construct,
BAC 581D24 - HvARM containing BAC clone,
BAC 632F23 - "empty" BAC control (BAC does not hybridize with any known EST).

For the DNA coating, 2.18 mg of gold particles (diameter 1.0 μm, particle density 25 mg ml$^{-1}$ in 50% (v/v) glycerol) were mixed with 14-21 μg of supercoiled DNA and treated with 1 M Ca(NO$_3$)$_2$ pH 10 so that the final Ca(NO$_3$)$_2$ concentration was 0.5 M (all per shot). After centrifugation and washing with 70% (v/v) ethanol, the particles were resuspended in 96% (v/v) ethanol and distributed on the 7 macrocarriers. In a vacuum (3.6×10$^3$ Pa), the particles were introduced to in each case 7 leaf segments of 7-day old barley or wheat plants (barley: cultivar Golden Promise; wheat: cultivar Kanzler) by means of a helium pressurewave of 7.6×10$^6$ Pa. For the bombardment, the leaf segments were placed, in a Petri dist on 0.5% (w/v) Phytoagar which had been treated with 20 μg ml$^{-1}$ benzimidazole. The leaves were then incubated for 4 h at +20° C. and indirect daylight.

2) Inoculation of the Leaf Segments

The bombarded leaves were transferred to polycarbonate dishes 20×20 cm in size on 1% (w/v) Phytoagar supplemented with 20 μg ml$^{-1}$ benzimidazole. In an inoculation tower, the barley leaves were infected with barley mildew spores and the wheat leaves with wheat mildew spores by shaking spores from severely infected barley and wheat leaves into the tower. The inoculum density was approximately 200 spores/mm$^2$. After 5 min, the dishes were removed, sealed and incubated for 40-48 h at +20° C. and indirect daylight.

3) Histochemical GUS Detection

The leaves were infiltrated in vacuo with the GUS detection solution (10 mM EDTA, 1.4 mM K$_3$[Fe(CN)$_6$], 1.4 mM K$_4$[Fe(CN)$_6$], 0.1% (v/v) Triton X-100, 20% (v/v) methanol, 1 mg/ml 5-bromo-4-chloro-3-indolyl-β-D-glucuronic acid, 100 mM sodium phosphate buffer, pH 7.0) and incubated overnight at +37° C. After the detection solution had been removed, the leaves were destained for 15 min at +20° C. with a solution of 7.5% (w/v) trichloroacetic acid and 50% (v/v) methanol 4) Determination of the Susceptibility of Bombarded Epidermal Cells Light microscopy was performed with a Zeiss Axiolab at 200× magnification. The cell contents of cells with GUS expression is stained blue. The number of GUS-stained cells and the number of GUS-stained cells which contain at least 1 haustorium of the wheat mildew fungus are counted for each shot by means of quantitative microscopy. The susceptibility index was calculated from the number of haustorium-containing GUS-positive cells/all GUS-positive cells.

Results: increase of the mildew resistance of wheat by expression of HvARM repeat protein

TABLE 1

Complementation data HvARM (='Rnr5')

|  |  | Relative susceptibility (%) Mean | Relative susceptibility (%) Standard deviation |
|---|---|---|---|
| Barley | pIPKTA9 | 100.00 |  |
| Barley | pGY1_TaPERO | 36.71 | 5.04136 |
| Barley | BAC_632F23 | 149.60 | 13.9 |
| Barley | BAC_581D24 | 147.69 | 19.04006 |
| Barley | pIPKTA9_Rnr5 | 104.97 | 15.22278 |
| Wheat | pIPKTA9 | 100 |  |
| Wheat | pGY1_TaPERO | 25.48284139 | 2.973353 |
| Wheat | BAC_632F23 | 107.8383963 | 11.40531 |
| Wheat | BAC_581D24 | 48.48787766 | 4.162226 |
| Wheat | pIPKTA9_Rnr5 | 66.78504562 | 3.821332 |

In the transient assay, the expression of TaPERO (WO 2005/035766) acted as the positive control for successful mildew resistance.

FIG. 4 provides a summary of the data from Table 1.

Example 7

Expression in Wheat by Means of Particle Bombardment

Transgenic wheat (*Triticum aestivum*) was generated by means of particle bombardment by methods known to the skilled worker. For the expression, the armadillo repeat genes were fused to the wheat RbcS promoter (ribose-1,5-bisphosphate carboxylase small unit). Employing customary methods, this gave seedlings of the T1 generation, which were tested for their resistance to *Blumeria graminis* f.sp. *tritici*. To this end, the seedlings were planted into soil and, after seven days, inoculated with *Blumeria graminis* f.sp. *tritici* spores as already described above. After a further seven to ten days, the plants infected thus were studied for attack by *Blumeria graminis* f.sp. *tritici*. Three of the transgenic wheat lines obtained thus were virtually disease-free (disease level 5% in comparison with the wild-type control).

We claim:

1. A method of generating or increasing the resistance to one or more pathogen(s) in a plant, a part of a plant, or a plant cell, comprising introducing a nucleotide sequence which codes for an armadillo repeat ARM1 protein or part thereof into a plant, a part of a plant, or a plant cell, and expressing said nucleotide sequence in the plant, the part of the plant, or the plant cell;

wherein the nucleotide sequence which codes for an armadillo repeat ARM1 protein or part thereof is increased in the plant, the part of the plant, or the plant cell in comparison with the corresponding wild-type plant, part of the plant, or plant cell; and wherein the nucleotide sequence comprises at least one nucleic acid molecule selected from the group consisting of:

a) a nucleic acid molecule which codes for at least one polypeptide comprising the sequence of SEQ ID NO: 2;

b) a nucleic acid molecule which comprises at least one polynucleotide comprising the sequence of SEQ ID NO: 1;

c) a nucleic acid molecule which codes for a polypeptide comprising an amino acid sequence having at least 90% identity to the sequence of SEQ ID NO: 2; and d) a nucleic acid molecule which hybridizes under stringent conditions of about 0.2×SSC at 65° C. with the complement of the nucleic acid molecule of (a) or (b);

the nucleotide sequence being such that a pathogen resistance is generated or increased thereby.

2. The method of claim 1, wherein a fungal pathogen resistance is generated or increased.

3. The method of claim 2, wherein the fungal pathogen is a penetrating fungal pathogen.

4. The method of claim 1, wherein the part of the plant is mesophyll cells and/or epidermal cells.

5. The method of claim 1, wherein the part of the plant is the lemma, palea, and/or glume.

6. The method of claim 1, wherein the armadillo repeat ARM1 protein comprises two or more armadillo repeats.

7. The method of claim 1, wherein the one or more pathogen(s) is selected from the group consisting of the families Pucciniaceae, Mycosphaerellaceae, and Hypocreaceae.

8. The method of claim 1, wherein the nucleic acid molecule is introduced in a recombinant expression cassette comprising said nucleic acid molecule in an operable linkage with a promoter which is active in plants, the method further comprising a) regenerating a plant from the plant cell, and b) expressing said nucleic acid molecule to generate or to increase a pathogen resistance in said plant.

9. The method of claim 8, wherein the promoter is a pathogen-inducible promoter or an epidermis- or mesophyll-specific promoter.

10. The method of claim 1, wherein the activity of a Bax inhibitor 1, ROR2, SnAP34, and/or lumenal binding protein BiP is additionally increased in the plant, the part of the plant, or the plant cell.

11. The method of claim 1, wherein the activity of a RacB, CSL1, HvNaOX and/or MLO is additionally reduced in the plant, the part of the plant, or the plant cell.

12. The method of claim 10, wherein the Bax inhibitor 1 is expressed in the mesophyll.

13. The method of claim 10, wherein the Bax inhibitor 1 is expressed in the roots.

14. The method of claim 1, wherein the pathogen is selected from the group consisting of the species *Blumeria graminis*, *Puccinia triticina*, *Puccinia striiformis*, *Mycosphaerella graminicola*, *Stagonospora nodorum*, *Fusarium graminearum*, *Fusarium culmorum*, *Fusarium avenaceum*, *Fusarium poae*, and *Microdochium nivale*.

15. The method of claim 14, wherein the pathogen is *Blumeria graminis*.

16. The method of claim 15, wherein the pathogen is *Blumeria graminis* (DC) Speer f.sp, *hordei* or *Blumeria graminis* (DC) Speer f.sp, *tritici*.

17. The method of claim 1, wherein the plant is selected from the group consisting of the plant genera *Hordeum, Avena, Secale, Triticum, Sorghum, Zea, Saccharum,* and *Oryza*.

18. The method of claim 1, wherein the pathogen is *Blumeria graminis* (DC) Speer f.sp, *hordei* and the plant is from the genus *Hordeum*.

19. The method of claim 1, wherein the pathogen is *Blumeria graminis* (DC) Speer f.sp, tritici and the plant is from the genus *Triticum* or is *Triticum aestivum*.

20. The method of claim 19, wherein the armadillo repeat ARM1 nucleotide sequence is derived from barley.

21. A nucleic acid molecule coding for an armadillo repeat ARM1 protein, comprising at least one nucleic acid molecule selected from the group consisting of:
   a) a nucleic acid molecule which codes for at least one polypeptide comprising the sequence of SEQ ID NO: 2;
   b) a nucleic acid molecule which comprises at least one polynucleotide comprising the sequence of SEQ ID NO: 1;
   c) a nucleic acid molecule which codes for a polypeptide comprising an amino acid sequence having at least 90% identity to the sequence of SEQ ID NO: 2; and
   d) a nucleic acid molecule which hybridizes under stringent conditions of about 0.2×SSC at 65° C. with the complement of the nucleic acid molecule of (a) or (b);
   wherein the nucleic acid molecule does not consist of the sequence shown in SEQ ID NO: 3, 5, 7, 9, 11, 13, 15, 17, 19, 21, 23, 25, 27, 29, 31, 33, 35, 37, 39, 41, or 43.

22. A nucleic acid construct comprising a nucleic acid molecule encoding an armadillo repeat ARM1 polypeptide in operable linkage with a pathogen-inducible promoter or an epidermis- and/or mesophyll-specific promoter, wherein the nucleic acid molecule comprises:
   a) a nucleic acid molecule which codes for at least one polypeptide comprising the sequence of SEQ ID NO: 2;
   b) a nucleic acid molecule which comprises at least one polynucleotide comprising the sequence of SEQ ID NO: 1;
   c) a nucleic acid molecule encoding a polypeptide comprising an amino acid sequence having at least 90% identity to the sequence of SEQ ID NO: 2; or
   d) a nucleic acid molecule which hybridizes under stringent conditions of about 0.2×SSC at 65° C. with the complement of the nucleic acid molecule of (a) or (b).

23. A DNA expression cassette comprising a nucleic acid molecule selected from the group consisting of:
   a) a nucleic acid molecule which codes for at least one polypeptide comprising the sequence of SEQ ID NO: 2;
   b) a nucleic acid molecule which comprises at least one polynucleotide comprising the sequence of SEQ ID NO: 1;
   c) a nucleic acid molecule which codes for a polypeptide comprising an amino acid sequence having at least 90% identity to the sequence of SEQ ID NO: 2; and
   d) a nucleic acid molecule which hybridizes under stringent conditions of about 0.2×SSC at 65° C. with the complement of the nucleic acid molecule of (a) or (b).

24. The DNA expression cassette of claim 23, where said nucleic acid sequence is in operable linkage with a promoter which is functional in a plant.

25. A DNA expression cassette comprising the nucleic acid construct of claim 22.

26. A vector comprising the expression cassette of claim 25.

27. A cell comprising a nucleic acid molecule, a DNA expression cassette comprising said nucleic acid molecule, or a vector comprising said expression cassette;
   wherein the nucleic acid molecule is selected from the group consisting of:
   a) a nucleic acid molecule which codes for at least one polypeptide comprising the sequence of SEQ ID NO: 2;
   b) a nucleic acid molecule which comprises at least one polynucleotide comprising the sequence of SEQ ID NO: 1;
   c) a nucleic acid molecule which codes for a polypeptide comprising an amino acid sequence having at least 90% identity to the sequence of SEQ ID NO: 2; and
   d) a nucleic acid molecule which hybridizes under stringent conditions of about 0.2×SSC at 65° C. with the complement of the nucleic acid molecule of (a) or (b).

28. A transgenic plant cell, plant, or part thereof, comprising a nucleic acid molecule, a DNA expression cassette comprising said nucleic acid molecule, or a vector comprising said expression cassette:
   wherein nucleic acid molecule comprises at least one nucleic acid molecule selected from the group consisting of:
   a) a nucleic acid molecule which codes for at least one polypeptide comprising the sequence of SEQ ID NO: 2;
   b) a nucleic acid molecule which comprises at least one polynucleotide comprising the sequence of SEQ ID NO: 1;
   c) a nucleic acid molecule which codes for a polypeptide comprising an amino acid sequence having at least 90% identity to the sequence of SEQ ID NO: 2; and
   d) a nucleic acid molecule which hybridizes under stringent conditions of about 0.2×SSC at 65° C. with the complement of the nucleic acid molecule of (a) or (b);
   the nucleic acid molecule being such that a pathogen resistance is generated or increased thereby.

29. The transgenic plant cell, plant, or part thereof of claim 28, which is a monocotyledonous plant cell, plant, or part thereof.

30. The transgenic plant cell, plant, or part thereof of claim 28, additionally comprising an increased Bax inhibitor 1 protein, ROR2 and/or SnAP34 activity and/or a reduced RacB, CSL1 and/or HvRBOHF activity.

31. The transgenic plant cell, plant, or part thereof of claim 28, comprising an increased Bax inhibitor 1, an ROR2 and/or SnAP34 activity and/or a reduced RacB, CSL1 and/or HvRBOHF activity in mesophyll cells and/or root cells.

32. The plant cell, plant, or part thereof of claim 28, selected from the group consisting of the species *Hordeum vulgare* (barley), *Triticum aestivum* (wheat), *Triticum aestivum* subsp, *spelta* (spelt), *Triticale, Avena sativa* (oats), *Secale cereale* (rye), *Sorghum bicolor* (sorghum), *Zea mays* (maize), *Saccharum officinarum* (sugarcane), and *Oryza sativa* (rice).

33. A method for generating a plant which is resistant to mesophyll-cell-penetrating pathogens, comprising introducing a nucleic acid molecule, a DNA expression cassette comprising said nucleic acid molecule, a vector comprising said expression cassette, or a cell comprising said nucleic acid molecule, said expression cassette, or said vector into a plant, part of the plant, or plant cell;
   wherein the nucleic acid molecule is selected from the group consisting of:

a) a nucleic acid molecule which codes for at least one polypeptide comprising the sequence of SEQ ID NO: 2;
b) a nucleic acid molecule which comprises at least one polynucleotide comprising the sequence of SEQ ID NO: 1;
c) a nucleic acid molecule which codes for a polypeptide comprising an amino acid sequence having at least 90% identity to the sequence of SEQ ID NO: 2; and
d) a nucleic acid molecule which hybridizes under stringent conditions of about 0.2×SSC at 65° C. with the complement of the nucleic acid molecule of (a) or (b).

34. A crop, propagation material or composition comprising a nucleic acid molecule, a DNA expression cassette comprising said nucleic acid molecule, or a vector comprising said expression cassette, or comprising a cell comprising said nucleic acid molecule, said expression cassette, or said vector;
wherein the nucleic acid molecule is selected from the group consisting of:
a) a nucleic acid molecule which codes for at least one polypeptide comprising the sequence of SEQ ID NO: 2;
b) a nucleic acid molecule which comprises at least one polynucleotide comprising the sequence of SEQ ID NO: 1;
c) a nucleic acid molecule which codes for a polypeptide comprising an amino acid sequence having at least 90% identity to the sequence of SEQ ID NO: 2; and
d) a nucleic acid molecule which hybridizes under stringent conditions of about 0.2×SSC at 65° C. with the complement of the nucleic acid molecule of (a) or (b).

35. The method of claim 1, wherein the nucleic acid molecule encodes a polypeptide comprising an amino acid sequence having at least 90% identity to the sequence of SEQ ID NO: 2.

36. The method of claim 1, wherein the nucleic acid molecule encodes a polypeptide comprising an amino acid sequence having at least 95% identity to the sequence of SEQ ID NO: 2.

37. The method of claim 1, wherein the nucleic acid molecule encodes a polypeptide comprising the sequence of SEQ ID NO: 2.

38. The transgenic plant cell, plant, or part thereof of claim 28, wherein the nucleic acid molecule encodes a polypeptide comprising an amino acid sequence having at least 90% identity to the sequence of SEQ ID NO: 2.

39. The transgenic plant cell, plant, or part thereof of claim 28, wherein the nucleic acid molecule encodes a polypeptide comprising an amino acid sequence having at least 95% identity to the sequence of SEQ ID NO: 2.

40. The transgenic plant cell, plant, or part thereof of claim 28, wherein the nucleic acid molecule encodes a polypeptide comprising the sequence of SEQ ID NO: 2.

* * * * *

SEQUENCE LISTING

<160> NUMBER OF SEQ ID NOS: 72

<210> SEQ ID NO 1
<211> LENGTH: 1329
<212> TYPE: DNA
<213> ORGANISM: Hordeum vulgare
<220> FEATURE:
<221> NAME/KEY: CDS
<222> LOCATION: (1)..(1329)

<400> SEQUENCE: 1

```
atg caa atg gct ctg cta gca agg ctt tct ctt gca agt tct gaa gga        48
Met Gln Met Ala Leu Leu Ala Arg Leu Ser Leu Ala Ser Ser Glu Gly
1               5                  10                  15 aga gag tct agt ttg gaa gaa aga cat gct ggt tct gat gaa caa act        96
Arg Glu Ser Ser Leu Glu Glu Arg His Ala Gly Ser Asp Glu Gln Thr
            20                  25                  30 tca gaa caa tca acg aag gaa gca ttt caa gca tct cat ttt gac agt       144
Ser Glu Gln Ser Thr Lys Glu Ala Phe Gln Ala Ser His Phe Asp Ser
        35                  40                  45 gat tca cag gtt cgt cta ggc aga tct tca gtt aat gat aat ctt cct       192
Asp Ser Gln Val Arg Leu Gly Arg Ser Ser Val Asn Asp Asn Leu Pro
    50                  55                  60 aat acc cgt cag ctt gac gag gag tgt gac atc aac gat ggg atg ata       240
Asn Thr Arg Gln Leu Asp Glu Glu Cys Asp Ile Asn Asp Gly Met Ile
65                  70                  75                  80 cga gtt cca ggt gat agg aca aat tat agt agt gat gcg tct gga gag       288
Arg Val Pro Gly Asp Arg Thr Asn Tyr Ser Ser Asp Ala Ser Gly Glu
                85                  90                  95 gtt gct gac cgt ggg ctt tct atc tct tct gcc cct caa agg gaa aat       336
Val Ala Asp Arg Gly Leu Ser Ile Ser Ser Ala Pro Gln Arg Glu Asn
            100                 105                 110 gta atc ctg cca aga ttg ggt cat gtc tgc atg gag gga cca ttt gtt       384
Val Ile Leu Pro Arg Leu Gly His Val Cys Met Glu Gly Pro Phe Val
        115                 120                 125 cag cgg caa aca tct gac aag gga ttc ccg aga ata att tcg tcg tta       432
Gln Arg Gln Thr Ser Asp Lys Gly Phe Pro Arg Ile Ile Ser Ser Leu
    130                 135                 140 tcc atg gat gcc cgg gat gat ttc tct gcc atc gag aat cag gta cgc       480
Ser Met Asp Ala Arg Asp Asp Phe Ser Ala Ile Glu Asn Gln Val Arg
145                 150                 155                 160 gag cta atc aat gat ttg gga agt gat tcc ata gaa ggt cag aga tca       528
Glu Leu Ile Asn Asp Leu Gly Ser Asp Ser Ile Glu Gly Gln Arg Ser
                165                 170                 175 gca aca tca gag att cgc ctt cta gct aag cac aac atg gag aac agg       576
Ala Thr Ser Glu Ile Arg Leu Leu Ala Lys His Asn Met Glu Asn Arg
            180                 185                 190 att gcc att gct aat tgt ggg gct ata aac ttg ctg gtt ggc ctt ctt       624
Ile Ala Ile Ala Asn Cys Gly Ala Ile Asn Leu Leu Val Gly Leu Leu
        195                 200                 205 cat tca ccc gat gcc aaa atc caa gaa aat gca gtg aca gcc ctc ctt       672
His Ser Pro Asp Ala Lys Ile Gln Glu Asn Ala Val Thr Ala Leu Leu
    210                 215                 220 aat ttg tca ctc agt gat atc aat aag att gcc atc gtg aat gca gat       720
Asn Leu Ser Leu Ser Asp Ile Asn Lys Ile Ala Ile Val Asn Ala Asp
225                 230                 235                 240 gct att gat cct ctc atc cat gtc ctg gaa aca ggg aac cct gaa gct       768
Ala Ile Asp Pro Leu Ile His Val Leu Glu Thr Gly Asn Pro Glu Ala
                245                 250                 255 aaa gag aat tca gca gct act ttg ttc agt ctc tca att att gaa gaa       816
Lys Glu Asn Ser Ala Ala Thr Leu Phe Ser Leu Ser Ile Ile Glu Glu
```

```
Lys Glu Asn Ser Ala Ala Thr Leu Phe Ser Leu Ser Ile Ile Glu Glu
                260                 265                 270 aac aga gtg agg ata ggg cga tct ggt gct gta aag cct ctc gtg gac    864
Asn Arg Val Arg Ile Gly Arg Ser Gly Ala Val Lys Pro Leu Val Asp
            275                 280                 285 ttg ctg gga aat ggg agc cca cga gga aag aaa gat gcg gtt act gca    912
Leu Leu Gly Asn Gly Ser Pro Arg Gly Lys Lys Asp Ala Val Thr Ala
        290                 295                 300 ttg ttt aat tta tcc ata ctt cat gag aac aag ggt cga att gtg caa    960
Leu Phe Asn Leu Ser Ile Leu His Glu Asn Lys Gly Arg Ile Val Gln
305                 310                 315                 320 gct gat gca ttg aag cac cta gtt gag ctt atg gac cct gct gct gga   1008
Ala Asp Ala Leu Lys His Leu Val Glu Leu Met Asp Pro Ala Ala Gly
                325                 330                 335 atg gtc gat aaa gct gta gct gtc ttg gca aat ctt gct acg ata cca   1056
Met Val Asp Lys Ala Val Ala Val Leu Ala Asn Leu Ala Thr Ile Pro
            340                 345                 350 gaa gga agg act gcg att ggg cag gcg cgt ggt att ccg gcc ctt gtt   1104
Glu Gly Arg Thr Ala Ile Gly Gln Ala Arg Gly Ile Pro Ala Leu Val
        355                 360                 365 gaa gtt gtc gaa ctg ggt tca gcg aaa gcg aag gaa aat gct acc gcg   1152
Glu Val Val Glu Leu Gly Ser Ala Lys Ala Lys Glu Asn Ala Thr Ala
370                 375                 380 gca ttg ctt cag cta tgc aca aac agc agc agg ttt tgc aac ata gtt   1200
Ala Leu Leu Gln Leu Cys Thr Asn Ser Ser Arg Phe Cys Asn Ile Val
385                 390                 395                 400 ctt caa gag gat gcc gtg ccc cct tta gtc gca ctg tca cag tca gga   1248
Leu Gln Glu Asp Ala Val Pro Pro Leu Val Ala Leu Ser Gln Ser Gly
                405                 410                 415 aca cca cgc gca aga gaa aag gcg cag gtt ctc ctc agc tat ttc cgc   1296
Thr Pro Arg Ala Arg Glu Lys Ala Gln Val Leu Leu Ser Tyr Phe Arg
            420                 425                 430 agc caa aga cat ggg aac tcg gga agg aga tga                       1329
Ser Gln Arg His Gly Asn Ser Gly Arg Arg
        435                 440

<210> SEQ ID NO 2
<211> LENGTH: 442
<212> TYPE: PRT
<213> ORGANISM: Hordeum vulgare

<400> SEQUENCE: 2

Met Gln Met Ala Leu Leu Ala Arg Leu Ser Leu Ala Ser Ser Glu Gly
1               5                   10                  15

Arg Glu Ser Ser Leu Glu Glu Arg His Ala Gly Ser Asp Glu Gln Thr
            20                  25                  30

Ser Glu Gln Ser Thr Lys Glu Ala Phe Gln Ala Ser His Phe Asp Ser
        35                  40                  45

Asp Ser Gln Val Arg Leu Gly Arg Ser Val Asn Asp Asn Leu Pro
    50                  55                  60

Asn Thr Arg Gln Leu Asp Glu Glu Cys Asp Ile Asn Asp Gly Met Ile
65                  70                  75                  80

Arg Val Pro Gly Asp Arg Thr Asn Tyr Ser Ser Asp Ala Ser Gly Glu
                85                  90                  95

Val Ala Asp Arg Gly Leu Ser Ile Ser Ser Ala Pro Gln Arg Glu Asn
            100                 105                 110

Val Ile Leu Pro Arg Leu Gly His Val Cys Met Glu Gly Pro Phe Val
        115                 120                 125

Gln Arg Gln Thr Ser Asp Lys Gly Phe Pro Arg Ile Ile Ser Ser Leu
```

```
                130                 135                 140
Ser Met Asp Ala Arg Asp Phe Ser Ala Ile Glu Asn Gln Val Arg
145                 150                 155                 160

Glu Leu Ile Asn Asp Leu Gly Ser Asp Ser Ile Glu Gly Gln Arg Ser
                165                 170                 175

Ala Thr Ser Glu Ile Arg Leu Leu Ala Lys His Asn Met Glu Asn Arg
            180                 185                 190

Ile Ala Ile Ala Asn Cys Gly Ala Ile Asn Leu Leu Val Gly Leu Leu
        195                 200                 205

His Ser Pro Asp Ala Lys Ile Gln Glu Asn Ala Val Thr Ala Leu Leu
    210                 215                 220

Asn Leu Ser Leu Ser Asp Ile Asn Lys Ile Ala Ile Val Asn Ala Asp
225                 230                 235                 240

Ala Ile Asp Pro Leu Ile His Val Leu Glu Thr Gly Asn Pro Glu Ala
                245                 250                 255

Lys Glu Asn Ser Ala Ala Thr Leu Phe Ser Leu Ser Ile Ile Glu Glu
            260                 265                 270

Asn Arg Val Arg Ile Gly Arg Ser Gly Ala Val Lys Pro Leu Val Asp
        275                 280                 285

Leu Leu Gly Asn Gly Ser Pro Arg Gly Lys Lys Asp Ala Val Thr Ala
    290                 295                 300

Leu Phe Asn Leu Ser Ile His Glu Asn Lys Gly Arg Ile Val Gln
305                 310                 315                 320

Ala Asp Ala Leu Lys His Leu Val Glu Leu Met Asp Pro Ala Ala Gly
                325                 330                 335

Met Val Asp Lys Ala Val Ala Val Leu Ala Asn Leu Ala Thr Ile Pro
            340                 345                 350

Glu Gly Arg Thr Ala Ile Gly Gln Ala Arg Gly Ile Pro Ala Leu Val
        355                 360                 365

Glu Val Val Glu Leu Gly Ser Ala Lys Ala Lys Glu Asn Ala Thr Ala
    370                 375                 380

Ala Leu Leu Gln Leu Cys Thr Asn Ser Ser Arg Phe Cys Asn Ile Val
385                 390                 395                 400

Leu Gln Glu Asp Ala Val Pro Pro Leu Val Ala Leu Ser Gln Ser Gly
                405                 410                 415

Thr Pro Arg Ala Arg Glu Lys Ala Gln Val Leu Leu Ser Tyr Phe Arg
            420                 425                 430

Ser Gln Arg His Gly Asn Ser Gly Arg Arg
        435                 440
```

<210> SEQ ID NO 3
<211> LENGTH: 2475
<212> TYPE: DNA
<213> ORGANISM: Oryza sativa
<220> FEATURE:
<221> NAME/KEY: CDS
<222> LOCATION: (1)..(2475)

<400> SEQUENCE: 3

```
atg gaa aat ttc tcc ccg aga acc ctg ctc aat agt atc ttg cgt atc      48
Met Glu Asn Phe Ser Pro Arg Thr Leu Leu Asn Ser Ile Leu Arg Ile
1               5                   10                  15 act gtc tta acc tcc gat ggc tct act gca agg ccc aag ccc att cag     96
Thr Val Leu Thr Ser Asp Gly Ser Thr Ala Arg Pro Lys Pro Ile Gln
            20                  25                  30 aag tac tgc caa aat gtg tgt gat atc tca agc att gtg agc cct ctc    144
Lys Tyr Cys Gln Asn Val Cys Asp Ile Ser Ser Ile Val Ser Pro Leu
```

```
                 35                  40                  45
ata gag gat cta tgt gag tct cct gaa gag caa ctc aat gag gtg tta      192
Ile Glu Asp Leu Cys Glu Ser Pro Glu Glu Gln Leu Asn Glu Val Leu
 50                  55                  60 agg gag ctt ggc act gct att aac aga gct tca ggg ctt att ggg aac      240
Arg Glu Leu Gly Thr Ala Ile Asn Arg Ala Ser Gly Leu Ile Gly Asn
 65                  70                  75                  80 tgg caa cag aca acc agc aaa ata tat ttt ata tgg cag att gaa tca      288
Trp Gln Gln Thr Thr Ser Lys Ile Tyr Phe Ile Trp Gln Ile Glu Ser
                     85                  90                  95 gta atc tca gat atc cag gga tgt tct cta cag ctg tgc cag ctt gtt      336
Val Ile Ser Asp Ile Gln Gly Cys Ser Leu Gln Leu Cys Gln Leu Val
                100                 105                 110 aac tct cta tta cct tct ttg act ggc cgt gca tgc aca tgt att gag      384
Asn Ser Leu Leu Pro Ser Leu Thr Gly Arg Ala Cys Thr Cys Ile Glu
            115                 120                 125 aaa ctc caa gac ata aat tat gaa aac atg ttt gat ctg gta aag gag      432
Lys Leu Gln Asp Ile Asn Tyr Glu Asn Met Phe Asp Leu Val Lys Glu
130                 135                 140 tct tca ttg gag cta gtt gag acg gac aca aca agt cct gag aat ctg      480
Ser Ser Leu Glu Leu Val Glu Thr Asp Thr Thr Ser Pro Glu Asn Leu
145                 150                 155                 160 tcg aga cta tct agt tca ttg agt ttg tca act aac ctg gaa ttt tac      528
Ser Arg Leu Ser Ser Ser Leu Ser Leu Ser Thr Asn Leu Glu Phe Tyr
                165                 170                 175 atg gaa gct gtt tcc ctt gag aat ctc aga gca agg gca atg cgg agt      576
Met Glu Ala Val Ser Leu Glu Asn Leu Arg Ala Arg Ala Met Arg Ser
                180                 185                 190 gag aac cgt gaa gaa atg gat ctg gct gac aag atg atc ccc ctg gtc      624
Glu Asn Arg Glu Glu Met Asp Leu Ala Asp Lys Met Ile Pro Leu Val
            195                 200                 205 aac tat atg cat gac cac ctt ctg agg gaa aca caa ctg ctt agc atc      672
Asn Tyr Met His Asp His Leu Leu Arg Glu Thr Gln Leu Leu Ser Ile
210                 215                 220 aat ggg gtg ccc att cct gca gat ttt tgc tgc ccg ctg tcc cta gag      720
Asn Gly Val Pro Ile Pro Ala Asp Phe Cys Cys Pro Leu Ser Leu Glu
225                 230                 235                 240 ctg atg tca gat cct gtt att gta gca tct ggt cag aca tat gag cgg      768
Leu Met Ser Asp Pro Val Ile Val Ala Ser Gly Gln Thr Tyr Glu Arg
                245                 250                 255 gtt tat atc aag tta tgg ctt gat gag ggt ttt act atc tgc ccg aag      816
Val Tyr Ile Lys Leu Trp Leu Asp Glu Gly Phe Thr Ile Cys Pro Lys
                260                 265                 270 aca cgc caa aga ctt ggt cac tcc aat tta att cca aat tac acc gtg      864
Thr Arg Gln Arg Leu Gly His Ser Asn Leu Ile Pro Asn Tyr Thr Val
            275                 280                 285 aaa gct ttg ata gct aat tgg tgc gaa tca cac aac att agg ctt cct      912
Lys Ala Leu Ile Ala Asn Trp Cys Glu Ser His Asn Ile Arg Leu Pro
290                 295                 300 gat cct atg aaa tcc ttg aaa ttg aac ttc cct ttg gct gcg tct gct      960
Asp Pro Met Lys Ser Leu Lys Leu Asn Phe Pro Leu Ala Ala Ser Ala
305                 310                 315                 320 ctc cag gat tcg agc acc aca gga agc agc cct cta cat cct act gtc     1008
Leu Gln Asp Ser Ser Thr Thr Gly Ser Ser Pro Leu His Pro Thr Val
                325                 330                 335 gct gct aag ggt aat att cct ggg tcc ccg gaa gct gac ctt tat atg     1056
Ala Ala Lys Gly Asn Ile Pro Gly Ser Pro Glu Ala Asp Leu Tyr Met
                340                 345                 350 aga agc ttg aat aga gca tct cct cca cac agt gta gtc cat cag aat     1104
Arg Ser Leu Asn Arg Ala Ser Pro Pro His Ser Val Val His Gln Asn
```

```
                    355                 360                 365
tct cat gcg cat gtg aac cgt gct ggt cat gaa gcc tcc att aag caa    1152
Ser His Ala His Val Asn Arg Ala Gly His Glu Ala Ser Ile Lys Gln
    370                 375                 380 tct tca gaa aat gct aat ggt tct gca tca gat gtt tca agg tta tct    1200
Ser Ser Glu Asn Ala Asn Gly Ser Ala Ser Asp Val Ser Arg Leu Ser
385                 390                 395                 400 ctt gca ggt tct gaa aca aga gag tct agt ctg gaa gaa aga aat gct    1248
Leu Ala Gly Ser Glu Thr Arg Glu Ser Ser Leu Glu Glu Arg Asn Ala
                405                 410                 415 ggt tct atc ggt caa act tca gaa cag tca att gag gaa gca ttt caa    1296
Gly Ser Ile Gly Gln Thr Ser Glu Gln Ser Ile Glu Glu Ala Phe Gln
            420                 425                 430 gca tct aat ttg gac agg gat tca cat gac cat gtg ggt agt tct tcg    1344
Ala Ser Asn Leu Asp Arg Asp Ser His Asp His Val Gly Ser Ser Ser
        435                 440                 445 gtg aat ggt agc ctt cca aat agc ggt caa ctt gat gca gaa tgt gac    1392
Val Asn Gly Ser Leu Pro Asn Ser Gly Gln Leu Asp Ala Glu Cys Asp
    450                 455                 460 aat ggg cca agc gaa agg aca aat tac agt agt gat gca tct gga gaa    1440
Asn Gly Pro Ser Glu Arg Thr Asn Tyr Ser Ser Asp Ala Ser Gly Glu
465                 470                 475                 480 gtt aca gat ggg cct tca gca tct tct gct cct cag agg gag cat cta    1488
Val Thr Asp Gly Pro Ser Ala Ser Ser Ala Pro Gln Arg Glu His Leu
                485                 490                 495 atc cct tct aga ttg gct gat gtt cgt agt aga ggc caa ttt gtt cgg    1536
Ile Pro Ser Arg Leu Ala Asp Val Arg Ser Arg Gly Gln Phe Val Arg
            500                 505                 510 cga cca tct gaa agg ggt ttc ccc aga ata ata tct tcc tca tcc atg    1584
Arg Pro Ser Glu Arg Gly Phe Pro Arg Ile Ile Ser Ser Ser Ser Met
        515                 520                 525 gat aca cgg agt gat ctt tcc gcc atc gag aat cag gtc cgc aag tta    1632
Asp Thr Arg Ser Asp Leu Ser Ala Ile Glu Asn Gln Val Arg Lys Leu
    530                 535                 540 gtt gat gat tta aga agt gat tct gta gat gtt caa aga tca gcg aca    1680
Val Asp Asp Leu Arg Ser Asp Ser Val Asp Val Gln Arg Ser Ala Thr
545                 550                 555                 560 tca gat atc cgc ctt tta gct aag cac aac atg gag aac agg atc atc    1728
Ser Asp Ile Arg Leu Leu Ala Lys His Asn Met Glu Asn Arg Ile Ile
                565                 570                 575 att gca aac tgt gga gct ata aac ttg ctg gtt ggt ctt ctt cat tcg    1776
Ile Ala Asn Cys Gly Ala Ile Asn Leu Leu Val Gly Leu Leu His Ser
            580                 585                 590 cca gat tcc aaa acc caa gag cat gcc gtg aca gcc ctt ctg aat ttg    1824
Pro Asp Ser Lys Thr Gln Glu His Ala Val Thr Ala Leu Leu Asn Leu
        595                 600                 605 tca atc aat gat aat aat aag att gcc att gca aat gct gat gct gtt    1872
Ser Ile Asn Asp Asn Asn Lys Ile Ala Ile Ala Asn Ala Asp Ala Val
    610                 615                 620 gac ccc ctc atc cat gtc ctt gag act ggg aac cct gaa gcc aag gag    1920
Asp Pro Leu Ile His Val Leu Glu Thr Gly Asn Pro Glu Ala Lys Glu
625                 630                 635                 640 aat tca gcg gct aca tta ttc agt ctc tcg gtt att gaa gaa aac aaa    1968
Asn Ser Ala Ala Thr Leu Phe Ser Leu Ser Val Ile Glu Glu Asn Lys
                645                 650                 655 gtg agg att gga aga tcc ggt gcc atc aaa cct ctc gtc gac cta cta    2016
Val Arg Ile Gly Arg Ser Gly Ala Ile Lys Pro Leu Val Asp Leu Leu
            660                 665                 670 gga aat ggg acc cct cga gga aag aaa gat gca gct act gca ttg ttt    2064
Gly Asn Gly Thr Pro Arg Gly Lys Lys Asp Ala Ala Thr Ala Leu Phe
```

```
                        675                 680                 685
aat tta tcc ata tta cat gag aac aag gcg cgt att gtg cag gct gac       2112
Asn Leu Ser Ile Leu His Glu Asn Lys Ala Arg Ile Val Gln Ala Asp
690                 695                 700 gct gtg aag tac cta gtt gaa ctt atg gac cct gct gct gga atg gtt       2160
Ala Val Lys Tyr Leu Val Glu Leu Met Asp Pro Ala Ala Gly Met Val
705                 710                 715                 720 gac aaa gct gtg gct gtt ttg gca aac ctt gct acc ata cca gaa ggg       2208
Asp Lys Ala Val Ala Val Leu Ala Asn Leu Ala Thr Ile Pro Glu Gly
                725                 730                 735 agg aca gca att ggt caa gcg cgt ggt att cca gcc ctt gtt gaa gtt       2256
Arg Thr Ala Ile Gly Gln Ala Arg Gly Ile Pro Ala Leu Val Glu Val
                740                 745                 750 gtt gaa ctc ggt tca gca agg ggg aag gaa aat gcg gct gca gca ttg       2304
Val Glu Leu Gly Ser Ala Arg Gly Lys Glu Asn Ala Ala Ala Ala Leu
                755                 760                 765 ctt cag cta tgt aca aac agc agc aga ttt tgc agt ata gtt ctt caa       2352
Leu Gln Leu Cys Thr Asn Ser Ser Arg Phe Cys Ser Ile Val Leu Gln
        770                 775                 780 gag ggt gct gtg cct cct cta gtt gca ttg tca cag tca ggc acg cca       2400
Glu Gly Ala Val Pro Pro Leu Val Ala Leu Ser Gln Ser Gly Thr Pro
785                 790                 795                 800 cgg gca aga gag aag gca cag gct ctt ctc agc tac ttt cgc agc caa       2448
Arg Ala Arg Glu Lys Ala Gln Ala Leu Leu Ser Tyr Phe Arg Ser Gln
                805                 810                 815 agg cac ggg aat tca gca agg aga tga                                    2475
Arg His Gly Asn Ser Ala Arg Arg
                820

<210> SEQ ID NO 4
<211> LENGTH: 824
<212> TYPE: PRT
<213> ORGANISM: Oryza sativa

<400> SEQUENCE: 4

Met Glu Asn Phe Ser Pro Arg Thr Leu Leu Asn Ser Ile Leu Arg Ile
1               5                   10                  15

Thr Val Leu Thr Ser Asp Gly Ser Thr Ala Arg Pro Lys Pro Ile Gln
                20                  25                  30

Lys Tyr Cys Gln Asn Val Cys Asp Ile Ser Ser Ile Val Ser Pro Leu
            35                  40                  45

Ile Glu Asp Leu Cys Glu Ser Pro Glu Glu Gln Leu Asn Glu Val Leu
        50                  55                  60

Arg Glu Leu Gly Thr Ala Ile Asn Arg Ala Ser Gly Leu Ile Gly Asn
65                  70                  75                  80

Trp Gln Gln Thr Thr Ser Lys Ile Tyr Phe Ile Trp Gln Ile Glu Ser
                85                  90                  95

Val Ile Ser Asp Ile Gln Gly Cys Ser Leu Gln Leu Cys Gln Leu Val
            100                 105                 110

Asn Ser Leu Leu Pro Ser Leu Thr Gly Arg Ala Cys Thr Cys Ile Glu
        115                 120                 125

Lys Leu Gln Asp Ile Asn Tyr Glu Asn Met Phe Asp Leu Val Lys Glu
    130                 135                 140

Ser Ser Leu Glu Leu Val Glu Thr Asp Thr Thr Ser Pro Glu Asn Leu
145                 150                 155                 160

Ser Arg Leu Ser Ser Ser Leu Ser Leu Ser Thr Asn Leu Glu Phe Tyr
                165                 170                 175

Met Glu Ala Val Ser Leu Glu Asn Leu Arg Ala Arg Ala Met Arg Ser
```

```
                180                 185                 190
Glu Asn Arg Glu Glu Met Asp Leu Ala Asp Lys Met Ile Pro Leu Val
            195                 200                 205
Asn Tyr Met His Asp His Leu Leu Arg Glu Thr Gln Leu Leu Ser Ile
        210                 215                 220
Asn Gly Val Pro Ile Pro Ala Asp Phe Cys Cys Pro Leu Ser Leu Glu
225                 230                 235                 240
Leu Met Ser Asp Pro Val Ile Val Ala Ser Gly Gln Thr Tyr Glu Arg
                245                 250                 255
Val Tyr Ile Lys Leu Trp Leu Asp Glu Gly Phe Thr Ile Cys Pro Lys
            260                 265                 270
Thr Arg Gln Arg Leu Gly His Ser Asn Leu Ile Pro Asn Tyr Thr Val
        275                 280                 285
Lys Ala Leu Ile Ala Asn Trp Cys Glu Ser His Asn Ile Arg Leu Pro
290                 295                 300
Asp Pro Met Lys Ser Leu Lys Leu Asn Phe Pro Leu Ala Ala Ser Ala
305                 310                 315                 320
Leu Gln Asp Ser Ser Thr Thr Gly Ser Ser Pro Leu His Pro Thr Val
                325                 330                 335
Ala Ala Lys Gly Asn Ile Pro Gly Ser Pro Glu Ala Asp Leu Tyr Met
            340                 345                 350
Arg Ser Leu Asn Arg Ala Ser Pro His Ser Val His Gln Asn
        355                 360                 365
Ser His Ala His Val Asn Arg Ala Gly His Glu Ala Ser Ile Lys Gln
        370                 375                 380
Ser Ser Glu Asn Ala Asn Gly Ser Ala Ser Asp Val Ser Arg Leu Ser
385                 390                 395                 400
Leu Ala Gly Ser Glu Thr Arg Glu Ser Ser Leu Glu Glu Arg Asn Ala
                405                 410                 415
Gly Ser Ile Gly Gln Thr Ser Glu Gln Ser Ile Glu Glu Ala Phe Gln
            420                 425                 430
Ala Ser Asn Leu Asp Arg Asp Ser His Asp His Val Gly Ser Ser Ser
        435                 440                 445
Val Asn Gly Ser Leu Pro Asn Ser Gly Gln Leu Asp Ala Glu Cys Asp
450                 455                 460
Asn Gly Pro Ser Glu Arg Thr Asn Tyr Ser Ser Asp Ala Ser Gly Glu
465                 470                 475                 480
Val Thr Asp Gly Pro Ser Ala Ser Ser Ala Pro Gln Arg Glu His Leu
                485                 490                 495
Ile Pro Ser Arg Leu Ala Asp Val Arg Ser Arg Gly Gln Phe Val Arg
            500                 505                 510
Arg Pro Ser Glu Arg Gly Phe Pro Arg Ile Ile Ser Ser Ser Ser Met
        515                 520                 525
Asp Thr Arg Ser Asp Leu Ser Ala Ile Glu Asn Gln Val Arg Lys Leu
        530                 535                 540
Val Asp Asp Leu Arg Ser Asp Ser Val Asp Val Gln Arg Ser Ala Thr
545                 550                 555                 560
Ser Asp Ile Arg Leu Leu Ala Lys His Asn Met Glu Asn Arg Ile Ile
                565                 570                 575
Ile Ala Asn Cys Gly Ala Ile Asn Leu Leu Val Gly Leu Leu His Ser
            580                 585                 590
Pro Asp Ser Lys Thr Gln Glu His Ala Val Thr Ala Leu Leu Asn Leu
        595                 600                 605
```

```
Ser Ile Asn Asp Asn Asn Lys Ile Ala Ile Ala Asn Ala Asp Ala Val
            610                 615                 620

Asp Pro Leu Ile His Val Leu Glu Thr Gly Asn Pro Glu Ala Lys Glu
625                 630                 635                 640

Asn Ser Ala Ala Thr Leu Phe Ser Leu Ser Val Ile Glu Glu Asn Lys
                645                 650                 655

Val Arg Ile Gly Arg Ser Gly Ala Ile Lys Pro Leu Val Asp Leu Leu
            660                 665                 670

Gly Asn Gly Thr Pro Arg Gly Lys Lys Asp Ala Ala Thr Ala Leu Phe
        675                 680                 685

Asn Leu Ser Ile Leu His Glu Asn Lys Ala Arg Ile Val Gln Ala Asp
            690                 695                 700

Ala Val Lys Tyr Leu Val Glu Leu Met Asp Pro Ala Ala Gly Met Val
705                 710                 715                 720

Asp Lys Ala Val Ala Val Leu Ala Asn Leu Ala Thr Ile Pro Glu Gly
                725                 730                 735

Arg Thr Ala Ile Gly Gln Ala Arg Gly Ile Pro Ala Leu Val Glu Val
            740                 745                 750

Val Glu Leu Gly Ser Ala Arg Gly Lys Glu Asn Ala Ala Ala Ala Leu
        755                 760                 765

Leu Gln Leu Cys Thr Asn Ser Ser Arg Phe Cys Ser Ile Val Leu Gln
    770                 775                 780

Glu Gly Ala Val Pro Pro Leu Val Ala Leu Ser Gln Ser Gly Thr Pro
785                 790                 795                 800

Arg Ala Arg Glu Lys Ala Gln Ala Leu Leu Ser Tyr Phe Arg Ser Gln
                805                 810                 815

Arg His Gly Asn Ser Ala Arg Arg
            820

<210> SEQ ID NO 5
<211> LENGTH: 2370
<212> TYPE: DNA
<213> ORGANISM: Oryza sativa
<220> FEATURE:
<221> NAME/KEY: CDS
<222> LOCATION: (1)..(2370)

<400> SEQUENCE: 5 atg gcg ttt gtt tgt ggt ggt ggg caa gtg atg gat tca gtg tca ttg        48
Met Ala Phe Val Cys Gly Gly Gly Gln Val Met Asp Ser Val Ser Leu
1               5                   10                  15 tca cta ctc gat agt att tca aat ttc cgg gtg ctg tct tca agc aat        96
Ser Leu Leu Asp Ser Ile Ser Asn Phe Arg Val Leu Ser Ser Ser Asn
            20                  25                  30 gcc tcg aaa aca gag cta gtt aag aaa tat tgc caa acg atg gat ggc       144
Ala Ser Lys Thr Glu Leu Val Lys Lys Tyr Cys Gln Thr Met Asp Gly
        35                  40                  45 atc ctt gat cac ttg gag gtg gcc cta aac aga gct ttt cct cag att       192
Ile Leu Asp His Leu Glu Val Ala Leu Asn Arg Ala Phe Pro Gln Ile
    50                  55                  60 act cca gat ggt gaa cta agt aaa gtt att cag gct gat tca att att       240
Thr Pro Asp Gly Glu Leu Ser Lys Val Ile Gln Ala Asp Ser Ile Ile
65                  70                  75                  80 gcc aag atg cag ata tat gta ttc gaa tta tgc caa att gtc aat tct       288
Ala Lys Met Gln Ile Tyr Val Phe Glu Leu Cys Gln Ile Val Asn Ser
                85                  90                  95 ctc atg cag att gag tca atg cat ttg gag gat ctt gaa cac gat agc       336
Leu Met Gln Ile Glu Ser Met His Leu Glu Asp Leu Glu His Asp Ser
            100                 105                 110
```

| | |
|---|---|
| tgt gga aaa att tca gat gtc att agg gag gct tcc agg gct tta gca<br>Cys Gly Lys Ile Ser Asp Val Ile Arg Glu Ala Ser Arg Ala Leu Ala<br>              115                    120                    125 | 384 |
| ggg gaa gtt atg cca aat tca gag gaa ttt gga aag att caa act act<br>Gly Glu Val Met Pro Asn Ser Glu Glu Phe Gly Lys Ile Gln Thr Thr<br>130                    135                    140 | 432 |
| ttg agc tta tcc aca aat cag gag ttg ctg atg gaa tat gtt gca ctt<br>Leu Ser Leu Ser Thr Asn Gln Glu Leu Leu Met Glu Tyr Val Ala Leu<br>145                    150                    155                    160 | 480 |
| gtt aag gtt aaa aca aaa ggt aat cat gaa gat aac aaa gaa atg gat<br>Val Lys Val Lys Thr Lys Gly Asn His Glu Asp Asn Lys Glu Met Asp<br>              165                    170                    175 | 528 |
| gat att aac gat att gtt gaa tta gtc aac cat atg ctt gac aaa cat<br>Asp Ile Asn Asp Ile Val Glu Leu Val Asn His Met Leu Asp Lys His<br>                  180                    185                    190 | 576 |
| gtg gaa gaa aag caa aca cgt agc att aat gga gtg acc att cct gct<br>Val Glu Glu Lys Gln Thr Arg Ser Ile Asn Gly Val Thr Ile Pro Ala<br>              195                    200                    205 | 624 |
| gat ttt tgt tgt cct ctt tcc ctt gaa cta atg tcg gat cca gtg att<br>Asp Phe Cys Cys Pro Leu Ser Leu Glu Leu Met Ser Asp Pro Val Ile<br>210                    215                    220 | 672 |
| gtg gca tct ggt caa acg tat gag cat gtt ttt atc aga aaa tgg ttt<br>Val Ala Ser Gly Gln Thr Tyr Glu His Val Phe Ile Arg Lys Trp Phe<br>225                    230                    235                    240 | 720 |
| gat ctg gga tac aac att tgt cca aag aca cgc caa ata ttg gga cac<br>Asp Leu Gly Tyr Asn Ile Cys Pro Lys Thr Arg Gln Ile Leu Gly His<br>                      245                    250                    255 | 768 |
| acc aaa ttg att cct aac ttc act gtc aaa cag ttg att gaa aat tgg<br>Thr Lys Leu Ile Pro Asn Phe Thr Val Lys Gln Leu Ile Glu Asn Trp<br>                  260                    265                    270 | 816 |
| tgt gag gta cat ggt ata atg cta cca gat cct gtt aaa ctc ttg agt<br>Cys Glu Val His Gly Ile Met Leu Pro Asp Pro Val Lys Leu Leu Ser<br>              275                    280                    285 | 864 |
| ttg tgc ttc cct gtt tcc ctc aac atc aca gat gga agt gca agt gca<br>Leu Cys Phe Pro Val Ser Leu Asn Ile Thr Asp Gly Ser Ala Ser Ala<br>290                    295                    300 | 912 |
| gac aag tct gga tca cca gaa cac tgc caa ttg gta gct gca ttg cat<br>Asp Lys Ser Gly Ser Pro Glu His Cys Gln Leu Val Ala Ala Leu His<br>305                    310                    315                    320 | 960 |
| cca aaa gca cag tgc gca tcg gat gat agt cat cat tat aat ttg ata<br>Pro Lys Ala Gln Cys Ala Ser Asp Asp Ser His His Tyr Asn Leu Ile<br>                  325                    330                    335 | 1008 |
| cat gaa aac tct gat tca gat gat aga gtg tca tca ttt gga gac aca<br>His Glu Asn Ser Asp Ser Asp Asp Arg Val Ser Ser Phe Gly Asp Thr<br>                  340                    345                    350 | 1056 |
| gat gat tct gaa cct gat tct tta aga tta tca aca gaa act act gca<br>Asp Asp Ser Glu Pro Asp Ser Leu Arg Leu Ser Thr Glu Thr Thr Ala<br>              355                    360                    365 | 1104 |
| gca aac aaa tct cta ctt gat gaa aaa act gat cgt tct gat ggt ctt<br>Ala Asn Lys Ser Leu Leu Asp Glu Lys Thr Asp Arg Ser Asp Gly Leu<br>370                    375                    380 | 1152 |
| aag caa ttg aga gac aat ggt ttt caa gtt tct gat gag gaa cag tat<br>Lys Gln Leu Arg Asp Asn Gly Phe Gln Val Ser Asp Glu Glu Gln Tyr<br>385                    390                    395                    400 | 1200 |
| ctc gaa agg aat ggt aaa agt cat atc agc agc cat cat caa ctt gaa<br>Leu Glu Arg Asn Gly Lys Ser His Ile Ser Ser His His Gln Leu Glu<br>                      405                    410                    415 | 1248 |
| gtt gat gga gag aat gtc agg gta caa gca tca agt gac atc aat gca<br>Val Asp Gly Glu Asn Val Arg Val Gln Ala Ser Ser Asp Ile Asn Ala<br>              420                    425                    430 | 1296 |

| | | |
|---|---|---|
| tct gaa gtt atg caa gat gat ccg gtc acc aca tgt tca aag gta tca<br>Ser Glu Val Met Gln Asp Asp Pro Val Thr Thr Cys Ser Lys Val Ser<br>435                   440                   445 | 1344 |
| gat aac cct cct aga ttg ggt ggt gtt cgt tct cga aat cag cca aac<br>Asp Asn Pro Pro Arg Leu Gly Gly Val Arg Ser Arg Asn Gln Pro Asn<br>450                   455                   460 | 1392 |
| tgg tgg aga cag tct aat aaa act att cct agg atc gga ttg tca tct<br>Trp Trp Arg Gln Ser Asn Lys Thr Ile Pro Arg Ile Gly Leu Ser Ser<br>465                     470                   475                   480 | 1440 |
| tcg aca gat tca aaa cca gat ttt tct ggc aat gat gct aaa gtg cgt<br>Ser Thr Asp Ser Lys Pro Asp Phe Ser Gly Asn Asp Ala Lys Val Arg<br>                   485                   490                   495 | 1488 |
| aat ctt atc gag gaa ctg aaa agt gat tct gct gag gtc caa agg tca<br>Asn Leu Ile Glu Glu Leu Lys Ser Asp Ser Ala Glu Val Gln Arg Ser<br>500                   505                   510 | 1536 |
| gca aca gga gag ctc cgc att ctt tct aga cac agc ttg gag aat aga<br>Ala Thr Gly Glu Leu Arg Ile Leu Ser Arg His Ser Leu Glu Asn Arg<br>               515                   520                   525 | 1584 |
| att gcc atc gca aac tgc gga gca atc ccc ttc ttg gtg agt cta ctt<br>Ile Ala Ile Ala Asn Cys Gly Ala Ile Pro Phe Leu Val Ser Leu Leu<br>530                   535                   540 | 1632 |
| cat tct aca gac ccc agc aca caa gaa aat gct gtg aca att ctc ctg<br>His Ser Thr Asp Pro Ser Thr Gln Glu Asn Ala Val Thr Ile Leu Leu<br>545                     550                   555                   560 | 1680 |
| aat ttg tca ttg gat gac aat aac aag att gcc ata gca agt gct gag<br>Asn Leu Ser Leu Asp Asp Asn Asn Lys Ile Ala Ile Ala Ser Ala Glu<br>                   565                   570                   575 | 1728 |
| gcc att gag cct ctc atc ttc gtt ctt cag gtg gga aac ccc gaa gcg<br>Ala Ile Glu Pro Leu Ile Phe Val Leu Gln Val Gly Asn Pro Glu Ala<br>580                   585                   590 | 1776 |
| aaa gcc aac tca gct gca act tta ttc agc ctc tca gtc att gaa gag<br>Lys Ala Asn Ser Ala Ala Thr Leu Phe Ser Leu Ser Val Ile Glu Glu<br>595                   600                   605 | 1824 |
| aac aag atc aag att gga cgt tcc ggt gcc atc gaa cca tta gta gat<br>Asn Lys Ile Lys Ile Gly Arg Ser Gly Ala Ile Glu Pro Leu Val Asp<br>610                   615                   620 | 1872 |
| tta ctg gga gaa ggt acc ccg caa ggg aag aag gat gca gct act gca<br>Leu Leu Gly Glu Gly Thr Pro Gln Gly Lys Lys Asp Ala Ala Thr Ala<br>625                   630                   635                   640 | 1920 |
| ctc ttc aat ctg tcg ata ttt cat gaa cac aag acc cgc att gtt cag<br>Leu Phe Asn Leu Ser Ile Phe His Glu His Lys Thr Arg Ile Val Gln<br>                   645                   650                   655 | 1968 |
| gct ggg gct gtc aac cac ctg gtg gag ctg atg gat cca gct gct ggg<br>Ala Gly Ala Val Asn His Leu Val Glu Leu Met Asp Pro Ala Ala Gly<br>660                   665                   670 | 2016 |
| atg gtt gat aaa gct gtt gct gtt ctg gca aac ctt gcg act gtg cat<br>Met Val Asp Lys Ala Val Ala Val Leu Ala Asn Leu Ala Thr Val His<br>675                   680                   685 | 2064 |
| gat gga agg aat gcc att gct cag gca gga ggc atc cga gta ctg gtt<br>Asp Gly Arg Asn Ala Ile Ala Gln Ala Gly Gly Ile Arg Val Leu Val<br>                   690                   695                   700 | 2112 |
| gag gtt gtt gag ctg ggt tct gca cgt tca aag gag aat gcc gct gct<br>Glu Val Val Glu Leu Gly Ser Ala Arg Ser Lys Glu Asn Ala Ala Ala<br>705                   710                   715                   720 | 2160 |
| gcc ctg cta caa ctc tgc aca aac agt aac agg ttt tgc acc ctg gtt<br>Ala Leu Leu Gln Leu Cys Thr Asn Ser Asn Arg Phe Cys Thr Leu Val<br>                   725                   730                   735 | 2208 |
| ctt caa gaa ggc gtc gtg cca cct ttg gtt gca ttg tcg caa tca ggc<br>Leu Gln Glu Gly Val Val Pro Pro Leu Val Ala Leu Ser Gln Ser Gly<br>740                   745                   750 | 2256 |

-continued

```
aca gcc cgt gca aga gag aag gct cag gtt ctt cta agc tat ttt cgc    2304
Thr Ala Arg Ala Arg Glu Lys Ala Gln Val Leu Leu Ser Tyr Phe Arg
        755                 760                 765 aac cag cgc cac gtc agg gtt ggg aga ggg ctt agc ttg cta tta gag    2352
Asn Gln Arg His Val Arg Val Gly Arg Gly Leu Ser Leu Leu Leu Glu
    770                 775                 780 tta aaa cgg acc aca taa                                            2370
Leu Lys Arg Thr Thr
785

<210> SEQ ID NO 6
<211> LENGTH: 789
<212> TYPE: PRT
<213> ORGANISM: Oryza sativa

<400> SEQUENCE: 6

Met Ala Phe Val Cys Gly Gly Gln Val Met Asp Ser Val Ser Leu
1               5                   10                  15

Ser Leu Leu Asp Ser Ile Ser Asn Phe Arg Val Leu Ser Ser Ser Asn
                20                  25                  30

Ala Ser Lys Thr Glu Leu Val Lys Lys Tyr Cys Gln Thr Met Asp Gly
            35                  40                  45

Ile Leu Asp His Leu Glu Val Ala Leu Asn Arg Ala Phe Pro Gln Ile
        50                  55                  60

Thr Pro Asp Gly Glu Leu Ser Lys Val Ile Gln Ala Asp Ser Ile Ile
65                  70                  75                  80

Ala Lys Met Gln Ile Tyr Val Phe Glu Leu Cys Gln Ile Val Asn Ser
                85                  90                  95

Leu Met Gln Ile Glu Ser Met His Leu Glu Asp Leu Glu His Asp Ser
            100                 105                 110

Cys Gly Lys Ile Ser Asp Val Ile Arg Glu Ala Ser Arg Ala Leu Ala
        115                 120                 125

Gly Glu Val Met Pro Asn Ser Glu Glu Phe Gly Lys Ile Gln Thr Thr
    130                 135                 140

Leu Ser Leu Ser Thr Asn Gln Glu Leu Leu Met Glu Tyr Val Ala Leu
145                 150                 155                 160

Val Lys Val Lys Thr Lys Gly Asn His Glu Asp Asn Lys Glu Met Asp
                165                 170                 175

Asp Ile Asn Asp Ile Val Glu Leu Val Asn His Met Leu Asp Lys His
            180                 185                 190

Val Glu Glu Lys Gln Thr Arg Ser Ile Asn Gly Val Thr Ile Pro Ala
        195                 200                 205

Asp Phe Cys Cys Pro Leu Ser Leu Glu Leu Met Ser Asp Pro Val Ile
    210                 215                 220

Val Ala Ser Gly Gln Thr Tyr Glu His Val Phe Ile Arg Lys Trp Phe
225                 230                 235                 240

Asp Leu Gly Tyr Asn Ile Cys Pro Lys Thr Arg Gln Ile Leu Gly His
                245                 250                 255

Thr Lys Leu Ile Pro Asn Phe Thr Val Lys Gln Leu Ile Glu Asn Trp
            260                 265                 270

Cys Glu Val His Gly Ile Met Leu Pro Asp Pro Val Lys Leu Leu Ser
        275                 280                 285

Leu Cys Phe Pro Val Ser Leu Asn Ile Thr Asp Gly Ser Ala Ser Ala
    290                 295                 300

Asp Lys Ser Gly Ser Pro Glu His Cys Gln Leu Val Ala Ala Leu His
305                 310                 315                 320
```

```
Pro Lys Ala Gln Cys Ala Ser Asp Asp Ser His His Tyr Asn Leu Ile
            325                 330                 335
His Glu Asn Ser Asp Ser Asp Arg Val Ser Ser Phe Gly Asp Thr
        340                 345                 350
Asp Asp Ser Glu Pro Asp Ser Leu Arg Leu Ser Thr Glu Thr Thr Ala
    355                 360                 365
Ala Asn Lys Ser Leu Leu Asp Glu Lys Thr Asp Arg Ser Asp Gly Leu
370                 375                 380
Lys Gln Leu Arg Asp Asn Gly Phe Gln Val Ser Asp Glu Glu Gln Tyr
385                 390                 395                 400
Leu Glu Arg Asn Gly Lys Ser His Ile Ser Ser His His Gln Leu Glu
            405                 410                 415
Val Asp Gly Glu Asn Val Arg Val Gln Ala Ser Ser Asp Ile Asn Ala
        420                 425                 430
Ser Glu Val Met Gln Asp Asp Pro Val Thr Thr Cys Ser Lys Val Ser
    435                 440                 445
Asp Asn Pro Pro Arg Leu Gly Gly Val Arg Ser Arg Asn Gln Pro Asn
450                 455                 460
Trp Trp Arg Gln Ser Asn Lys Thr Ile Pro Arg Ile Gly Leu Ser Ser
465                 470                 475                 480
Ser Thr Asp Ser Lys Pro Asp Phe Ser Gly Asn Asp Ala Lys Val Arg
            485                 490                 495
Asn Leu Ile Glu Glu Leu Lys Ser Asp Ser Ala Glu Val Gln Arg Ser
        500                 505                 510
Ala Thr Gly Glu Leu Arg Ile Leu Ser Arg His Ser Leu Glu Asn Arg
    515                 520                 525
Ile Ala Ile Ala Asn Cys Gly Ala Ile Pro Phe Leu Val Ser Leu Leu
530                 535                 540
His Ser Thr Asp Pro Ser Thr Gln Glu Asn Ala Val Thr Ile Leu Leu
545                 550                 555                 560
Asn Leu Ser Leu Asp Asp Asn Asn Lys Ile Ala Ile Ala Ser Ala Glu
            565                 570                 575
Ala Ile Glu Pro Leu Ile Phe Val Leu Gln Val Gly Asn Pro Glu Ala
        580                 585                 590
Lys Ala Asn Ser Ala Ala Thr Leu Phe Ser Leu Ser Val Ile Glu Glu
    595                 600                 605
Asn Lys Ile Lys Ile Gly Arg Ser Gly Ala Ile Glu Pro Leu Val Asp
610                 615                 620
Leu Leu Gly Glu Gly Thr Pro Gln Gly Lys Lys Asp Ala Ala Thr Ala
625                 630                 635                 640
Leu Phe Asn Leu Ser Ile Phe His Glu His Lys Thr Arg Ile Val Gln
            645                 650                 655
Ala Gly Ala Val Asn His Leu Val Glu Leu Met Asp Pro Ala Ala Gly
        660                 665                 670
Met Val Asp Lys Ala Val Ala Val Leu Ala Asn Leu Ala Thr Val His
    675                 680                 685
Asp Gly Arg Asn Ala Ile Ala Gln Ala Gly Gly Ile Arg Val Leu Val
690                 695                 700
Glu Val Val Glu Leu Gly Ser Ala Arg Ser Lys Glu Asn Ala Ala Ala
705                 710                 715                 720
Ala Leu Leu Gln Leu Cys Thr Asn Ser Asn Arg Phe Cys Thr Leu Val
            725                 730                 735
Leu Gln Glu Gly Val Val Pro Pro Leu Val Ala Leu Ser Gln Ser Gly
```

```
                    740                 745                 750
Thr Ala Arg Ala Arg Glu Lys Ala Gln Val Leu Leu Ser Tyr Phe Arg
        755                 760                 765

Asn Gln Arg His Val Arg Val Gly Arg Gly Leu Ser Leu Leu Leu Glu
        770                 775                 780

Leu Lys Arg Thr Thr
785

<210> SEQ ID NO 7
<211> LENGTH: 2391
<212> TYPE: DNA
<213> ORGANISM: Oryza sativa
<220> FEATURE:
<221> NAME/KEY: CDS
<222> LOCATION: (1)..(2391)

<400> SEQUENCE: 7 atg gat tca gtg tca ttg tca cta ctc gat agt att tca aat ttc cgg      48
Met Asp Ser Val Ser Leu Ser Leu Leu Asp Ser Ile Ser Asn Phe Arg
1               5                   10                  15 gtg ctg tct tca agc aat gcc tcg aaa aca gag cta gtt aag aaa tat      96
Val Leu Ser Ser Ser Asn Ala Ser Lys Thr Glu Leu Val Lys Lys Tyr
            20                  25                  30 tgc caa acg atg gat ggc atc ctt gat cac ttg gag gtg gcc cta aac     144
Cys Gln Thr Met Asp Gly Ile Leu Asp His Leu Glu Val Ala Leu Asn
        35                  40                  45 aga gct ttt cct cag att act cca gat ggt gaa cta agt aaa gtg ctt     192
Arg Ala Phe Pro Gln Ile Thr Pro Asp Gly Glu Leu Ser Lys Val Leu
    50                  55                  60 gaa gaa ctt ggc gct acc atc aat gaa gcg act gag cta gtt gga ggc     240
Glu Glu Leu Gly Ala Thr Ile Asn Glu Ala Thr Glu Leu Val Gly Gly
65                  70                  75                  80 tgg aat caa atg atg agc aag att tat ttt gtt att cag gct gat tca     288
Trp Asn Gln Met Met Ser Lys Ile Tyr Phe Val Ile Gln Ala Asp Ser
                85                  90                  95 att att gcc aag atg cag ata tat gta ttc gaa tta tgc caa att gtc     336
Ile Ile Ala Lys Met Gln Ile Tyr Val Phe Glu Leu Cys Gln Ile Val
            100                 105                 110 aat tct ctc atg cag att gag tca atg cat ttg gag gat ctt gaa cac     384
Asn Ser Leu Met Gln Ile Glu Ser Met His Leu Glu Asp Leu Glu His
        115                 120                 125 gat agc tgt gga aaa att tca gat gtc att agg gag gct tcc agg gct     432
Asp Ser Cys Gly Lys Ile Ser Asp Val Ile Arg Glu Ala Ser Arg Ala
    130                 135                 140 tta gca ggg gaa gtt atg cca aat tca gag gaa ttt gga aag att caa     480
Leu Ala Gly Glu Val Met Pro Asn Ser Glu Glu Phe Gly Lys Ile Gln
145                 150                 155                 160 act act ttg agc tta tcc aca aat cag gag ttg ctg atg gaa tat gtt     528
Thr Thr Leu Ser Leu Ser Thr Asn Gln Glu Leu Leu Met Glu Tyr Val
                165                 170                 175 gca ctt gtt aag gtt aaa aca aaa ggt aat cat gaa gat aac aaa gaa     576
Ala Leu Val Lys Val Lys Thr Lys Gly Asn His Glu Asp Asn Lys Glu
            180                 185                 190 atg gat gat att aac gat att gtt gaa tta gtc aac cat atg ctt gac     624
Met Asp Asp Ile Asn Asp Ile Val Glu Leu Val Asn His Met Leu Asp
        195                 200                 205 aaa cat gtg gaa gaa aag caa aca cgt agc att aat gga gtg acc att     672
Lys His Val Glu Glu Lys Gln Thr Arg Ser Ile Asn Gly Val Thr Ile
    210                 215                 220 cct gct gat ttt tgt tgt cct ctt tcc ctt gaa cta atg tcg gat cca     720
Pro Ala Asp Phe Cys Cys Pro Leu Ser Leu Glu Leu Met Ser Asp Pro
```

|         |         |         |         |         |         |         |         |         |         |         |         |         |         |         |         |      |
|---------|---------|---------|---------|---------|---------|---------|---------|---------|---------|---------|---------|---------|---------|---------|---------|------|
|         |         |         |         | 225     |         |         |         | 230     |         |         |         | 235     |         |         | 240     |      |

```
gtg att gtg gca tct ggt caa acg tat gag cat gtt ttt atc aga aaa        768
Val Ile Val Ala Ser Gly Gln Thr Tyr Glu His Val Phe Ile Arg Lys
                    245                 250                 255 tgg ttt gat ctg gga tac aac att tgt cca aag aca cgc caa ata ttg        816
Trp Phe Asp Leu Gly Tyr Asn Ile Cys Pro Lys Thr Arg Gln Ile Leu
            260                 265                 270 gga cac acc aaa ttg att cct aac ttc act gtc aaa cag ttg att gaa        864
Gly His Thr Lys Leu Ile Pro Asn Phe Thr Val Lys Gln Leu Ile Glu
        275                 280                 285 aat tgg tgt gag gta cat ggt ata atg cta cca gat cct gtt aaa ctc        912
Asn Trp Cys Glu Val His Gly Ile Met Leu Pro Asp Pro Val Lys Leu
    290                 295                 300 ttg agt ttg tgc ttc cct gtt tcc ctc aac atc aca gat gga agt gca        960
Leu Ser Leu Cys Phe Pro Val Ser Leu Asn Ile Thr Asp Gly Ser Ala
305                 310                 315                 320 agt gca gac aag tct gga tca cca gaa cac tgc caa ttg gta gct gca       1008
Ser Ala Asp Lys Ser Gly Ser Pro Glu His Cys Gln Leu Val Ala Ala
                325                 330                 335 ttg cat cca aaa gca cag tgc gca tcg gat gat agt cat cat tat aat       1056
Leu His Pro Lys Ala Gln Cys Ala Ser Asp Asp Ser His His Tyr Asn
            340                 345                 350 ttg ata cat gaa aac tct gat tca gat gat aga gtg tca tca ttt gga       1104
Leu Ile His Glu Asn Ser Asp Ser Asp Asp Arg Val Ser Ser Phe Gly
        355                 360                 365 gac aca gat gat tct gaa cct gat tct tta aga tta tca aca gaa act       1152
Asp Thr Asp Asp Ser Glu Pro Asp Ser Leu Arg Leu Ser Thr Glu Thr
    370                 375                 380 act gca gca aac aaa tct cta ctt gat gaa aaa act gat cgt tct gat       1200
Thr Ala Ala Asn Lys Ser Leu Leu Asp Glu Lys Thr Asp Arg Ser Asp
385                 390                 395                 400 ggt ctt aag caa ttg aga gac aat ggt ttt caa gtt tct gat gag gaa       1248
Gly Leu Lys Gln Leu Arg Asp Asn Gly Phe Gln Val Ser Asp Glu Glu
                405                 410                 415 cag tat ctc gaa agg aat ggt aaa agt cat atc agc agc cat cat caa       1296
Gln Tyr Leu Glu Arg Asn Gly Lys Ser His Ile Ser Ser His His Gln
            420                 425                 430 ctt gaa gtt gat gga gag aat gtc agg gta caa gca tca agt gac atc       1344
Leu Glu Val Asp Gly Glu Asn Val Arg Val Gln Ala Ser Ser Asp Ile
        435                 440                 445 aat gca tct gaa gtt atg caa gat gat ccg gtc acc aca tgt tca aag       1392
Asn Ala Ser Glu Val Met Gln Asp Asp Pro Val Thr Thr Cys Ser Lys
    450                 455                 460 gta tca gat aac cct cct aga ttg ggt ggt gtt cgt tct cga aat cag       1440
Val Ser Asp Asn Pro Pro Arg Leu Gly Gly Val Arg Ser Arg Asn Gln
465                 470                 475                 480 cca aac tgg tgg aga cag tct aat aaa act att cct agg atc gga ttg       1488
Pro Asn Trp Trp Arg Gln Ser Asn Lys Thr Ile Pro Arg Ile Gly Leu
                485                 490                 495 tca tct tcg aca gat tca aaa cca gat ttt tct ggc aat gat gct aaa       1536
Ser Ser Ser Thr Asp Ser Lys Pro Asp Phe Ser Gly Asn Asp Ala Lys
            500                 505                 510 gtg cgt aat ctt atc gag gaa ctg aaa agt gat tct gct gag gtc caa       1584
Val Arg Asn Leu Ile Glu Glu Leu Lys Ser Asp Ser Ala Glu Val Gln
        515                 520                 525 agg tca gca aca gga gag ctc cgc att ctt tct aga cac agc ttg gag       1632
Arg Ser Ala Thr Gly Glu Leu Arg Ile Leu Ser Arg His Ser Leu Glu
    530                 535                 540 aat aga att gcc atc gca aac tgc gga gca atc ccc ttc ttg gtg agt       1680
Asn Arg Ile Ala Ile Ala Asn Cys Gly Ala Ile Pro Phe Leu Val Ser
```

|  |  |  |  |  |  |  |  |  |  |  |  |  |  |  |  |
|---|---|---|---|---|---|---|---|---|---|---|---|---|---|---|---|
| | | | | 545 | | | | 550 | | | | 555 | | | 560 |

```
cta ctt cat tct aca gac ccc agc aca caa gaa aat gct gtg aca att   1728
Leu Leu His Ser Thr Asp Pro Ser Thr Gln Glu Asn Ala Val Thr Ile
            565                 570                 575 ctc ctg aat ttg tca ttg gat gac aat aac aag att gcc ata gca agt   1776
Leu Leu Asn Leu Ser Leu Asp Asp Asn Asn Lys Ile Ala Ile Ala Ser
            580                 585                 590 gct gag gcc att gag cct ctc atc ttc gtt ctt cag gtg gga aac ccc   1824
Ala Glu Ala Ile Glu Pro Leu Ile Phe Val Leu Gln Val Gly Asn Pro
            595                 600                 605 gaa gcg aaa gcc aac tca gct gca act tta ttc agc ctc tca gtc att   1872
Glu Ala Lys Ala Asn Ser Ala Ala Thr Leu Phe Ser Leu Ser Val Ile
610                 615                 620 gaa gag aac aag atc aag att gga cgt tcc ggt gcc atc gaa cca tta   1920
Glu Glu Asn Lys Ile Lys Ile Gly Arg Ser Gly Ala Ile Glu Pro Leu
625                 630                 635                 640 gta gat tta ctg gga gaa ggt acc ccg caa ggg aag aag gat gca gct   1968
Val Asp Leu Leu Gly Glu Gly Thr Pro Gln Gly Lys Lys Asp Ala Ala
                645                 650                 655 act gca ctc ttc aat ctg tcg ata ttt cat gaa cac aag acc cgc att   2016
Thr Ala Leu Phe Asn Leu Ser Ile Phe His Glu His Lys Thr Arg Ile
            660                 665                 670 gtt cag gct ggg gct gtc aac cac ctg gtg gag ctg atg gat cca gct   2064
Val Gln Ala Gly Ala Val Asn His Leu Val Glu Leu Met Asp Pro Ala
            675                 680                 685 gct ggg atg gtt gat aaa gct gtt gct gtt ctg gca aac ctt gcg act   2112
Ala Gly Met Val Asp Lys Ala Val Ala Val Leu Ala Asn Leu Ala Thr
            690                 695                 700 gtg cat gat gga agg aat gcc att gct cag gca gga ggc atc cga gta   2160
Val His Asp Gly Arg Asn Ala Ile Ala Gln Ala Gly Gly Ile Arg Val
705                 710                 715                 720 ctg gtt gag gtt gtt gag ctg ggt tct gca cgt tca aag gag aat gcc   2208
Leu Val Glu Val Val Glu Leu Gly Ser Ala Arg Ser Lys Glu Asn Ala
                725                 730                 735 gct gct gcc ctg cta caa ctc tgc aca aac agt aac agg ttt tgc acc   2256
Ala Ala Ala Leu Leu Gln Leu Cys Thr Asn Ser Asn Arg Phe Cys Thr
            740                 745                 750 ctg gtt ctt caa gaa ggc gtc gtg cca cct ttg gtt gca ttg tcg caa   2304
Leu Val Leu Gln Glu Gly Val Val Pro Pro Leu Val Ala Leu Ser Gln
            755                 760                 765 tca ggc aca gcc cgt gca aga gag aag gct cag gtt ctt cta agc tat   2352
Ser Gly Thr Ala Arg Ala Arg Glu Lys Ala Gln Val Leu Leu Ser Tyr
            770                 775                 780 ttt cgc aac cag cgc cac gtc agg gtt ggg aga ggg taa                2391
Phe Arg Asn Gln Arg His Val Arg Val Gly Arg Gly
785                 790                 795
```

<210> SEQ ID NO 8
<211> LENGTH: 796
<212> TYPE: PRT
<213> ORGANISM: Oryza sativa

<400> SEQUENCE: 8

```
Met Asp Ser Val Ser Leu Ser Leu Leu Asp Ser Ile Ser Asn Phe Arg
1               5                   10                  15

Val Leu Ser Ser Ser Asn Ala Ser Lys Thr Glu Leu Val Lys Lys Tyr
            20                  25                  30

Cys Gln Thr Met Asp Gly Ile Leu Asp His Leu Glu Val Ala Leu Asn
        35                  40                  45

Arg Ala Phe Pro Gln Ile Thr Pro Asp Gly Glu Leu Ser Lys Val Leu
```

-continued

```
             50                  55                  60
Glu Glu Leu Gly Ala Thr Ile Asn Glu Ala Thr Glu Leu Val Gly Gly
 65                  70                  75                  80

Trp Asn Gln Met Met Ser Lys Ile Tyr Phe Val Ile Gln Ala Asp Ser
                 85                  90                  95

Ile Ile Ala Lys Met Gln Ile Tyr Val Phe Glu Leu Cys Gln Ile Val
            100                 105                 110

Asn Ser Leu Met Gln Ile Glu Ser Met His Leu Glu Asp Leu Glu His
        115                 120                 125

Asp Ser Cys Gly Lys Ile Ser Asp Val Ile Arg Glu Ala Ser Arg Ala
    130                 135                 140

Leu Ala Gly Glu Val Met Pro Asn Ser Glu Glu Phe Gly Lys Ile Gln
145                 150                 155                 160

Thr Thr Leu Ser Leu Ser Thr Asn Gln Glu Leu Leu Met Glu Tyr Val
                165                 170                 175

Ala Leu Val Lys Val Lys Thr Lys Gly Asn His Glu Asp Asn Lys Glu
            180                 185                 190

Met Asp Asp Ile Asn Asp Ile Val Glu Leu Val Asn His Met Leu Asp
        195                 200                 205

Lys His Val Glu Glu Lys Gln Thr Arg Ser Ile Asn Gly Val Thr Ile
    210                 215                 220

Pro Ala Asp Phe Cys Cys Pro Leu Ser Leu Glu Leu Met Ser Asp Pro
225                 230                 235                 240

Val Ile Val Ala Ser Gly Gln Thr Tyr Glu His Val Phe Ile Arg Lys
                245                 250                 255

Trp Phe Asp Leu Gly Tyr Asn Ile Cys Pro Lys Thr Arg Gln Ile Leu
            260                 265                 270

Gly His Thr Lys Leu Ile Pro Asn Phe Thr Val Lys Gln Leu Ile Glu
        275                 280                 285

Asn Trp Cys Glu Val His Gly Ile Met Leu Pro Asp Pro Val Lys Leu
    290                 295                 300

Leu Ser Leu Cys Phe Pro Val Ser Leu Asn Ile Thr Asp Gly Ser Ala
305                 310                 315                 320

Ser Ala Asp Lys Ser Gly Ser Pro Glu His Cys Gln Leu Val Ala Ala
                325                 330                 335

Leu His Pro Lys Ala Gln Cys Ala Ser Asp Asp Ser His His Tyr Asn
            340                 345                 350

Leu Ile His Glu Asn Ser Asp Ser Asp Asp Arg Val Ser Ser Phe Gly
        355                 360                 365

Asp Thr Asp Asp Ser Glu Pro Asp Ser Leu Arg Leu Ser Thr Glu Thr
    370                 375                 380

Thr Ala Ala Asn Lys Ser Leu Leu Asp Glu Lys Thr Asp Arg Ser Asp
385                 390                 395                 400

Gly Leu Lys Gln Leu Arg Asp Asn Gly Phe Gly Val Ser Asp Glu Glu
                405                 410                 415

Gln Tyr Leu Glu Arg Asn Gly Lys Ser His Ile Ser Ser His His Gln
            420                 425                 430

Leu Glu Val Asp Gly Glu Asn Val Arg Val Gln Ala Ser Ser Asp Ile
        435                 440                 445

Asn Ala Ser Glu Val Met Gln Asp Asp Pro Val Thr Thr Cys Ser Lys
    450                 455                 460

Val Ser Asp Asn Pro Pro Arg Leu Gly Gly Val Arg Ser Arg Asn Gln
465                 470                 475                 480
```

-continued

```
        Pro Asn Trp Trp Arg Gln Ser Asn Lys Thr Ile Pro Arg Ile Gly Leu
                        485                 490                 495

Ser Ser Ser Thr Asp Ser Lys Pro Asp Phe Ser Gly Asn Asp Ala Lys
                    500                 505                 510

Val Arg Asn Leu Ile Glu Glu Leu Lys Ser Asp Ser Ala Glu Val Gln
                515                 520                 525

Arg Ser Ala Thr Gly Glu Leu Arg Ile Leu Ser Arg His Ser Leu Glu
            530                 535                 540

Asn Arg Ile Ala Ile Ala Asn Cys Gly Ala Ile Pro Phe Leu Val Ser
        545                 550                 555                 560

Leu Leu His Ser Thr Asp Pro Ser Thr Gln Glu Asn Ala Val Thr Ile
                        565                 570                 575

Leu Leu Asn Leu Ser Leu Asp Asp Asn Asn Lys Ile Ala Ile Ala Ser
                    580                 585                 590

Ala Glu Ala Ile Glu Pro Leu Ile Phe Val Leu Gln Val Gly Asn Pro
                595                 600                 605

Glu Ala Lys Ala Asn Ser Ala Ala Thr Leu Phe Ser Leu Ser Val Ile
            610                 615                 620

Glu Glu Asn Lys Ile Lys Ile Gly Arg Ser Gly Ala Ile Glu Pro Leu
        625                 630                 635                 640

Val Asp Leu Leu Gly Glu Gly Thr Pro Gln Gly Lys Lys Asp Ala Ala
                        645                 650                 655

Thr Ala Leu Phe Asn Leu Ser Ile Phe His Glu His Lys Thr Arg Ile
                    660                 665                 670

Val Gln Ala Gly Ala Val Asn His Leu Val Glu Leu Met Asp Pro Ala
                675                 680                 685

Ala Gly Met Val Asp Lys Ala Val Ala Val Leu Ala Asn Leu Ala Thr
            690                 695                 700

Val His Asp Gly Arg Asn Ala Ile Ala Gln Ala Gly Gly Ile Arg Val
        705                 710                 715                 720

Leu Val Glu Val Val Glu Leu Gly Ser Ala Arg Ser Lys Glu Asn Ala
                        725                 730                 735

Ala Ala Ala Leu Leu Gln Leu Cys Thr Asn Ser Asn Arg Phe Cys Thr
                    740                 745                 750

Leu Val Leu Gln Glu Gly Val Val Pro Pro Leu Val Ala Leu Ser Gln
                755                 760                 765

Ser Gly Thr Ala Arg Ala Arg Glu Lys Ala Gln Val Leu Leu Ser Tyr
            770                 775                 780

Phe Arg Asn Gln Arg His Val Arg Val Gly Arg Gly
        785                 790                 795

<210> SEQ ID NO 9
<211> LENGTH: 1404
<212> TYPE: DNA
<213> ORGANISM: Oryza sativa
<220> FEATURE:
<221> NAME/KEY: CDS
<222> LOCATION: (1)..(1404)

<400> SEQUENCE: 9 atg gtg tcg cta gcc ggc tcc cag atc ccg tcg ccg ggg cag agt ccg     48
Met Val Ser Leu Ala Gly Ser Gln Ile Pro Ser Pro Gly Gln Ser Pro
1               5                   10                  15 tgc gcg gcg gcg cgg tcg cag cgc cgc ggc gcg ggg tac tcc atg cgg     96
Cys Ala Ala Ala Arg Ser Gln Arg Arg Gly Ala Gly Tyr Ser Met Arg
            20                  25                  30 acc atc cgg tcg gcg ctg ctg cag ccg gac tcc tgc ccg ggc tcg ccg    144
```

```
Thr Ile Arg Ser Ala Leu Leu Gln Pro Asp Ser Cys Pro Gly Ser Pro
        35                  40                  45 cat gtg gcg gcc gcg tac gac gcg gcg ggg gcg gac tcg gac atg gag      192
His Val Ala Ala Ala Tyr Asp Ala Ala Gly Ala Asp Ser Asp Met Glu
 50                  55                  60 aac ttg acg gac tcc gtg att gat ttc cat ctc agc gag ctg gcg gcc      240
Asn Leu Thr Asp Ser Val Ile Asp Phe His Leu Ser Glu Leu Ala Ala
 65                  70                  75                  80 acc gcg ggg ccc gcg cac ccc gcg gcg gtg gcc aag tcg tcg tcg gcc      288
Thr Ala Gly Pro Ala His Pro Ala Ala Val Ala Lys Ser Ser Ser Ala
                 85                  90                  95 aac gcg gcg gcc acg gag atg ctc gag ctc tcg cgg gac ttc agt gac      336
Asn Ala Ala Ala Thr Glu Met Leu Glu Leu Ser Arg Asp Phe Ser Asp
            100                 105                 110 tac tcg agc ttc aac tcg gat atc tcc ggc gag ctc gag cgg ctc gcg      384
Tyr Ser Ser Phe Asn Ser Asp Ile Ser Gly Glu Leu Glu Arg Leu Ala
        115                 120                 125 gcg gcg gcg gcg gcg gtg gtg acg ccc aga tcc gac gcg ccg cag gtg      432
Ala Ala Ala Ala Ala Val Val Thr Pro Arg Ser Asp Ala Pro Gln Val
130                 135                 140 ggc gcc gtg gat ctg aat gag ctt gag tcg atg gat ctg tcc gtc gag      480
Gly Ala Val Asp Leu Asn Glu Leu Glu Ser Met Asp Leu Ser Val Glu
145                 150                 155                 160 gcg gcg ccg ctg gag cgc gtg gag ccg ttc gtg ctg gcg tgc gtg cgg      528
Ala Ala Pro Leu Glu Arg Val Glu Pro Phe Val Leu Ala Cys Val Arg
                165                 170                 175 gcg ctg ggg ccc gac gcc gcg cca gac gcg cgg cgc acc gcg gcg gcg      576
Ala Leu Gly Pro Asp Ala Ala Pro Asp Ala Arg Arg Thr Ala Ala Ala
            180                 185                 190 agg ata agg ctg ctg gcg aag cac agg tcg gac atc cgc gag ctg atc      624
Arg Ile Arg Leu Leu Ala Lys His Arg Ser Asp Ile Arg Glu Leu Ile
        195                 200                 205 ggc gtg tcc ggc gcc atc ccg gcg ctg gtg ccg ctg ctg cgg agc acc      672
Gly Val Ser Gly Ala Ile Pro Ala Leu Val Pro Leu Leu Arg Ser Thr
210                 215                 220 gac ccg gtg gcg cag gag agc gcg gtg acg gcg ctg ctc aac ctc tcg      720
Asp Pro Val Ala Gln Glu Ser Ala Val Thr Ala Leu Leu Asn Leu Ser
225                 230                 235                 240 ctc gag gag cgg aac cgg tcg gcc atc acg gcg gcg ggg gcc atc aag      768
Leu Glu Glu Arg Asn Arg Ser Ala Ile Thr Ala Ala Gly Ala Ile Lys
                245                 250                 255 ccg ctc gtg tac gcg ctg cgg acg ggc acc gcg tcg gcc aag cag aac      816
Pro Leu Val Tyr Ala Leu Arg Thr Gly Thr Ala Ser Ala Lys Gln Asn
            260                 265                 270 gcc gcg tgc gcg ctg ctc agc ctc tcg ggc atc gag gag aac cgc gcc      864
Ala Ala Cys Ala Leu Leu Ser Leu Ser Gly Ile Glu Glu Asn Arg Ala
        275                 280                 285 acc atc ggc gcg tgc ggc gcc atc cct ccc ctc gtc gcg ctg ctc tcc      912
Thr Ile Gly Ala Cys Gly Ala Ile Pro Pro Leu Val Ala Leu Leu Ser
290                 295                 300 gcg ggc tcc acc cgc ggc aag aag gac gcg ctc acc acg ctc tac cgg      960
Ala Gly Ser Thr Arg Gly Lys Lys Asp Ala Leu Thr Thr Leu Tyr Arg
305                 310                 315                 320 ctc tgc tcg gcg cgc cgg aac aag gag cgc gcg gtc agc gcc ggc gcc     1008
Leu Cys Ser Ala Arg Arg Asn Lys Glu Arg Ala Val Ser Ala Gly Ala
                325                 330                 335 gtc gtg ccg ctc atc cac ctc gtc ggc gag cgt ggc agc ggg acg tcg     1056
Val Val Pro Leu Ile His Leu Val Gly Glu Arg Gly Ser Gly Thr Ser
            340                 345                 350 gag aag gca atg gtg gtc ctc gcc agc ctc gcg ggc atc gtc gag ggc     1104
```

```
                Glu Lys Ala Met Val Val Leu Ala Ser Leu Ala Gly Ile Val Glu Gly
                            355                 360                 365 cgc gac gcc gtg gtg gag gct ggc ggg ata ccg gcg ctt gtc gag acc          1152
Arg Asp Ala Val Val Glu Ala Gly Gly Ile Pro Ala Leu Val Glu Thr
            370                 375                 380 atc gag gac ggc ccg gcg agg gag agg gag ttc gcc gtg gtg gcg ctg          1200
Ile Glu Asp Gly Pro Ala Arg Glu Arg Glu Phe Ala Val Val Ala Leu
385                 390                 395                 400 ctg cag ctc tgc tcc gag tgc ccc cgc aac cgc gcg ctt ctt gtc cgt          1248
Leu Gln Leu Cys Ser Glu Cys Pro Arg Asn Arg Ala Leu Leu Val Arg
            405                 410                 415 gag ggc gcc atc cca ccg ctt gtc gcg ctc tcg cag tcc ggc tct gcc          1296
Glu Gly Ala Ile Pro Pro Leu Val Ala Leu Ser Gln Ser Gly Ser Ala
                420                 425                 430 cgt gcc aag cac aag gct gaa act ttg ctt ggg tat ctc cgc gag caa          1344
Arg Ala Lys His Lys Ala Glu Thr Leu Leu Gly Tyr Leu Arg Glu Gln
            435                 440                 445 cgg caa gga ggt ggt ggc tgc agg gtt gaa ccc gtg gca gct tcg agc          1392
Arg Gln Gly Gly Gly Gly Cys Arg Val Glu Pro Val Ala Ala Ser Ser
450                 455                 460 ttg gcc agg taa                                                           1404
Leu Ala Arg
465

<210> SEQ ID NO 10
<211> LENGTH: 467
<212> TYPE: PRT
<213> ORGANISM: Oryza sativa

<400> SEQUENCE: 10

Met Val Ser Leu Ala Gly Ser Gln Ile Pro Ser Pro Gly Gln Ser Pro
1               5                   10                  15

Cys Ala Ala Ala Arg Ser Gln Arg Arg Gly Ala Gly Tyr Ser Met Arg
            20                  25                  30

Thr Ile Arg Ser Ala Leu Leu Gln Pro Asp Ser Cys Pro Gly Ser Pro
        35                  40                  45

His Val Ala Ala Ala Tyr Asp Ala Ala Gly Ala Asp Ser Asp Met Glu
    50                  55                  60

Asn Leu Thr Asp Ser Val Ile Asp Phe His Leu Ser Glu Leu Ala Ala
65                  70                  75                  80

Thr Ala Gly Pro Ala His Pro Ala Ala Val Ala Lys Ser Ser Ser Ala
                85                  90                  95

Asn Ala Ala Ala Thr Glu Met Leu Glu Leu Ser Arg Asp Phe Ser Asp
            100                 105                 110

Tyr Ser Ser Phe Asn Ser Asp Ile Ser Gly Glu Leu Glu Arg Leu Ala
        115                 120                 125

Ala Ala Ala Ala Val Val Thr Pro Arg Ser Asp Ala Pro Gln Val
    130                 135                 140

Gly Ala Val Asp Leu Asn Glu Leu Glu Ser Met Asp Leu Ser Val Glu
145                 150                 155                 160

Ala Ala Pro Leu Glu Arg Val Glu Pro Phe Val Leu Ala Cys Val Arg
                165                 170                 175

Ala Leu Gly Pro Asp Ala Ala Pro Asp Ala Arg Arg Thr Ala Ala Ala
            180                 185                 190

Arg Ile Arg Leu Leu Ala Lys His Arg Ser Asp Ile Arg Glu Leu Ile
        195                 200                 205

Gly Val Ser Gly Ala Ile Pro Ala Leu Val Pro Leu Leu Arg Ser Thr
    210                 215                 220
```

```
Asp Pro Val Ala Gln Glu Ser Ala Val Thr Ala Leu Leu Asn Leu Ser
225                 230                 235                 240

Leu Glu Glu Arg Asn Arg Ser Ala Ile Thr Ala Gly Ala Ile Lys
            245                 250                 255

Pro Leu Val Tyr Ala Leu Arg Thr Gly Thr Ala Ser Ala Lys Gln Asn
            260                 265                 270

Ala Ala Cys Ala Leu Leu Ser Leu Ser Gly Ile Glu Glu Asn Arg Ala
        275                 280                 285

Thr Ile Gly Ala Cys Gly Ala Ile Pro Pro Leu Val Ala Leu Leu Ser
    290                 295                 300

Ala Gly Ser Thr Arg Gly Lys Lys Asp Ala Leu Thr Thr Leu Tyr Arg
305                 310                 315                 320

Leu Cys Ser Ala Arg Arg Asn Lys Glu Arg Ala Val Ser Ala Gly Ala
            325                 330                 335

Val Val Pro Leu Ile His Leu Val Gly Glu Arg Gly Ser Gly Thr Ser
            340                 345                 350

Glu Lys Ala Met Val Val Leu Ala Ser Leu Ala Gly Ile Val Glu Gly
        355                 360                 365

Arg Asp Ala Val Val Glu Ala Gly Gly Ile Pro Ala Leu Val Glu Thr
370                 375                 380

Ile Glu Asp Gly Pro Ala Arg Glu Arg Glu Phe Ala Val Val Ala Leu
385                 390                 395                 400

Leu Gln Leu Cys Ser Glu Cys Pro Arg Asn Arg Ala Leu Leu Val Arg
            405                 410                 415

Glu Gly Ala Ile Pro Pro Leu Val Ala Leu Ser Gln Ser Gly Ser Ala
            420                 425                 430

Arg Ala Lys His Lys Ala Glu Thr Leu Leu Gly Tyr Leu Arg Glu Gln
        435                 440                 445

Arg Gln Gly Gly Gly Gly Cys Arg Val Glu Pro Val Ala Ala Ser Ser
    450                 455                 460

Leu Ala Arg
465

<210> SEQ ID NO 11
<211> LENGTH: 2373
<212> TYPE: DNA
<213> ORGANISM: Nicotiana tabacum
<220> FEATURE:
<221> NAME/KEY: CDS
<222> LOCATION: (1)..(2373)

<400> SEQUENCE: 11 atg gag ata tca ttg tta aaa gtg ctt ctc aac aat atc tcc tgt ttt      48
Met Glu Ile Ser Leu Leu Lys Val Leu Leu Asn Asn Ile Ser Cys Phe
1               5                   10                  15 tcc cat tta tca tca agt gat cac ata agt ggt gaa ctg gtt cgt aga      96
Ser His Leu Ser Ser Ser Asp His Ile Ser Gly Glu Leu Val Arg Arg
            20                  25                  30 tat tat tgt aag att gag gat ata ctg aag ctt gta aag ccg att ctt     144
Tyr Tyr Cys Lys Ile Glu Asp Ile Leu Lys Leu Val Lys Pro Ile Leu
        35                  40                  45 gac gcc atc gtt gat gtt gaa gct gct tct ggt gag ctg ctt ctg aaa     192
Asp Ala Ile Val Asp Val Glu Ala Ala Ser Gly Glu Leu Leu Leu Lys
    50                  55                  60 gcg ttt gct ggg ctg gct caa tgt gtt gat gaa ctg agg gag cta ttc     240
Ala Phe Ala Gly Leu Ala Gln Cys Val Asp Glu Leu Arg Glu Leu Phe
65                  70                  75                  80
```

```
gaa acc ttg gaa ccg ctg tgc agt aaa gtt tat ttt gtc ctg caa gct      288
Glu Thr Leu Glu Pro Leu Cys Ser Lys Val Tyr Phe Val Leu Gln Ala
            85                  90                  95 gaa cca ttg att ggg aaa att cga tca tgt agc ctg gaa ata ctt gag      336
Glu Pro Leu Ile Gly Lys Ile Arg Ser Cys Ser Leu Glu Ile Leu Glu
        100                 105                 110 ctt ctt aaa tct tct cat aaa agc ctt cca gct gat gta act ttg aca      384
Leu Leu Lys Ser Ser His Lys Ser Leu Pro Ala Asp Val Thr Leu Thr
    115                 120                 125 act ctc gag ctc tat ata ctg aaa att aag tat gta gat tat gaa atg      432
Thr Leu Glu Leu Tyr Ile Leu Lys Ile Lys Tyr Val Asp Tyr Glu Met
130                 135                 140 ata tca gtg aca atc aca aag gtt att aaa gct caa gtg gaa ggc ttg      480
Ile Ser Val Thr Ile Thr Lys Val Ile Lys Ala Gln Val Glu Gly Leu
145                 150                 155                 160 gga acc agc tca gat agc ttt gcc aaa att gct gat tgc cta agc ttg      528
Gly Thr Ser Ser Asp Ser Phe Ala Lys Ile Ala Asp Cys Leu Ser Leu
                165                 170                 175 aac tca aac caa gag ctt ttg att gag ctt gtg gcc ctt gaa aaa ttg      576
Asn Ser Asn Gln Glu Leu Leu Ile Glu Leu Val Ala Leu Glu Lys Leu
            180                 185                 190 aaa gag aat gct gaa caa gct gaa aag agt gaa gtt gtt gaa tat att      624
Lys Glu Asn Ala Glu Gln Ala Glu Lys Ser Glu Val Val Glu Tyr Ile
        195                 200                 205 gag caa atg ata act ctt gtt tct cat atg cac gat tgc ttt gtt act      672
Glu Gln Met Ile Thr Leu Val Ser His Met His Asp Cys Phe Val Thr
    210                 215                 220 aca aaa cag tcc cag agt tgt acc gct gtg cca ata cct cct gat ttt      720
Thr Lys Gln Ser Gln Ser Cys Thr Ala Val Pro Ile Pro Pro Asp Phe
225                 230                 235                 240 tgc tgt cct ctt tca ctt gag ttg atg act gac cct gta att gtc gct      768
Cys Cys Pro Leu Ser Leu Glu Leu Met Thr Asp Pro Val Ile Val Ala
                245                 250                 255 tct ggt caa acc tat gag agg gct ttt att agg aga tgg att gat ctt      816
Ser Gly Gln Thr Tyr Glu Arg Ala Phe Ile Arg Arg Trp Ile Asp Leu
            260                 265                 270 ggc ctc act gtt tgc ccc aaa aca cgg caa act ctg gga cat aca aat      864
Gly Leu Thr Val Cys Pro Lys Thr Arg Gln Thr Leu Gly His Thr Asn
        275                 280                 285 ctc att cct aat tac act gtt aag gca ctg atc gca aac tgg tgc gaa      912
Leu Ile Pro Asn Tyr Thr Val Lys Ala Leu Ile Ala Asn Trp Cys Glu
    290                 295                 300 ata aac aat gta aag ctg cct gat ccc atg aag tct ttg agc ttg aac      960
Ile Asn Asn Val Lys Leu Pro Asp Pro Met Lys Ser Leu Ser Leu Asn
305                 310                 315                 320 cag cca tct ttg tca cca gac tcc acg caa tct tca ggt tct ccg aga     1008
Gln Pro Ser Leu Ser Pro Asp Ser Thr Gln Ser Ser Gly Ser Pro Arg
                325                 330                 335 aag agt ttg att tca tca act gta agc caa aga gaa gaa tca tct cca     1056
Lys Ser Leu Ile Ser Ser Thr Val Ser Gln Arg Glu Glu Ser Ser Pro
            340                 345                 350 tct cat ccc cgt tcc tct tca gag gaa tct tta cct gga gtt ggt ggt     1104
Ser His Pro Arg Ser Ser Ser Glu Glu Ser Leu Pro Gly Val Gly Gly
        355                 360                 365 aat att ctt gct ttt gat gtt gaa agg atg cgt att aag agt gaa gac     1152
Asn Ile Leu Ala Phe Asp Val Glu Arg Met Arg Ile Lys Ser Glu Asp
    370                 375                 380 cgg atg gcc cac tcc gga gag ata agt tca cat ggt cat agt aca tta     1200
Arg Met Ala His Ser Gly Glu Ile Ser Ser His Gly His Ser Thr Leu
385                 390                 395                 400
```

```
gta gct gat gac cag ttc cct ctg ggt cat aat cga aca acc tcg gca      1248
Val Ala Asp Asp Gln Phe Pro Leu Gly His Asn Arg Thr Thr Ser Ala
            405                 410                 415 cct agc acg ctt tct aat tca aac ttt tcc ccg gta att cct ggt gat      1296
Pro Ser Thr Leu Ser Asn Ser Asn Phe Ser Pro Val Ile Pro Gly Asp
        420                 425                 430 gga aac aag ttg tca gaa gat tct tct gtt gct tca ggg gat gtt ggg      1344
Gly Asn Lys Leu Ser Glu Asp Ser Ser Val Ala Ser Gly Asp Val Gly
            435                 440                 445 ttg gat tcc aag cct gct gct tct gtc ctt cca aag gag cca gaa ttt      1392
Leu Asp Ser Lys Pro Ala Ala Ser Val Leu Pro Lys Glu Pro Glu Phe
        450                 455                 460 cca tat aca cca gag atg aga cct cgt aat caa ctg atc tgg cgc aga      1440
Pro Tyr Thr Pro Glu Met Arg Pro Arg Asn Gln Leu Ile Trp Arg Arg
465                 470                 475                 480 cca acc gag agg ttt cca aga ata gtt tct tcc gct aca gtt gaa aga      1488
Pro Thr Glu Arg Phe Pro Arg Ile Val Ser Ser Ala Thr Val Glu Arg
                485                 490                 495 agg gct gat ctt tca gaa gtt gag gag caa gta aaa aag ttg att gag      1536
Arg Ala Asp Leu Ser Glu Val Glu Glu Gln Val Lys Lys Leu Ile Glu
            500                 505                 510 gag ttg aag agc act tcc ctt gat atg cag aga aat gct aca gct gaa      1584
Glu Leu Lys Ser Thr Ser Leu Asp Met Gln Arg Asn Ala Thr Ala Glu
        515                 520                 525 ctc cgg tta ctt gcc aag cat aat atg gat aac cgt atg gta att gca      1632
Leu Arg Leu Leu Ala Lys His Asn Met Asp Asn Arg Met Val Ile Ala
            530                 535                 540 aat tgt ggc gct atc agc tcg ttg gtt aac cta ctt cac tca aaa gac      1680
Asn Cys Gly Ala Ile Ser Ser Leu Val Asn Leu Leu His Ser Lys Asp
545                 550                 555                 560 atg aaa gta cag gaa gat gct gtt act gca ctt ctc aac ttg tca att      1728
Met Lys Val Gln Glu Asp Ala Val Thr Ala Leu Leu Asn Leu Ser Ile
                565                 570                 575 aat gac aac aac aag tgt gcc att gca aat gct gat gca atc gaa cct      1776
Asn Asp Asn Asn Lys Cys Ala Ile Ala Asn Ala Asp Ala Ile Glu Pro
            580                 585                 590 ctg att cat gtc ctc caa aca ggg agc gcc gag gcc aaa gaa aat tct      1824
Leu Ile His Val Leu Gln Thr Gly Ser Ala Glu Ala Lys Glu Asn Ser
        595                 600                 605 gct gct act ctt ttt agc ctt tcc gtg atg gag gaa aac aag atg aag      1872
Ala Ala Thr Leu Phe Ser Leu Ser Val Met Glu Glu Asn Lys Met Lys
            610                 615                 620 att ggg agg tct gga gca atc aaa cct ctt gtt gat tta ctg gga aat      1920
Ile Gly Arg Ser Gly Ala Ile Lys Pro Leu Val Asp Leu Leu Gly Asn
625                 630                 635                 640 gga act cca agg ggc aag aaa gat gca gcg aca gct tta ttt aac ttg      1968
Gly Thr Pro Arg Gly Lys Lys Asp Ala Ala Thr Ala Leu Phe Asn Leu
                645                 650                 655 tca ata ctt cat gag aac aag tct cgt ata ata cag gct ggt gcg gta      2016
Ser Ile Leu His Glu Asn Lys Ser Arg Ile Ile Gln Ala Gly Ala Val
            660                 665                 670 aag tat ctc gta gag ttg atg gac cct gct act ggg atg gtt gac aag      2064
Lys Tyr Leu Val Glu Leu Met Asp Pro Ala Thr Gly Met Val Asp Lys
        675                 680                 685 gct gtt gca gtt ttg tcc aac ctt gct acc att ccc gag gga cga gca      2112
Ala Val Ala Val Leu Ser Asn Leu Ala Thr Ile Pro Glu Gly Arg Ala
            690                 695                 700 gaa atc ggt cag gaa gga ggg att cct ctt ctt gtt gag gtt gtt gag      2160
Glu Ile Gly Gln Glu Gly Gly Ile Pro Leu Leu Val Glu Val Val Glu
705                 710                 715                 720
```

```
ctg ggc tcc gca agg ggt aag gag aat gca gca gct gct ctc ttg caa    2208
Leu Gly Ser Ala Arg Gly Lys Glu Asn Ala Ala Ala Ala Leu Leu Gln
            725                 730                 735 cta tgc act aac agt agc agg ttc tgc aac atg gtt ctc cag gaa gga    2256
Leu Cys Thr Asn Ser Ser Arg Phe Cys Asn Met Val Leu Gln Glu Gly
        740                 745                 750 gct gta cct cca tta gtg gca ttg tca cag tcc ggc acc cca aga gca    2304
Ala Val Pro Pro Leu Val Ala Leu Ser Gln Ser Gly Thr Pro Arg Ala
    755                 760                 765 aga gaa aag gct caa caa cta ctt agc tac ttc cga aat caa cgc cat    2352
Arg Glu Lys Ala Gln Gln Leu Leu Ser Tyr Phe Arg Asn Gln Arg His
770                 775                 780 ggt aat gca gga aga ggt tga                                        2373
Gly Asn Ala Gly Arg Gly
785                 790

<210> SEQ ID NO 12
<211> LENGTH: 790
<212> TYPE: PRT
<213> ORGANISM: Nicotiana tabacum

<400> SEQUENCE: 12

Met Glu Ile Ser Leu Leu Lys Val Leu Leu Asn Asn Ile Ser Cys Phe
1               5                   10                  15

Ser His Leu Ser Ser Ser Asp His Ile Ser Gly Glu Leu Val Arg Arg
            20                  25                  30

Tyr Tyr Cys Lys Ile Glu Asp Ile Leu Lys Leu Val Lys Pro Ile Leu
        35                  40                  45

Asp Ala Ile Val Asp Val Glu Ala Ala Ser Gly Glu Leu Leu Leu Lys
    50                  55                  60

Ala Phe Ala Gly Leu Ala Gln Cys Val Asp Glu Leu Arg Glu Leu Phe
65                  70                  75                  80

Glu Thr Leu Glu Pro Leu Cys Ser Lys Val Tyr Phe Val Leu Gln Ala
                85                  90                  95

Glu Pro Leu Ile Gly Lys Ile Arg Ser Cys Ser Leu Glu Ile Leu Glu
            100                 105                 110

Leu Leu Lys Ser Ser His Lys Ser Leu Pro Ala Asp Val Thr Leu Thr
        115                 120                 125

Thr Leu Glu Leu Tyr Ile Leu Lys Ile Lys Tyr Val Asp Tyr Glu Met
    130                 135                 140

Ile Ser Val Thr Ile Thr Lys Val Ile Lys Ala Gln Val Glu Gly Leu
145                 150                 155                 160

Gly Thr Ser Ser Asp Ser Phe Ala Lys Ile Ala Asp Cys Leu Ser Leu
                165                 170                 175

Asn Ser Asn Gln Glu Leu Leu Ile Glu Leu Val Ala Leu Glu Lys Leu
            180                 185                 190

Lys Glu Asn Ala Glu Gln Ala Glu Lys Ser Glu Val Val Glu Tyr Ile
        195                 200                 205

Glu Gln Met Ile Thr Leu Val Ser His Met His Asp Cys Phe Val Thr
    210                 215                 220

Thr Lys Gln Ser Gln Ser Cys Thr Ala Val Pro Ile Pro Pro Asp Phe
225                 230                 235                 240

Cys Cys Pro Leu Ser Leu Glu Leu Met Thr Asp Pro Val Ile Val Ala
                245                 250                 255

Ser Gly Gln Thr Tyr Glu Arg Ala Phe Ile Arg Arg Trp Ile Asp Leu
            260                 265                 270

Gly Leu Thr Val Cys Pro Lys Thr Arg Gln Thr Leu Gly His Thr Asn
```

-continued

```
            275                 280                 285
Leu Ile Pro Asn Tyr Thr Val Lys Ala Leu Ile Ala Asn Trp Cys Glu
290                 295                 300
Ile Asn Val Lys Leu Pro Asp Pro Met Lys Ser Leu Ser Leu Asn
305                 310                 315                 320
Gln Pro Ser Leu Ser Pro Asp Ser Thr Gln Ser Ser Gly Ser Pro Arg
                    325                 330                 335
Lys Ser Leu Ile Ser Ser Thr Val Ser Gln Arg Glu Glu Ser Ser Pro
                    340                 345                 350
Ser His Pro Arg Ser Ser Glu Glu Ser Leu Pro Gly Val Gly Gly
                    355                 360                 365
Asn Ile Leu Ala Phe Asp Val Glu Arg Met Arg Ile Lys Ser Glu Asp
370                 375                 380
Arg Met Ala His Ser Gly Glu Ile Ser Ser His Gly His Ser Thr Leu
385                 390                 395                 400
Val Ala Asp Asp Gln Phe Pro Leu Gly His Asn Arg Thr Thr Ser Ala
                    405                 410                 415
Pro Ser Thr Leu Ser Asn Ser Asn Phe Ser Pro Val Ile Pro Gly Asp
                    420                 425                 430
Gly Asn Lys Leu Ser Glu Asp Ser Ser Val Ala Ser Gly Asp Val Gly
                    435                 440                 445
Leu Asp Ser Lys Pro Ala Ala Ser Val Leu Pro Lys Glu Pro Glu Phe
450                 455                 460
Pro Tyr Thr Pro Glu Met Arg Pro Arg Asn Gln Leu Ile Trp Arg Arg
465                 470                 475                 480
Pro Thr Glu Arg Phe Pro Arg Ile Val Ser Ser Ala Thr Val Glu Arg
                    485                 490                 495
Arg Ala Asp Leu Ser Glu Val Glu Glu Gln Val Lys Lys Leu Ile Glu
                    500                 505                 510
Glu Leu Lys Ser Thr Ser Leu Asp Met Gln Arg Asn Ala Thr Ala Glu
                    515                 520                 525
Leu Arg Leu Leu Ala Lys His Asn Met Asp Asn Arg Met Val Ile Ala
530                 535                 540
Asn Cys Gly Ala Ile Ser Ser Leu Val Asn Leu Leu His Ser Lys Asp
545                 550                 555                 560
Met Lys Val Gln Glu Asp Ala Val Thr Ala Leu Leu Asn Leu Ser Ile
                    565                 570                 575
Asn Asp Asn Asn Lys Cys Ala Ile Ala Asn Ala Asp Ala Ile Glu Pro
                    580                 585                 590
Leu Ile His Val Leu Gln Thr Gly Ser Ala Glu Ala Lys Glu Asn Ser
                    595                 600                 605
Ala Ala Thr Leu Phe Ser Leu Ser Val Met Glu Glu Asn Lys Met Lys
610                 615                 620
Ile Gly Arg Ser Gly Ala Ile Lys Pro Leu Val Asp Leu Leu Gly Asn
625                 630                 635                 640
Gly Thr Pro Arg Gly Lys Lys Asp Ala Ala Thr Ala Leu Phe Asn Leu
                    645                 650                 655
Ser Ile Leu His Glu Asn Lys Ser Arg Ile Ile Gln Ala Gly Ala Val
                    660                 665                 670
Lys Tyr Leu Val Glu Leu Met Asp Pro Ala Thr Gly Met Val Asp Lys
                    675                 680                 685
Ala Val Ala Val Leu Ser Asn Leu Ala Thr Ile Pro Glu Gly Arg Ala
                    690                 695                 700
```

```
Glu Ile Gly Gln Glu Gly Gly Ile Pro Leu Leu Val Glu Val Val Glu
705                 710                 715                 720

Leu Gly Ser Ala Arg Gly Lys Glu Asn Ala Ala Ala Leu Leu Gln
            725                 730                 735

Leu Cys Thr Asn Ser Ser Arg Phe Cys Asn Met Val Leu Gln Glu Gly
            740                 745                 750

Ala Val Pro Pro Leu Val Ala Leu Ser Gln Ser Gly Thr Pro Arg Ala
            755                 760                 765

Arg Glu Lys Ala Gln Gln Leu Leu Ser Tyr Phe Arg Asn Gln Arg His
            770                 775                 780

Gly Asn Ala Gly Arg Gly
785                 790

<210> SEQ ID NO 13
<211> LENGTH: 2436
<212> TYPE: DNA
<213> ORGANISM: Arabidopsis thaliana
<220> FEATURE:
<221> NAME/KEY: CDS
<222> LOCATION: (1)..(2436)

<400> SEQUENCE: 13
```

| | | | | | | | | | | | | | | | | |
|---|---|---|---|---|---|---|---|---|---|---|---|---|---|---|---|---|
| atg | gaa | gtt | ctt | ctc | aga | agt | atc | tcg | tcg | ttt | cta | aat | ctg | tca | tct | 48 |
| Met | Glu | Val | Leu | Leu | Arg | Ser | Ile | Ser | Ser | Phe | Leu | Asn | Leu | Ser | Ser | |
| 1 | | | | 5 | | | | | 10 | | | | | 15 | | |
| tct | aaa | cat | att | gat | tta | gac | ccg | ttt | gag | aag | tac | tat | aag | aga | gtt | 96 |
| Ser | Lys | His | Ile | Asp | Leu | Asp | Pro | Phe | Glu | Lys | Tyr | Tyr | Lys | Arg | Val | |
| | | | 20 | | | | | 25 | | | | | 30 | | | |
| gaa | gag | tta | ttg | aga | gtg | ttg | aag | cct | ata | gca | gat | gtt | gtt | gtt | acc | 144 |
| Glu | Glu | Leu | Leu | Arg | Val | Leu | Lys | Pro | Ile | Ala | Asp | Val | Val | Val | Thr | |
| | | 35 | | | | | 40 | | | | | 45 | | | | |
| tct | gat | ttt | gtt | ttt | gat | gag | aaa | ctt | ggt | aaa | gca | ttt | gaa | gaa | ttg | 192 |
| Ser | Asp | Phe | Val | Phe | Asp | Glu | Lys | Leu | Gly | Lys | Ala | Phe | Glu | Glu | Leu | |
| | 50 | | | | | 55 | | | | | 60 | | | | | |
| act | cag | gat | gtt | gat | caa | tcc | att | gat | ctt | ttc | agg | agt | tgg | caa | gct | 240 |
| Thr | Gln | Asp | Val | Asp | Gln | Ser | Ile | Asp | Leu | Phe | Arg | Ser | Trp | Gln | Ala | |
| 65 | | | | | 70 | | | | | 75 | | | | | 80 | |
| ttc | tct | agt | aaa | gtc | tat | ttc | gtt | ctt | caa | att | gaa | tct | ttg | cta | cca | 288 |
| Phe | Ser | Ser | Lys | Val | Tyr | Phe | Val | Leu | Gln | Ile | Glu | Ser | Leu | Leu | Pro | |
| | | | | 85 | | | | | 90 | | | | | 95 | | |
| aag | atg | cgg | gac | acc | att | gtg | gat | act | ttt | cag | ttt | ctc | atg | tct | tct | 336 |
| Lys | Met | Arg | Asp | Thr | Ile | Val | Asp | Thr | Phe | Gln | Phe | Leu | Met | Ser | Ser | |
| | | | 100 | | | | | 105 | | | | | 110 | | | |
| aag | aac | cat | cta | cct | gat | gag | cta | agc | cca | gct | tct | ctt | gag | caa | tgt | 384 |
| Lys | Asn | His | Leu | Pro | Asp | Glu | Leu | Ser | Pro | Ala | Ser | Leu | Glu | Gln | Cys | |
| | | 115 | | | | | 120 | | | | | 125 | | | | |
| cta | gag | aag | att | aag | cat | ctt | agt | tat | gaa | gaa | ata | tct | tct | gtc | att | 432 |
| Leu | Glu | Lys | Ile | Lys | His | Leu | Ser | Tyr | Glu | Glu | Ile | Ser | Ser | Val | Ile | |
| | 130 | | | | | 135 | | | | | 140 | | | | | |
| gac | ggt | gct | ttg | agg | gat | cag | aga | gat | ggt | gtt | gga | cct | agc | cct | gag | 480 |
| Asp | Gly | Ala | Leu | Arg | Asp | Gln | Arg | Asp | Gly | Val | Gly | Pro | Ser | Pro | Glu | |
| 145 | | | | | 150 | | | | | 155 | | | | | 160 | |
| atc | ttg | gtg | aaa | att | gga | gag | aac | act | ggt | ctt | aga | tca | aac | cag | gag | 528 |
| Ile | Leu | Val | Lys | Ile | Gly | Glu | Asn | Thr | Gly | Leu | Arg | Ser | Asn | Gln | Glu | |
| | | | | 165 | | | | | 170 | | | | | 175 | | |
| att | ctg | att | gaa | gct | gtt | gct | cta | gag | agg | cag | aaa | gag | atg | gct | gag | 576 |
| Ile | Leu | Ile | Glu | Ala | Val | Ala | Leu | Glu | Arg | Gln | Lys | Glu | Met | Ala | Glu | |
| | | | 180 | | | | | 185 | | | | | 190 | | | |
| cag | tct | gag | aat | aat | gca | gaa | gtc | gag | ttc | ctt | gac | caa | ctg | att | gtt | 624 |
| Gln | Ser | Glu | Asn | Asn | Ala | Glu | Val | Glu | Phe | Leu | Asp | Gln | Leu | Ile | Val | |
| | | 195 | | | | | 200 | | | | | 205 | | | | |

```
att gta aac cgc atg cat gaa cgt ctt ctt ctg atc aaa cag act cag      672
Ile Val Asn Arg Met His Glu Arg Leu Leu Leu Ile Lys Gln Thr Gln
    210                 215                 220 act tct agt gtc gcc att ctt gcc gac ttc ttt tgc cct ctg tca ctt      720
Thr Ser Ser Val Ala Ile Leu Ala Asp Phe Phe Cys Pro Leu Ser Leu
225                 230                 235                 240 gaa gta atg act gat cca gtg att gtg tca tca gga caa aca tat gaa      768
Glu Val Met Thr Asp Pro Val Ile Val Ser Ser Gly Gln Thr Tyr Glu
                245                 250                 255 aag gcg ttt atc aag aga tgg att gat ttg ggt tta aaa gtg tgt ccc      816
Lys Ala Phe Ile Lys Arg Trp Ile Asp Leu Gly Leu Lys Val Cys Pro
            260                 265                 270 aag act cga cag acc ctg act cac act act cta ata ccc aat tac acc      864
Lys Thr Arg Gln Thr Leu Thr His Thr Thr Leu Ile Pro Asn Tyr Thr
        275                 280                 285 gtg aag gcc tta atc gct aac tgg tgt gag aca aac gat gtc aag ctg      912
Val Lys Ala Leu Ile Ala Asn Trp Cys Glu Thr Asn Asp Val Lys Leu
    290                 295                 300 cct gat ccc aat aaa tca aca agt tta aat gag ctt tct cct ctt tta      960
Pro Asp Pro Asn Lys Ser Thr Ser Leu Asn Glu Leu Ser Pro Leu Leu
305                 310                 315                 320 tca tgt aca gac tcc att cct agc acg ggt gct gat gtt tct gct cgt     1008
Ser Cys Thr Asp Ser Ile Pro Ser Thr Gly Ala Asp Val Ser Ala Arg
                325                 330                 335 aaa gtt agc aac aag tca cat gat tgg gat gct tct tca agt gaa acc     1056
Lys Val Ser Asn Lys Ser His Asp Trp Asp Ala Ser Ser Ser Glu Thr
            340                 345                 350 ggt aag ccc tcg ttc tca agc cga gca act gaa aga gaa ggt gct tct     1104
Gly Lys Pro Ser Phe Ser Ser Arg Ala Thr Glu Arg Glu Gly Ala Ser
        355                 360                 365 cct tca cgt cct gct tct gcc ttg ggt gct tct tca ccg ggt ata tct     1152
Pro Ser Arg Pro Ala Ser Ala Leu Gly Ala Ser Ser Pro Gly Ile Ser
    370                 375                 380 gga aat ggt tac ggt ttg gac gcc agg agg gga tca cta aat gat ttt     1200
Gly Asn Gly Tyr Gly Leu Asp Ala Arg Arg Gly Ser Leu Asn Asp Phe
385                 390                 395                 400 gaa gat aga tca aac gat tct cga gaa ctg agg aca gat gca cct ggt     1248
Glu Asp Arg Ser Asn Asp Ser Arg Glu Leu Arg Thr Asp Ala Pro Gly
                405                 410                 415 agg tca tct gta tct tca act aca cga ggc tca gta gaa aat gga caa     1296
Arg Ser Ser Val Ser Ser Thr Thr Arg Gly Ser Val Glu Asn Gly Gln
            420                 425                 430 aca tct gag aac cac cat cat agg tcc cct tct gct act agc act gtt     1344
Thr Ser Glu Asn His His His Arg Ser Pro Ser Ala Thr Ser Thr Val
        435                 440                 445 tcc aat gag gag ttt cca agg gca gat gcg aat gag aat tca gaa gaa     1392
Ser Asn Glu Glu Phe Pro Arg Ala Asp Ala Asn Glu Asn Ser Glu Glu
    450                 455                 460 tca gct cat gct aca cct tac agc agt gat gct tca gga gaa att aga     1440
Ser Ala His Ala Thr Pro Tyr Ser Ser Asp Ala Ser Gly Glu Ile Arg
465                 470                 475                 480 tca ggg cct ctt gct gca acc act tca gca gct act cgc cga gat ttg     1488
Ser Gly Pro Leu Ala Ala Thr Thr Ser Ala Ala Thr Arg Arg Asp Leu
                485                 490                 495 tct gat ttt tcc cca aaa ttc atg gat aga cgt acc cgt ggt caa ttt     1536
Ser Asp Phe Ser Pro Lys Phe Met Asp Arg Arg Thr Arg Gly Gln Phe
            500                 505                 510 tgg cga cgt cca tca gag aga ctc ggt tca agg att gtt tca gcg cct     1584
Trp Arg Arg Pro Ser Glu Arg Leu Gly Ser Arg Ile Val Ser Ala Pro
        515                 520                 525
```

| | | | | | | | | | | | | | | | | |
|---|---|---|---|---|---|---|---|---|---|---|---|---|---|---|---|---|
| tcg | aat | gag | aca | aga | cgt | gat | ctt | tct | gag | gtc | gaa | act | caa | gtt | aag | 1632 |
| Ser | Asn | Glu | Thr | Arg | Arg | Asp | Leu | Ser | Glu | Val | Glu | Thr | Gln | Val | Lys | |
| 530 | | | | | 535 | | | | | 540 | | | | | | |
| aag | ttg | gtg | gag | gag | ttg | aaa | agc | agc | tca | ttg | gat | act | cag | aga | caa | 1680 |
| Lys | Leu | Val | Glu | Glu | Leu | Lys | Ser | Ser | Ser | Leu | Asp | Thr | Gln | Arg | Gln | |
| 545 | | | | 550 | | | | | 555 | | | | | 560 | | |
| gca | acc | gca | gaa | cta | agg | ttg | cta | gcc | aag | cac | aac | atg | gat | aat | cgg | 1728 |
| Ala | Thr | Ala | Glu | Leu | Arg | Leu | Leu | Ala | Lys | His | Asn | Met | Asp | Asn | Arg | |
| | | | 565 | | | | | 570 | | | | | 575 | | | |
| ata | gtc | att | ggg | aac | tct | gga | gca | atc | gtc | tta | ttg | gtg | gaa | cta | ctt | 1776 |
| Ile | Val | Ile | Gly | Asn | Ser | Gly | Ala | Ile | Val | Leu | Leu | Val | Glu | Leu | Leu | |
| | | 580 | | | | | 585 | | | | | 590 | | | | |
| tac | tca | act | gac | tca | gct | aca | cag | gaa | aac | gct | gtt | acc | gca | ctt | ctc | 1824 |
| Tyr | Ser | Thr | Asp | Ser | Ala | Thr | Gln | Glu | Asn | Ala | Val | Thr | Ala | Leu | Leu | |
| 595 | | | | | 600 | | | | | 605 | | | | | | |
| aac | tta | tct | atc | aat | gac | aac | aac | aaa | aaa | gca | att | gct | gat | gct | ggt | 1872 |
| Asn | Leu | Ser | Ile | Asn | Asp | Asn | Asn | Lys | Lys | Ala | Ile | Ala | Asp | Ala | Gly | |
| 610 | | | | | 615 | | | | | 620 | | | | | | |
| gca | att | gag | ccg | ctc | att | cac | gtg | ctt | gaa | aat | ggg | agc | tct | gaa | gcc | 1920 |
| Ala | Ile | Glu | Pro | Leu | Ile | His | Val | Leu | Glu | Asn | Gly | Ser | Ser | Glu | Ala | |
| 625 | | | | | 630 | | | | | 635 | | | | | 640 | |
| aag | gag | aat | tca | gct | gct | act | ctc | ttc | agc | ctc | tct | gta | ata | gaa | gaa | 1968 |
| Lys | Glu | Asn | Ser | Ala | Ala | Thr | Leu | Phe | Ser | Leu | Ser | Val | Ile | Glu | Glu | |
| | | | | 645 | | | | | 650 | | | | | 655 | | |
| aac | aag | att | aag | att | ggt | cag | tcg | ggt | gca | atc | ggg | cct | ctt | gta | gat | 2016 |
| Asn | Lys | Ile | Lys | Ile | Gly | Gln | Ser | Gly | Ala | Ile | Gly | Pro | Leu | Val | Asp | |
| | | 660 | | | | | 665 | | | | | 670 | | | | |
| ctt | ctc | ggt | aac | ggt | acc | cct | cgg | ggt | aag | aaa | gac | gct | gct | act | gcc | 2064 |
| Leu | Leu | Gly | Asn | Gly | Thr | Pro | Arg | Gly | Lys | Lys | Asp | Ala | Ala | Thr | Ala | |
| | | 675 | | | | | 680 | | | | | 685 | | | | |
| ttg | ttt | aat | cta | tcg | ata | cat | caa | gaa | aac | aag | gcg | atg | atc | gtg | caa | 2112 |
| Leu | Phe | Asn | Leu | Ser | Ile | His | Gln | Glu | Asn | Lys | Ala | Met | Ile | Val | Gln | |
| 690 | | | | | 695 | | | | | 700 | | | | | | |
| tca | ggt | gct | gtg | aga | tat | ctt | att | gat | ctg | atg | gac | cca | gca | gct | ggg | 2160 |
| Ser | Gly | Ala | Val | Arg | Tyr | Leu | Ile | Asp | Leu | Met | Asp | Pro | Ala | Ala | Gly | |
| 705 | | | | 710 | | | | | 715 | | | | | 720 | | |
| atg | gtg | gat | aaa | gca | gtt | gct | gtt | ttg | gca | aat | cta | gct | aca | att | ccg | 2208 |
| Met | Val | Asp | Lys | Ala | Val | Ala | Val | Leu | Ala | Asn | Leu | Ala | Thr | Ile | Pro | |
| | | | 725 | | | | | 730 | | | | | 735 | | | |
| gaa | gga | aga | aac | gcg | att | ggt | caa | gaa | ggc | gga | atc | cct | ctt | ctt | gtt | 2256 |
| Glu | Gly | Arg | Asn | Ala | Ile | Gly | Gln | Glu | Gly | Gly | Ile | Pro | Leu | Leu | Val | |
| | | | 740 | | | | | 745 | | | | | 750 | | | |
| gaa | gtc | gtt | gag | ttg | ggt | tca | gct | aga | ggg | aaa | gaa | aac | gca | gca | gca | 2304 |
| Glu | Val | Val | Glu | Leu | Gly | Ser | Ala | Arg | Gly | Lys | Glu | Asn | Ala | Ala | Ala | |
| | | 755 | | | | | 760 | | | | | 765 | | | | |
| gct | ctt | ctt | caa | ctt | tca | acc | aac | agt | ggt | cgg | ttc | tgc | aac | atg | gtt | 2352 |
| Ala | Leu | Leu | Gln | Leu | Ser | Thr | Asn | Ser | Gly | Arg | Phe | Cys | Asn | Met | Val | |
| | | 770 | | | | | 775 | | | | | 780 | | | | |
| ctt | caa | gaa | ggc | gcc | gtt | cct | cca | ctc | gtc | gct | ctc | tca | cag | tct | ggt | 2400 |
| Leu | Gln | Glu | Gly | Ala | Val | Pro | Pro | Leu | Val | Ala | Leu | Ser | Gln | Ser | Gly | |
| 785 | | | | 790 | | | | | 795 | | | | | 800 | | |
| act | cct | aga | gct | aga | gaa | aag | gta | caa | act | tta | taa | | | | | 2436 |
| Thr | Pro | Arg | Ala | Arg | Glu | Lys | Val | Gln | Thr | Leu | | | | | | |
| | | | 805 | | | | | 810 | | | | | | | | |

<210> SEQ ID NO 14
<211> LENGTH: 811
<212> TYPE: PRT
<213> ORGANISM: Arabidopsis thaliana

<400> SEQUENCE: 14

```
Met Glu Val Leu Leu Arg Ser Ile Ser Ser Phe Leu Asn Leu Ser Ser
1               5                   10                  15

Ser Lys His Ile Asp Leu Asp Pro Phe Glu Lys Tyr Tyr Lys Arg Val
            20                  25                  30

Glu Glu Leu Leu Arg Val Leu Lys Pro Ile Ala Asp Val Val Thr
        35                  40                  45

Ser Asp Phe Val Phe Asp Glu Lys Leu Gly Lys Ala Phe Glu Glu Leu
50                  55                  60

Thr Gln Asp Val Asp Gln Ser Ile Asp Leu Phe Arg Ser Trp Gln Ala
65                  70                  75                  80

Phe Ser Ser Lys Val Tyr Phe Val Leu Gln Ile Glu Ser Leu Leu Pro
                85                  90                  95

Lys Met Arg Asp Thr Ile Val Asp Thr Phe Gln Phe Leu Met Ser Ser
            100                 105                 110

Lys Asn His Leu Pro Asp Glu Leu Ser Pro Ala Ser Leu Glu Gln Cys
            115                 120                 125

Leu Glu Lys Ile Lys His Leu Ser Tyr Glu Glu Ile Ser Ser Val Ile
        130                 135                 140

Asp Gly Ala Leu Arg Asp Gln Arg Asp Gly Val Gly Pro Ser Pro Glu
145                 150                 155                 160

Ile Leu Val Lys Ile Gly Glu Asn Thr Gly Leu Arg Ser Asn Gln Glu
                165                 170                 175

Ile Leu Ile Glu Ala Val Ala Leu Glu Arg Gln Lys Glu Met Ala Glu
            180                 185                 190

Gln Ser Glu Asn Asn Ala Glu Val Glu Phe Leu Asp Gln Leu Ile Val
        195                 200                 205

Ile Val Asn Arg Met His Glu Arg Leu Leu Leu Ile Lys Gln Thr Gln
210                 215                 220

Thr Ser Ser Val Ala Ile Leu Ala Asp Phe Phe Cys Pro Leu Ser Leu
225                 230                 235                 240

Glu Val Met Thr Asp Pro Val Ile Val Ser Ser Gly Gln Thr Tyr Glu
                245                 250                 255

Lys Ala Phe Ile Lys Arg Trp Ile Asp Leu Gly Leu Lys Val Cys Pro
            260                 265                 270

Lys Thr Arg Gln Thr Leu Thr His Thr Thr Leu Ile Pro Asn Tyr Thr
        275                 280                 285

Val Lys Ala Leu Ile Ala Asn Trp Cys Glu Thr Asn Asp Val Lys Leu
290                 295                 300

Pro Asp Pro Asn Lys Ser Thr Ser Leu Asn Glu Leu Ser Pro Leu Leu
305                 310                 315                 320

Ser Cys Thr Asp Ser Ile Pro Ser Thr Gly Ala Asp Val Ser Ala Arg
                325                 330                 335

Lys Val Ser Asn Lys Ser His Asp Trp Asp Ala Ser Ser Ser Glu Thr
            340                 345                 350

Gly Lys Pro Ser Phe Ser Ser Arg Ala Thr Glu Arg Glu Gly Ala Ser
        355                 360                 365

Pro Ser Arg Pro Ala Ser Ala Leu Gly Ala Ser Ser Pro Gly Ile Ser
370                 375                 380

Gly Asn Gly Tyr Gly Leu Asp Ala Arg Arg Gly Ser Leu Asn Asp Phe
385                 390                 395                 400

Glu Asp Arg Ser Asn Asp Ser Arg Glu Leu Arg Thr Asp Ala Pro Gly
                405                 410                 415

Arg Ser Ser Val Ser Ser Thr Thr Arg Gly Ser Val Glu Asn Gly Gln
```

```
                    420             425             430
Thr Ser Glu Asn His His Arg Ser Pro Ala Thr Ser Thr Val
            435                 440             445
Ser Asn Glu Glu Phe Pro Arg Ala Asp Ala Asn Glu Asn Ser Glu Glu
450                     455                 460
Ser Ala His Ala Thr Pro Tyr Ser Ser Asp Ala Ser Gly Glu Ile Arg
465                     470                 475                 480
Ser Gly Pro Leu Ala Ala Thr Thr Ser Ala Ala Thr Arg Arg Asp Leu
                485                 490                 495
Ser Asp Phe Ser Pro Lys Phe Met Asp Arg Arg Thr Arg Gly Gln Phe
            500                 505                 510
Trp Arg Arg Pro Ser Glu Arg Leu Gly Ser Arg Ile Val Ser Ala Pro
            515                 520                 525
Ser Asn Glu Thr Arg Arg Asp Leu Ser Glu Val Glu Thr Gln Val Lys
            530                 535                 540
Lys Leu Val Glu Glu Leu Lys Ser Ser Ser Leu Asp Thr Gln Arg Gln
545                 550                 555                 560
Ala Thr Ala Glu Leu Arg Leu Leu Ala Lys His Asn Met Asp Asn Arg
                565                 570                 575
Ile Val Ile Gly Asn Ser Gly Ala Ile Val Leu Leu Val Glu Leu Leu
                580                 585                 590
Tyr Ser Thr Asp Ser Ala Thr Gln Glu Asn Ala Val Thr Ala Leu Leu
            595                 600                 605
Asn Leu Ser Ile Asn Asp Asn Asn Lys Lys Ala Ile Ala Asp Ala Gly
            610                 615                 620
Ala Ile Glu Pro Leu Ile His Val Leu Glu Asn Gly Ser Ser Glu Ala
625                 630                 635                 640
Lys Glu Asn Ser Ala Ala Thr Leu Phe Ser Leu Ser Val Ile Glu Glu
                645                 650                 655
Asn Lys Ile Lys Ile Gly Gln Ser Gly Ala Ile Gly Pro Leu Val Asp
                660                 665                 670
Leu Leu Gly Asn Gly Thr Pro Arg Gly Lys Lys Asp Ala Ala Thr Ala
            675                 680                 685
Leu Phe Asn Leu Ser Ile His Gln Glu Asn Lys Ala Met Ile Val Gln
            690                 695                 700
Ser Gly Ala Val Arg Tyr Leu Ile Asp Leu Met Asp Pro Ala Ala Gly
705                 710                 715                 720
Met Val Asp Lys Ala Val Ala Val Leu Ala Asn Leu Ala Thr Ile Pro
                725                 730                 735
Glu Gly Arg Asn Ala Ile Gly Gln Glu Gly Gly Ile Pro Leu Leu Val
                740                 745                 750
Glu Val Val Glu Leu Gly Ser Ala Arg Gly Lys Glu Asn Ala Ala Ala
            755                 760                 765
Ala Leu Leu Gln Leu Ser Thr Asn Ser Gly Arg Phe Cys Asn Met Val
            770                 775                 780
Leu Gln Glu Gly Ala Val Pro Pro Leu Val Ala Leu Ser Gln Ser Gly
785                 790                 795                 800
Thr Pro Arg Ala Arg Glu Lys Val Gln Thr Leu
                805                 810

<210> SEQ ID NO 15
<211> LENGTH: 2775
<212> TYPE: DNA
<213> ORGANISM: Arabidopsis thaliana
<220> FEATURE:
```

-continued

```
<221> NAME/KEY: CDS
<222> LOCATION: (1)..(2775)

<400> SEQUENCE: 15 atg att ttg cgg ttt tgg cgg gaa aac att att ttg cgg ttt tgg cgg        48
Met Ile Leu Arg Phe Trp Arg Glu Asn Ile Ile Leu Arg Phe Trp Arg
1               5                   10                  15 aaa atc cat gat ttt gcg gtt ttg aaa ctc att cag atg tat cat cca        96
Lys Ile His Asp Phe Ala Val Leu Lys Leu Ile Gln Met Tyr His Pro
                20                  25                  30 gat gat cca tcc aaa tac ttg tta aat tat aaa aaa caa aca tca ttt       144
Asp Asp Pro Ser Lys Tyr Leu Leu Asn Tyr Lys Lys Gln Thr Ser Phe
            35                  40                  45 ttc atc tgc att tgg atg aat cat ttg gat gaa aaa caa aca agg tct       192
Phe Ile Cys Ile Trp Met Asn His Leu Asp Glu Lys Gln Thr Arg Ser
        50                  55                  60 gag tct gat ttc aca gtt tcc aaa aga gat ata aga agg gtg gaa atg       240
Glu Ser Asp Phe Thr Val Ser Lys Arg Asp Ile Arg Arg Val Glu Met
65                  70                  75                  80 gaa gtt ctt ctc aga agt atc tcg tcg ttt cta aat ctg tca tct tct       288
Glu Val Leu Leu Arg Ser Ile Ser Ser Phe Leu Asn Leu Ser Ser Ser
                85                  90                  95 aaa cat att gat tta gac ccg ttt gag aag tac tat aag aga gtt gaa       336
Lys His Ile Asp Leu Asp Pro Phe Glu Lys Tyr Tyr Lys Arg Val Glu
                100                 105                 110 gag tta ttg aga gtg ttg aag cct ata gca gat gtt gtt gtt acc tct       384
Glu Leu Leu Arg Val Leu Lys Pro Ile Ala Asp Val Val Val Thr Ser
            115                 120                 125 gat ttt gtt ttt gat gag aaa ctt ggt aaa gca ttt gaa gaa ttg act       432
Asp Phe Val Phe Asp Glu Lys Leu Gly Lys Ala Phe Glu Glu Leu Thr
        130                 135                 140 cag gat gtt gat caa tcc att gat ctt ttc agg agt tgg caa gct ttc       480
Gln Asp Val Asp Gln Ser Ile Asp Leu Phe Arg Ser Trp Gln Ala Phe
145                 150                 155                 160 tct agt aaa gtc tat ttc gtt ctt caa att gaa tct ttg cta cca aag       528
Ser Ser Lys Val Tyr Phe Val Leu Gln Ile Glu Ser Leu Leu Pro Lys
                165                 170                 175 atg cgg gac acc att gtg gat act ttt cag ttt ctc atg tct tct aag       576
Met Arg Asp Thr Ile Val Asp Thr Phe Gln Phe Leu Met Ser Ser Lys
                180                 185                 190 aac cat cta cct gat gag cta agc cca gct tct ctt gag caa tgt cta       624
Asn His Leu Pro Asp Glu Leu Ser Pro Ala Ser Leu Glu Gln Cys Leu
            195                 200                 205 gag aag att aag cat ctt agt tat gaa gaa ata tct tct gtc att gac       672
Glu Lys Ile Lys His Leu Ser Tyr Glu Glu Ile Ser Ser Val Ile Asp
        210                 215                 220 ggt gct ttg agg gat cag aga gat ggt gtt gga cct agc cct gag atc       720
Gly Ala Leu Arg Asp Gln Arg Asp Gly Val Gly Pro Ser Pro Glu Ile
225                 230                 235                 240 ttg gtg aaa att gga gag aac act ggt ctt aga tca aac cag gag att       768
Leu Val Lys Ile Gly Glu Asn Thr Gly Leu Arg Ser Asn Gln Glu Ile
                245                 250                 255 ctg att gaa gct gtt gct cta gag agg cag aaa gag atg gct gag cag       816
Leu Ile Glu Ala Val Ala Leu Glu Arg Gln Lys Glu Met Ala Glu Gln
                260                 265                 270 tct gag aat aat gca gaa gtc gag ttc ctt gac caa ctg att gtt att       864
Ser Glu Asn Asn Ala Glu Val Glu Phe Leu Asp Gln Leu Ile Val Ile
            275                 280                 285 gta aac cgc atg cat gaa cgt ctt ctt ctg atc aaa cag act cag act       912
Val Asn Arg Met His Glu Arg Leu Leu Leu Ile Lys Gln Thr Gln Thr
        290                 295                 300
```

| | | | | | | | | | | | | | | | | |
|---|---|---|---|---|---|---|---|---|---|---|---|---|---|---|---|---|
| tct | agt | gtc | gcc | att | ctt | gcc | gac | ttc | ttt | tgc | cct | ctg | tca | ctt | gaa | 960 |
| Ser | Ser | Val | Ala | Ile | Leu | Ala | Asp | Phe | Phe | Cys | Pro | Leu | Ser | Leu | Glu | |
| 305 | | | | 310 | | | | 315 | | | | 320 | | | | |
| gta | atg | act | gat | cca | gtg | att | gtg | tca | tca | gga | caa | aca | tat | gaa | aag | 1008 |
| Val | Met | Thr | Asp | Pro | Val | Ile | Val | Ser | Ser | Gly | Gln | Thr | Tyr | Glu | Lys | |
| | | | 325 | | | | | 330 | | | | | 335 | | | |
| gcg | ttt | atc | aag | aga | tgg | att | gat | ttg | ggt | tta | aaa | gtg | tgt | ccc | aag | 1056 |
| Ala | Phe | Ile | Lys | Arg | Trp | Ile | Asp | Leu | Gly | Leu | Lys | Val | Cys | Pro | Lys | |
| | | 340 | | | | | 345 | | | | | 350 | | | | |
| act | cga | cag | acc | ctg | act | cac | act | act | cta | ata | ccc | aat | tac | acc | gtg | 1104 |
| Thr | Arg | Gln | Thr | Leu | Thr | His | Thr | Thr | Leu | Ile | Pro | Asn | Tyr | Thr | Val | |
| | | 355 | | | | | 360 | | | | | 365 | | | | |
| aag | gcc | tta | atc | gct | aac | tgg | tgt | gag | aca | aac | gat | gtc | aag | ctg | cct | 1152 |
| Lys | Ala | Leu | Ile | Ala | Asn | Trp | Cys | Glu | Thr | Asn | Asp | Val | Lys | Leu | Pro | |
| 370 | | | | | 375 | | | | | 380 | | | | | | |
| gat | ccc | aat | aaa | tca | aca | agt | tta | aat | gag | ctt | tct | cct | ctt | tta | tca | 1200 |
| Asp | Pro | Asn | Lys | Ser | Thr | Ser | Leu | Asn | Glu | Leu | Ser | Pro | Leu | Leu | Ser | |
| 385 | | | | | 390 | | | | | 395 | | | | | 400 | |
| tgt | aca | gac | tcc | att | cct | agc | acg | ggt | gct | gat | gtt | tct | gct | cgt | aaa | 1248 |
| Cys | Thr | Asp | Ser | Ile | Pro | Ser | Thr | Gly | Ala | Asp | Val | Ser | Ala | Arg | Lys | |
| | | | | 405 | | | | | 410 | | | | | 415 | | |
| gtt | agc | aac | aag | tca | cat | gat | tgg | gat | gct | tct | tca | agt | gaa | acc | ggt | 1296 |
| Val | Ser | Asn | Lys | Ser | His | Asp | Trp | Asp | Ala | Ser | Ser | Ser | Glu | Thr | Gly | |
| | | | 420 | | | | | 425 | | | | | 430 | | | |
| aag | ccc | tcg | ttc | tca | agc | cga | gca | act | gaa | aga | gaa | ggt | gct | tct | cct | 1344 |
| Lys | Pro | Ser | Phe | Ser | Ser | Arg | Ala | Thr | Glu | Arg | Glu | Gly | Ala | Ser | Pro | |
| | | 435 | | | | | 440 | | | | | 445 | | | | |
| tca | cgt | cct | gct | tct | gcc | ttg | ggt | gct | tct | tca | ccg | ggt | ata | tct | gga | 1392 |
| Ser | Arg | Pro | Ala | Ser | Ala | Leu | Gly | Ala | Ser | Ser | Pro | Gly | Ile | Ser | Gly | |
| 450 | | | | | 455 | | | | | 460 | | | | | | |
| aat | ggt | tac | ggt | ttg | gac | gcc | agg | agg | gga | tca | cta | aat | gat | ttt | gaa | 1440 |
| Asn | Gly | Tyr | Gly | Leu | Asp | Ala | Arg | Arg | Gly | Ser | Leu | Asn | Asp | Phe | Glu | |
| 465 | | | | | 470 | | | | | 475 | | | | | 480 | |
| gat | aga | tca | aac | gat | tct | cga | gaa | ctg | agg | aca | gat | gca | cct | ggt | agg | 1488 |
| Asp | Arg | Ser | Asn | Asp | Ser | Arg | Glu | Leu | Arg | Thr | Asp | Ala | Pro | Gly | Arg | |
| | | | | 485 | | | | | 490 | | | | | 495 | | |
| tca | tct | gta | tct | tca | act | aca | cga | ggc | tca | gta | gaa | aat | gga | caa | aca | 1536 |
| Ser | Ser | Val | Ser | Ser | Thr | Thr | Arg | Gly | Ser | Val | Glu | Asn | Gly | Gln | Thr | |
| | | | 500 | | | | | 505 | | | | | 510 | | | |
| tct | gag | aac | cac | cat | cat | agg | tcc | cct | tct | gct | act | agc | act | gtt | tcc | 1584 |
| Ser | Glu | Asn | His | His | His | Arg | Ser | Pro | Ser | Ala | Thr | Ser | Thr | Val | Ser | |
| | | 515 | | | | | 520 | | | | | 525 | | | | |
| aat | gag | gag | ttt | cca | agg | gca | gat | gcg | aat | gag | aat | tca | gaa | gaa | tca | 1632 |
| Asn | Glu | Glu | Phe | Pro | Arg | Ala | Asp | Ala | Asn | Glu | Asn | Ser | Glu | Glu | Ser | |
| | 530 | | | | | 535 | | | | | 540 | | | | | |
| gct | cat | gct | aca | cct | tac | agc | agt | gat | gct | tca | gga | gaa | att | aga | tca | 1680 |
| Ala | His | Ala | Thr | Pro | Tyr | Ser | Ser | Asp | Ala | Ser | Gly | Glu | Ile | Arg | Ser | |
| 545 | | | | 550 | | | | | 555 | | | | | 560 | | |
| ggg | cct | ctt | gct | gca | acc | act | tca | gca | gct | act | cgc | cga | gat | ttg | tct | 1728 |
| Gly | Pro | Leu | Ala | Ala | Thr | Thr | Ser | Ala | Ala | Thr | Arg | Arg | Asp | Leu | Ser | |
| | | | | 565 | | | | | 570 | | | | | 575 | | |
| gat | ttt | tcc | cca | aaa | ttc | atg | gat | aga | cgt | acc | cgt | ggt | caa | ttt | tgg | 1776 |
| Asp | Phe | Ser | Pro | Lys | Phe | Met | Asp | Arg | Arg | Thr | Arg | Gly | Gln | Phe | Trp | |
| | | | 580 | | | | | 585 | | | | | 590 | | | |
| cga | cgt | cca | tca | gag | aga | ctc | ggt | tca | agg | att | gtt | tca | gcg | cct | tcg | 1824 |
| Arg | Arg | Pro | Ser | Glu | Arg | Leu | Gly | Ser | Arg | Ile | Val | Ser | Ala | Pro | Ser | |
| | | 595 | | | | | 600 | | | | | 605 | | | | |
| aat | gag | aca | aga | cgt | gat | ctt | tct | gag | gtc | gaa | act | caa | gtt | aag | aag | 1872 |
| Asn | Glu | Thr | Arg | Arg | Asp | Leu | Ser | Glu | Val | Glu | Thr | Gln | Val | Lys | Lys | |
| 610 | | | | | 615 | | | | | 620 | | | | | | |

```
ttg gtg gag gag ttg aaa agc agc tca ttg gat act cag aga caa gca      1920
Leu Val Glu Glu Leu Lys Ser Ser Ser Leu Asp Thr Gln Arg Gln Ala
625                 630                 635                 640 acc gca gaa cta agg ttg cta gcc aag cac aac atg gat aat cgg ata      1968
Thr Ala Glu Leu Arg Leu Leu Ala Lys His Asn Met Asp Asn Arg Ile
                645                 650                 655 gtc att ggg aac tct gga gca atc gtc tta ttg gtg gaa cta ctt tac      2016
Val Ile Gly Asn Ser Gly Ala Ile Val Leu Leu Val Glu Leu Leu Tyr
            660                 665                 670 tca act gac tca gct aca cag gaa aac gct gtt acc gca ctt ctc aac      2064
Ser Thr Asp Ser Ala Thr Gln Glu Asn Ala Val Thr Ala Leu Leu Asn
        675                 680                 685 tta tct atc aat gac aac aac aaa aaa gca att gct gat gct ggt gca      2112
Leu Ser Ile Asn Asp Asn Asn Lys Lys Ala Ile Ala Asp Ala Gly Ala
    690                 695                 700 att gag ccg ctc att cac gtg ctt gaa aat ggg agc tct gaa gcc aag      2160
Ile Glu Pro Leu Ile His Val Leu Glu Asn Gly Ser Ser Glu Ala Lys
705                 710                 715                 720 gag aat tca gct gct act ctc ttc agc ctc tct gta ata gaa gaa aac      2208
Glu Asn Ser Ala Ala Thr Leu Phe Ser Leu Ser Val Ile Glu Glu Asn
                725                 730                 735 aag att aag att ggt cag tcg ggt gca atc ggg cct ctt gta gat ctt      2256
Lys Ile Lys Ile Gly Gln Ser Gly Ala Ile Gly Pro Leu Val Asp Leu
            740                 745                 750 ctc ggt aac ggt acc cct cgg ggt aag aaa gac gct gct act gcc ttg      2304
Leu Gly Asn Gly Thr Pro Arg Gly Lys Lys Asp Ala Ala Thr Ala Leu
        755                 760                 765 ttt aat cta tcg ata cat caa gaa aac aag gcg atg atc gtg caa tca      2352
Phe Asn Leu Ser Ile His Gln Glu Asn Lys Ala Met Ile Val Gln Ser
    770                 775                 780 ggt gct gtg aga tat ctt att gat ctg atg gac cca gca gct ggg atg      2400
Gly Ala Val Arg Tyr Leu Ile Asp Leu Met Asp Pro Ala Ala Gly Met
785                 790                 795                 800 gtg gat aaa gca gtt gct gtt ttg gca aat cta gct aca att ccg gaa      2448
Val Asp Lys Ala Val Ala Val Leu Ala Asn Leu Ala Thr Ile Pro Glu
                805                 810                 815 gga aga aac gcg att ggt caa gaa ggc gga atc cct ctt ctt gtt gaa      2496
Gly Arg Asn Ala Ile Gly Gln Glu Gly Gly Ile Pro Leu Leu Val Glu
            820                 825                 830 gtc gtt gag ttg ggt tca gct aga ggg aaa gaa aac gca gca gca gct      2544
Val Val Glu Leu Gly Ser Ala Arg Gly Lys Glu Asn Ala Ala Ala Ala
        835                 840                 845 ctt ctt caa ctt tca acc aac agt ggt cgg ttc tgc aac atg gtt ctt      2592
Leu Leu Gln Leu Ser Thr Asn Ser Gly Arg Phe Cys Asn Met Val Leu
    850                 855                 860 caa gaa ggc gcc gtt cct cca ctc gtc gct ctc tca cag tct ggt act      2640
Gln Glu Gly Ala Val Pro Pro Leu Val Ala Leu Ser Gln Ser Gly Thr
865                 870                 875                 880 cct aga gct aga gaa aag aaa cca acg gca tgg aaa cgc tgg gcg tgg      2688
Pro Arg Ala Arg Glu Lys Lys Pro Thr Ala Trp Lys Arg Trp Ala Trp
                885                 890                 895 ctg atg atg gat gat gat gat gat gat gtt gat gat gca cag att         2736
Leu Met Met Asp Asp Asp Asp Asp Asp Val Asp Asp Ala Gln Ile
            900                 905                 910 ctg gtc tct cag tgc cta ttt tta tgt ttt gtc ttg tga                  2775
Leu Val Ser Gln Cys Leu Phe Leu Cys Phe Val Leu
            915                 920

<210> SEQ ID NO 16
<211> LENGTH: 924
```

```
<212> TYPE: PRT
<213> ORGANISM: Arabidopsis thaliana

<400> SEQUENCE: 16

Met Ile Leu Arg Phe Trp Arg Glu Asn Ile Ile Leu Arg Phe Trp Arg
1               5                   10                  15

Lys Ile His Asp Phe Ala Val Leu Lys Leu Ile Gln Met Tyr His Pro
            20                  25                  30

Asp Asp Pro Ser Lys Tyr Leu Asn Tyr Lys Lys Gln Thr Ser Phe
        35                  40                  45

Phe Ile Cys Ile Trp Met Asn His Leu Asp Glu Lys Gln Thr Arg Ser
    50                  55                  60

Glu Ser Asp Phe Thr Val Ser Lys Arg Asp Ile Arg Arg Val Glu Met
65                  70                  75                  80

Glu Val Leu Leu Arg Ser Ile Ser Ser Phe Leu Asn Leu Ser Ser Ser
                85                  90                  95

Lys His Ile Asp Leu Asp Pro Phe Glu Lys Tyr Tyr Lys Arg Val Glu
            100                 105                 110

Glu Leu Leu Arg Val Leu Lys Pro Ile Ala Asp Val Val Thr Ser
        115                 120                 125

Asp Phe Val Phe Asp Glu Lys Leu Gly Lys Ala Phe Glu Glu Leu Thr
130                 135                 140

Gln Asp Val Asp Gln Ser Ile Asp Leu Phe Arg Ser Trp Gln Ala Phe
145                 150                 155                 160

Ser Ser Lys Val Tyr Phe Val Leu Gln Ile Glu Ser Leu Leu Pro Lys
                165                 170                 175

Met Arg Asp Thr Ile Val Asp Thr Phe Gln Phe Leu Met Ser Ser Lys
            180                 185                 190

Asn His Leu Pro Asp Glu Leu Ser Pro Ala Ser Leu Glu Gln Cys Leu
        195                 200                 205

Glu Lys Ile Lys His Leu Ser Tyr Glu Glu Ile Ser Ser Val Ile Asp
210                 215                 220

Gly Ala Leu Arg Asp Gln Arg Asp Gly Val Gly Pro Ser Pro Glu Ile
225                 230                 235                 240

Leu Val Lys Ile Gly Glu Asn Thr Gly Leu Arg Ser Asn Gln Glu Ile
                245                 250                 255

Leu Ile Glu Ala Val Ala Leu Glu Arg Gln Lys Glu Met Ala Glu Gln
            260                 265                 270

Ser Glu Asn Asn Ala Glu Val Glu Phe Leu Asp Gln Leu Ile Val Ile
        275                 280                 285

Val Asn Arg Met His Glu Arg Leu Leu Leu Ile Lys Gln Thr Gln Thr
290                 295                 300

Ser Ser Val Ala Ile Leu Ala Asp Phe Phe Cys Pro Leu Ser Leu Glu
305                 310                 315                 320

Val Met Thr Asp Pro Val Ile Val Ser Ser Gly Gln Thr Tyr Glu Lys
                325                 330                 335

Ala Phe Ile Lys Arg Trp Ile Asp Leu Gly Leu Lys Val Cys Pro Lys
            340                 345                 350

Thr Arg Gln Thr Leu Thr His Thr Thr Leu Ile Pro Asn Tyr Thr Val
        355                 360                 365

Lys Ala Leu Ile Ala Asn Trp Cys Glu Thr Asn Asp Val Lys Leu Pro
370                 375                 380

Asp Pro Asn Lys Ser Thr Ser Leu Asn Glu Leu Ser Pro Leu Leu Ser
385                 390                 395                 400
```

-continued

```
Cys Thr Asp Ser Ile Pro Ser Thr Gly Ala Asp Val Ser Ala Arg Lys
                405                 410                 415

Val Ser Asn Lys Ser His Asp Trp Asp Ala Ser Ser Glu Thr Gly
        420                 425                 430

Lys Pro Ser Phe Ser Ser Arg Ala Thr Glu Arg Glu Gly Ala Ser Pro
            435                 440                 445

Ser Arg Pro Ala Ser Ala Leu Gly Ala Ser Pro Gly Ile Ser Gly
    450                 455                 460

Asn Gly Tyr Gly Leu Asp Ala Arg Arg Gly Ser Leu Asn Asp Phe Glu
465                 470                 475                 480

Asp Arg Ser Asn Asp Ser Arg Glu Leu Arg Thr Asp Ala Pro Gly Arg
                485                 490                 495

Ser Ser Val Ser Ser Thr Thr Arg Gly Ser Val Glu Asn Gly Gln Thr
            500                 505                 510

Ser Glu Asn His His His Arg Ser Pro Ser Ala Thr Ser Thr Val Ser
        515                 520                 525

Asn Glu Glu Phe Pro Arg Ala Asp Ala Asn Glu Asn Ser Glu Glu Ser
    530                 535                 540

Ala His Ala Thr Pro Tyr Ser Ser Asp Ala Ser Gly Glu Ile Arg Ser
545                 550                 555                 560

Gly Pro Leu Ala Ala Thr Thr Ser Ala Ala Thr Arg Arg Asp Leu Ser
                565                 570                 575

Asp Phe Ser Pro Lys Phe Met Asp Arg Arg Thr Arg Gly Gln Phe Trp
            580                 585                 590

Arg Arg Pro Ser Glu Arg Leu Gly Ser Arg Ile Val Ser Ala Pro Ser
    595                 600                 605

Asn Glu Thr Arg Arg Asp Leu Ser Glu Val Glu Thr Gln Val Lys Lys
610                 615                 620

Leu Val Glu Glu Leu Lys Ser Ser Ser Leu Asp Thr Gln Arg Gln Ala
625                 630                 635                 640

Thr Ala Glu Leu Arg Leu Leu Ala Lys His Asn Met Asp Asn Arg Ile
                645                 650                 655

Val Ile Gly Asn Ser Gly Ala Ile Val Leu Leu Val Glu Leu Leu Tyr
            660                 665                 670

Ser Thr Asp Ser Ala Thr Gln Glu Asn Ala Val Thr Ala Leu Leu Asn
    675                 680                 685

Leu Ser Ile Asn Asp Asn Asn Lys Lys Ala Ile Ala Asp Ala Gly Ala
690                 695                 700

Ile Glu Pro Leu Ile His Val Leu Glu Asn Gly Ser Ser Glu Ala Lys
705                 710                 715                 720

Glu Asn Ser Ala Ala Thr Leu Phe Ser Leu Ser Val Ile Glu Glu Asn
                725                 730                 735

Lys Ile Lys Ile Gly Gln Ser Gly Ala Ile Gly Pro Leu Val Asp Leu
            740                 745                 750

Leu Gly Asn Gly Thr Pro Arg Gly Lys Lys Asp Ala Ala Thr Ala Leu
    755                 760                 765

Phe Asn Leu Ser Ile His Gln Glu Asn Lys Ala Met Ile Val Gln Ser
    770                 775                 780

Gly Ala Val Arg Tyr Leu Ile Asp Leu Met Asp Pro Ala Ala Gly Met
785                 790                 795                 800

Val Asp Lys Ala Val Ala Val Leu Ala Asn Leu Ala Thr Ile Pro Glu
                805                 810                 815

Gly Arg Asn Ala Ile Gly Gln Glu Gly Gly Ile Pro Leu Leu Val Glu
            820                 825                 830
```

| | | | | | | | | | | | | |
|---|---|---|---|---|---|---|---|---|---|---|---|---|
| Val | Val | Glu | Leu | Gly | Ser | Ala | Arg | Gly | Lys | Glu | Asn | Ala Ala Ala |
| | | 835 | | | 840 | | | | 845 | | | |
| Leu | Leu | Gln | Leu | Ser | Thr | Asn | Ser | Gly | Arg | Phe | Cys | Asn Met Val Leu |
| | | 850 | | | 855 | | | | 860 | | | |
| Gln | Glu | Gly | Ala | Val | Pro | Pro | Leu | Val | Ala | Leu | Ser | Gln Ser Gly Thr |
| 865 | | | | 870 | | | | 875 | | | | 880 |
| Pro | Arg | Ala | Arg | Glu | Lys | Lys | Pro | Thr | Ala | Trp | Lys | Arg Trp Ala Trp |
| | | | 885 | | | | 890 | | | | 895 | |
| Leu | Met | Met | Asp | Asp | Asp | Asp | Asp | Val | Asp | Asp | Ala | Gln Ile |
| | | | 900 | | | 905 | | | | 910 | | |
| Leu | Val | Ser | Gln | Cys | Leu | Phe | Leu | Cys | Phe | Val | Leu | |
| | | | 915 | | | 920 | | | | | | |

```
<210> SEQ ID NO 17
<211> LENGTH: 2124
<212> TYPE: DNA
<213> ORGANISM: Arabidopsis thaliana
<220> FEATURE:
<221> NAME/KEY: CDS
<222> LOCATION: (1)..(2124)

<400> SEQUENCE: 17
```

| | | | | | | | | | | | | | | | | |
|---|---|---|---|---|---|---|---|---|---|---|---|---|---|---|---|---|
| atg | atg | gta | cat | atg | gag | gtg | tct | tgg | tta | aga | gtt | ctt | cta | gat | aac | 48 |
| Met | Met | Val | His | Met | Glu | Val | Ser | Trp | Leu | Arg | Val | Leu | Leu | Asp | Asn | |
| 1 | | | | 5 | | | | | 10 | | | | | 15 | | |
| atc | tcc | tcc | tat | cta | agt | tta | tca | tct | atg | gac | gat | tta | tct | tca | aac | 96 |
| Ile | Ser | Ser | Tyr | Leu | Ser | Leu | Ser | Ser | Met | Asp | Asp | Leu | Ser | Ser | Asn | |
| | | | 20 | | | | | 25 | | | | | 30 | | | |
| cct | gct | cat | aag | tac | tac | acc | aga | gga | gaa | gat | ata | gga | aag | ctt | atc | 144 |
| Pro | Ala | His | Lys | Tyr | Tyr | Thr | Arg | Gly | Glu | Asp | Ile | Gly | Lys | Leu | Ile | |
| | 35 | | | | | 40 | | | | | 45 | | | | | |
| aag | cct | gtt | ctt | gag | aac | ctc | att | gac | tct | gac | gcg | gct | cct | agc | gag | 192 |
| Lys | Pro | Val | Leu | Glu | Asn | Leu | Ile | Asp | Ser | Asp | Ala | Ala | Pro | Ser | Glu | |
| 50 | | | | | 55 | | | | | 60 | | | | | | |
| ttg | ctt | aac | aat | ggt | ttt | gaa | gaa | tta | gct | caa | tac | gtt | gat | gaa | ctt | 240 |
| Leu | Leu | Asn | Asn | Gly | Phe | Glu | Glu | Leu | Ala | Gln | Tyr | Val | Asp | Glu | Leu | |
| 65 | | | | 70 | | | | | 75 | | | | | 80 | | |
| aga | gaa | cag | ttt | cag | agt | tgg | caa | cct | ctt | tca | act | aga | atc | ttt | tat | 288 |
| Arg | Glu | Gln | Phe | Gln | Ser | Trp | Gln | Pro | Leu | Ser | Thr | Arg | Ile | Phe | Tyr | |
| | | | 85 | | | | | 90 | | | | | 95 | | | |
| gtt | ctt | cga | att | gaa | tca | tta | gca | tca | aag | tta | cga | gaa | tcc | agt | ttg | 336 |
| Val | Leu | Arg | Ile | Glu | Ser | Leu | Ala | Ser | Lys | Leu | Arg | Glu | Ser | Ser | Leu | |
| | | | 100 | | | | | 105 | | | | | 110 | | | |
| gaa | gtc | ttt | cag | ctc | ctc | aaa | cac | tgc | gaa | caa | cat | ttg | cct | gct | gac | 384 |
| Glu | Val | Phe | Gln | Leu | Leu | Lys | His | Cys | Glu | Gln | His | Leu | Pro | Ala | Asp | |
| | | 115 | | | | | 120 | | | | | 125 | | | | |
| ttg | atc | tca | cct | tct | ttt | gag | gag | tgc | att | gaa | ttg | gtg | aag | tta | gtg | 432 |
| Leu | Ile | Ser | Pro | Ser | Phe | Glu | Glu | Cys | Ile | Glu | Leu | Val | Lys | Leu | Val | |
| | 130 | | | | | 135 | | | | | 140 | | | | | |
| gca | aga | gac | gaa | ata | tcg | tat | act | att | gat | caa | gct | cta | aaa | gat | caa | 480 |
| Ala | Arg | Asp | Glu | Ile | Ser | Tyr | Thr | Ile | Asp | Gln | Ala | Leu | Lys | Asp | Gln | |
| 145 | | | | | 150 | | | | | 155 | | | | | 160 | |
| aag | aaa | ggt | gtt | gga | cct | act | tca | gag | gtt | ctg | gtg | aaa | att | gcc | gag | 528 |
| Lys | Lys | Gly | Val | Gly | Pro | Thr | Ser | Glu | Val | Leu | Val | Lys | Ile | Ala | Glu | |
| | | | | 165 | | | | | 170 | | | | | 175 | | |
| agt | act | ggt | tta | aga | tcc | aac | cag | gag | att | ctt | gtt | gaa | ggt | gtg | gta | 576 |
| Ser | Thr | Gly | Leu | Arg | Ser | Asn | Gln | Glu | Ile | Leu | Val | Glu | Gly | Val | Val | |
| | | | 180 | | | | | 185 | | | | | 190 | | | |
| ctt | aca | aac | atg | aag | gag | gat | gct | gag | ctt | acc | gat | aat | gac | acc | gaa | 624 |
| Leu | Thr | Asn | Met | Lys | Glu | Asp | Ala | Glu | Leu | Thr | Asp | Asn | Asp | Thr | Glu | |

```
                195                     200                     205
gcc gag tat cta gac gga ttg atc tct cta aca aca caa atg cat gag    672
Ala Glu Tyr Leu Asp Gly Leu Ile Ser Leu Thr Thr Gln Met His Glu
210                     215                     220 tac ctt agc gac ata aag cag gct cag tta cgt tgt cca gta cgc gta    720
Tyr Leu Ser Asp Ile Lys Gln Ala Gln Leu Arg Cys Pro Val Arg Val
225                     230                     235                     240 cct tct gat ttc cgc tgc tct cta tct ctt gag ctt atg act gat cca    768
Pro Ser Asp Phe Arg Cys Ser Leu Ser Leu Glu Leu Met Thr Asp Pro
                245                     250                     255 gtc att gta gca tct ggt caa aca ttc gaa cgg gtt ttt atc cag aaa    816
Val Ile Val Ala Ser Gly Gln Thr Phe Glu Arg Val Phe Ile Gln Lys
        260                     265                     270 tgg atc gat atg gga ctc atg gtt tgt cca aag aca agg cag gct tta    864
Trp Ile Asp Met Gly Leu Met Val Cys Pro Lys Thr Arg Gln Ala Leu
        275                     280                     285 tct cat acc act ttg aca cct aat ttc att gtc aga gct ttt ctt gca    912
Ser His Thr Thr Leu Thr Pro Asn Phe Ile Val Arg Ala Phe Leu Ala
        290                     295                     300 agt tgg tgt gaa act aac aat gtc tat cct cct gat cca ttg gag ttg    960
Ser Trp Cys Glu Thr Asn Asn Val Tyr Pro Pro Asp Pro Leu Glu Leu
305                     310                     315                     320 att cac tca agt gag cca ttc cct ctt ctt gtt gaa tca gtg aga gct   1008
Ile His Ser Ser Glu Pro Phe Pro Leu Leu Val Glu Ser Val Arg Ala
                325                     330                     335 tca tca tca gag aat ggc cat tca gaa tct tta gat gca gag gaa ctg   1056
Ser Ser Ser Glu Asn Gly His Ser Glu Ser Leu Asp Ala Glu Glu Leu
                340                     345                     350 cgt cag gtc ttt agt agg tct gct tcg gcg cca ggc att gtc tct gaa   1104
Arg Gln Val Phe Ser Arg Ser Ala Ser Ala Pro Gly Ile Val Ser Glu
        355                     360                     365 gtg gtt tgc aaa acc aaa aga aac aac aat gct gct gca gat aga tca   1152
Val Val Cys Lys Thr Lys Arg Asn Asn Asn Ala Ala Ala Asp Arg Ser
        370                     375                     380 ctg aca cgg agt aat acc cct tgg aaa ttt cca gaa gag agg cat tgg   1200
Leu Thr Arg Ser Asn Thr Pro Trp Lys Phe Pro Glu Glu Arg His Trp
385                     390                     395                     400 cgt cac ccc ggg atc atc cca gcg acc gta aga gaa aca gga agc agt   1248
Arg His Pro Gly Ile Ile Pro Ala Thr Val Arg Glu Thr Gly Ser Ser
                405                     410                     415 tca agt atc gaa acc gag gtg aag aaa ctc att gat gat ctc aag agt   1296
Ser Ser Ile Glu Thr Glu Val Lys Lys Leu Ile Asp Asp Leu Lys Ser
                420                     425                     430 tct tca ttg gat aca cag aga gag gcc aca gct aga atc agg ata cta   1344
Ser Ser Leu Asp Thr Gln Arg Glu Ala Thr Ala Arg Ile Arg Ile Leu
        435                     440                     445 gca aga aac agt aca gac aat cgc att gtc att gcg cgg tgc gaa gca   1392
Ala Arg Asn Ser Thr Asp Asn Arg Ile Val Ile Ala Arg Cys Glu Ala
450                     455                     460 atc cct tcg tta gtc agt ctt ctt tac tca acg gat gag aga atc caa   1440
Ile Pro Ser Leu Val Ser Leu Leu Tyr Ser Thr Asp Glu Arg Ile Gln
465                     470                     475                     480 gca gac gca gtg act tgc tta cta aac tta tcc atc aac gac aac aac   1488
Ala Asp Ala Val Thr Cys Leu Leu Asn Leu Ser Ile Asn Asp Asn Asn
                485                     490                     495 aag tcc ctc atc gcg gaa agt gga gcc atc gta ccg ctt att cac gtt   1536
Lys Ser Leu Ile Ala Glu Ser Gly Ala Ile Val Pro Leu Ile His Val
                500                     505                     510 ctc aaa aca gga tac tta gaa gaa gct aaa gca aac tca gca gca act   1584
Leu Lys Thr Gly Tyr Leu Glu Glu Ala Lys Ala Asn Ser Ala Ala Thr
```

```
cta ttc agc ttg tcg gtg atc gaa gag tac aag aca gag ata gga gaa      1632
Leu Phe Ser Leu Ser Val Ile Glu Glu Tyr Lys Thr Glu Ile Gly Glu
530                 535                 540 gca gga gct ata gag cca ctt gtt gac ctc tta gga agt gga agt ctc      1680
Ala Gly Ala Ile Glu Pro Leu Val Asp Leu Leu Gly Ser Gly Ser Leu
545                 550                 555                 560 agt ggg aag aaa gat gca gcc acg gct tta ttc aac ctc tca ata cac      1728
Ser Gly Lys Lys Asp Ala Ala Thr Ala Leu Phe Asn Leu Ser Ile His
                565                 570                 575 cat gag aac aaa acg aaa gta atc gaa gct gga gca gtg aga tac tta      1776
His Glu Asn Lys Thr Lys Val Ile Glu Ala Gly Ala Val Arg Tyr Leu
            580                 585                 590 gtt gaa ctg atg gat cct gct ttt ggg atg gtg gag aaa gct gtg gtg      1824
Val Glu Leu Met Asp Pro Ala Phe Gly Met Val Glu Lys Ala Val Val
        595                 600                 605 gtg cta gcg aat ctt gca acg gtt aga gaa gga aag att gcg ata ggc      1872
Val Leu Ala Asn Leu Ala Thr Val Arg Glu Gly Lys Ile Ala Ile Gly
    610                 615                 620 gaa gaa gga gga ata ccg gta ttg gtg gaa gtt gtg gag tta ggt tca      1920
Glu Glu Gly Gly Ile Pro Val Leu Val Glu Val Val Glu Leu Gly Ser
625                 630                 635                 640 gca aga ggc aaa gag aat gca act gca gca cta ttg cag ctt tgt acg      1968
Ala Arg Gly Lys Glu Asn Ala Thr Ala Ala Leu Leu Gln Leu Cys Thr
                645                 650                 655 cat agc ccg aaa ttc tgc aac aat gtc ata aga gaa gga gtg att cca      2016
His Ser Pro Lys Phe Cys Asn Asn Val Ile Arg Glu Gly Val Ile Pro
            660                 665                 670 cct ctt gtg gca ctt act aaa tca gga aca gct aga ggc aaa gag aag      2064
Pro Leu Val Ala Leu Thr Lys Ser Gly Thr Ala Arg Gly Lys Glu Lys
        675                 680                 685 gca cag aat ctt ctg aag tac ttt aaa gca cac aga caa agc aat cag      2112
Ala Gln Asn Leu Leu Lys Tyr Phe Lys Ala His Arg Gln Ser Asn Gln
    690                 695                 700 agg aga ggc tga                                                       2124
Arg Arg Gly
705
```

<210> SEQ ID NO 18
<211> LENGTH: 707
<212> TYPE: PRT
<213> ORGANISM: Arabidopsis thaliana

<400> SEQUENCE: 18

```
Met Met Val His Met Glu Val Ser Trp Leu Arg Val Leu Leu Asp Asn
1               5                   10                  15

Ile Ser Ser Tyr Leu Ser Leu Ser Ser Met Asp Asp Leu Ser Ser Asn
                20                  25                  30

Pro Ala His Lys Tyr Tyr Thr Arg Gly Glu Asp Ile Gly Lys Leu Ile
            35                  40                  45

Lys Pro Val Leu Glu Asn Leu Ile Asp Ser Asp Ala Ala Pro Ser Glu
        50                  55                  60

Leu Leu Asn Asn Gly Phe Glu Glu Leu Ala Gln Tyr Val Asp Glu Leu
65                  70                  75                  80

Arg Glu Gln Phe Gln Ser Trp Gln Pro Leu Ser Thr Arg Ile Phe Tyr
                85                  90                  95

Val Leu Arg Ile Glu Ser Leu Ala Ser Lys Leu Arg Glu Ser Ser Leu
            100                 105                 110

Glu Val Phe Gln Leu Leu Lys His Cys Glu Gln His Leu Pro Ala Asp
```

-continued

```
            115                 120                 125
Leu Ile Ser Pro Ser Phe Glu Glu Cys Ile Glu Leu Val Lys Leu Val
130                 135                 140
Ala Arg Asp Glu Ile Ser Tyr Thr Ile Asp Gln Ala Leu Lys Asp Gln
145                 150                 155                 160
Lys Lys Gly Val Gly Pro Thr Ser Glu Val Leu Val Lys Ile Ala Glu
                    165                 170                 175
Ser Thr Gly Leu Arg Ser Asn Gln Glu Ile Leu Val Glu Gly Val Val
                180                 185                 190
Leu Thr Asn Met Lys Glu Asp Ala Glu Leu Thr Asp Asn Asp Thr Glu
            195                 200                 205
Ala Glu Tyr Leu Asp Gly Leu Ile Ser Leu Thr Thr Gln Met His Glu
210                 215                 220
Tyr Leu Ser Asp Ile Lys Gln Ala Gln Leu Arg Cys Pro Val Arg Val
225                 230                 235                 240
Pro Ser Asp Phe Arg Cys Ser Leu Ser Leu Glu Leu Met Thr Asp Pro
                    245                 250                 255
Val Ile Val Ala Ser Gly Gln Thr Phe Glu Arg Val Phe Ile Gln Lys
                260                 265                 270
Trp Ile Asp Met Gly Leu Met Val Cys Pro Lys Thr Arg Gln Ala Leu
            275                 280                 285
Ser His Thr Thr Leu Thr Pro Asn Phe Ile Val Arg Ala Phe Leu Ala
290                 295                 300
Ser Trp Cys Glu Thr Asn Asn Val Tyr Pro Pro Asp Pro Leu Glu Leu
305                 310                 315                 320
Ile His Ser Ser Glu Pro Phe Pro Leu Leu Val Glu Ser Val Arg Ala
                    325                 330                 335
Ser Ser Ser Glu Asn Gly His Ser Glu Ser Leu Asp Ala Glu Glu Leu
                340                 345                 350
Arg Gln Val Phe Ser Arg Ser Ala Ser Ala Pro Gly Ile Val Ser Glu
            355                 360                 365
Val Val Cys Lys Thr Lys Arg Asn Asn Asn Ala Ala Ala Asp Arg Ser
370                 375                 380
Leu Thr Arg Ser Asn Thr Pro Trp Lys Phe Pro Glu Glu Arg His Trp
385                 390                 395                 400
Arg His Pro Gly Ile Ile Pro Ala Thr Val Arg Glu Thr Gly Ser Ser
                    405                 410                 415
Ser Ser Ile Glu Thr Glu Val Lys Lys Leu Ile Asp Asp Leu Lys Ser
                420                 425                 430
Ser Ser Leu Asp Thr Gln Arg Glu Ala Thr Ala Arg Ile Arg Ile Leu
            435                 440                 445
Ala Arg Asn Ser Thr Asp Asn Arg Ile Val Ile Ala Arg Cys Glu Ala
450                 455                 460
Ile Pro Ser Leu Val Ser Leu Leu Tyr Ser Thr Asp Glu Arg Ile Gln
465                 470                 475                 480
Ala Asp Ala Val Thr Cys Leu Leu Asn Leu Ser Ile Asn Asp Asn Asn
                    485                 490                 495
Lys Ser Leu Ile Ala Glu Ser Gly Ala Ile Val Pro Leu Ile His Val
                500                 505                 510
Leu Lys Thr Gly Tyr Leu Glu Glu Ala Lys Ala Asn Ser Ala Ala Thr
            515                 520                 525
Leu Phe Ser Leu Ser Val Ile Glu Glu Tyr Lys Thr Glu Ile Gly Glu
530                 535                 540
```

```
Ala Gly Ala Ile Glu Pro Leu Val Asp Leu Leu Gly Ser Gly Ser Leu
545                 550                 555                 560

Ser Gly Lys Lys Asp Ala Ala Thr Ala Leu Phe Asn Leu Ser Ile His
            565                 570                 575

His Glu Asn Lys Thr Lys Val Ile Glu Ala Gly Ala Val Arg Tyr Leu
        580                 585                 590

Val Glu Leu Met Asp Pro Ala Phe Gly Met Val Glu Lys Ala Val Val
    595                 600                 605

Val Leu Ala Asn Leu Ala Thr Val Arg Glu Gly Lys Ile Ala Ile Gly
610                 615                 620

Glu Glu Gly Gly Ile Pro Val Leu Val Glu Val Val Glu Leu Gly Ser
625                 630                 635                 640

Ala Arg Gly Lys Glu Asn Ala Thr Ala Ala Leu Leu Gln Leu Cys Thr
            645                 650                 655

His Ser Pro Lys Phe Cys Asn Asn Val Ile Arg Glu Gly Val Ile Pro
        660                 665                 670

Pro Leu Val Ala Leu Thr Lys Ser Gly Thr Ala Arg Gly Lys Glu Lys
    675                 680                 685

Ala Gln Asn Leu Leu Lys Tyr Phe Lys Ala His Arg Gln Ser Asn Gln
690                 695                 700

Arg Arg Gly
705

<210> SEQ ID NO 19
<211> LENGTH: 2097
<212> TYPE: DNA
<213> ORGANISM: Arabidopsis thaliana
<220> FEATURE:
<221> NAME/KEY: CDS
<222> LOCATION: (1)..(2097)

<400> SEQUENCE: 19 atg gag gtg tct tgg tta aga gtt ctt cta gat aac atc tcc tcc tat      48
Met Glu Val Ser Trp Leu Arg Val Leu Leu Asp Asn Ile Ser Ser Tyr
1               5                   10                  15 cta agt tta tca tct atg gac gat tta tct tca aac cct gct cat aag      96
Leu Ser Leu Ser Ser Met Asp Asp Leu Ser Ser Asn Pro Ala His Lys
            20                  25                  30 tac tac acc aga gga gaa gat ata gga aag ctt atc aag cct gtt ctt     144
Tyr Tyr Thr Arg Gly Glu Asp Ile Gly Lys Leu Ile Lys Pro Val Leu
        35                  40                  45 gag aac ctc att gac tct gac gcg gct cct agc gag ttg ctt aac aat     192
Glu Asn Leu Ile Asp Ser Asp Ala Ala Pro Ser Glu Leu Leu Asn Asn
    50                  55                  60 ggt ttt gaa gaa tta gct caa tac gtt gat gaa ctt aga gaa cag ttt     240
Gly Phe Glu Glu Leu Ala Gln Tyr Val Asp Glu Leu Arg Glu Gln Phe
65                  70                  75                  80 cag agt tgg caa cct ctt tca act aga atc ttt tat gtt ctt cga att     288
Gln Ser Trp Gln Pro Leu Ser Thr Arg Ile Phe Tyr Val Leu Arg Ile
                85                  90                  95 gaa tca tta gca tca aag tta cga gaa tcc agt ttg gaa gtc ttt cag     336
Glu Ser Leu Ala Ser Lys Leu Arg Glu Ser Ser Leu Glu Val Phe Gln
            100                 105                 110 ctc ctc aaa cac tgc gaa caa cat ttg cct gct gac ttg atc tca cct     384
Leu Leu Lys His Cys Glu Gln His Leu Pro Ala Asp Leu Ile Ser Pro
        115                 120                 125 tct ttt gag gag tgc att gaa ttg gtg aag tta gtg gca aga gac gaa     432
Ser Phe Glu Glu Cys Ile Glu Leu Val Lys Leu Val Ala Arg Asp Glu
    130                 135                 140
```

```
ata tcg tat act att gat caa gct cta aaa gat caa aag aaa ggt gtt        480
Ile Ser Tyr Thr Ile Asp Gln Ala Leu Lys Asp Gln Lys Lys Gly Val
145                 150                 155                 160 gga cct act tca gag gtt ctg gtg aaa att gcc gag agt act ggt tta        528
Gly Pro Thr Ser Glu Val Leu Val Lys Ile Ala Glu Ser Thr Gly Leu
                165                 170                 175 aga tcc aac cag gag att ctt gtt gaa ggt gtg gta ctt aca aac atg        576
Arg Ser Asn Gln Glu Ile Leu Val Glu Gly Val Val Leu Thr Asn Met
            180                 185                 190 aag gag gat gct gag ctt acc gat aat gac acc gaa gcc gag tat cta        624
Lys Glu Asp Ala Glu Leu Thr Asp Asn Asp Thr Glu Ala Glu Tyr Leu
        195                 200                 205 gac gga ttg atc tct cta aca aca caa atg cat gag tac ctt agc gac        672
Asp Gly Leu Ile Ser Leu Thr Thr Gln Met His Glu Tyr Leu Ser Asp
    210                 215                 220 ata aag cag gct cag tta cgt tgt cca gta cgc gta cct tct gat ttc        720
Ile Lys Gln Ala Gln Leu Arg Cys Pro Val Arg Val Pro Ser Asp Phe
225                 230                 235                 240 cgc tgc tct cta tct ctt gag ctt atg act gat cca gtc att gta gca        768
Arg Cys Ser Leu Ser Leu Glu Leu Met Thr Asp Pro Val Ile Val Ala
                245                 250                 255 tct ggt caa aca ttc gaa cgg gtt ttt atc cag aaa tgg atc gat atg        816
Ser Gly Gln Thr Phe Glu Arg Val Phe Ile Gln Lys Trp Ile Asp Met
            260                 265                 270 gga ctc atg gtt tgt cca aag aca agg cag gct tta tct cat acc act        864
Gly Leu Met Val Cys Pro Lys Thr Arg Gln Ala Leu Ser His Thr Thr
        275                 280                 285 ttg aca cct aat ttc att gtc aga gct ttt ctt gca agt tgg tgt gaa        912
Leu Thr Pro Asn Phe Ile Val Arg Ala Phe Leu Ala Ser Trp Cys Glu
    290                 295                 300 act aac aat gtc tat cct cct gat cca ttg gag ttg att cac tca agt        960
Thr Asn Asn Val Tyr Pro Pro Asp Pro Leu Glu Leu Ile His Ser Ser
305                 310                 315                 320 gag cca ttc cct ctt ctt gtt gaa tca gtg aga gct tca tca tca gag       1008
Glu Pro Phe Pro Leu Leu Val Glu Ser Val Arg Ala Ser Ser Ser Glu
                325                 330                 335 aat ggc cat tca gaa tct tta gat gca gag gaa ctg cgt cag gtc ttt       1056
Asn Gly His Ser Glu Ser Leu Asp Ala Glu Glu Leu Arg Gln Val Phe
            340                 345                 350 agt agg tct gct tcg gcg cca ggc att gtc tct gaa gtg gtt tgc aaa       1104
Ser Arg Ser Ala Ser Ala Pro Gly Ile Val Ser Glu Val Val Cys Lys
        355                 360                 365 acc aaa aga aac aac aat gct gct gca gat aga tca ctg aca cgg agt       1152
Thr Lys Arg Asn Asn Asn Ala Ala Ala Asp Arg Ser Leu Thr Arg Ser
    370                 375                 380 aat acc cct tgg aaa ttt cca gaa gag agg cat tgg cgt cac ccc ggg       1200
Asn Thr Pro Trp Lys Phe Pro Glu Glu Arg His Trp Arg His Pro Gly
385                 390                 395                 400 atc atc cca gcg acc gta aga gaa aca gga agc agt tca agt atc gaa       1248
Ile Ile Pro Ala Thr Val Arg Glu Thr Gly Ser Ser Ser Ser Ile Glu
                405                 410                 415 acc gag gtg aag aaa ctc att gat gat ctc aag agt tct tca ttg gat       1296
Thr Glu Val Lys Lys Leu Ile Asp Asp Leu Lys Ser Ser Ser Leu Asp
            420                 425                 430 aca cag aga gag gcc aca gct aga atc agg ata cta gca aga aac agt       1344
Thr Gln Arg Glu Ala Thr Ala Arg Ile Arg Ile Leu Ala Arg Asn Ser
        435                 440                 445 aca gac aat cgc att gtc att gcg cgg tgc gaa gca atc cct tcg tta       1392
Thr Asp Asn Arg Ile Val Ile Ala Arg Cys Glu Ala Ile Pro Ser Leu
    450                 455                 460
```

```
gtc agt ctt ctt tac tca acg gat gag aga atc caa gca gac gca gtg      1440
Val Ser Leu Leu Tyr Ser Thr Asp Glu Arg Ile Gln Ala Asp Ala Val
465                 470                 475                 480 act tgc tta cta aac tta tcc atc aac gac aac aac aag tcc ctc atc      1488
Thr Cys Leu Leu Asn Leu Ser Ile Asn Asp Asn Asn Lys Ser Leu Ile
                485                 490                 495 gcg gaa agt gga gcc atc gta ccg ctt att cac gtt ctc aaa aca gga      1536
Ala Glu Ser Gly Ala Ile Val Pro Leu Ile His Val Leu Lys Thr Gly
            500                 505                 510 tac tta gaa gaa gct aaa gca aac tca gca gca act cta ttc agc ttg      1584
Tyr Leu Glu Glu Ala Lys Ala Asn Ser Ala Ala Thr Leu Phe Ser Leu
        515                 520                 525 tcg gtg atc gaa gag tac aag aca gag ata gga gaa gca gga gct ata      1632
Ser Val Ile Glu Glu Tyr Lys Thr Glu Ile Gly Glu Ala Gly Ala Ile
    530                 535                 540 gag cca ctt gtt gac ctc tta gga agt gga agt ctc agt ggg aag aaa      1680
Glu Pro Leu Val Asp Leu Leu Gly Ser Gly Ser Leu Ser Gly Lys Lys
545                 550                 555                 560 gat gca gcc acg gct tta ttc aac ctc tca ata cac cat gag aac aaa      1728
Asp Ala Ala Thr Ala Leu Phe Asn Leu Ser Ile His His Glu Asn Lys
                565                 570                 575 acg aaa gta atc gaa gct gga gca gtg aga tac tta gtt gaa ctg atg      1776
Thr Lys Val Ile Glu Ala Gly Ala Val Arg Tyr Leu Val Glu Leu Met
            580                 585                 590 gat cct gct ttt ggg atg gtg gag aaa gct gtg gtg gtg cta gcg aat      1824
Asp Pro Ala Phe Gly Met Val Glu Lys Ala Val Val Val Leu Ala Asn
        595                 600                 605 ctt gca acg gtt aga gaa gga aag att gcg ata ggc gaa gaa gga gga      1872
Leu Ala Thr Val Arg Glu Gly Lys Ile Ala Ile Gly Glu Glu Gly Gly
    610                 615                 620 ata ccg gta ttg gtg gaa gtt gtg gag tta ggt tca gca aga ggc aaa      1920
Ile Pro Val Leu Val Glu Val Val Glu Leu Gly Ser Ala Arg Gly Lys
625                 630                 635                 640 gag aat gca act gca gca cta ttg cag ctt tgt acg cat agc ccg aaa      1968
Glu Asn Ala Thr Ala Ala Leu Leu Gln Leu Cys Thr His Ser Pro Lys
                645                 650                 655 ttc tgc aac aat gtc ata aga gaa gga gtg att cca cct ctt gtg gca      2016
Phe Cys Asn Asn Val Ile Arg Glu Gly Val Ile Pro Pro Leu Val Ala
            660                 665                 670 ctt act aaa tca gga aca gct aga ggc aaa gag aag gtt ctt ttt ttg      2064
Leu Thr Lys Ser Gly Thr Ala Arg Gly Lys Glu Lys Val Leu Phe Leu
        675                 680                 685 ttt cct ctt ctt tgt ttg gta aat gtc tca tga                          2097
Phe Pro Leu Leu Cys Leu Val Asn Val Ser
    690                 695

<210> SEQ ID NO 20
<211> LENGTH: 698
<212> TYPE: PRT
<213> ORGANISM: Arabidopsis thaliana

<400> SEQUENCE: 20

Met Glu Val Ser Trp Leu Arg Val Leu Leu Asp Asn Ile Ser Ser Tyr
1               5                   10                  15

Leu Ser Leu Ser Ser Met Asp Asp Leu Ser Ser Asn Pro Ala His Lys
            20                  25                  30

Tyr Tyr Thr Arg Gly Glu Asp Ile Gly Lys Leu Ile Lys Pro Val Leu
        35                  40                  45

Glu Asn Leu Ile Asp Ser Asp Ala Ala Pro Ser Glu Leu Leu Asn Asn
    50                  55                  60
```

-continued

```
Gly Phe Glu Glu Leu Ala Gln Tyr Val Asp Glu Leu Arg Glu Gln Phe
 65                  70                  75                  80
Gln Ser Trp Gln Pro Leu Ser Thr Arg Ile Phe Tyr Val Leu Arg Ile
                 85                  90                  95
Glu Ser Leu Ala Ser Lys Leu Arg Glu Ser Ser Leu Glu Val Phe Gln
            100                 105                 110
Leu Leu Lys His Cys Glu Gln His Leu Pro Ala Asp Leu Ile Ser Pro
        115                 120                 125
Ser Phe Glu Glu Cys Ile Glu Leu Val Lys Leu Val Ala Arg Asp Glu
130                 135                 140
Ile Ser Tyr Thr Ile Asp Gln Ala Leu Lys Asp Gln Lys Lys Gly Val
145                 150                 155                 160
Gly Pro Thr Ser Glu Val Leu Val Lys Ile Ala Glu Ser Thr Gly Leu
                165                 170                 175
Arg Ser Asn Gln Glu Ile Leu Val Glu Gly Val Val Leu Thr Asn Met
            180                 185                 190
Lys Glu Asp Ala Glu Leu Thr Asp Asn Asp Thr Glu Ala Glu Tyr Leu
        195                 200                 205
Asp Gly Leu Ile Ser Leu Thr Thr Gln Met His Glu Tyr Leu Ser Asp
210                 215                 220
Ile Lys Gln Ala Gln Leu Arg Cys Pro Val Arg Val Pro Ser Asp Phe
225                 230                 235                 240
Arg Cys Ser Leu Ser Leu Glu Leu Met Thr Asp Pro Val Ile Val Ala
                245                 250                 255
Ser Gly Gln Thr Phe Glu Arg Val Phe Ile Gln Lys Trp Ile Asp Met
            260                 265                 270
Gly Leu Met Val Cys Pro Lys Thr Arg Gln Ala Leu Ser His Thr Thr
        275                 280                 285
Leu Thr Pro Asn Phe Ile Val Arg Ala Phe Leu Ala Ser Trp Cys Glu
290                 295                 300
Thr Asn Asn Val Tyr Pro Pro Asp Pro Leu Glu Leu Ile His Ser Ser
305                 310                 315                 320
Glu Pro Phe Pro Leu Leu Val Glu Ser Val Arg Ala Ser Ser Ser Glu
                325                 330                 335
Asn Gly His Ser Glu Ser Leu Asp Ala Glu Glu Leu Arg Gln Val Phe
            340                 345                 350
Ser Arg Ser Ala Ser Ala Pro Gly Ile Val Ser Glu Val Val Cys Lys
        355                 360                 365
Thr Lys Arg Asn Asn Ala Ala Asp Arg Ser Leu Thr Arg Ser
370                 375                 380
Asn Thr Pro Trp Lys Phe Pro Glu Glu Arg His Trp Arg His Pro Gly
385                 390                 395                 400
Ile Ile Pro Ala Thr Val Arg Glu Thr Gly Ser Ser Ser Ile Glu
                405                 410                 415
Thr Glu Val Lys Lys Leu Ile Asp Asp Leu Lys Ser Ser Leu Asp
            420                 425                 430
Thr Gln Arg Glu Ala Thr Ala Arg Ile Arg Ile Leu Ala Arg Asn Ser
        435                 440                 445
Thr Asp Asn Arg Ile Val Ile Ala Arg Cys Glu Ala Ile Pro Ser Leu
450                 455                 460
Val Ser Leu Leu Tyr Ser Thr Asp Glu Arg Ile Gln Ala Asp Ala Val
465                 470                 475                 480
Thr Cys Leu Leu Asn Leu Ser Ile Asn Asp Asn Lys Ser Leu Ile
                485                 490                 495
```

```
Ala Glu Ser Gly Ala Ile Val Pro Leu Ile His Val Leu Lys Thr Gly
                500                 505                 510

Tyr Leu Glu Glu Ala Lys Ala Asn Ser Ala Ala Thr Leu Phe Ser Leu
            515                 520                 525

Ser Val Ile Glu Glu Tyr Lys Thr Glu Ile Gly Ala Gly Ala Ile
530                 535                 540

Glu Pro Leu Val Asp Leu Leu Gly Ser Gly Leu Ser Gly Lys Lys
545                 550                 555                 560

Asp Ala Ala Thr Ala Leu Phe Asn Leu Ser Ile His His Glu Asn Lys
                565                 570                 575

Thr Lys Val Ile Glu Ala Gly Ala Val Arg Tyr Leu Val Glu Leu Met
                580                 585                 590

Asp Pro Ala Phe Gly Met Val Glu Lys Ala Val Val Leu Ala Asn
                595                 600                 605

Leu Ala Thr Val Arg Glu Gly Lys Ile Ala Ile Gly Glu Gly Gly
    610                 615                 620

Ile Pro Val Leu Val Glu Val Glu Leu Gly Ser Ala Arg Gly Lys
625                 630                 635                 640

Glu Asn Ala Thr Ala Ala Leu Leu Gln Leu Cys Thr His Ser Pro Lys
                645                 650                 655

Phe Cys Asn Asn Val Ile Arg Glu Gly Val Ile Pro Pro Leu Val Ala
                660                 665                 670

Leu Thr Lys Ser Gly Thr Ala Arg Gly Lys Glu Lys Val Leu Phe Leu
                675                 680                 685

Phe Pro Leu Leu Cys Leu Val Asn Val Ser
690                 695

<210> SEQ ID NO 21
<211> LENGTH: 2283
<212> TYPE: DNA
<213> ORGANISM: Arabidopsis thaliana
<220> FEATURE:
<221> NAME/KEY: CDS
<222> LOCATION: (1)..(2283)

<400> SEQUENCE: 21 atg gat cct gtt cct gtt cga tgt ctt ctt aac agt ata tct cgg tat      48
Met Asp Pro Val Pro Val Arg Cys Leu Leu Asn Ser Ile Ser Arg Tyr
1               5                   10                  15 ctt cat ctg gtt gcg tgc cag act ata aga ttt aat cct att caa aca      96
Leu His Leu Val Ala Cys Gln Thr Ile Arg Phe Asn Pro Ile Gln Thr
            20                  25                  30 tgt att gga aat atg gtt ctc ttg ttg aag ctc ttg aaa ccg ttg ctc     144
Cys Ile Gly Asn Met Val Leu Leu Leu Lys Leu Leu Lys Pro Leu Leu
        35                  40                  45 gat gaa gtt gtt gat tgc aag ata cct tct gat gac tgt tta tat aaa     192
Asp Glu Val Val Asp Cys Lys Ile Pro Ser Asp Asp Cys Leu Tyr Lys
50                  55                  60 gga tgt gaa gac ctt gat tct gtt gtt aac cag gct cgg gag ttc tta     240
Gly Cys Glu Asp Leu Asp Ser Val Val Asn Gln Ala Arg Glu Phe Leu
65                  70                  75                  80 gag gac tgg tca cca aag ttg agc aag ttg ttt ggt gtg ttt caa tgc     288
Glu Asp Trp Ser Pro Lys Leu Ser Lys Leu Phe Gly Val Phe Gln Cys
                85                  90                  95 gag gtt ttg ttg gga aag gtc cag act tgt tcg ttg gag att agt cgc     336
Glu Val Leu Leu Gly Lys Val Gln Thr Cys Ser Leu Glu Ile Ser Arg
            100                 105                 110 ata ctt ctt cag tta tca cag tca agt ccg gtt act tca agc gta caa     384
```

```
Ile Leu Leu Gln Leu Ser Gln Ser Ser Pro Val Thr Ser Val Gln
            115                 120                 125 agt gtt gag cgc tgc gtg cag gag act gag agt ttt aag caa gag ggg    432
Ser Val Glu Arg Cys Val Gln Glu Thr Glu Ser Phe Lys Gln Glu Gly
130                 135                 140 aca tta atg gaa ctc atg gag aat gct tta cgg aat cag aaa gat gat    480
Thr Leu Met Glu Leu Met Glu Asn Ala Leu Arg Asn Gln Lys Asp Asp
145                 150                 155                 160 att acc tct ttg gat aac aat cat ctg gaa agc ata att caa atg ctt    528
Ile Thr Ser Leu Asp Asn Asn His Leu Glu Ser Ile Ile Gln Met Leu
                165                 170                 175 gga ttg ata tca aac caa gat ctc tta aag gaa agc att act gtg gag    576
Gly Leu Ile Ser Asn Gln Asp Leu Leu Lys Glu Ser Ile Thr Val Glu
            180                 185                 190 aaa gag agg ata aga tcc cag gcc agt aag tca gaa gaa gat atg gaa    624
Lys Glu Arg Ile Arg Ser Gln Ala Ser Lys Ser Glu Glu Asp Met Glu
        195                 200                 205 caa acc gaa cag ttg ata gaa ctc gtc ttg tgc atc cgt gaa cac atg    672
Gln Thr Glu Gln Leu Ile Glu Leu Val Leu Cys Ile Arg Glu His Met
210                 215                 220 ctt aaa act gag ttt ctt gaa gtg gct aaa ggt atc tcg ata ccc ccg    720
Leu Lys Thr Glu Phe Leu Glu Val Ala Lys Gly Ile Ser Ile Pro Pro
225                 230                 235                 240 tat ttc cgg tgt cct ttg tca aca gaa ctc atg ctg gat ccg gta ata    768
Tyr Phe Arg Cys Pro Leu Ser Thr Glu Leu Met Leu Asp Pro Val Ile
                245                 250                 255 gta gct tca gga cag aca ttt gac aga aca tcc att aag aaa tgg ctt    816
Val Ala Ser Gly Gln Thr Phe Asp Arg Thr Ser Ile Lys Lys Trp Leu
            260                 265                 270 gat aac ggg tta gct gtt tgt cca agg acg cgg cag gtg ctg act cat    864
Asp Asn Gly Leu Ala Val Cys Pro Arg Thr Arg Gln Val Leu Thr His
        275                 280                 285 caa gaa ctc att ccc aat tac acg gtt aag gct atg ata gcg agt tgg    912
Gln Glu Leu Ile Pro Asn Tyr Thr Val Lys Ala Met Ile Ala Ser Trp
290                 295                 300 ttg gag gca aac agg atc aac ctt gct act aac tct tgt cat cag tat    960
Leu Glu Ala Asn Arg Ile Asn Leu Ala Thr Asn Ser Cys His Gln Tyr
305                 310                 315                 320 gat ggt ggt gat gct tca tcc atg gct aat aat atg ggt tct caa gac   1008
Asp Gly Gly Asp Ala Ser Ser Met Ala Asn Asn Met Gly Ser Gln Asp
                325                 330                 335 ttt aac cgc acc gag agt ttt cgt ttt tct tta cgg agc agc agt tta   1056
Phe Asn Arg Thr Glu Ser Phe Arg Phe Ser Leu Arg Ser Ser Ser Leu
            340                 345                 350 acc tca aga tca tct ctt gaa act gga aat ggg ttt gag aaa ctg aag   1104
Thr Ser Arg Ser Ser Leu Glu Thr Gly Asn Gly Phe Glu Lys Leu Lys
        355                 360                 365 att aac gtg tct gcc agt tta tgc ggg gaa tct caa agc aag gat ctt   1152
Ile Asn Val Ser Ala Ser Leu Cys Gly Glu Ser Gln Ser Lys Asp Leu
370                 375                 380 gaa ata ttc gag ctt ttg tct ccg ggg cag tct tac act cac agc agg   1200
Glu Ile Phe Glu Leu Leu Ser Pro Gly Gln Ser Tyr Thr His Ser Arg
385                 390                 395                 400 agt gaa tca gtt tgc agt gtt gtc tcg tct gtt gat tat gta cct tcg   1248
Ser Glu Ser Val Cys Ser Val Val Ser Ser Val Asp Tyr Val Pro Ser
                405                 410                 415 gtg aca cat gag aca gaa agt ata cta ggg aat cac caa agc tcc agt   1296
Val Thr His Glu Thr Glu Ser Ile Leu Gly Asn His Gln Ser Ser Ser
            420                 425                 430 gag atg tct ccc aag aaa aac tta gaa agt tca aac aat gta aat cat   1344
```

|     |     |     |     |     |     |     |     |     |     |     |     |     |     |      |
|-----|-----|-----|-----|-----|-----|-----|-----|-----|-----|-----|-----|-----|-----|------|
| Glu | Met | Ser | Pro | Lys | Lys | Asn | Leu | Glu | Ser | Ser | Asn | Asn | Val | Asn His |
|     |     | 435 |     |     |     | 440 |     |     |     | 445 |     |     |     |      |

```
gag cat agc gca gca aag act tat gag tgt tct gta cat gat tta gat    1392
Glu His Ser Ala Ala Lys Thr Tyr Glu Cys Ser Val His Asp Leu Asp
    450                 455                 460 gat tca gga aca atg acg act tca cat acc ata aaa ttg gta gaa gat    1440
Asp Ser Gly Thr Met Thr Thr Ser His Thr Ile Lys Leu Val Glu Asp
465                 470                 475                 480 ctt aaa agc ggg tct aac aaa gtg aag act gct gct gca gct gaa ata    1488
Leu Lys Ser Gly Ser Asn Lys Val Lys Thr Ala Ala Ala Ala Glu Ile
                    485                 490                 495 cgt cat ctc acc att aac agc att gaa aat cgt gtt cac atc ggg cgt    1536
Arg His Leu Thr Ile Asn Ser Ile Glu Asn Arg Val His Ile Gly Arg
                500                 505                 510 tgt ggt gct att act cca ctg ctg tca ctt tta tac tca gaa gaa aag    1584
Cys Gly Ala Ile Thr Pro Leu Leu Ser Leu Leu Tyr Ser Glu Glu Lys
            515                 520                 525 cta act caa gaa cac gca gtc acg gct ctt ttg aat ctt tcc atc agt    1632
Leu Thr Gln Glu His Ala Val Thr Ala Leu Leu Asn Leu Ser Ile Ser
530                 535                 540 gaa cta aac aaa gcc atg att gtg gaa gtc ggg gcg ata gaa ccg ctt    1680
Glu Leu Asn Lys Ala Met Ile Val Glu Val Gly Ala Ile Glu Pro Leu
545                 550                 555                 560 gtt cat gtt ttg aac aca gga aat gac aga gcc aaa gag aat tca gca    1728
Val His Val Leu Asn Thr Gly Asn Asp Arg Ala Lys Glu Asn Ser Ala
                565                 570                 575 gca tca ttg ttc agt ctg tct gtt ctg cag gtc aac aga gaa cga ata    1776
Ala Ser Leu Phe Ser Leu Ser Val Leu Gln Val Asn Arg Glu Arg Ile
                580                 585                 590 ggc cag tct aac gca gcg ata caa gct ctg gtg aat ctt ctt ggt aaa    1824
Gly Gln Ser Asn Ala Ala Ile Gln Ala Leu Val Asn Leu Leu Gly Lys
            595                 600                 605 gga aca ttt aga gga aag aaa gac gcc gcc tct gct ttg ttc aat cta    1872
Gly Thr Phe Arg Gly Lys Lys Asp Ala Ala Ser Ala Leu Phe Asn Leu
                    610                 615                 620 tcg att act cat gat aac aag gcc cgt atc gtg caa gct aag gcg gtt    1920
Ser Ile Thr His Asp Asn Lys Ala Arg Ile Val Gln Ala Lys Ala Val
625                 630                 635                 640 aag tac ctt gtg gag ctg tta gac cca gat tta gag atg gtt gat aaa    1968
Lys Tyr Leu Val Glu Leu Leu Asp Pro Asp Leu Glu Met Val Asp Lys
                    645                 650                 655 gca gtt gct ctt ctt gca aat ctt tct gca gtt gga gaa ggg cgt caa    2016
Ala Val Ala Leu Leu Ala Asn Leu Ser Ala Val Gly Glu Gly Arg Gln
                660                 665                 670 gcc atc gtg agg gaa ggt ggg att cca tta ctt gtt gaa act gtt gac    2064
Ala Ile Val Arg Glu Gly Gly Ile Pro Leu Leu Val Glu Thr Val Asp
            675                 680                 685 tta gga tct cag aga ggg aaa gag aat gca gct tct gtg ctg ctt cag    2112
Leu Gly Ser Gln Arg Gly Lys Glu Asn Ala Ala Ser Val Leu Leu Gln
        690                 695                 700 ttg tgt ctg aac agt ccc aag ttt tgc act ctg gtc ttg caa gaa ggc    2160
Leu Cys Leu Asn Ser Pro Lys Phe Cys Thr Leu Val Leu Gln Glu Gly
705                 710                 715                 720 gcc ata cct ccg ctt gtt gcc ttg tct cag tct ggt aca cag aga gca    2208
Ala Ile Pro Pro Leu Val Ala Leu Ser Gln Ser Gly Thr Gln Arg Ala
                    725                 730                 735 aaa gag aag gca cag caa ctt ctt agc cac ttc cga aac cag aga gat    2256
Lys Glu Lys Ala Gln Gln Leu Leu Ser His Phe Arg Asn Gln Arg Asp
                740                 745                 750 gca agg atg aag aaa ggt aga tca tga                                2283
```

Ala Arg Met Lys Lys Gly Arg Ser
        755                 760

<210> SEQ ID NO 22
<211> LENGTH: 760
<212> TYPE: PRT
<213> ORGANISM: Arabidopsis thaliana

<400> SEQUENCE: 22

Met Asp Pro Val Pro Val Arg Cys Leu Leu Asn Ser Ile Ser Arg Tyr
1               5                   10                  15

Leu His Leu Val Ala Cys Gln Thr Ile Arg Phe Asn Pro Ile Gln Thr
            20                  25                  30

Cys Ile Gly Asn Met Val Leu Leu Lys Leu Leu Lys Pro Leu Leu
        35                  40                  45

Asp Glu Val Val Asp Cys Lys Ile Pro Ser Asp Asp Cys Leu Tyr Lys
    50                  55                  60

Gly Cys Glu Asp Leu Asp Ser Val Val Asn Gln Ala Arg Glu Phe Leu
65                  70                  75                  80

Glu Asp Trp Ser Pro Lys Leu Ser Lys Leu Phe Gly Val Phe Gln Cys
                85                  90                  95

Glu Val Leu Leu Gly Lys Val Gln Thr Cys Ser Leu Glu Ile Ser Arg
            100                 105                 110

Ile Leu Leu Gln Leu Ser Gln Ser Ser Pro Val Thr Ser Ser Val Gln
        115                 120                 125

Ser Val Glu Arg Cys Val Gln Glu Thr Glu Ser Phe Lys Gln Glu Gly
    130                 135                 140

Thr Leu Met Glu Leu Met Glu Asn Ala Leu Arg Asn Gln Lys Asp Asp
145                 150                 155                 160

Ile Thr Ser Leu Asp Asn Asn His Leu Glu Ser Ile Ile Gln Met Leu
                165                 170                 175

Gly Leu Ile Ser Asn Gln Asp Leu Leu Lys Glu Ser Ile Thr Val Glu
            180                 185                 190

Lys Glu Arg Ile Arg Ser Gln Ala Ser Lys Ser Glu Glu Asp Met Glu
        195                 200                 205

Gln Thr Glu Gln Leu Ile Glu Leu Val Leu Cys Ile Arg Glu His Met
    210                 215                 220

Leu Lys Thr Glu Phe Leu Glu Val Ala Lys Gly Ile Ser Ile Pro Pro
225                 230                 235                 240

Tyr Phe Arg Cys Pro Leu Ser Thr Glu Leu Met Leu Asp Pro Val Ile
                245                 250                 255

Val Ala Ser Gly Gln Thr Phe Asp Arg Thr Ser Ile Lys Lys Trp Leu
            260                 265                 270

Asp Asn Gly Leu Ala Val Cys Pro Arg Thr Arg Gln Val Leu Thr His
        275                 280                 285

Gln Glu Leu Ile Pro Asn Tyr Thr Val Lys Ala Met Ile Ala Ser Trp
    290                 295                 300

Leu Glu Ala Asn Arg Ile Asn Leu Ala Thr Asn Ser Cys His Gln Tyr
305                 310                 315                 320

Asp Gly Gly Asp Ala Ser Ser Met Ala Asn Asn Met Gly Ser Gln Asp
                325                 330                 335

Phe Asn Arg Thr Glu Ser Phe Arg Phe Ser Leu Arg Ser Ser Ser Leu
            340                 345                 350

Thr Ser Arg Ser Ser Leu Glu Thr Gly Asn Gly Phe Glu Lys Leu Lys
        355                 360                 365

```
Ile Asn Val Ser Ala Ser Leu Cys Gly Glu Ser Gln Ser Lys Asp Leu
        370                 375                 380

Glu Ile Phe Glu Leu Leu Ser Pro Gly Gln Ser Tyr Thr His Ser Arg
385                 390                 395                 400

Ser Glu Ser Val Cys Ser Val Ser Ser Val Asp Tyr Val Pro Ser
                405                 410                 415

Val Thr His Glu Thr Glu Ser Ile Leu Gly Asn His Gln Ser Ser Ser
                420                 425                 430

Glu Met Ser Pro Lys Lys Asn Leu Glu Ser Ser Asn Val Asn His
        435                 440                 445

Glu His Ser Ala Ala Lys Thr Tyr Glu Cys Ser Val His Asp Leu Asp
        450                 455                 460

Asp Ser Gly Thr Met Thr Thr Ser His Thr Ile Lys Leu Val Glu Asp
465                 470                 475                 480

Leu Lys Ser Gly Ser Asn Lys Val Lys Thr Ala Ala Ala Glu Ile
                485                 490                 495

Arg His Leu Thr Ile Asn Ser Ile Glu Asn Arg Val His Ile Gly Arg
                500                 505                 510

Cys Gly Ala Ile Thr Pro Leu Leu Ser Leu Leu Tyr Ser Glu Glu Lys
        515                 520                 525

Leu Thr Gln Glu His Ala Val Thr Ala Leu Leu Asn Leu Ser Ile Ser
        530                 535                 540

Glu Leu Asn Lys Ala Met Ile Val Glu Val Gly Ala Ile Glu Pro Leu
545                 550                 555                 560

Val His Val Leu Asn Thr Gly Asn Asp Arg Ala Lys Glu Asn Ser Ala
                565                 570                 575

Ala Ser Leu Phe Ser Leu Ser Val Leu Gln Val Asn Arg Glu Arg Ile
                580                 585                 590

Gly Gln Ser Asn Ala Ala Ile Gln Ala Leu Val Asn Leu Leu Gly Lys
        595                 600                 605

Gly Thr Phe Arg Gly Lys Lys Asp Ala Ala Ser Ala Leu Phe Asn Leu
        610                 615                 620

Ser Ile Thr His Asp Asn Lys Ala Arg Ile Val Gln Ala Lys Ala Val
625                 630                 635                 640

Lys Tyr Leu Val Glu Leu Leu Asp Pro Asp Leu Glu Met Val Asp Lys
                645                 650                 655

Ala Val Ala Leu Leu Ala Asn Leu Ser Ala Val Gly Glu Gly Arg Gln
                660                 665                 670

Ala Ile Val Arg Glu Gly Gly Ile Pro Leu Leu Val Glu Thr Val Asp
        675                 680                 685

Leu Gly Ser Gln Arg Gly Lys Glu Asn Ala Ala Ser Val Leu Leu Gln
        690                 695                 700

Leu Cys Leu Asn Ser Pro Lys Phe Cys Thr Leu Val Leu Gln Glu Gly
705                 710                 715                 720

Ala Ile Pro Pro Leu Val Ala Leu Ser Gln Ser Gly Thr Gln Arg Ala
                725                 730                 735

Lys Glu Lys Ala Gln Gln Leu Leu Ser His Phe Arg Asn Gln Arg Asp
        740                 745                 750

Ala Arg Met Lys Lys Gly Arg Ser
        755                 760

<210> SEQ ID NO 23
<211> LENGTH: 2283
<212> TYPE: DNA
<213> ORGANISM: Arabidopsis thaliana
```

```
<220> FEATURE:
<221> NAME/KEY: CDS
<222> LOCATION: (1)..(2283)

<400> SEQUENCE: 23 atg gat cct gtt cct gtt cga tgt ctt ctt aac agt ata tct cgg tat      48
Met Asp Pro Val Pro Val Arg Cys Leu Leu Asn Ser Ile Ser Arg Tyr
1               5                   10                  15 ctt cat ctg gtt gcg tgc cag act ata aga ttt aat cct att caa aca      96
Leu His Leu Val Ala Cys Gln Thr Ile Arg Phe Asn Pro Ile Gln Thr
                20                  25                  30 tgt att gga aat atg gtt ctc ttg ttg aag ctc ttg aaa ccg ttg ctc     144
Cys Ile Gly Asn Met Val Leu Leu Leu Lys Leu Leu Lys Pro Leu Leu
            35                  40                  45 gat gaa gtt gtt gat tgc aag ata cct tct gat gac tgt tta tat aaa     192
Asp Glu Val Val Asp Cys Lys Ile Pro Ser Asp Asp Cys Leu Tyr Lys
        50                  55                  60 gga cgt gaa gac ctt gat tct gtt gtt aac cag gct cgg gag ttc tta     240
Gly Arg Glu Asp Leu Asp Ser Val Val Asn Gln Ala Arg Glu Phe Leu
65                  70                  75                  80 gag gac tgg tca cca aag ttg agc aag ttg ttt ggt gtg ttt caa tgc     288
Glu Asp Trp Ser Pro Lys Leu Ser Lys Leu Phe Gly Val Phe Gln Cys
                85                  90                  95 gag gtt ttg ttg gga aag gtc cag act tgt tcg ttg gag att agt cgc     336
Glu Val Leu Leu Gly Lys Val Gln Thr Cys Ser Leu Glu Ile Ser Arg
                100                 105                 110 ata ctt ctt cag tta tca cag tca agt ccg gtt act tca agc gta caa     384
Ile Leu Leu Gln Leu Ser Gln Ser Ser Pro Val Thr Ser Ser Val Gln
            115                 120                 125 agt gtt gag cgc tgc gtg cag gag act gag agt ttt aag caa gag ggg     432
Ser Val Glu Arg Cys Val Gln Glu Thr Glu Ser Phe Lys Gln Glu Gly
        130                 135                 140 aca tta atg gaa ctc atg gag aat gct tta cgg aat cag aaa gat gat     480
Thr Leu Met Glu Leu Met Glu Asn Ala Leu Arg Asn Gln Lys Asp Asp
145                 150                 155                 160 att acc tct ttg gat aac aat cat ctg gaa agc ata att caa atg ctt     528
Ile Thr Ser Leu Asp Asn Asn His Leu Glu Ser Ile Ile Gln Met Leu
                165                 170                 175 gga ttg ata tca aac caa gat ctc tta aag gaa agc att act gtg gag     576
Gly Leu Ile Ser Asn Gln Asp Leu Leu Lys Glu Ser Ile Thr Val Glu
                180                 185                 190 aaa gag agg ata aga tcc cag gcc agt aag tca gaa gaa gat atg gaa     624
Lys Glu Arg Ile Arg Ser Gln Ala Ser Lys Ser Glu Glu Asp Met Glu
            195                 200                 205 caa acc gaa cag ttg ata gaa ctc gtc ttg tgc atc cgt gaa cac atg     672
Gln Thr Glu Gln Leu Ile Glu Leu Val Leu Cys Ile Arg Glu His Met
        210                 215                 220 ctt aaa act gag ttt ctt gaa gtg gct aaa ggt atc tcg ata ccc ccg     720
Leu Lys Thr Glu Phe Leu Glu Val Ala Lys Gly Ile Ser Ile Pro Pro
225                 230                 235                 240 tat ttc cgg tgt cct ttg tca aca gaa ctc atg ctg gat ccg gta ata     768
Tyr Phe Arg Cys Pro Leu Ser Thr Glu Leu Met Leu Asp Pro Val Ile
                245                 250                 255 gta gct tca gga cag aca ttt gac aga aca tcc att aag aaa tgg ctt     816
Val Ala Ser Gly Gln Thr Phe Asp Arg Thr Ser Ile Lys Lys Trp Leu
                260                 265                 270 gat aac ggg tta gct gtt tgt cca agg acg cgg cag gtg ctg act cat     864
Asp Asn Gly Leu Ala Val Cys Pro Arg Thr Arg Gln Val Leu Thr His
            275                 280                 285 caa gaa ctc att ccc aat tac acg gtt aag gct atg ata gcg agt tgg     912
Gln Glu Leu Ile Pro Asn Tyr Thr Val Lys Ala Met Ile Ala Ser Trp
```

-continued

```
                290                      295                      300
ttg gag gca aac agg atc aac ctt gct act aac tct tgt cat cag tat         960
Leu Glu Ala Asn Arg Ile Asn Leu Ala Thr Asn Ser Cys His Gln Tyr
305                     310                      315                    320 gat ggt ggt gat gct tca tcc atg gct aat aat atg ggt tct caa gac        1008
Asp Gly Gly Asp Ala Ser Ser Met Ala Asn Asn Met Gly Ser Gln Asp
                        325                      330                    335 ttt aac cgc acc gag agt ttt cgt ttt tct tta cgg agc agc agt tta        1056
Phe Asn Arg Thr Glu Ser Phe Arg Phe Ser Leu Arg Ser Ser Ser Leu
                340                      345                      350 acc tca aga tca tct ctt gaa act gga aat ggg ttt gag aaa ctg aag        1104
Thr Ser Arg Ser Ser Leu Glu Thr Gly Asn Gly Phe Glu Lys Leu Lys
            355                      360                      365 att aac gtg tct gcc agt tta tgc ggg gaa tct caa agc aag gat ctt        1152
Ile Asn Val Ser Ala Ser Leu Cys Gly Glu Ser Gln Ser Lys Asp Leu
370                      375                      380 gaa ata ttc gag ctt ttg tct ccg ggg cag tct tac act cac agc agg        1200
Glu Ile Phe Glu Leu Leu Ser Pro Gly Gln Ser Tyr Thr His Ser Arg
385                      390                      395                    400 agt gaa tca gtt tgc agt gtt gtc tcg tct gtt gat tat gta cct tcg        1248
Ser Glu Ser Val Cys Ser Val Val Ser Ser Val Asp Tyr Val Pro Ser
                        405                      410                    415 gtg aca cat gag aca gaa agt ata cta ggg aat cac caa agc tcc agt        1296
Val Thr His Glu Thr Glu Ser Ile Leu Gly Asn His Gln Ser Ser Ser
                420                      425                      430 gag atg tct ccc aag aaa aac tta gaa agt tca aac aat gta aat cat        1344
Glu Met Ser Pro Lys Lys Asn Leu Glu Ser Ser Asn Asn Val Asn His
            435                      440                      445 gag cat agc gca gca aag act tat gag tgt tct gta cat gat tta gat        1392
Glu His Ser Ala Ala Lys Thr Tyr Glu Cys Ser Val His Asp Leu Asp
450                      455                      460 gat tca gga aca atg acg act tca cat acc ata aaa ttg gta gaa gat        1440
Asp Ser Gly Thr Met Thr Thr Ser His Thr Ile Lys Leu Val Glu Asp
465                      470                      475                    480 ctt aaa agc ggg tct aac aaa gtg aag act gct gct gca gct gaa ata        1488
Leu Lys Ser Gly Ser Asn Lys Val Lys Thr Ala Ala Ala Ala Glu Ile
                        485                      490                    495 cgt cat ctc acc att aac agc att gaa aat cgt gtt cac atc ggg cgt        1536
Arg His Leu Thr Ile Asn Ser Ile Glu Asn Arg Val His Ile Gly Arg
                500                      505                      510 tgt ggt gct att act cca ctg ctg tca ctt tta tac tca gaa gaa aag        1584
Cys Gly Ala Ile Thr Pro Leu Leu Ser Leu Leu Tyr Ser Glu Glu Lys
            515                      520                      525 cta act caa gaa cac gca gtc acg gct ctt ttg aat ctt tcc atc agt        1632
Leu Thr Gln Glu His Ala Val Thr Ala Leu Leu Asn Leu Ser Ile Ser
530                      535                      540 gaa cta aac aaa gcc atg att gtg gaa gtc ggg gcg gta gaa ccg ctt        1680
Glu Leu Asn Lys Ala Met Ile Val Glu Val Gly Ala Val Glu Pro Leu
545                      550                      555                    560 gtt cat gtt ttg aac aca gga aat gac aga gcc aaa gag aat tca gca        1728
Val His Val Leu Asn Thr Gly Asn Asp Arg Ala Lys Glu Asn Ser Ala
                        565                      570                    575 gca tca ttg ttc agt ctg tct gtt ctg cag gtc aac aga gaa cga ata        1776
Ala Ser Leu Phe Ser Leu Ser Val Leu Gln Val Asn Arg Glu Arg Ile
                580                      585                      590 ggc cag tct aac gca gcg ata caa gct ctg gtg aat ctt ctt ggt aaa        1824
Gly Gln Ser Asn Ala Ala Ile Gln Ala Leu Val Asn Leu Leu Gly Lys
            595                      600                      605 gga aca ttt aga gga aag aaa gac gcc gcc tct gct ttg ttc aat cta        1872
Gly Thr Phe Arg Gly Lys Lys Asp Ala Ala Ser Ala Leu Phe Asn Leu
```

```
                610                 615                 620
tcg att act cat gat aac aag gcc cgt atc gtg caa gct aag gcg gtt      1920
Ser Ile Thr His Asp Asn Lys Ala Arg Ile Val Gln Ala Lys Ala Val
625                 630                 635                 640 aag tac ctt gtg gag ctg tta gac cca gat tta gag atg gtt gat aaa      1968
Lys Tyr Leu Val Glu Leu Leu Asp Pro Asp Leu Glu Met Val Asp Lys
                645                 650                 655 gca gtt gct ctt ctt gca aat ctt tct gca gtt gga gaa ggg cgt caa      2016
Ala Val Ala Leu Leu Ala Asn Leu Ser Ala Val Gly Glu Gly Arg Gln
            660                 665                 670 gcc atc gtg agg gaa ggt ggg att cca tta ctt gtt gaa act gtt gac      2064
Ala Ile Val Arg Glu Gly Gly Ile Pro Leu Leu Val Glu Thr Val Asp
        675                 680                 685 tta gga tct cag aga ggg aaa gag aat gca gct tct gtg ctg ctt cag      2112
Leu Gly Ser Gln Arg Gly Lys Glu Asn Ala Ala Ser Val Leu Leu Gln
690                 695                 700 ttg tgt ctg aac agt ccc aag ttt tgc act ctg gtc ttg caa gaa ggc      2160
Leu Cys Leu Asn Ser Pro Lys Phe Cys Thr Leu Val Leu Gln Glu Gly
705                 710                 715                 720 gcc ata cct ccg ctt gtt gcc ttg tct cag tct ggt aca cag aga gca      2208
Ala Ile Pro Pro Leu Val Ala Leu Ser Gln Ser Gly Thr Gln Arg Ala
                725                 730                 735 aaa gag aag gca cag caa ctt ctt agc cac ttc cga aac cag aga gat      2256
Lys Glu Lys Ala Gln Gln Leu Leu Ser His Phe Arg Asn Gln Arg Asp
            740                 745                 750 gca agg atg aag aaa ggt aga tca tga                                  2283
Ala Arg Met Lys Lys Gly Arg Ser
        755                 760

<210> SEQ ID NO 24
<211> LENGTH: 760
<212> TYPE: PRT
<213> ORGANISM: Arabidopsis thaliana

<400> SEQUENCE: 24

Met Asp Pro Val Pro Val Arg Cys Leu Leu Asn Ser Ile Ser Arg Tyr
1               5                   10                  15

Leu His Leu Val Ala Cys Gln Thr Ile Arg Phe Asn Pro Ile Gln Thr
            20                  25                  30

Cys Ile Gly Asn Met Val Leu Leu Leu Lys Leu Leu Lys Pro Leu Leu
        35                  40                  45

Asp Glu Val Val Asp Cys Lys Ile Pro Ser Asp Cys Leu Tyr Lys
    50                  55                  60

Gly Arg Glu Asp Leu Asp Ser Val Val Asn Gln Ala Arg Glu Phe Leu
65                  70                  75                  80

Glu Asp Trp Ser Pro Lys Leu Ser Lys Leu Phe Gly Val Phe Gln Cys
                85                  90                  95

Glu Val Leu Leu Gly Lys Val Gln Thr Cys Ser Leu Glu Ile Ser Arg
            100                 105                 110

Ile Leu Leu Gln Leu Ser Gln Ser Ser Pro Val Thr Ser Ser Val Gln
        115                 120                 125

Ser Val Glu Arg Cys Val Gln Glu Thr Glu Ser Phe Lys Gln Glu Gly
    130                 135                 140

Thr Leu Met Glu Leu Met Glu Asn Ala Leu Arg Asn Gln Lys Asp Asp
145                 150                 155                 160

Ile Thr Ser Leu Asp Asn Asn His Leu Glu Ser Ile Ile Gln Met Leu
                165                 170                 175

Gly Leu Ile Ser Asn Gln Asp Leu Leu Lys Glu Ser Ile Thr Val Glu
```

```
                    180                 185                 190
Lys Glu Arg Ile Arg Ser Gln Ala Ser Lys Ser Glu Glu Asp Met Glu
                195                 200                 205

Gln Thr Glu Gln Leu Ile Glu Leu Val Leu Cys Ile Arg Glu His Met
    210                 215                 220

Leu Lys Thr Glu Phe Leu Glu Val Ala Lys Gly Ile Ser Ile Pro Pro
225                 230                 235                 240

Tyr Phe Arg Cys Pro Leu Ser Thr Glu Leu Met Leu Asp Pro Val Ile
                245                 250                 255

Val Ala Ser Gly Gln Thr Phe Asp Arg Thr Ser Ile Lys Lys Trp Leu
            260                 265                 270

Asp Asn Gly Leu Ala Val Cys Pro Arg Thr Arg Gln Val Leu Thr His
        275                 280                 285

Gln Glu Leu Ile Pro Asn Tyr Thr Val Lys Ala Met Ile Ala Ser Trp
    290                 295                 300

Leu Glu Ala Asn Arg Ile Asn Leu Ala Thr Asn Ser Cys His Gln Tyr
305                 310                 315                 320

Asp Gly Gly Asp Ala Ser Ser Met Ala Asn Asn Met Gly Ser Gln Asp
                325                 330                 335

Phe Asn Arg Thr Glu Ser Phe Arg Phe Ser Leu Arg Ser Ser Ser Leu
            340                 345                 350

Thr Ser Arg Ser Ser Leu Glu Thr Gly Asn Gly Phe Glu Lys Leu Lys
        355                 360                 365

Ile Asn Val Ser Ala Ser Leu Cys Gly Glu Ser Gln Ser Lys Asp Leu
    370                 375                 380

Glu Ile Phe Glu Leu Leu Ser Pro Gly Gln Ser Tyr Thr His Ser Arg
385                 390                 395                 400

Ser Glu Ser Val Cys Ser Val Val Ser Val Asp Tyr Val Pro Ser
                405                 410                 415

Val Thr His Glu Thr Glu Ser Ile Leu Gly Asn His Gln Ser Ser Ser
            420                 425                 430

Glu Met Ser Pro Lys Lys Asn Leu Glu Ser Ser Asn Val Asn His
        435                 440                 445

Glu His Ser Ala Ala Lys Thr Tyr Glu Cys Ser Val His Asp Leu Asp
    450                 455                 460

Asp Ser Gly Thr Met Thr Thr Ser His Thr Ile Lys Leu Val Glu Asp
465                 470                 475                 480

Leu Lys Ser Gly Ser Asn Lys Val Lys Thr Ala Ala Ala Glu Ile
                485                 490                 495

Arg His Leu Thr Ile Asn Ser Ile Glu Asn Arg Val His Ile Gly Arg
            500                 505                 510

Cys Gly Ala Ile Thr Pro Leu Leu Ser Leu Leu Tyr Ser Glu Glu Lys
        515                 520                 525

Leu Thr Gln Glu His Ala Val Thr Ala Leu Leu Asn Leu Ser Ile Ser
    530                 535                 540

Glu Leu Asn Lys Ala Met Ile Val Glu Val Gly Ala Val Glu Pro Leu
545                 550                 555                 560

Val His Val Leu Asn Thr Gly Asn Asp Arg Ala Lys Glu Asn Ser Ala
                565                 570                 575

Ala Ser Leu Phe Ser Leu Ser Val Leu Gln Val Asn Arg Glu Arg Ile
            580                 585                 590

Gly Gln Ser Asn Ala Ala Ile Gln Ala Leu Val Asn Leu Leu Gly Lys
        595                 600                 605
```

```
Gly Thr Phe Arg Gly Lys Lys Asp Ala Ala Ser Ala Leu Phe Asn Leu
        610                 615                 620

Ser Ile Thr His Asp Asn Lys Ala Arg Ile Val Gln Ala Lys Ala Val
625                 630                 635                 640

Lys Tyr Leu Val Glu Leu Leu Asp Pro Asp Leu Glu Met Val Asp Lys
                645                 650                 655

Ala Val Ala Leu Leu Ala Asn Leu Ser Ala Val Gly Glu Gly Arg Gln
                660                 665                 670

Ala Ile Val Arg Glu Gly Gly Ile Pro Leu Leu Val Glu Thr Val Asp
            675                 680                 685

Leu Gly Ser Gln Arg Gly Lys Glu Asn Ala Ala Ser Val Leu Leu Gln
        690                 695                 700

Leu Cys Leu Asn Ser Pro Lys Phe Cys Thr Leu Val Leu Gln Glu Gly
705                 710                 715                 720

Ala Ile Pro Pro Leu Val Ala Leu Ser Gln Ser Gly Thr Gln Arg Ala
                725                 730                 735

Lys Glu Lys Ala Gln Gln Leu Leu Ser His Phe Arg Asn Gln Arg Asp
                740                 745                 750

Ala Arg Met Lys Lys Gly Arg Ser
            755                 760

<210> SEQ ID NO 25
<211> LENGTH: 2184
<212> TYPE: DNA
<213> ORGANISM: Arabidopsis thaliana
<220> FEATURE:
<221> NAME/KEY: CDS
<222> LOCATION: (1)..(2184)

<400> SEQUENCE: 25 atg gtt ctc ttg ttg aag ctc ttg aaa ccg ttg ctc gat gaa gtt gtt        48
Met Val Leu Leu Leu Lys Leu Leu Lys Pro Leu Leu Asp Glu Val Val
1               5                   10                  15 gat tgc aag ata cct tct gat gac tgt tta tat aaa gga tgt gaa gac        96
Asp Cys Lys Ile Pro Ser Asp Asp Cys Leu Tyr Lys Gly Cys Glu Asp
            20                  25                  30 ctt gat tct gtt gtt aac cag gct cgg gag ttc tta gag gac tgg tca       144
Leu Asp Ser Val Val Asn Gln Ala Arg Glu Phe Leu Glu Asp Trp Ser
        35                  40                  45 cca aag ttg agc aag ttg ttt ggt gtg ttt caa tgc gag gtt ttg ttg       192
Pro Lys Leu Ser Lys Leu Phe Gly Val Phe Gln Cys Glu Val Leu Leu
    50                  55                  60 gga aag gtc cag act tgt tcg ttg gag att agt cgc ata ctt ctt cag       240
Gly Lys Val Gln Thr Cys Ser Leu Glu Ile Ser Arg Ile Leu Leu Gln
65                  70                  75                  80 tta tca cag tca agt ccg gtt act tca agc gta caa agt gtt gag cgc       288
Leu Ser Gln Ser Ser Pro Val Thr Ser Ser Val Gln Ser Val Glu Arg
                85                  90                  95 tgc gtg cag gag act gag agt ttt aag caa gag ggg aca tta atg gaa       336
Cys Val Gln Glu Thr Glu Ser Phe Lys Gln Glu Gly Thr Leu Met Glu
            100                 105                 110 ctc atg gag aat gct tta cgg aat cag aaa gat gat att acc tct ttg       384
Leu Met Glu Asn Ala Leu Arg Asn Gln Lys Asp Asp Ile Thr Ser Leu
        115                 120                 125 gat aac aat cat ctg gaa agc ata att caa atg ctt gga ttg ata tca       432
Asp Asn Asn His Leu Glu Ser Ile Ile Gln Met Leu Gly Leu Ile Ser
    130                 135                 140 aac caa gat ctc tta aag gaa agc att act gtg gag aaa gag agg ata       480
Asn Gln Asp Leu Leu Lys Glu Ser Ile Thr Val Glu Lys Glu Arg Ile
145                 150                 155                 160
```

| | | |
|---|---|---|
| aga tcc cag gcc agt aag tca gaa gaa gat atg gaa caa acc gaa cag<br>Arg Ser Gln Ala Ser Lys Ser Glu Glu Asp Met Glu Gln Thr Glu Gln<br>                165                        170                      175 | 528 | |
| ttg ata gaa ctc gtc ttg tgc atc cgt gaa cac atg ctt aaa act gag<br>Leu Ile Glu Leu Val Leu Cys Ile Arg Glu His Met Leu Lys Thr Glu<br>        180                        185                        190 | 576 | |
| ttt ctt gaa gtg gct aaa ggt atc tcg ata ccc ccg tat ttc cgg tgt<br>Phe Leu Glu Val Ala Lys Gly Ile Ser Ile Pro Pro Tyr Phe Arg Cys<br>            195                        200                      205 | 624 | |
| cct ttg tca aca gaa ctc atg ctg gat ccg gta ata gta gct tca gga<br>Pro Leu Ser Thr Glu Leu Met Leu Asp Pro Val Ile Val Ala Ser Gly<br>210                        215                        220 | 672 | |
| cag aca ttt gac aga aca tcc att aag aaa tgg ctt gat aac ggg tta<br>Gln Thr Phe Asp Arg Thr Ser Ile Lys Lys Trp Leu Asp Asn Gly Leu<br>225                        230                        235                        240 | 720 | |
| gct gtt tgt cca agg acg cgg cag gtg ctg act cat caa gaa ctc att<br>Ala Val Cys Pro Arg Thr Arg Gln Val Leu Thr His Gln Glu Leu Ile<br>                      245                        250                      255 | 768 | |
| ccc aat tac acg gtt aag gct atg ata gcg agt tgg ttg gag gca aac<br>Pro Asn Tyr Thr Val Lys Ala Met Ile Ala Ser Trp Leu Glu Ala Asn<br>        260                        265                        270 | 816 | |
| agg atc aac ctt gct act aac tct tgt cat cag tat gat ggt ggt gat<br>Arg Ile Asn Leu Ala Thr Asn Ser Cys His Gln Tyr Asp Gly Gly Asp<br>            275                        280                      285 | 864 | |
| gct tca tcc atg gct aat aat atg ggt tct caa gac ttt aac cgc acc<br>Ala Ser Ser Met Ala Asn Asn Met Gly Ser Gln Asp Phe Asn Arg Thr<br>290                        295                        300 | 912 | |
| gag agt ttt cgt ttt tct tta cgg agc agc agt tta acc tca aga tca<br>Glu Ser Phe Arg Phe Ser Leu Arg Ser Ser Ser Leu Thr Ser Arg Ser<br>305                        310                        315                        320 | 960 | |
| tct ctt gaa act gga aat ggg ttt gag aaa ctg aag att aac gtg tct<br>Ser Leu Glu Thr Gly Asn Gly Phe Glu Lys Leu Lys Ile Asn Val Ser<br>                      325                        330                      335 | 1008 | |
| gcc agt tta tgc ggg gaa tct caa agc aag gat ctt gaa ata ttc gag<br>Ala Ser Leu Cys Gly Glu Ser Gln Ser Lys Asp Leu Glu Ile Phe Glu<br>        340                        345                        350 | 1056 | |
| ctt ttg tct ccg ggg cag tct tac act cac agc agg agt gaa tca gtt<br>Leu Leu Ser Pro Gly Gln Ser Tyr Thr His Ser Arg Ser Glu Ser Val<br>            355                        360                      365 | 1104 | |
| tgc agt gtt gtc tcg tct gtt gat tat gta cct tcg gtg aca cat gag<br>Cys Ser Val Val Ser Ser Val Asp Tyr Val Pro Ser Val Thr His Glu<br>370                        375                        380 | 1152 | |
| aca gaa agt ata cta ggg aat cac caa agc tcc agt gag atg tct ccc<br>Thr Glu Ser Ile Leu Gly Asn His Gln Ser Ser Ser Glu Met Ser Pro<br>385                        390                        395                        400 | 1200 | |
| aag aaa aac tta gaa agt tca aac aat gta aat cat gag cat agc gca<br>Lys Lys Asn Leu Glu Ser Ser Asn Asn Val Asn His Glu His Ser Ala<br>                      405                        410                      415 | 1248 | |
| gca aag act tat gag tgt tct gta cat gat tta gat gat tca gga aca<br>Ala Lys Thr Tyr Glu Cys Ser Val His Asp Leu Asp Asp Ser Gly Thr<br>                  420                        425                      430 | 1296 | |
| atg acg act tca cat acc ata aaa ttg gta gaa gat ctt aaa agc ggg<br>Met Thr Thr Ser His Thr Ile Lys Leu Val Glu Asp Leu Lys Ser Gly<br>                435                        440                      445 | 1344 | |
| tct aac aaa gtg aag act gct gct gca gct gaa ata cgt cat ctc acc<br>Ser Asn Lys Val Lys Thr Ala Ala Ala Ala Glu Ile Arg His Leu Thr<br>450                        455                        460 | 1392 | |
| att aac agc att gaa aat cgt gtt cac atc ggg cgt tgt ggt gct att<br>Ile Asn Ser Ile Glu Asn Arg Val His Ile Gly Arg Cys Gly Ala Ile<br>465                        470                        475                      480 | 1440 | |

```
act cca ctg ctg tca ctt tta tac tca gaa gaa aag cta act caa gaa    1488
Thr Pro Leu Leu Ser Leu Leu Tyr Ser Glu Glu Lys Leu Thr Gln Glu
                485                 490                 495 cac gca gtc acg gct ctt ttg aat ctt tcc atc agt gaa cta aac aaa    1536
His Ala Val Thr Ala Leu Leu Asn Leu Ser Ile Ser Glu Leu Asn Lys
            500                 505                 510 gcc atg att gtg gaa gtc ggg gcg ata gaa ccg ctt gtt cat gtt ttg    1584
Ala Met Ile Val Glu Val Gly Ala Ile Glu Pro Leu Val His Val Leu
        515                 520                 525 aac aca gga aat gac aga gcc aaa gag aat tca gca gca tca ttg ttc    1632
Asn Thr Gly Asn Asp Arg Ala Lys Glu Asn Ser Ala Ala Ser Leu Phe
    530                 535                 540 agt ctg tct gtt ctg cag gtc aac aga gaa cga ata ggc cag tct aac    1680
Ser Leu Ser Val Leu Gln Val Asn Arg Glu Arg Ile Gly Gln Ser Asn
545                 550                 555                 560 gca gcg ata caa gct ctg gtg aat ctt ctt ggt aaa gga aca ttt aga    1728
Ala Ala Ile Gln Ala Leu Val Asn Leu Leu Gly Lys Gly Thr Phe Arg
                565                 570                 575 gga aag aaa gac gcc gcc tct gct ttg ttc aat cta tcg att act cat    1776
Gly Lys Lys Asp Ala Ala Ser Ala Leu Phe Asn Leu Ser Ile Thr His
            580                 585                 590 gat aac aag gcc cgt atc gtg caa gct aag gcg gtt aag tac ctt gtg    1824
Asp Asn Lys Ala Arg Ile Val Gln Ala Lys Ala Val Lys Tyr Leu Val
        595                 600                 605 gag ctg tta gac cca gat tta gag atg gtt gat aaa gca gtt gct ctt    1872
Glu Leu Leu Asp Pro Asp Leu Glu Met Val Asp Lys Ala Val Ala Leu
    610                 615                 620 ctt gca aat ctt tct gca gtt gga gaa ggg cgt caa gcc atc gtg agg    1920
Leu Ala Asn Leu Ser Ala Val Gly Glu Gly Arg Gln Ala Ile Val Arg
625                 630                 635                 640 gaa ggt ggg att cca tta ctt gtt gaa act gtt gac tta gga tct cag    1968
Glu Gly Gly Ile Pro Leu Leu Val Glu Thr Val Asp Leu Gly Ser Gln
                645                 650                 655 aga ggg aaa gag aat gca gct tct gtg ctg ctt cag ttg tgt ctg aac    2016
Arg Gly Lys Glu Asn Ala Ala Ser Val Leu Leu Gln Leu Cys Leu Asn
            660                 665                 670 agt ccc aag ttt tgc act ctg gtc ttg caa gaa ggc gcc ata cct ccg    2064
Ser Pro Lys Phe Cys Thr Leu Val Leu Gln Glu Gly Ala Ile Pro Pro
        675                 680                 685 ctt gtt gcc ttg tct cag tct ggt aca cag aga gca aaa gag aag gta    2112
Leu Val Ala Leu Ser Gln Ser Gly Thr Gln Arg Ala Lys Glu Lys Val
    690                 695                 700 tat act ata ttc ttc ttc tgc ggt tac acg aaa aca cac caa gtt cag    2160
Tyr Thr Ile Phe Phe Phe Cys Gly Tyr Thr Lys Thr His Gln Val Gln
705                 710                 715                 720 ttt ctt att gat cga gat atc tga                                    2184
Phe Leu Ile Asp Arg Asp Ile
                725

<210> SEQ ID NO 26
<211> LENGTH: 727
<212> TYPE: PRT
<213> ORGANISM: Arabidopsis thaliana

<400> SEQUENCE: 26

Met Val Leu Leu Leu Lys Leu Leu Lys Pro Leu Leu Asp Glu Val Val
1               5                   10                  15

Asp Cys Lys Ile Pro Ser Asp Cys Leu Tyr Lys Gly Cys Glu Asp
            20                  25                  30

Leu Asp Ser Val Val Asn Gln Ala Arg Glu Phe Leu Glu Asp Trp Ser
```

-continued

```
             35                  40                  45
Pro Lys Leu Ser Lys Leu Phe Gly Val Phe Gln Cys Glu Val Leu Leu
 50                  55                  60
Gly Lys Val Gln Thr Cys Ser Leu Glu Ile Ser Arg Ile Leu Leu Gln
 65                  70                  75                  80
Leu Ser Gln Ser Ser Pro Val Thr Ser Ser Val Gln Ser Val Glu Arg
                 85                  90                  95
Cys Val Gln Glu Thr Glu Ser Phe Lys Gln Glu Gly Thr Leu Met Glu
                100                 105                 110
Leu Met Glu Asn Ala Leu Arg Asn Gln Lys Asp Asp Ile Thr Ser Leu
            115                 120                 125
Asp Asn Asn His Leu Glu Ser Ile Ile Gln Met Leu Gly Leu Ile Ser
130                 135                 140
Asn Gln Asp Leu Leu Lys Glu Ser Ile Thr Val Glu Lys Glu Arg Ile
145                 150                 155                 160
Arg Ser Gln Ala Ser Lys Ser Glu Glu Asp Met Glu Gln Thr Glu Gln
                165                 170                 175
Leu Ile Glu Leu Val Leu Cys Ile Arg Glu His Met Leu Lys Thr Glu
                180                 185                 190
Phe Leu Glu Val Ala Lys Gly Ile Ser Ile Pro Pro Tyr Phe Arg Cys
            195                 200                 205
Pro Leu Ser Thr Glu Leu Met Leu Asp Pro Val Ile Val Ala Ser Gly
            210                 215                 220
Gln Thr Phe Asp Arg Thr Ser Ile Lys Lys Trp Leu Asp Asn Gly Leu
225                 230                 235                 240
Ala Val Cys Pro Arg Thr Arg Gln Val Leu Thr His Gln Glu Leu Ile
                245                 250                 255
Pro Asn Tyr Thr Val Lys Ala Met Ile Ala Ser Trp Leu Glu Ala Asn
            260                 265                 270
Arg Ile Asn Leu Ala Thr Asn Ser Cys His Gln Tyr Asp Gly Gly Asp
            275                 280                 285
Ala Ser Ser Met Ala Asn Asn Met Gly Ser Gln Asp Phe Asn Arg Thr
290                 295                 300
Glu Ser Phe Arg Phe Ser Leu Arg Ser Ser Ser Leu Thr Ser Arg Ser
305                 310                 315                 320
Ser Leu Glu Thr Gly Asn Gly Phe Glu Lys Leu Lys Ile Asn Val Ser
                325                 330                 335
Ala Ser Leu Cys Gly Glu Ser Gln Ser Lys Asp Leu Glu Ile Phe Glu
            340                 345                 350
Leu Leu Ser Pro Gly Gln Ser Tyr Thr His Ser Arg Ser Glu Ser Val
            355                 360                 365
Cys Ser Val Val Ser Ser Val Asp Tyr Val Pro Ser Val Thr His Glu
370                 375                 380
Thr Glu Ser Ile Leu Gly Asn His Gln Ser Ser Ser Glu Met Ser Pro
385                 390                 395                 400
Lys Lys Asn Leu Glu Ser Ser Asn Asn Val Asn His Glu His Ser Ala
                405                 410                 415
Ala Lys Thr Tyr Glu Cys Ser Val His Asp Leu Asp Asp Ser Gly Thr
            420                 425                 430
Met Thr Thr Ser His Thr Ile Lys Leu Val Glu Asp Leu Lys Ser Gly
            435                 440                 445
Ser Asn Lys Val Lys Thr Ala Ala Ala Glu Ile Arg His Leu Thr
450                 455                 460
```

```
Ile Asn Ser Ile Glu Asn Arg Val His Ile Gly Arg Cys Gly Ala Ile
465                 470                 475                 480

Thr Pro Leu Leu Ser Leu Leu Tyr Ser Glu Lys Leu Thr Gln Glu
            485                 490                 495

His Ala Val Thr Ala Leu Leu Asn Leu Ser Ile Ser Glu Leu Asn Lys
            500                 505                 510

Ala Met Ile Val Glu Val Gly Ala Ile Glu Pro Leu Val His Val Leu
515                 520                 525

Asn Thr Gly Asn Asp Arg Ala Lys Glu Asn Ser Ala Ala Ser Leu Phe
530                 535                 540

Ser Leu Ser Val Leu Gln Val Asn Arg Glu Arg Ile Gly Gln Ser Asn
545                 550                 555                 560

Ala Ala Ile Gln Ala Leu Val Asn Leu Leu Gly Lys Gly Thr Phe Arg
                565                 570                 575

Gly Lys Lys Asp Ala Ala Ser Ala Leu Phe Asn Leu Ser Ile Thr His
            580                 585                 590

Asp Asn Lys Ala Arg Ile Val Gln Ala Lys Ala Val Lys Tyr Leu Val
            595                 600                 605

Glu Leu Leu Asp Pro Asp Leu Glu Met Val Asp Lys Ala Val Ala Leu
610                 615                 620

Leu Ala Asn Leu Ser Ala Val Gly Glu Gly Arg Gln Ala Ile Val Arg
625                 630                 635                 640

Glu Gly Gly Ile Pro Leu Leu Val Glu Thr Val Asp Leu Gly Ser Gln
                645                 650                 655

Arg Gly Lys Glu Asn Ala Ala Ser Val Leu Leu Gln Leu Cys Leu Asn
            660                 665                 670

Ser Pro Lys Phe Cys Thr Leu Val Leu Gln Glu Gly Ala Ile Pro Pro
            675                 680                 685

Leu Val Ala Leu Ser Gln Ser Gly Thr Gln Arg Ala Lys Glu Lys Val
690                 695                 700

Tyr Thr Ile Phe Phe Phe Cys Gly Tyr Thr Lys Thr His Gln Val Gln
705                 710                 715                 720

Phe Leu Ile Asp Arg Asp Ile
                725

<210> SEQ ID NO 27
<211> LENGTH: 1983
<212> TYPE: DNA
<213> ORGANISM: Arabidopsis thaliana
<220> FEATURE:
<221> NAME/KEY: CDS
<222> LOCATION: (1)..(1983)

<400> SEQUENCE: 27 atg gag gaa gag aaa gct tct gct gca cag agc tta atc gat gta gtt    48
Met Glu Glu Glu Lys Ala Ser Ala Ala Gln Ser Leu Ile Asp Val Val
1               5                   10                  15 aac gag att gct gcg att tct gat tat cgt ata aca gtg aag aag ctt    96
Asn Glu Ile Ala Ala Ile Ser Asp Tyr Arg Ile Thr Val Lys Lys Leu
            20                  25                  30 tgt tat aat cta gcg agg aga tta aag ctg ctt gtt cct atg ttt gag   144
Cys Tyr Asn Leu Ala Arg Arg Leu Lys Leu Leu Val Pro Met Phe Glu
        35                  40                  45 gaa att aga gaa agt aac gaa ccg atc agc gaa gat acg ttg aag act   192
Glu Ile Arg Glu Ser Asn Glu Pro Ile Ser Glu Asp Thr Leu Lys Thr
    50                  55                  60 ttg atg aat ttg aag gaa gct atg tgt tca gcg aag gat tat ctc aaa   240
Leu Met Asn Leu Lys Glu Ala Met Cys Ser Ala Lys Asp Tyr Leu Lys
```

```
                65                  70                  75                  80
ttt tgt agc caa ggg agc aag att tat ctg gtg atg gag agg gaa caa          288
Phe Cys Ser Gln Gly Ser Lys Ile Tyr Leu Val Met Glu Arg Glu Gln
                    85                  90                  95 gtg aca agt aaa ttg atg gag gtg tct gtt aag tta gaa caa tct tta          336
Val Thr Ser Lys Leu Met Glu Val Ser Val Lys Leu Glu Gln Ser Leu
            100                 105                 110 agc cag att cca tat gaa gaa ctc gat ata tcg gat gaa gtt aga gaa          384
Ser Gln Ile Pro Tyr Glu Glu Leu Asp Ile Ser Asp Glu Val Arg Glu
        115                 120                 125 cag gtt gag ctg gtt ctt agt cag ttt cgg cga gct aaa gga aga gta          432
Gln Val Glu Leu Val Leu Ser Gln Phe Arg Arg Ala Lys Gly Arg Val
    130                 135                 140 gat gta tca gat gat gag cta tat gaa gat ctt cag tcg ctt tgc aac          480
Asp Val Ser Asp Asp Glu Leu Tyr Glu Asp Leu Gln Ser Leu Cys Asn
145                 150                 155                 160 aaa agt agt gat gta gat gct tat cag cct gtg cta gag cgg gtt gcg          528
Lys Ser Ser Asp Val Asp Ala Tyr Gln Pro Val Leu Glu Arg Val Ala
                    165                 170                 175 aag aag tta cat ttg atg gag att cct gac cta gct caa gaa tca gtg          576
Lys Lys Leu His Leu Met Glu Ile Pro Asp Leu Ala Gln Glu Ser Val
                180                 185                 190 gct ctg cat gaa atg gtt gct tca agc ggt gga gat gtt ggt gaa aat          624
Ala Leu His Glu Met Val Ala Ser Ser Gly Gly Asp Val Gly Glu Asn
            195                 200                 205 att gag gag atg gca atg gta tta aag atg att aag gat ttt gtg cag          672
Ile Glu Glu Met Ala Met Val Leu Lys Met Ile Lys Asp Phe Val Gln
        210                 215                 220 acg gag gat gat aat ggc gag gag cag aaa gta gga gtt aac tct aga          720
Thr Glu Asp Asp Asn Gly Glu Glu Gln Lys Val Gly Val Asn Ser Arg
225                 230                 235                 240 agc aat gga cag act tct acg gca gcg agt cag aag ata cct gtg att          768
Ser Asn Gly Gln Thr Ser Thr Ala Ala Ser Gln Lys Ile Pro Val Ile
                    245                 250                 255 cct gat gat ttt cgc tgt ccg att tcg ctg gaa atg atg aga gat cca          816
Pro Asp Asp Phe Arg Cys Pro Ile Ser Leu Glu Met Met Arg Asp Pro
                260                 265                 270 gtt att gtt tca tca ggg cag aca tac gaa cgc aca tgt att gag aaa          864
Val Ile Val Ser Ser Gly Gln Thr Tyr Glu Arg Thr Cys Ile Glu Lys
            275                 280                 285 tgg ata gaa ggt gga cac tcg aca tgt cca aaa aca cag cag gcg cta          912
Trp Ile Glu Gly Gly His Ser Thr Cys Pro Lys Thr Gln Gln Ala Leu
        290                 295                 300 aca agc aca acc ctc aca cca aac tat gtt ctc cgt agt ctc ata gct          960
Thr Ser Thr Thr Leu Thr Pro Asn Tyr Val Leu Arg Ser Leu Ile Ala
305                 310                 315                 320 cag tgg tgc gag gcc aac gat att gag cct cca aag cct ccg agc agt         1008
Gln Trp Cys Glu Ala Asn Asp Ile Glu Pro Pro Lys Pro Pro Ser Ser
                    325                 330                 335 tta aga ccc aga aaa gta tcg tcc ttc tca tct ccc gca gaa gcg aac         1056
Leu Arg Pro Arg Lys Val Ser Ser Phe Ser Ser Pro Ala Glu Ala Asn
                340                 345                 350 aag att gaa gat ctt atg tgg aga ctt gcg tac gga aac ccc gag gac         1104
Lys Ile Glu Asp Leu Met Trp Arg Leu Ala Tyr Gly Asn Pro Glu Asp
            355                 360                 365 caa cga tct gca gct ggg gaa atc cgc ctt ctt gca aaa cga aat gca         1152
Gln Arg Ser Ala Ala Gly Glu Ile Arg Leu Leu Ala Lys Arg Asn Ala
        370                 375                 380 gac aac cgc gtg gcc ata gcc gaa gct gga gcc ata cct ctt ctc gta         1200
Asp Asn Arg Val Ala Ile Ala Glu Ala Gly Ala Ile Pro Leu Leu Val
```

```
                385             390             395             400
ggt ctc ctc tca act cct gat tct cgt att caa gaa cat tcg gta aca    1248
Gly Leu Leu Ser Thr Pro Asp Ser Arg Ile Gln Glu His Ser Val Thr
                405             410             415 gct ctt cta aac ctc tcc ata tgt gag aac aac aaa gga gcc att gtt    1296
Ala Leu Leu Asn Leu Ser Ile Cys Glu Asn Asn Lys Gly Ala Ile Val
                420             425             430 tca gct gga gct att cct ggt ata gtt caa gtg ctt aag aaa gga agc    1344
Ser Ala Gly Ala Ile Pro Gly Ile Val Gln Val Leu Lys Lys Gly Ser
            435             440             445 atg gag gcc aga gag aat gcg gcg gct aca ctt ttc agt cta tca gtg    1392
Met Glu Ala Arg Glu Asn Ala Ala Ala Thr Leu Phe Ser Leu Ser Val
        450             455             460 atc gat gaa aat aaa gtg act atc ggt gcc tta gga gca att ccg cca    1440
Ile Asp Glu Asn Lys Val Thr Ile Gly Ala Leu Gly Ala Ile Pro Pro
465             470             475             480 ctc gtt gta tta ctt aat gaa ggt aca caa aga ggc aag aaa gat gct    1488
Leu Val Val Leu Leu Asn Glu Gly Thr Gln Arg Gly Lys Lys Asp Ala
                485             490             495 gct act gca ctc ttt aac ctc tgt ata tac caa gga aac aaa gga aaa    1536
Ala Thr Ala Leu Phe Asn Leu Cys Ile Tyr Gln Gly Asn Lys Gly Lys
                500             505             510 gct ata cgt gca gga gtg att ccc acg ttg act aga ctc ttg aca gag    1584
Ala Ile Arg Ala Gly Val Ile Pro Thr Leu Thr Arg Leu Leu Thr Glu
            515             520             525 ccc gga agc gga atg gtc gat gag gca ctc gcg att ttg gcg att ctc    1632
Pro Gly Ser Gly Met Val Asp Glu Ala Leu Ala Ile Leu Ala Ile Leu
        530             535             540 tct agc cac ccc gaa gga aaa gca atc ata gga tcc tct gat gca gtc    1680
Ser Ser His Pro Glu Gly Lys Ala Ile Ile Gly Ser Ser Asp Ala Val
545             550             555             560 cca agt ttg gtt gag ttt atc aga act ggc tcg cct aga aac aga gaa    1728
Pro Ser Leu Val Glu Phe Ile Arg Thr Gly Ser Pro Arg Asn Arg Glu
                565             570             575 aac gca gct gct gtt cta gtc cac ctc tgt tct gga gac cca caa cat    1776
Asn Ala Ala Ala Val Leu Val His Leu Cys Ser Gly Asp Pro Gln His
                580             585             590 ctt gtc gaa gcg cag aaa ctc ggc ctt atg ggt cca ttg ata gat tta    1824
Leu Val Glu Ala Gln Lys Leu Gly Leu Met Gly Pro Leu Ile Asp Leu
            595             600             605 gct gga aat ggg acg gat aga ggg aaa cga aaa gca gcg cag ttg ctt    1872
Ala Gly Asn Gly Thr Asp Arg Gly Lys Arg Lys Ala Ala Gln Leu Leu
        610             615             620 gaa cgc atc agc cgt ctc gct gaa cag cag aag gaa acg gct gtg tca    1920
Glu Arg Ile Ser Arg Leu Ala Glu Gln Gln Lys Glu Thr Ala Val Ser
625             630             635             640 caa ccg gaa gaa gaa gct gaa cca aca cat cca gaa tcc acc aca gaa    1968
Gln Pro Glu Glu Glu Ala Glu Pro Thr His Pro Glu Ser Thr Thr Glu
                645             650             655 gct gca gat act taa                                                1983
Ala Ala Asp Thr
                660

<210> SEQ ID NO 28
<211> LENGTH: 660
<212> TYPE: PRT
<213> ORGANISM: Arabidopsis thaliana

<400> SEQUENCE: 28

Met Glu Glu Glu Lys Ala Ser Ala Ala Gln Ser Leu Ile Asp Val Val
1               5                   10                  15
```

Asn Glu Ile Ala Ala Ile Ser Asp Tyr Arg Ile Thr Val Lys Lys Leu
            20                  25                  30

Cys Tyr Asn Leu Ala Arg Arg Leu Lys Leu Leu Val Pro Met Phe Glu
                35                  40                  45

Glu Ile Arg Glu Ser Asn Glu Pro Ile Ser Glu Asp Thr Leu Lys Thr
 50                  55                  60

Leu Met Asn Leu Lys Glu Ala Met Cys Ser Ala Lys Asp Tyr Leu Lys
 65                  70                  75                  80

Phe Cys Ser Gln Gly Ser Lys Ile Tyr Leu Val Met Glu Arg Glu Gln
                85                  90                  95

Val Thr Ser Lys Leu Met Glu Val Ser Val Lys Leu Glu Gln Ser Leu
                100                 105                 110

Ser Gln Ile Pro Tyr Glu Glu Leu Asp Ile Ser Asp Glu Val Arg Glu
                115                 120                 125

Gln Val Glu Leu Val Leu Ser Gln Phe Arg Arg Ala Lys Gly Arg Val
            130                 135                 140

Asp Val Ser Asp Asp Glu Leu Tyr Glu Asp Leu Gln Ser Leu Cys Asn
145                 150                 155                 160

Lys Ser Ser Asp Val Asp Ala Tyr Gln Pro Val Leu Glu Arg Val Ala
                165                 170                 175

Lys Lys Leu His Leu Met Glu Ile Pro Asp Leu Ala Gln Glu Ser Val
                180                 185                 190

Ala Leu His Glu Met Val Ala Ser Ser Gly Gly Asp Val Gly Glu Asn
            195                 200                 205

Ile Glu Glu Met Ala Met Val Leu Lys Met Ile Lys Asp Phe Val Gln
            210                 215                 220

Thr Glu Asp Asp Asn Gly Glu Leu Gln Lys Val Gly Val Asn Ser Arg
225                 230                 235                 240

Ser Asn Gly Gln Thr Ser Thr Ala Ala Ser Gln Lys Ile Pro Val Ile
                245                 250                 255

Pro Asp Asp Phe Arg Cys Pro Ile Ser Leu Glu Met Met Arg Asp Pro
                260                 265                 270

Val Ile Val Ser Ser Gly Gln Thr Tyr Glu Arg Thr Cys Ile Glu Lys
            275                 280                 285

Trp Ile Glu Gly Gly His Ser Thr Cys Pro Lys Thr Gln Gln Ala Leu
            290                 295                 300

Thr Ser Thr Thr Leu Thr Pro Asn Tyr Val Leu Arg Ser Leu Ile Ala
305                 310                 315                 320

Gln Trp Cys Glu Ala Asn Asp Ile Glu Pro Pro Lys Pro Ser Ser
                325                 330                 335

Leu Arg Pro Arg Lys Val Ser Ser Phe Ser Ser Pro Ala Glu Ala Asn
                340                 345                 350

Lys Ile Glu Asp Leu Met Trp Arg Leu Ala Tyr Gly Asn Pro Glu Asp
                355                 360                 365

Gln Arg Ser Ala Ala Gly Glu Ile Arg Leu Leu Ala Lys Arg Asn Ala
            370                 375                 380

Asp Asn Arg Val Ala Ile Ala Glu Ala Gly Ala Ile Pro Leu Leu Val
385                 390                 395                 400

Gly Leu Leu Ser Thr Pro Asp Ser Arg Ile Gln Glu His Ser Val Thr
                405                 410                 415

Ala Leu Leu Asn Leu Ser Ile Cys Glu Asn Asn Lys Gly Ala Ile Val
                420                 425                 430

Ser Ala Gly Ala Ile Pro Gly Ile Val Gln Val Leu Lys Lys Gly Ser

```
                        435                 440                 445
Met Glu Ala Arg Glu Asn Ala Ala Thr Leu Phe Ser Leu Ser Val
                450                 455                 460

Ile Asp Glu Asn Lys Val Thr Ile Gly Ala Leu Gly Ala Ile Pro Pro
465                 470                 475                 480

Leu Val Val Leu Leu Asn Glu Gly Thr Gln Arg Gly Lys Lys Asp Ala
                485                 490                 495

Ala Thr Ala Leu Phe Asn Leu Cys Ile Tyr Gln Gly Asn Lys Gly Lys
                500                 505                 510

Ala Ile Arg Ala Gly Val Ile Pro Thr Leu Thr Arg Leu Leu Thr Glu
                515                 520                 525

Pro Gly Ser Gly Met Val Asp Glu Ala Leu Ala Ile Leu Ala Ile Leu
                530                 535                 540

Ser Ser His Pro Glu Gly Lys Ala Ile Ile Gly Ser Ser Asp Ala Val
545                 550                 555                 560

Pro Ser Leu Val Glu Phe Ile Arg Thr Gly Ser Pro Arg Asn Arg Glu
                565                 570                 575

Asn Ala Ala Ala Val Leu Val His Leu Cys Ser Gly Asp Pro Gln His
                580                 585                 590

Leu Val Glu Ala Gln Lys Leu Gly Leu Met Gly Pro Leu Ile Asp Leu
                595                 600                 605

Ala Gly Asn Gly Thr Asp Arg Gly Lys Arg Lys Ala Ala Gln Leu Leu
                610                 615                 620

Glu Arg Ile Ser Arg Leu Ala Glu Gln Gln Lys Glu Thr Ala Val Ser
625                 630                 635                 640

Gln Pro Glu Glu Glu Ala Glu Pro Thr His Pro Glu Ser Thr Thr Glu
                645                 650                 655

Ala Ala Asp Thr
                660

<210> SEQ ID NO 29
<211> LENGTH: 1068
<212> TYPE: DNA
<213> ORGANISM: Arabidopsis thaliana
<220> FEATURE:
<221> NAME/KEY: CDS
<222> LOCATION: (1)..(1068)

<400> SEQUENCE: 29 atg gag atg gag aat cac cgc ccc ggc agt ttc acc tac atg ggc cgc      48
Met Glu Met Glu Asn His Arg Pro Gly Ser Phe Thr Tyr Met Gly Arg
1               5                   10                  15 aaa ttc agc gat tta agt ctc aac gat gac tcc tct gct ttc agc gat      96
Lys Phe Ser Asp Leu Ser Leu Asn Asp Asp Ser Ser Ala Phe Ser Asp
                20                  25                  30 tgt aac agc gac aga tcc ggc gaa ttc ccc act gct tcc tcc gag agc     144
Cys Asn Ser Asp Arg Ser Gly Glu Phe Pro Thr Ala Ser Ser Glu Ser
            35                  40                  45 cgt cgt ctc ctc ctc tct tgc gcc tct gag aat tcc gat gat ctc atc     192
Arg Arg Leu Leu Leu Ser Cys Ala Ser Glu Asn Ser Asp Asp Leu Ile
        50                  55                  60 aat cat ctc gtg tcg cat ctt gat tcc tcc tat tcg atc gat gag cag     240
Asn His Leu Val Ser His Leu Asp Ser Ser Tyr Ser Ile Asp Glu Gln
65                  70                  75                  80 aag caa gct gct atg gag atc agg ctc tta tcc aag aac aaa cct gag     288
Lys Gln Ala Ala Met Glu Ile Arg Leu Leu Ser Lys Asn Lys Pro Glu
                85                  90                  95 aat cgg atc aaa atc gcc aag gcc ggt gcg att aag ccg ttg att tct     336
```

```
Asn Arg Ile Lys Ile Ala Lys Ala Gly Ala Ile Lys Pro Leu Ile Ser
            100                 105                 110 ctg atc tct tct tcg gat ctt cag ctt cag gag tat ggt gtc act gca      384
Leu Ile Ser Ser Ser Asp Leu Gln Leu Gln Glu Tyr Gly Val Thr Ala
            115                 120                 125 atc ttg aat cta tct ctc tgc gac gag aac aaa gag tcg att gct tct      432
Ile Leu Asn Leu Ser Leu Cys Asp Glu Asn Lys Glu Ser Ile Ala Ser
            130                 135                 140 tcc ggt gcg att aag ccg ctt gtc agg gct ttg aaa atg gga aca ccg      480
Ser Gly Ala Ile Lys Pro Leu Val Arg Ala Leu Lys Met Gly Thr Pro
145                 150                 155                 160 act gct aaa gag aac gct gct tgt gct ctg ctc cgt cta tcg cag atc      528
Thr Ala Lys Glu Asn Ala Ala Cys Ala Leu Leu Arg Leu Ser Gln Ile
                165                 170                 175 gag gag aac aaa gtc gcc atc ggg aga tcc gga gcg att cct ctg ttg      576
Glu Glu Asn Lys Val Ala Ile Gly Arg Ser Gly Ala Ile Pro Leu Leu
            180                 185                 190 gtg aac ctt cta gaa aca ggc gga ttc aga gcg aag aag gac gcg tcg      624
Val Asn Leu Leu Glu Thr Gly Gly Phe Arg Ala Lys Lys Asp Ala Ser
            195                 200                 205 acg gct ctg tac tcg ttg tgc tca gct aaa gag aac aaa atc aga gcc      672
Thr Ala Leu Tyr Ser Leu Cys Ser Ala Lys Glu Asn Lys Ile Arg Ala
210                 215                 220 gtg caa tcg gga att atg aag ccg ctt gtt gaa ttg atg gcg gat ttc      720
Val Gln Ser Gly Ile Met Lys Pro Leu Val Glu Leu Met Ala Asp Phe
225                 230                 235                 240 gga tca aac atg gtg gat aaa tcg gcg ttt gtg atg agt ctg tta atg      768
Gly Ser Asn Met Val Asp Lys Ser Ala Phe Val Met Ser Leu Leu Met
                245                 250                 255 tcg gtg ccg gaa tcg aaa ccg gcg att gtg gag gaa gga gga gtt ccg      816
Ser Val Pro Glu Ser Lys Pro Ala Ile Val Glu Glu Gly Gly Val Pro
            260                 265                 270 gtg ctg gtg gag ata gta gag gtg gga aca cag aga cag aaa gag atg      864
Val Leu Val Glu Ile Val Glu Val Gly Thr Gln Arg Gln Lys Glu Met
            275                 280                 285 gct gtg tcg ata ttg cta cag ctt tgt gag gag agt gtt gtg tat aga      912
Ala Val Ser Ile Leu Leu Gln Leu Cys Glu Glu Ser Val Val Tyr Arg
            290                 295                 300 aca atg gtg gct aga gaa gga gcg ata cct ccg cta gtg gct ctg tcg      960
Thr Met Val Ala Arg Glu Gly Ala Ile Pro Pro Leu Val Ala Leu Ser
305                 310                 315                 320 cag gca gga aca agt cga gct aag caa aag gct gag gcg ttg att gag     1008
Gln Ala Gly Thr Ser Arg Ala Lys Gln Lys Ala Glu Ala Leu Ile Glu
                325                 330                 335 ctt cta agg caa cca aga tcc att agt aat ggt ggt gct aga tca tcg     1056
Leu Leu Arg Gln Pro Arg Ser Ile Ser Asn Gly Gly Ala Arg Ser Ser
            340                 345                 350 tcc caa ctc tga                                                     1068
Ser Gln Leu
        355

<210> SEQ ID NO 30
<211> LENGTH: 355
<212> TYPE: PRT
<213> ORGANISM: Arabidopsis thaliana

<400> SEQUENCE: 30

Met Glu Met Glu Asn His Arg Pro Gly Ser Phe Thr Tyr Met Gly Arg
1               5                   10                  15

Lys Phe Ser Asp Leu Ser Leu Asn Asp Asp Ser Ser Ala Phe Ser Asp
            20                  25                  30
```

| | | | | | | | | | | | | |
|---|---|---|---|---|---|---|---|---|---|---|---|---|
|Cys|Asn|Ser|Asp|Arg|Ser|Gly|Glu|Phe|Pro|Thr|Ala|Ser|Ser|Glu|Ser|
| |35| | | |40| | | |45| | | | | | |

Cys Asn Ser Asp Arg Ser Gly Glu Phe Pro Thr Ala Ser Ser Glu Ser
      35                      40                      45

Arg Arg Leu Leu Leu Ser Cys Ala Ser Glu Asn Ser Asp Asp Leu Ile
50                     55                     60

Asn His Leu Val Ser His Leu Asp Ser Ser Tyr Ser Ile Asp Glu Gln
65                     70                     75                     80

Lys Gln Ala Ala Met Glu Ile Arg Leu Leu Ser Lys Asn Lys Pro Glu
      85                      90                     95

Asn Arg Ile Lys Ile Ala Lys Ala Gly Ala Ile Lys Pro Leu Ile Ser
      100                   105                110

Leu Ile Ser Ser Ser Asp Leu Gln Leu Gln Glu Tyr Gly Val Thr Ala
      115                   120                125

Ile Leu Asn Leu Ser Leu Cys Asp Glu Asn Lys Glu Ser Ile Ala Ser
      130                   135                140

Ser Gly Ala Ile Lys Pro Leu Val Arg Ala Leu Lys Met Gly Thr Pro
145                   150                   155                160

Thr Ala Lys Glu Asn Ala Ala Cys Ala Leu Leu Arg Leu Ser Gln Ile
      165                   170                175

Glu Glu Asn Lys Val Ala Ile Gly Arg Ser Gly Ala Ile Pro Leu Leu
      180                   185                190

Val Asn Leu Leu Glu Thr Gly Gly Phe Arg Ala Lys Lys Asp Ala Ser
      195                   200                205

Thr Ala Leu Tyr Ser Leu Cys Ser Ala Lys Glu Asn Lys Ile Arg Ala
210                   215                   220

Val Gln Ser Gly Ile Met Lys Pro Leu Val Glu Leu Met Ala Asp Phe
225                   230                   235                240

Gly Ser Asn Met Val Asp Lys Ser Ala Phe Val Met Ser Leu Leu Met
      245                   250                255

Ser Val Pro Glu Ser Lys Pro Ala Ile Val Glu Glu Gly Gly Val Pro
      260                   265                270

Val Leu Val Glu Ile Val Glu Val Gly Thr Gln Arg Gln Lys Glu Met
      275                   280                285

Ala Val Ser Ile Leu Leu Gln Leu Cys Glu Glu Ser Val Val Tyr Arg
      290                   295                300

Thr Met Val Ala Arg Glu Gly Ala Ile Pro Pro Leu Val Ala Leu Ser
305                   310                   315                320

Gln Ala Gly Thr Ser Arg Ala Lys Gln Lys Ala Glu Ala Leu Ile Glu
      325                   330                335

Leu Leu Arg Gln Pro Arg Ser Ile Ser Asn Gly Gly Ala Arg Ser Ser
      340                   345                350

Ser Gln Leu
      355

```
<210> SEQ ID NO 31
<211> LENGTH: 1068
<212> TYPE: DNA
<213> ORGANISM: Arabidopsis thaliana
<220> FEATURE:
<221> NAME/KEY: CDS
<222> LOCATION: (1)..(1068)

<400> SEQUENCE: 31 atg gag atg gag aat cac cgc ccc ggc agt ttc acc tac atg ggc cgc      48
Met Glu Met Glu Asn His Arg Pro Gly Ser Phe Thr Tyr Met Gly Arg
1               5                   10                  15 aaa ttc agc gat tta agt ctc aac gat gac tcc tct gct ttc agc gat      96
```

-continued

| | | |
|---|---|---|
| Lys Phe Ser Asp Leu Ser Leu Asn Asp Asp Ser Ser Ala Phe Ser Asp<br>20 25 30 | | |
| tgt aac agc gac aga tcc ggc gaa ttc ccc act gct tcc tcc gag agc<br>Cys Asn Ser Asp Arg Ser Gly Glu Phe Pro Thr Ala Ser Ser Glu Ser<br>35 40 45 | 144 | |
| cgt cgt ctc ctc ctc tct tgc gcc tct gag aat tcc gat gat ctc atc<br>Arg Arg Leu Leu Leu Ser Cys Ala Ser Glu Asn Ser Asp Asp Leu Ile<br>50 55 60 | 192 | |
| aat cat ctc gtg tcg cat ctt gat tcc tcc tat tcg atc gat gag cag<br>Asn His Leu Val Ser His Leu Asp Ser Ser Tyr Ser Ile Asp Glu Gln<br>65 70 75 80 | 240 | |
| aag caa gct gct atg gag atc agg ctc tta tcc aag aac aaa cct gag<br>Lys Gln Ala Ala Met Glu Ile Arg Leu Leu Ser Lys Asn Lys Pro Glu<br>85 90 95 | 288 | |
| aat cgg atc aaa atc gcc aag gcc ggt gcg att aag ccg ttg att tct<br>Asn Arg Ile Lys Ile Ala Lys Ala Gly Ala Ile Lys Pro Leu Ile Ser<br>100 105 110 | 336 | |
| ctg atc tct tct tcg gat ctt cag ctt cag gag tat ggt gtc act gca<br>Leu Ile Ser Ser Ser Asp Leu Gln Leu Gln Glu Tyr Gly Val Thr Ala<br>115 120 125 | 384 | |
| atc ttg aat cta tct ctc tgc gac gag aac aaa gag tcg att gct tct<br>Ile Leu Asn Leu Ser Leu Cys Asp Glu Asn Lys Glu Ser Ile Ala Ser<br>130 135 140 | 432 | |
| tcc ggt gcg att aag ccg ctt gtc agg gct ttg aaa atg gga aca ccg<br>Ser Gly Ala Ile Lys Pro Leu Val Arg Ala Leu Lys Met Gly Thr Pro<br>145 150 155 160 | 480 | |
| act gct aaa gag aac gct gct tgt gct ctg ctc cgt cta tcg cag atc<br>Thr Ala Lys Glu Asn Ala Ala Cys Ala Leu Leu Arg Leu Ser Gln Ile<br>165 170 175 | 528 | |
| gag gag aac aaa gtc gcc atc ggg aga tcc gga gcg att cct ctg ttg<br>Glu Glu Asn Lys Val Ala Ile Gly Arg Ser Gly Ala Ile Pro Leu Leu<br>180 185 190 | 576 | |
| gtg aac ctt cta gaa aca ggc gga ttc aga gcg aag aag gac gcg tcg<br>Val Asn Leu Leu Glu Thr Gly Gly Phe Arg Ala Lys Lys Asp Ala Ser<br>195 200 205 | 624 | |
| acg gct ctg tac tcg ttg tgc tca gct aaa gag aac aaa atc aga gcc<br>Thr Ala Leu Tyr Ser Leu Cys Ser Ala Lys Glu Asn Lys Ile Arg Ala<br>210 215 220 | 672 | |
| gtg caa tcg gga att atg aag ccg ctt gtt gaa ttg atg gcg gat ttc<br>Val Gln Ser Gly Ile Met Lys Pro Leu Val Glu Leu Met Ala Asp Phe<br>225 230 235 240 | 720 | |
| gga tca aac atg gtg gat aaa tcg gcg ttt gtg atg agt ctg tta atg<br>Gly Ser Asn Met Val Asp Lys Ser Ala Phe Val Met Ser Leu Leu Met<br>245 250 255 | 768 | |
| tcg gtg ccg gaa tcg aaa ccg gcg att gtg gag gaa gga gga gtt ccg<br>Ser Val Pro Glu Ser Lys Pro Ala Ile Val Glu Glu Gly Gly Val Pro<br>260 265 270 | 816 | |
| gtg ctg gtg gag ata gta gag gtg gga aca cag aga cag aaa gag atg<br>Val Leu Val Glu Ile Val Glu Val Gly Thr Gln Arg Gln Lys Glu Met<br>275 280 285 | 864 | |
| gct gtg tcg ata ttg cta cag ctt tgt gag gag agt gtt gta tat aga<br>Ala Val Ser Ile Leu Leu Gln Leu Cys Glu Glu Ser Val Val Tyr Arg<br>290 295 300 | 912 | |
| aca atg gtg gct aga gaa gga gcg ata cct ccg cta gtg gct ctg tcg<br>Thr Met Val Ala Arg Glu Gly Ala Ile Pro Pro Leu Val Ala Leu Ser<br>305 310 315 320 | 960 | |
| cag gca gga aca agt cga gct aag caa aag gct gag gcg ttg att gag<br>Gln Ala Gly Thr Ser Arg Ala Lys Gln Lys Ala Glu Ala Leu Ile Glu<br>325 330 335 | 1008 | |
| ctt cta agg caa cta aga tcc att agt aat ggt ggt gct aga tca tcg | 1056 | |

Leu Leu Arg Gln Leu Arg Ser Ile Ser Asn Gly Gly Ala Arg Ser Ser
            340                 345                 350 tcc caa ctc tga                                                         1068
Ser Gln Leu
        355

<210> SEQ ID NO 32
<211> LENGTH: 355
<212> TYPE: PRT
<213> ORGANISM: Arabidopsis thaliana

<400> SEQUENCE: 32

Met Glu Met Glu Asn His Arg Pro Gly Ser Phe Thr Tyr Met Gly Arg
1               5                   10                  15

Lys Phe Ser Asp Leu Ser Leu Asn Asp Asp Ser Ser Ala Phe Ser Asp
            20                  25                  30

Cys Asn Ser Asp Arg Ser Gly Glu Phe Pro Thr Ala Ser Ser Glu Ser
        35                  40                  45

Arg Arg Leu Leu Leu Ser Cys Ala Ser Glu Asn Ser Asp Asp Leu Ile
    50                  55                  60

Asn His Leu Val Ser His Leu Asp Ser Ser Tyr Ser Ile Asp Glu Gln
65                  70                  75                  80

Lys Gln Ala Ala Met Glu Ile Arg Leu Leu Ser Lys Asn Lys Pro Glu
                85                  90                  95

Asn Arg Ile Lys Ile Ala Lys Ala Gly Ala Ile Lys Pro Leu Ile Ser
            100                 105                 110

Leu Ile Ser Ser Ser Asp Leu Gln Leu Gln Glu Tyr Gly Val Thr Ala
        115                 120                 125

Ile Leu Asn Leu Ser Leu Cys Asp Glu Asn Lys Glu Ser Ile Ala Ser
    130                 135                 140

Ser Gly Ala Ile Lys Pro Leu Val Arg Ala Leu Lys Met Gly Thr Pro
145                 150                 155                 160

Thr Ala Lys Glu Asn Ala Ala Cys Ala Leu Leu Arg Leu Ser Gln Ile
                165                 170                 175

Glu Glu Asn Lys Val Ala Ile Gly Arg Ser Gly Ala Ile Pro Leu Leu
            180                 185                 190

Val Asn Leu Leu Glu Thr Gly Gly Phe Arg Ala Lys Lys Asp Ala Ser
        195                 200                 205

Thr Ala Leu Tyr Ser Leu Cys Ser Ala Lys Glu Asn Lys Ile Arg Ala
    210                 215                 220

Val Gln Ser Gly Ile Met Lys Pro Leu Val Glu Leu Met Ala Asp Phe
225                 230                 235                 240

Gly Ser Asn Met Val Asp Lys Ser Ala Phe Val Met Ser Leu Leu Met
                245                 250                 255

Ser Val Pro Glu Ser Lys Pro Ala Ile Val Glu Glu Gly Gly Val Pro
            260                 265                 270

Val Leu Val Glu Ile Val Glu Val Gly Thr Gln Arg Gln Lys Glu Met
        275                 280                 285

Ala Val Ser Ile Leu Leu Gln Leu Cys Glu Glu Ser Val Val Tyr Arg
    290                 295                 300

Thr Met Val Ala Arg Glu Gly Ala Ile Pro Pro Leu Val Ala Leu Ser
305                 310                 315                 320

Gln Ala Gly Thr Ser Arg Ala Lys Gln Lys Ala Glu Ala Leu Ile Glu
                325                 330                 335

Leu Leu Arg Gln Leu Arg Ser Ile Ser Asn Gly Gly Ala Arg Ser Ser
            340                 345                 350

```
                                           Ser Gln Leu
                                                   355

<210> SEQ ID NO 33
<211> LENGTH: 1068
<212> TYPE: DNA
<213> ORGANISM: Arabidopsis thaliana
<220> FEATURE:
<221> NAME/KEY: CDS
<222> LOCATION: (1)..(1068)

<400> SEQUENCE: 33 atg gag atg gag aat cac cgc ccc ggc agt ttc acc tac atg ggc cgc      48
Met Glu Met Glu Asn His Arg Pro Gly Ser Phe Thr Tyr Met Gly Arg
1               5                  10                  15 aaa ttc agc gat tta agt ctc aac gat gac tcc tct gct ttc agc gat      96
Lys Phe Ser Asp Leu Ser Leu Asn Asp Asp Ser Ser Ala Phe Ser Asp
            20                  25                  30 tgt aac agc gac aga tcc ggc gaa ttc ccc act gct tcc tcc gag agc     144
Cys Asn Ser Asp Arg Ser Gly Glu Phe Pro Thr Ala Ser Ser Glu Ser
        35                  40                  45 cgt cgt ctc ctc ctc tct tgc gcc tct gag aat tcc gat gat ctc atc     192
Arg Arg Leu Leu Leu Ser Cys Ala Ser Glu Asn Ser Asp Asp Leu Ile
    50                  55                  60 aat cat ctc gtg tcg cat ctt gat tcc tcc tat tcg atc gat gag cag     240
Asn His Leu Val Ser His Leu Asp Ser Ser Tyr Ser Ile Asp Glu Gln
65                  70                  75                  80 aag caa gct gct atg gag atc agg ctc tta tcc aag aac aaa cct gag     288
Lys Gln Ala Ala Met Glu Ile Arg Leu Leu Ser Lys Asn Lys Pro Glu
                85                  90                  95 aat cgg atc aaa atc gcc aag gcc ggt gcg att aag ccg ttg att tct     336
Asn Arg Ile Lys Ile Ala Lys Ala Gly Ala Ile Lys Pro Leu Ile Ser
            100                 105                 110 ctg atc tct tct tcg gat ctt cag ctt cag gag tat ggt gtc act gcw     384
Leu Ile Ser Ser Ser Asp Leu Gln Leu Gln Glu Tyr Gly Val Thr Ala
        115                 120                 125 atc ttg aat cta tct ctc tgc gac gag aac aaa gag tcg att gct tct     432
Ile Leu Asn Leu Ser Leu Cys Asp Glu Asn Lys Glu Ser Ile Ala Ser
    130                 135                 140 tcc ggt gcg att aag ccg ctt gtc agg gct ttg aaa atg gga aca ccg     480
Ser Gly Ala Ile Lys Pro Leu Val Arg Ala Leu Lys Met Gly Thr Pro
145                 150                 155                 160 act gct aaa gat aac gct gct tgt gct ctg ctc cgt cta tcg cag atc     528
Thr Ala Lys Asp Asn Ala Ala Cys Ala Leu Leu Arg Leu Ser Gln Ile
                165                 170                 175 gag gag aac aaa gtc gcc atc ggg aga tcc gga gcg att cct ctg ttg     576
Glu Glu Asn Lys Val Ala Ile Gly Arg Ser Gly Ala Ile Pro Leu Leu
            180                 185                 190 gtg aac ctt cta gaa aca ggc gga ttc aga gcg aag aag gac gcg tcg     624
Val Asn Leu Leu Glu Thr Gly Gly Phe Arg Ala Lys Lys Asp Ala Ser
        195                 200                 205 acg gct ctg tac tcg ttg tgc tca gct aaa gag aac aaa atc aga gcc     672
Thr Ala Leu Tyr Ser Leu Cys Ser Ala Lys Glu Asn Lys Ile Arg Ala
    210                 215                 220 gtg caa tcg gga att atg aag ccg ctt gtt gaa ttg atg gcg gat ttc     720
Val Gln Ser Gly Ile Met Lys Pro Leu Val Glu Leu Met Ala Asp Phe
225                 230                 235                 240 gga tca aac atg gtg gat aaa tcg gcg ttt gtg atg agt ctg tta atg     768
Gly Ser Asn Met Val Asp Lys Ser Ala Phe Val Met Ser Leu Leu Met
                245                 250                 255 tcg gtg ccg gaa tcg aaa ccg gcg att gtg gag gaa gga gga gtt ccg     816
Ser Val Pro Glu Ser Lys Pro Ala Ile Val Glu Glu Gly Gly Val Pro
```

```
Ser Val Pro Glu Ser Lys Pro Ala Ile Val Glu Glu Gly Gly Val Pro
        260             265             270 gtg ctg gtg gag ata gta gag gtg gga aca cag aga cag aaa gag atg     864
Val Leu Val Glu Ile Val Glu Val Gly Thr Gln Arg Gln Lys Glu Met
        275             280             285 gct gtg tcg ata ttg cta cag ctt tgt gag gag agt gtt gtg tat aga     912
Ala Val Ser Ile Leu Leu Gln Leu Cys Glu Glu Ser Val Val Tyr Arg
        290             295             300 aca atg gtg gct aga gaa gga gcg ata cct ccg cta gtg gct ctg tcg     960
Thr Met Val Ala Arg Glu Gly Ala Ile Pro Pro Leu Val Ala Leu Ser
305             310             315             320 cag gca gga aca agt cga gct aag caa aag gct gag gcg ttg att gag    1008
Gln Ala Gly Thr Ser Arg Ala Lys Gln Lys Ala Glu Ala Leu Ile Glu
                325             330             335 ctt cta agg caa cca aga tcc att agt aat ggt ggt gct aga tca tcg    1056
Leu Leu Arg Gln Pro Arg Ser Ile Ser Asn Gly Gly Ala Arg Ser Ser
                340             345             350 tcc caa ctc tga                                                    1068
Ser Gln Leu
        355

<210> SEQ ID NO 34
<211> LENGTH: 355
<212> TYPE: PRT
<213> ORGANISM: Arabidopsis thaliana

<400> SEQUENCE: 34

Met Glu Met Glu Asn His Arg Pro Gly Ser Phe Thr Tyr Met Gly Arg
1               5                   10                  15

Lys Phe Ser Asp Leu Ser Leu Asn Asp Asp Ser Ser Ala Phe Ser Asp
            20                  25                  30

Cys Asn Ser Asp Arg Ser Gly Glu Phe Pro Thr Ala Ser Ser Glu Ser
        35                  40                  45

Arg Arg Leu Leu Leu Ser Cys Ala Ser Glu Asn Ser Asp Asp Leu Ile
    50                  55                  60

Asn His Leu Val Ser His Leu Asp Ser Ser Tyr Ser Ile Asp Glu Gln
65                  70                  75                  80

Lys Gln Ala Ala Met Glu Ile Arg Leu Leu Ser Lys Asn Lys Pro Glu
                85                  90                  95

Asn Arg Ile Lys Ile Ala Lys Ala Gly Ala Ile Lys Pro Leu Ile Ser
            100                 105                 110

Leu Ile Ser Ser Ser Asp Leu Gln Leu Gln Glu Tyr Gly Val Thr Ala
        115                 120                 125

Ile Leu Asn Leu Ser Leu Cys Asp Glu Asn Lys Glu Ser Ile Ala Ser
    130                 135                 140

Ser Gly Ala Ile Lys Pro Leu Val Arg Ala Leu Lys Met Gly Thr Pro
145                 150                 155                 160

Thr Ala Lys Asp Asn Ala Ala Cys Ala Leu Leu Arg Leu Ser Gln Ile
                165                 170                 175

Glu Glu Asn Lys Val Ala Ile Gly Arg Ser Gly Ala Ile Pro Leu Leu
            180                 185                 190

Val Asn Leu Leu Glu Thr Gly Gly Phe Arg Ala Lys Lys Asp Ala Ser
        195                 200                 205

Thr Ala Leu Tyr Ser Leu Cys Ser Ala Lys Glu Asn Lys Ile Arg Ala
    210                 215                 220

Val Gln Ser Gly Ile Met Lys Pro Leu Val Glu Leu Met Ala Asp Phe
225                 230                 235                 240
```

-continued

```
Gly Ser Asn Met Val Asp Lys Ser Ala Phe Val Met Ser Leu Leu Met
            245                 250                 255

Ser Val Pro Glu Ser Lys Pro Ala Ile Val Glu Glu Gly Gly Val Pro
        260                 265                 270

Val Leu Val Glu Ile Val Glu Val Gly Thr Gln Arg Gln Lys Glu Met
    275                 280                 285

Ala Val Ser Ile Leu Leu Gln Leu Cys Glu Glu Ser Val Val Tyr Arg
290                 295                 300

Thr Met Val Ala Arg Glu Gly Ala Ile Pro Pro Leu Val Ala Leu Ser
305                 310                 315                 320

Gln Ala Gly Thr Ser Arg Ala Lys Gln Lys Ala Glu Ala Leu Ile Glu
                325                 330                 335

Leu Leu Arg Gln Pro Arg Ser Ile Ser Asn Gly Gly Ala Arg Ser Ser
            340                 345                 350

Ser Gln Leu
        355

<210> SEQ ID NO 35
<211> LENGTH: 1971
<212> TYPE: DNA
<213> ORGANISM: Arabidopsis thaliana
<220> FEATURE:
<221> NAME/KEY: CDS
<222> LOCATION: (1)..(1971)

<400> SEQUENCE: 35 atg gat aca gat gaa gaa gcc aca gga gat gca gag aac cgt gat gaa      48
Met Asp Thr Asp Glu Glu Ala Thr Gly Asp Ala Glu Asn Arg Asp Glu
1               5                   10                  15 gaa gtt acc gca gaa gaa ccg att cac gat gag gtt gtg gat gcg gtg      96
Glu Val Thr Ala Glu Glu Pro Ile His Asp Glu Val Val Asp Ala Val
                20                  25                  30 gag att cat gag gaa gaa gtg aaa gaa gat gat gat gat tgt gaa gga     144
Glu Ile His Glu Glu Glu Val Lys Glu Asp Asp Asp Asp Cys Glu Gly
            35                  40                  45 ttg gtg agc gat atc gta tcg att gtc gag ttt ttg gat cag att aac     192
Leu Val Ser Asp Ile Val Ser Ile Val Glu Phe Leu Asp Gln Ile Asn
        50                  55                  60 ggt tat cga aga aca caa caa aaa gaa tgt ttt aat ctc gtt aga cga     240
Gly Tyr Arg Arg Thr Gln Gln Lys Glu Cys Phe Asn Leu Val Arg Arg
65                  70                  75                  80 ttg aag att ctt att cca ttt ttg gat gag att cga ggt ttt gaa tca     288
Leu Lys Ile Leu Ile Pro Phe Leu Asp Glu Ile Arg Gly Phe Glu Ser
                85                  90                  95 cca agt tgc aag cat ttt tta aat cgt ttg agg aaa gtg ttt ctt gct     336
Pro Ser Cys Lys His Phe Leu Asn Arg Leu Arg Lys Val Phe Leu Ala
            100                 105                 110 gcc aag aaa tta tta gaa act tgc agc aat ggc agt aaa atc tat atg     384
Ala Lys Lys Leu Leu Glu Thr Cys Ser Asn Gly Ser Lys Ile Tyr Met
        115                 120                 125 gca ttg gat ggc gaa aca atg atg acg aga ttt cat tcg att tac gaa     432
Ala Leu Asp Gly Glu Thr Met Met Thr Arg Phe His Ser Ile Tyr Glu
    130                 135                 140 aag ttg aat cgt gtt ctt gtt aaa gct cct ttt gat gaa tta atg att     480
Lys Leu Asn Arg Val Leu Val Lys Ala Pro Phe Asp Glu Leu Met Ile
145                 150                 155                 160 tct ggt gat gcg aaa gac gag att gat tca ttg tgt aaa caa ctg aaa     528
Ser Gly Asp Ala Lys Asp Glu Ile Asp Ser Leu Cys Lys Gln Leu Lys
                165                 170                 175 aaa gca aaa aga aga aca gat aca caa gac ata gag cta gca gta gac     576
```

```
Lys Ala Lys Arg Arg Thr Asp Thr Gln Asp Ile Glu Leu Ala Val Asp
            180                 185                 190 atg atg gtg gta ttc tca aaa acc gat cct cga aac gca gat agc gcg        624
Met Met Val Val Phe Ser Lys Thr Asp Pro Arg Asn Ala Asp Ser Ala
        195                 200                 205 ata ata gag agg cta gcg aaa aag ctt gag cta caa aca att gat gat        672
Ile Ile Glu Arg Leu Ala Lys Lys Leu Glu Leu Gln Thr Ile Asp Asp
    210                 215                 220 tta aag aca gaa act ata gcc ata caa agc tta atc caa gac aaa gga        720
Leu Lys Thr Glu Thr Ile Ala Ile Gln Ser Leu Ile Gln Asp Lys Gly
225                 230                 235                 240 ggt ttg aac ata gag act aaa caa cat atc att gag ctt ctt aac aag        768
Gly Leu Asn Ile Glu Thr Lys Gln His Ile Ile Glu Leu Leu Asn Lys
                245                 250                 255 ttc aag aag ctt caa ggt ctt gaa gct acc gac att ctc tac caa ccc        816
Phe Lys Lys Leu Gln Gly Leu Glu Ala Thr Asp Ile Leu Tyr Gln Pro
            260                 265                 270 gtc atc aat aaa gca atc acc aag tca acg tct cta ata tta cct cat        864
Val Ile Asn Lys Ala Ile Thr Lys Ser Thr Ser Leu Ile Leu Pro His
        275                 280                 285 gag ttt ttg tgt cct ata aca ctc gaa ata atg ctt gac ccg gtt atc        912
Glu Phe Leu Cys Pro Ile Thr Leu Glu Ile Met Leu Asp Pro Val Ile
    290                 295                 300 atc gcc act gga cag aca tat gag aag gag agt ata cag aaa tgg ttt        960
Ile Ala Thr Gly Gln Thr Tyr Glu Lys Glu Ser Ile Gln Lys Trp Phe
305                 310                 315                 320 gac gca gga cat aag act tgt cct aaa aca aga cag gag tta gat cat       1008
Asp Ala Gly His Lys Thr Cys Pro Lys Thr Arg Gln Glu Leu Asp His
                325                 330                 335 ctc tct ctt gca cct aac ttc gct tta aag aac ttg att atg cag tgg       1056
Leu Ser Leu Ala Pro Asn Phe Ala Leu Lys Asn Leu Ile Met Gln Trp
            340                 345                 350 tgt gag aag aac aat ttc aag att cca gag aaa gaa gta agt cct gac       1104
Cys Glu Lys Asn Asn Phe Lys Ile Pro Glu Lys Glu Val Ser Pro Asp
        355                 360                 365 tca caa aat gag cag aaa gat gag gtc tct ttg ctg gtg gaa gcg tta       1152
Ser Gln Asn Glu Gln Lys Asp Glu Val Ser Leu Leu Val Glu Ala Leu
    370                 375                 380 tcg tca agc caa ctg gaa gaa caa cga aga tca gtg aag cag atg cgt       1200
Ser Ser Ser Gln Leu Glu Glu Gln Arg Arg Ser Val Lys Gln Met Arg
385                 390                 395                 400 ttg cta gcc aga gaa aat ccc gag aac cgc gtt tta ata gcg aat gca       1248
Leu Leu Ala Arg Glu Asn Pro Glu Asn Arg Val Leu Ile Ala Asn Ala
                405                 410                 415 gga gcg att cct ttg tta gtt caa ctc ctt tct tac cct gat tca gga       1296
Gly Ala Ile Pro Leu Leu Val Gln Leu Leu Ser Tyr Pro Asp Ser Gly
            420                 425                 430 atc caa gaa aac gcg gta acg aca ttg ttg aat cta tct atc gac gag       1344
Ile Gln Glu Asn Ala Val Thr Thr Leu Leu Asn Leu Ser Ile Asp Glu
        435                 440                 445 gtc aac aag aaa ctc att tca aat gaa gga gct att cca aac att att       1392
Val Asn Lys Lys Leu Ile Ser Asn Glu Gly Ala Ile Pro Asn Ile Ile
    450                 455                 460 gaa atc ctt gaa aat gga aac aga gag gca aga gag aac tct gct gca       1440
Glu Ile Leu Glu Asn Gly Asn Arg Glu Ala Arg Glu Asn Ser Ala Ala
465                 470                 475                 480 gct ttg ttt agt tta tcg atg ctc gat gag aac aaa gta act atc gga       1488
Ala Leu Phe Ser Leu Ser Met Leu Asp Glu Asn Lys Val Thr Ile Gly
                485                 490                 495 tta tcg aat ggg ata ccg cct tta gtc gat tta cta caa cat ggg aca       1536
```

```
Leu Ser Asn Gly Ile Pro Pro Leu Val Asp Leu Leu Gln His Gly Thr
                500                 505                 510 tta aga ggg aag aaa gat gct ctc act gca ctc ttt aac ttg tct ctt      1584
Leu Arg Gly Lys Lys Asp Ala Leu Thr Ala Leu Phe Asn Leu Ser Leu
            515                 520                 525 aac tca gct aat aaa gga aga gct atc gat gct ggt att gtt caa cct      1632
Asn Ser Ala Asn Lys Gly Arg Ala Ile Asp Ala Gly Ile Val Gln Pro
        530                 535                 540 ttg ctt aac ctt ctt aaa gat aaa aac tta ggg atg atc gat gaa gcg      1680
Leu Leu Asn Leu Leu Lys Asp Lys Asn Leu Gly Met Ile Asp Glu Ala
545                 550                 555                 560 ctt tcg att ctg ttg ctg ctt gca tca cac cct gaa gga cgt caa gcc      1728
Leu Ser Ile Leu Leu Leu Leu Ala Ser His Pro Glu Gly Arg Gln Ala
                565                 570                 575 att gga caa ctc tcc ttc att gaa aca ctt gtg gaa ttc atc aga caa      1776
Ile Gly Gln Leu Ser Phe Ile Glu Thr Leu Val Glu Phe Ile Arg Gln
            580                 585                 590 ggc acc ccg aaa aac aaa gag tgt gcg acc tcg gtg ctg ctt gaa cta      1824
Gly Thr Pro Lys Asn Lys Glu Cys Ala Thr Ser Val Leu Leu Glu Leu
        595                 600                 605 ggc tct aac aac tcg tct ttt atc ctc gca gcg ctt caa ttc gga gtt      1872
Gly Ser Asn Asn Ser Ser Phe Ile Leu Ala Ala Leu Gln Phe Gly Val
610                 615                 620 tat gaa tat ctg gta gaa ata acc acc tct gga aca aac aga gct cag      1920
Tyr Glu Tyr Leu Val Glu Ile Thr Thr Ser Gly Thr Asn Arg Ala Gln
625                 630                 635                 640 aga aaa gca aat gct ctt ata caa ctc ata agc aaa tct gaa caa att      1968
Arg Lys Ala Asn Ala Leu Ile Gln Leu Ile Ser Lys Ser Glu Gln Ile
                645                 650                 655 tag                                                                   1971

<210> SEQ ID NO 36
<211> LENGTH: 656
<212> TYPE: PRT
<213> ORGANISM: Arabidopsis thaliana

<400> SEQUENCE: 36

Met Asp Thr Asp Glu Ala Thr Gly Asp Ala Glu Asn Arg Asp Glu
1               5                   10                  15

Glu Val Thr Ala Glu Glu Pro Ile His Asp Glu Val Asp Ala Val
                20                  25                  30

Glu Ile His Glu Glu Val Lys Glu Asp Asp Asp Cys Glu Gly
            35                  40                  45

Leu Val Ser Asp Ile Val Ser Ile Val Glu Phe Leu Asp Gln Ile Asn
    50                  55                  60

Gly Tyr Arg Arg Thr Gln Lys Glu Cys Phe Asn Leu Val Arg Arg
65                  70                  75                  80

Leu Lys Ile Leu Ile Pro Phe Leu Asp Glu Ile Arg Gly Phe Glu Ser
                85                  90                  95

Pro Ser Cys Lys His Phe Leu Asn Arg Leu Arg Lys Val Phe Leu Ala
            100                 105                 110

Ala Lys Lys Leu Leu Glu Thr Cys Ser Asn Gly Ser Lys Ile Tyr Met
        115                 120                 125

Ala Leu Asp Gly Glu Thr Met Met Thr Arg Phe His Ser Ile Tyr Glu
    130                 135                 140

Lys Leu Asn Arg Val Leu Val Lys Ala Pro Phe Asp Glu Leu Met Ile
145                 150                 155                 160

Ser Gly Asp Ala Lys Asp Glu Ile Asp Ser Leu Cys Lys Gln Leu Lys
```

```
                     165                 170                 175
Lys Ala Lys Arg Arg Thr Asp Thr Gln Asp Ile Glu Leu Ala Val Asp
            180                 185                 190

Met Met Val Val Phe Ser Lys Thr Asp Pro Arg Asn Ala Asp Ser Ala
            195                 200                 205

Ile Ile Glu Arg Leu Ala Lys Lys Leu Glu Leu Gln Thr Ile Asp Asp
            210                 215                 220

Leu Lys Thr Glu Thr Ile Ala Ile Gln Ser Leu Ile Gln Asp Lys Gly
225                 230                 235                 240

Gly Leu Asn Ile Glu Thr Lys Gln His Ile Ile Glu Leu Leu Asn Lys
                245                 250                 255

Phe Lys Lys Leu Gln Gly Leu Glu Ala Thr Asp Ile Leu Tyr Gln Pro
            260                 265                 270

Val Ile Asn Lys Ala Ile Thr Lys Ser Thr Ser Leu Ile Leu Pro His
            275                 280                 285

Glu Phe Leu Cys Pro Ile Thr Leu Glu Ile Met Leu Asp Pro Val Ile
    290                 295                 300

Ile Ala Thr Gly Gln Thr Tyr Glu Lys Glu Ser Ile Gln Lys Trp Phe
305                 310                 315                 320

Asp Ala Gly His Lys Thr Cys Pro Lys Thr Arg Gln Glu Leu Asp His
                325                 330                 335

Leu Ser Leu Ala Pro Asn Phe Ala Leu Lys Asn Leu Ile Met Gln Trp
            340                 345                 350

Cys Glu Lys Asn Asn Phe Lys Ile Pro Glu Lys Glu Val Ser Pro Asp
            355                 360                 365

Ser Gln Asn Glu Gln Lys Asp Glu Val Ser Leu Leu Val Glu Ala Leu
    370                 375                 380

Ser Ser Ser Gln Leu Glu Glu Gln Arg Arg Ser Val Lys Gln Met Arg
385                 390                 395                 400

Leu Leu Ala Arg Glu Asn Pro Gly Asn Arg Val Leu Ile Ala Asn Ala
                405                 410                 415

Gly Ala Ile Pro Leu Leu Val Gln Leu Leu Ser Tyr Pro Asp Ser Gly
            420                 425                 430

Ile Gln Glu Asn Ala Val Thr Thr Leu Leu Asn Leu Ser Ile Asp Glu
            435                 440                 445

Val Asn Lys Lys Leu Ile Ser Asn Glu Gly Ala Ile Pro Asn Ile Ile
    450                 455                 460

Glu Ile Leu Glu Asn Gly Asn Arg Glu Ala Arg Glu Asn Ser Ala Ala
465                 470                 475                 480

Ala Leu Phe Ser Leu Ser Met Leu Asp Glu Asn Lys Val Thr Ile Gly
                485                 490                 495

Leu Ser Asn Gly Ile Pro Pro Leu Val Asp Leu Leu Gln His Gly Thr
            500                 505                 510

Leu Arg Gly Lys Lys Asp Ala Leu Thr Ala Leu Phe Asn Leu Ser Leu
            515                 520                 525

Asn Ser Ala Asn Lys Gly Arg Ala Ile Asp Ala Gly Ile Val Gln Pro
    530                 535                 540

Leu Leu Asn Leu Leu Lys Asp Lys Asn Leu Gly Met Ile Asp Glu Ala
545                 550                 555                 560

Leu Ser Ile Leu Leu Leu Ala Ser His Pro Glu Gly Arg Gln Ala
                565                 570                 575

Ile Gly Gln Leu Ser Phe Ile Glu Thr Leu Val Glu Phe Ile Arg Gln
            580                 585                 590
```

```
Gly Thr Pro Lys Asn Lys Glu Cys Ala Thr Ser Val Leu Leu Glu Leu
            595                 600                 605

Gly Ser Asn Asn Ser Ser Phe Ile Leu Ala Ala Leu Gln Phe Gly Val
            610                 615                 620

Tyr Glu Tyr Leu Val Glu Ile Thr Thr Ser Gly Thr Asn Arg Ala Gln
625                 630                 635                 640

Arg Lys Ala Asn Ala Leu Ile Gln Leu Ile Ser Lys Ser Glu Gln Ile
                645                 650                 655

<210> SEQ ID NO 37
<211> LENGTH: 1983
<212> TYPE: DNA
<213> ORGANISM: Arabidopsis thaliana
<220> FEATURE:
<221> NAME/KEY: CDS
<222> LOCATION: (1)..(1983)

<400> SEQUENCE: 37 atg gtc gat gtg atg gat aca gat gaa gaa gcc aca gga gat gca gag      48
Met Val Asp Val Met Asp Thr Asp Glu Glu Ala Thr Gly Asp Ala Glu
1               5                   10                  15 agc cgt gat gaa gaa gtt acc gca gaa gaa ccg att cac gat gag gtt      96
Ser Arg Asp Glu Glu Val Thr Ala Glu Glu Pro Ile His Asp Glu Val
                20                  25                  30 gtg gat gcg gtg gag att cat gag gaa gaa gtg aaa gaa gat gat gat     144
Val Asp Ala Val Glu Ile His Glu Glu Glu Val Lys Glu Asp Asp Asp
            35                  40                  45 gat tgt gaa gga ttg gtg agc gat atc gta tcg att gtc gag ttt ttg     192
Asp Cys Glu Gly Leu Val Ser Asp Ile Val Ser Ile Val Glu Phe Leu
        50                  55                  60 gat cag att aac ggt tat cga aga aca caa caa aaa gaa tgt ttt aat     240
Asp Gln Ile Asn Gly Tyr Arg Arg Thr Gln Gln Lys Glu Cys Phe Asn
65                  70                  75                  80 ctc gtt aga cga ttg aag att ctt att cca ttt ttg gat gag att cga     288
Leu Val Arg Arg Leu Lys Ile Leu Ile Pro Phe Leu Asp Glu Ile Arg
                85                  90                  95 ggt ttt gaa tca cca agt tgc aag cat ttt tta aat cgt ttg agg aaa     336
Gly Phe Glu Ser Pro Ser Cys Lys His Phe Leu Asn Arg Leu Arg Lys
            100                 105                 110 gtg ttt ctt gct gcc aag aaa tta tta gaa act tgc agc aat ggc agt     384
Val Phe Leu Ala Ala Lys Lys Leu Leu Glu Thr Cys Ser Asn Gly Ser
        115                 120                 125 aaa atc tat atg gca ttg gat ggc gaa aca atg atg acg aga ttt cat     432
Lys Ile Tyr Met Ala Leu Asp Gly Glu Thr Met Met Thr Arg Phe His
130                 135                 140 tcg att tac gaa aag ttg aat cgt gtt ctt gtt aaa gct cct ttt gat     480
Ser Ile Tyr Glu Lys Leu Asn Arg Val Leu Val Lys Ala Pro Phe Asp
145                 150                 155                 160 gaa tta atg att tct ggt gat gcg aaa gac gag att gat tca ttg tgt     528
Glu Leu Met Ile Ser Gly Asp Ala Lys Asp Glu Ile Asp Ser Leu Cys
                165                 170                 175 aaa caa ctg aaa aaa gca aaa aga aga aca gat aca caa gac ata gag     576
Lys Gln Leu Lys Lys Ala Lys Arg Arg Thr Asp Thr Gln Asp Ile Glu
            180                 185                 190 cta gca gta gac atg atg gtg gta ttc tca aaa acc gat cct cga aac     624
Leu Ala Val Asp Met Met Val Val Phe Ser Lys Thr Asp Pro Arg Asn
        195                 200                 205 gca gat agc gcg ata ata gag agg cta gcg aaa aag ctt gag cta caa     672
Ala Asp Ser Ala Ile Ile Glu Arg Leu Ala Lys Lys Leu Glu Leu Gln
210                 215                 220 aca att gat gat tta aag aca gaa act ata gcc ata caa agc tta atc     720
```

|     |     |     |     |     |     |     |     |     |     |     |     |     |     |     |     |
| --- | --- | --- | --- | --- | --- | --- | --- | --- | --- | --- | --- | --- | --- | --- | --- |
| Thr | Ile | Asp | Asp | Leu | Lys | Thr | Glu | Thr | Ile | Ala | Ile | Gln | Ser | Leu | Ile |
| 225 |     |     |     | 230 |     |     |     |     | 235 |     |     |     |     | 240 |     |

| caa | gac | aaa | gga | ggt | ttg | aac | ata | gag | act | aaa | caa | cat | atc | att | gag | 768 |
|---|---|---|---|---|---|---|---|---|---|---|---|---|---|---|---|---|
| Gln | Asp | Lys | Gly | Gly | Leu | Asn | Ile | Glu | Thr | Lys | Gln | His | Ile | Ile | Glu |  |
|  |  |  |  | 245 |  |  |  |  | 250 |  |  |  |  | 255 |  |  |

| ctt | ctt | aac | aag | ttc | aag | aag | ctt | caa | ggt | ctt | gaa | gct | acc | gac | att | 816 |
|---|---|---|---|---|---|---|---|---|---|---|---|---|---|---|---|---|
| Leu | Leu | Asn | Lys | Phe | Lys | Lys | Leu | Gln | Gly | Leu | Glu | Ala | Thr | Asp | Ile |  |
|  |  |  | 260 |  |  |  |  | 265 |  |  |  |  | 270 |  |  |  |

| ctc | tac | caa | ccc | gtc | atc | aat | aaa | gca | atc | acc | aag | tca | acg | tct | cta | 864 |
|---|---|---|---|---|---|---|---|---|---|---|---|---|---|---|---|---|
| Leu | Tyr | Gln | Pro | Val | Ile | Asn | Lys | Ala | Ile | Thr | Lys | Ser | Thr | Ser | Leu |  |
|  |  | 275 |  |  |  |  | 280 |  |  |  |  | 285 |  |  |  |  |

| ata | tta | cct | cat | gag | ttt | ttg | tgt | cct | ata | aca | ctc | gga | ata | atg | ctt | 912 |
|---|---|---|---|---|---|---|---|---|---|---|---|---|---|---|---|---|
| Ile | Leu | Pro | His | Glu | Phe | Leu | Cys | Pro | Ile | Thr | Leu | Gly | Ile | Met | Leu |  |
|  | 290 |  |  |  |  | 295 |  |  |  |  | 300 |  |  |  |  |  |

| gac | ccg | gtt | atc | atc | gcc | act | gga | cag | aca | tat | gag | aag | gag | agt | ata | 960 |
|---|---|---|---|---|---|---|---|---|---|---|---|---|---|---|---|---|
| Asp | Pro | Val | Ile | Ile | Ala | Thr | Gly | Gln | Thr | Tyr | Glu | Lys | Glu | Ser | Ile |  |
| 305 |  |  |  | 310 |  |  |  |  | 315 |  |  |  |  | 320 |  |  |

| cag | aaa | tgg | ttt | gac | gca | gga | cat | aag | act | tgt | cct | aaa | aca | aga | cag | 1008 |
|---|---|---|---|---|---|---|---|---|---|---|---|---|---|---|---|---|
| Gln | Lys | Trp | Phe | Asp | Ala | Gly | His | Lys | Thr | Cys | Pro | Lys | Thr | Arg | Gln |  |
|  |  |  | 325 |  |  |  |  | 330 |  |  |  |  | 335 |  |  |  |

| gag | tta | gat | cat | ctc | tct | ctt | gca | cct | aac | ttc | gct | tta | aag | aac | ttg | 1056 |
|---|---|---|---|---|---|---|---|---|---|---|---|---|---|---|---|---|
| Glu | Leu | Asp | His | Leu | Ser | Leu | Ala | Pro | Asn | Phe | Ala | Leu | Lys | Asn | Leu |  |
|  |  | 340 |  |  |  |  | 345 |  |  |  |  | 350 |  |  |  |  |

| att | atg | cag | tgg | tgt | gag | aag | aac | aat | ttc | aag | att | cca | gag | aaa | gaa | 1104 |
|---|---|---|---|---|---|---|---|---|---|---|---|---|---|---|---|---|
| Ile | Met | Gln | Trp | Cys | Glu | Lys | Asn | Asn | Phe | Lys | Ile | Pro | Glu | Lys | Glu |  |
|  | 355 |  |  |  |  | 360 |  |  |  |  | 365 |  |  |  |  |  |

| gta | agt | cct | gac | tca | caa | aat | gag | cag | aaa | gat | gag | gtc | tct | ttg | ctg | 1152 |
|---|---|---|---|---|---|---|---|---|---|---|---|---|---|---|---|---|
| Val | Ser | Pro | Asp | Ser | Gln | Asn | Glu | Gln | Lys | Asp | Glu | Val | Ser | Leu | Leu |  |
| 370 |  |  |  |  | 375 |  |  |  |  | 380 |  |  |  |  |  |  |

| gtg | gaa | gcg | tta | tcg | tca | agc | caa | ctg | gaa | gaa | caa | cga | aga | tca | gtg | 1200 |
|---|---|---|---|---|---|---|---|---|---|---|---|---|---|---|---|---|
| Val | Glu | Ala | Leu | Ser | Ser | Ser | Gln | Leu | Glu | Glu | Gln | Arg | Arg | Ser | Val |  |
| 385 |  |  |  |  | 390 |  |  |  |  | 395 |  |  |  |  | 400 |  |

| aag | cag | atg | cgt | ttg | cta | gcc | aga | gaa | aat | ccc | gag | aac | cgc | gtt | tta | 1248 |
|---|---|---|---|---|---|---|---|---|---|---|---|---|---|---|---|---|
| Lys | Gln | Met | Arg | Leu | Leu | Ala | Arg | Glu | Asn | Pro | Glu | Asn | Arg | Val | Leu |  |
|  |  |  | 405 |  |  |  |  | 410 |  |  |  |  | 415 |  |  |  |

| ata | gcg | aat | gca | gga | gcg | att | cct | ttg | tta | gtt | caa | ctc | ctt | tct | tac | 1296 |
|---|---|---|---|---|---|---|---|---|---|---|---|---|---|---|---|---|
| Ile | Ala | Asn | Ala | Gly | Ala | Ile | Pro | Leu | Leu | Val | Gln | Leu | Leu | Ser | Tyr |  |
|  |  | 420 |  |  |  |  | 425 |  |  |  |  | 430 |  |  |  |  |

| cct | gat | tca | gga | atc | caa | gaa | aac | gcg | gta | acg | aca | ttg | ttg | aat | cta | 1344 |
|---|---|---|---|---|---|---|---|---|---|---|---|---|---|---|---|---|
| Pro | Asp | Ser | Gly | Ile | Gln | Glu | Asn | Ala | Val | Thr | Thr | Leu | Leu | Asn | Leu |  |
|  |  | 435 |  |  |  |  | 440 |  |  |  |  | 445 |  |  |  |  |

| tct | atc | gac | gag | gtc | aac | aag | aaa | ctc | att | tca | aat | gaa | gga | gct | att | 1392 |
|---|---|---|---|---|---|---|---|---|---|---|---|---|---|---|---|---|
| Ser | Ile | Asp | Glu | Val | Asn | Lys | Lys | Leu | Ile | Ser | Asn | Glu | Gly | Ala | Ile |  |
|  | 450 |  |  |  |  | 455 |  |  |  |  | 460 |  |  |  |  |  |

| cca | aac | att | att | gaa | atc | ctt | gaa | aat | gga | aac | aga | gag | gca | aga | gag | 1440 |
|---|---|---|---|---|---|---|---|---|---|---|---|---|---|---|---|---|
| Pro | Asn | Ile | Ile | Glu | Ile | Leu | Glu | Asn | Gly | Asn | Arg | Glu | Ala | Arg | Glu |  |
| 465 |  |  |  | 470 |  |  |  |  | 475 |  |  |  |  | 480 |  |  |

| aac | tct | gct | gca | gct | ttg | ttt | agt | tta | tcg | atg | ctc | gat | gag | aac | aaa | 1488 |
|---|---|---|---|---|---|---|---|---|---|---|---|---|---|---|---|---|
| Asn | Ser | Ala | Ala | Ala | Leu | Phe | Ser | Leu | Ser | Met | Leu | Asp | Glu | Asn | Lys |  |
|  |  |  | 485 |  |  |  |  | 490 |  |  |  |  | 495 |  |  |  |

| gta | act | atc | gga | tta | tcg | aat | ggg | ata | ccg | cct | tta | gtc | gat | tta | cta | 1536 |
|---|---|---|---|---|---|---|---|---|---|---|---|---|---|---|---|---|
| Val | Thr | Ile | Gly | Leu | Ser | Asn | Gly | Ile | Pro | Pro | Leu | Val | Asp | Leu | Leu |  |
|  |  | 500 |  |  |  |  | 505 |  |  |  |  | 510 |  |  |  |  |

| caa | cat | ggg | aca | tta | aga | ggg | aag | aaa | gat | gct | ctc | act | gca | ctc | ttt | 1584 |
|---|---|---|---|---|---|---|---|---|---|---|---|---|---|---|---|---|
| Gln | His | Gly | Thr | Leu | Arg | Gly | Lys | Lys | Asp | Ala | Leu | Thr | Ala | Leu | Phe |  |
|  |  | 515 |  |  |  |  | 520 |  |  |  |  | 525 |  |  |  |  |

| aac | ttg | tct | ctt | aac | tca | gct | aat | aaa | gga | aga | gct | atc | gat | gct | ggt | 1632 |
|---|---|---|---|---|---|---|---|---|---|---|---|---|---|---|---|---|
| Asn | Leu | Ser | Leu | Asn | Ser | Ala | Asn | Lys | Gly | Arg | Ala | Ile | Asp | Ala | Gly |  |
|  | 530 |  |  |  |  | 535 |  |  |  |  | 540 |  |  |  |  |  |

| att | gtt | caa | cct | ttg | ctt | aac | ctt | ctt | aaa | gat | aaa | aac | tta | ggg | atg | 1680 |
|---|---|---|---|---|---|---|---|---|---|---|---|---|---|---|---|---|

```
Ile Val Gln Pro Leu Leu Asn Leu Leu Lys Asp Lys Asn Leu Gly Met
545                 550                 555                 560 atc gat gaa gcg ctt tcg att ctg ttg ctg ctt gca tca cac cct gaa    1728
Ile Asp Glu Ala Leu Ser Ile Leu Leu Leu Leu Ala Ser His Pro Glu
                565                 570                 575 gga cgt caa gcc att gga caa ctc tcc ttc att gaa aca ctt gtg gaa    1776
Gly Arg Gln Ala Ile Gly Gln Leu Ser Phe Ile Glu Thr Leu Val Glu
                580                 585                 590 ttc atc aga caa ggc acc ccg aaa aac aaa gag tgt gcg acc tcg gtg    1824
Phe Ile Arg Gln Gly Thr Pro Lys Asn Lys Glu Cys Ala Thr Ser Val
            595                 600                 605 ctg ctt gaa cta ggc tct aac aac tcg tct ttt atc ctc gca gcg ctt    1872
Leu Leu Glu Leu Gly Ser Asn Asn Ser Ser Phe Ile Leu Ala Ala Leu
        610                 615                 620 caa ttc gga gtt tat gaa tat ctg gta gaa ata acc acc tct gga aca    1920
Gln Phe Gly Val Tyr Glu Tyr Leu Val Glu Ile Thr Thr Ser Gly Thr
625                 630                 635                 640 aac aga gct cag aga aaa gca aat gct ctt ata caa ctc ata agc aaa    1968
Asn Arg Ala Gln Arg Lys Ala Asn Ala Leu Ile Gln Leu Ile Ser Lys
                645                 650                 655 tct gaa caa att tag                                                 1983
Ser Glu Gln Ile
            660

<210> SEQ ID NO 38
<211> LENGTH: 660
<212> TYPE: PRT
<213> ORGANISM: Arabidopsis thaliana

<400> SEQUENCE: 38

Met Val Asp Val Met Asp Thr Asp Glu Glu Ala Thr Gly Asp Ala Glu
1               5                   10                  15

Ser Arg Asp Glu Glu Val Thr Ala Glu Glu Pro Ile His Asp Glu Val
                20                  25                  30

Val Asp Ala Val Glu Ile His Glu Glu Val Lys Glu Asp Asp Asp
            35                  40                  45

Asp Cys Glu Gly Leu Val Ser Asp Ile Val Ser Ile Val Glu Phe Leu
50                  55                  60

Asp Gln Ile Asn Gly Tyr Arg Arg Thr Gln Lys Glu Cys Phe Asn
65                  70                  75                  80

Leu Val Arg Arg Leu Lys Ile Leu Ile Pro Phe Leu Asp Glu Ile Arg
                85                  90                  95

Gly Phe Glu Ser Pro Ser Cys Lys His Phe Leu Asn Arg Leu Arg Lys
                100                 105                 110

Val Phe Leu Ala Ala Lys Lys Leu Leu Glu Thr Cys Ser Asn Gly Ser
            115                 120                 125

Lys Ile Tyr Met Ala Leu Asp Gly Glu Thr Met Met Thr Arg Phe His
130                 135                 140

Ser Ile Tyr Glu Lys Leu Asn Arg Val Leu Val Lys Ala Pro Phe Asp
145                 150                 155                 160

Glu Leu Met Ile Ser Gly Asp Ala Lys Asp Ile Asp Ser Leu Cys
                165                 170                 175

Lys Gln Leu Lys Lys Ala Lys Arg Arg Thr Asp Thr Gln Asp Ile Glu
            180                 185                 190

Leu Ala Val Asp Met Met Val Val Phe Ser Lys Thr Asp Pro Arg Asn
        195                 200                 205

Ala Asp Ser Ala Ile Ile Glu Arg Leu Ala Lys Lys Leu Glu Leu Gln
    210                 215                 220
```

Thr Ile Asp Asp Leu Lys Thr Glu Thr Ile Ala Ile Gln Ser Leu Ile
225                 230                 235                 240

Gln Asp Lys Gly Gly Leu Asn Ile Glu Thr Lys Gln His Ile Ile Glu
            245                 250                 255

Leu Leu Asn Lys Phe Lys Lys Leu Gln Gly Leu Glu Ala Thr Asp Ile
                260                 265                 270

Leu Tyr Gln Pro Val Ile Asn Lys Ala Ile Thr Lys Ser Thr Ser Leu
        275                 280                 285

Ile Leu Pro His Glu Phe Leu Cys Pro Ile Thr Leu Gly Ile Met Leu
    290                 295                 300

Asp Pro Val Ile Ile Ala Thr Gly Gln Thr Tyr Glu Lys Glu Ser Ile
305                 310                 315                 320

Gln Lys Trp Phe Asp Ala Gly His Lys Thr Cys Pro Lys Thr Arg Gln
            325                 330                 335

Glu Leu Asp His Leu Ser Leu Ala Pro Asn Phe Ala Leu Lys Asn Leu
                340                 345                 350

Ile Met Gln Trp Cys Glu Lys Asn Asn Phe Lys Ile Pro Glu Lys Glu
        355                 360                 365

Val Ser Pro Asp Ser Gln Asn Glu Gln Lys Asp Glu Val Ser Leu Leu
    370                 375                 380

Val Glu Ala Leu Ser Ser Ser Gln Leu Glu Glu Gln Arg Arg Ser Val
385                 390                 395                 400

Lys Gln Met Arg Leu Leu Ala Arg Glu Asn Pro Glu Asn Arg Val Leu
            405                 410                 415

Ile Ala Asn Ala Gly Ala Ile Pro Leu Leu Val Gln Leu Leu Ser Tyr
                420                 425                 430

Pro Asp Ser Gly Ile Gln Glu Asn Ala Val Thr Thr Leu Leu Asn Leu
        435                 440                 445

Ser Ile Asp Glu Val Asn Lys Lys Leu Ile Ser Asn Glu Gly Ala Ile
    450                 455                 460

Pro Asn Ile Ile Glu Ile Leu Glu Asn Gly Asn Arg Glu Ala Arg Glu
465                 470                 475                 480

Asn Ser Ala Ala Ala Leu Phe Ser Leu Ser Met Leu Asp Glu Asn Lys
            485                 490                 495

Val Thr Ile Gly Leu Ser Asn Gly Ile Pro Pro Leu Val Asp Leu Leu
                500                 505                 510

Gln His Gly Thr Leu Arg Gly Lys Lys Asp Ala Leu Thr Ala Leu Phe
        515                 520                 525

Asn Leu Ser Leu Asn Ser Ala Asn Lys Gly Arg Ala Ile Asp Ala Gly
    530                 535                 540

Ile Val Gln Pro Leu Leu Asn Leu Leu Lys Asp Lys Asn Leu Gly Met
545                 550                 555                 560

Ile Asp Glu Ala Leu Ser Ile Leu Leu Leu Ala Ser His Pro Glu
            565                 570                 575

Gly Arg Gln Ala Ile Gly Gln Leu Ser Phe Ile Glu Thr Leu Val Glu
                580                 585                 590

Phe Ile Arg Gln Gly Thr Pro Lys Asn Lys Glu Cys Ala Thr Ser Val
        595                 600                 605

Leu Leu Glu Leu Gly Ser Asn Asn Ser Ser Phe Ile Leu Ala Ala Leu
    610                 615                 620

Gln Phe Gly Val Tyr Glu Tyr Leu Val Glu Ile Thr Thr Ser Gly Thr
625                 630                 635                 640

Asn Arg Ala Gln Arg Lys Ala Asn Ala Leu Ile Gln Leu Ile Ser Lys

Ser Glu Gln Ile
        660

<210> SEQ ID NO 39
<211> LENGTH: 1920
<212> TYPE: DNA
<213> ORGANISM: Arabidopsis thaliana
<220> FEATURE:
<221> NAME/KEY: CDS
<222> LOCATION: (1)..(1920)

<400> SEQUENCE: 39

| | | |
|---|---|---|
| atg gga tta acg aat tgt tgt tcc cac gag gag cta atg agt cga ctc<br>Met Gly Leu Thr Asn Cys Cys Ser His Glu Glu Leu Met Ser Arg Leu<br>1               5                   10                  15 | 48 | |
| gtt gac tcc gtt aaa gaa ata tca ggg ttt tca tct tca agg ggt ttt<br>Val Asp Ser Val Lys Glu Ile Ser Gly Phe Ser Ser Ser Arg Gly Phe<br>            20                  25                  30 | 96 | |
| att ggg aag atc caa ggc gat ctt gtt cgt agg atc acg ctt ctc agc<br>Ile Gly Lys Ile Gln Gly Asp Leu Val Arg Arg Ile Thr Leu Leu Ser<br>        35                  40                  45 | 144 | |
| cct ttc ttc gag gaa ttg att gac gtc aat gtt gaa ttg aaa aag gat<br>Pro Phe Phe Glu Glu Leu Ile Asp Val Asn Val Glu Leu Lys Lys Asp<br>50                  55                  60 | 192 | |
| cag att aca ggg ttt gag gct atg aga atc gct ctt gat tca agt ctt<br>Gln Ile Thr Gly Phe Glu Ala Met Arg Ile Ala Leu Asp Ser Ser Leu<br>65                  70                  75                  80 | 240 | |
| gag ctt ttt cga tcg gtt aat gga gga agc aag ctt ttt cag ctt ttc<br>Glu Leu Phe Arg Ser Val Asn Gly Gly Ser Lys Leu Phe Gln Leu Phe<br>                85                  90                  95 | 288 | |
| gat aga gat tct ctt gtg gag aag ttc cgt gac atg aca gtg gag ata<br>Asp Arg Asp Ser Leu Val Glu Lys Phe Arg Asp Met Thr Val Glu Ile<br>            100                 105                 110 | 336 | |
| gaa gca gcg tta agt cag att cct tat gag aag att gag gta tca gag<br>Glu Ala Ala Leu Ser Gln Ile Pro Tyr Glu Lys Ile Glu Val Ser Glu<br>        115                 120                 125 | 384 | |
| gaa gtc aga gaa cag gtt cag ctt ctg cat ttt cag ttc aag aga gca<br>Glu Val Arg Glu Gln Val Gln Leu Leu His Phe Gln Phe Lys Arg Ala<br>130                 135                 140 | 432 | |
| aaa gaa aga tgg gag gag tct gat cta cag ctt agc cat gat cta gct<br>Lys Glu Arg Trp Glu Glu Ser Asp Leu Gln Leu Ser His Asp Leu Ala<br>145                 150                 155                 160 | 480 | |
| atg gca gag aat gtg atg gat cct gac cct ata atc ctc aaa aga ctt<br>Met Ala Glu Asn Val Met Asp Pro Asp Pro Ile Ile Leu Lys Arg Leu<br>                165                 170                 175 | 528 | |
| tca caa gag ctc caa ctt act acc att gat gag ctg aag aaa gaa tcg<br>Ser Gln Glu Leu Gln Leu Thr Thr Ile Asp Glu Leu Lys Lys Glu Ser<br>            180                 185                 190 | 576 | |
| cat gcg ata cat gag tat ttt ctt tca tat gat gga gat cct gat gac<br>His Ala Ile His Glu Tyr Phe Leu Ser Tyr Asp Gly Asp Pro Asp Asp<br>        195                 200                 205 | 624 | |
| tgt ttc gag agg atg tct tca ctt ctt aaa aac ctg gta gac ttt gta<br>Cys Phe Glu Arg Met Ser Ser Leu Leu Lys Asn Leu Val Asp Phe Val<br>210                 215                 220 | 672 | |
| aca atg gaa agt tca gac cct gat cca tcc act ggc agc aga atc gtt<br>Thr Met Glu Ser Ser Asp Pro Asp Pro Ser Thr Gly Ser Arg Ile Val<br>225                 230                 235                 240 | 720 | |
| tcg aga cat cgt tct cct gtt ata cca gag tat ttt cgg tgt ccg ata<br>Ser Arg His Arg Ser Pro Val Ile Pro Glu Tyr Phe Arg Cys Pro Ile<br>                245                 250                 255 | 768 | |

-continued

| | |
|---|---|
| tca ctt gaa ctg atg aag gat cct gtt atc gtc tcc act gga cag ctg<br>Ser Leu Glu Leu Met Lys Asp Pro Val Ile Val Ser Thr Gly Gln Leu<br>           260                     265                270 | 816 |
| aat ttt tcg acc ttg cag aca tat gaa aga tca tca att cag aag tgg<br>Asn Phe Ser Thr Leu Gln Thr Tyr Glu Arg Ser Ser Ile Gln Lys Trp<br>        275                     280                285 | 864 |
| ctt gat gct ggt cat aaa aca tgt ccg aaa tct cag gag aca ctt tta<br>Leu Asp Ala Gly His Lys Thr Cys Pro Lys Ser Gln Glu Thr Leu Leu<br>        290                     295                300 | 912 |
| cat gct gga tta acc cct aat tat gtg tta aag agt ctc att gct ttg<br>His Ala Gly Leu Thr Pro Asn Tyr Val Leu Lys Ser Leu Ile Ala Leu<br>305                   310                 315                320 | 960 |
| tgg tgt gaa agc aac ggc att gag cta ccg caa aat caa ggg agc tgt<br>Trp Cys Glu Ser Asn Gly Ile Glu Leu Pro Gln Asn Gln Gly Ser Cys<br>                     325                330                335 | 1008 |
| aga acc aca aaa ata gga gga agc agc tct tca gat tgt gat cga aca<br>Arg Thr Thr Lys Ile Gly Gly Ser Ser Ser Ser Asp Cys Asp Arg Thr<br>                  340                     345                350 | 1056 |
| ttt gtc ctt tcc ttg tta gag aaa ttg gcc aac ggt act aca gaa cag<br>Phe Val Leu Ser Leu Leu Glu Lys Leu Ala Asn Gly Thr Thr Glu Gln<br>        355                     360                365 | 1104 |
| caa aga gct gca gct gga gaa tta agg tta cta gcc aag agg aac gtg<br>Gln Arg Ala Ala Ala Gly Glu Leu Arg Leu Leu Ala Lys Arg Asn Val<br>370                   375                 380 | 1152 |
| gat aac aga gtt tgt atc gct gag gct gga gcc ata cca ctc ctt gta<br>Asp Asn Arg Val Cys Ile Ala Glu Ala Gly Ala Ile Pro Leu Leu Val<br>385                   390                 395                400 | 1200 |
| gag ctt cta tcc tca cca gat cct cgg act cag gaa cat tct gtg aca<br>Glu Leu Leu Ser Ser Pro Asp Pro Arg Thr Gln Glu His Ser Val Thr<br>                  405                     410                415 | 1248 |
| gct ctt ctg aat ctt tcc ata aat gaa ggg aac aaa gga gcc att gtt<br>Ala Leu Leu Asn Leu Ser Ile Asn Glu Gly Asn Lys Gly Ala Ile Val<br>                  420                     425                430 | 1296 |
| gat gca gga gcc ata acg gat ata gta gaa gtc cta aag aac gga agc<br>Asp Ala Gly Ala Ile Thr Asp Ile Val Glu Val Leu Lys Asn Gly Ser<br>        435                     440                445 | 1344 |
| atg gaa gct aga gag aac gct gct gca acc ctt ttc agt tta tct gtt<br>Met Glu Ala Arg Glu Asn Ala Ala Ala Thr Leu Phe Ser Leu Ser Val<br>450                   455                 460 | 1392 |
| ata gat gaa aac aaa gtg gca ata ggt gct gct gga gct atc caa gca<br>Ile Asp Glu Asn Lys Val Ala Ile Gly Ala Ala Gly Ala Ile Gln Ala<br>465                   470                 475                480 | 1440 |
| ctt ata agc ttg ctt gag gaa gga acc cga aga ggc aaa aaa gat gct<br>Leu Ile Ser Leu Leu Glu Glu Gly Thr Arg Arg Gly Lys Lys Asp Ala<br>                  485                     490                495 | 1488 |
| gct aca gcg att ttc aac tta tgc ata tac cag ggg aac aaa tca agg<br>Ala Thr Ala Ile Phe Asn Leu Cys Ile Tyr Gln Gly Asn Lys Ser Arg<br>        500                     505                510 | 1536 |
| gcg gtt aaa ggc ggt att gtt gac cct ctg acc aga tta ctg aaa gat<br>Ala Val Lys Gly Gly Ile Val Asp Pro Leu Thr Arg Leu Leu Lys Asp<br>515                 520                 525 | 1584 |
| gca ggt ggc gga atg gtg gat gag gct ctg gcc att tta gca att ctt<br>Ala Gly Gly Gly Met Val Asp Glu Ala Leu Ala Ile Leu Ala Ile Leu<br>530                 535                540 | 1632 |
| tca act aac caa gaa ggg aaa aca gcg ata gct gaa gca gaa tct atc<br>Ser Thr Asn Gln Glu Gly Lys Thr Ala Ile Ala Glu Ala Glu Ser Ile<br>545                   550                 555                560 | 1680 |
| ccg gtt ttg gtt gag att ata agg aca ggg tca cca agg aac cgg gaa<br>Pro Val Leu Val Glu Ile Ile Arg Thr Gly Ser Pro Arg Asn Arg Glu<br>                  565                     570                575 | 1728 |

```
aat gct gca gca ata ctt tgg tat cta tgt att ggg aat ata gaa agg    1776
Asn Ala Ala Ala Ile Leu Trp Tyr Leu Cys Ile Gly Asn Ile Glu Arg
            580                 585                 590 cta aat gta gca aga gag gtt ggt gca gat gtg gcc ttg aag gaa ctt    1824
Leu Asn Val Ala Arg Glu Val Gly Ala Asp Val Ala Leu Lys Glu Leu
            595                 600                 605 act gag aat ggc act gat aga gca aag agg aaa gct gcg agc ttg ttg    1872
Thr Glu Asn Gly Thr Asp Arg Ala Lys Arg Lys Ala Ala Ser Leu Leu
        610                 615                 620 gag ctt att cag caa acc gaa ggt gtt gca gta act act gtt cca tga    1920
Glu Leu Ile Gln Gln Thr Glu Gly Val Ala Val Thr Thr Val Pro
625                 630                 635

<210> SEQ ID NO 40
<211> LENGTH: 639
<212> TYPE: PRT
<213> ORGANISM: Arabidopsis thaliana

<400> SEQUENCE: 40

Met Gly Leu Thr Asn Cys Cys Ser His Glu Leu Met Ser Arg Leu
1               5                   10                  15

Val Asp Ser Val Lys Glu Ile Ser Gly Phe Ser Ser Arg Gly Phe
            20                  25                  30

Ile Gly Lys Ile Gln Gly Asp Leu Val Arg Arg Ile Thr Leu Leu Ser
            35                  40                  45

Pro Phe Phe Glu Glu Leu Ile Asp Val Asn Val Glu Leu Lys Lys Asp
        50                  55                  60

Gln Ile Thr Gly Phe Glu Ala Met Arg Ile Ala Leu Asp Ser Ser Leu
65                  70                  75                  80

Glu Leu Phe Arg Ser Val Asn Gly Gly Ser Lys Leu Phe Gln Leu Phe
                85                  90                  95

Asp Arg Asp Ser Leu Val Glu Lys Phe Arg Asp Met Thr Val Glu Ile
            100                 105                 110

Glu Ala Ala Leu Ser Gln Ile Pro Tyr Glu Lys Ile Glu Val Ser Glu
        115                 120                 125

Glu Val Arg Glu Gln Val Gln Leu Leu His Phe Gln Phe Lys Arg Ala
    130                 135                 140

Lys Glu Arg Trp Glu Glu Ser Asp Leu Gln Leu Ser His Asp Leu Ala
145                 150                 155                 160

Met Ala Glu Asn Val Met Asp Pro Asp Pro Ile Ile Leu Lys Arg Leu
                165                 170                 175

Ser Gln Glu Leu Gln Leu Thr Thr Ile Asp Glu Leu Lys Lys Glu Ser
            180                 185                 190

His Ala Ile His Glu Tyr Phe Leu Ser Tyr Asp Gly Asp Pro Asp Asp
        195                 200                 205

Cys Phe Glu Arg Met Ser Ser Leu Leu Lys Asn Leu Val Asp Phe Val
    210                 215                 220

Thr Met Glu Ser Ser Asp Pro Asp Pro Ser Thr Gly Ser Arg Ile Val
225                 230                 235                 240

Ser Arg His Arg Ser Pro Val Ile Pro Glu Tyr Phe Arg Cys Pro Ile
                245                 250                 255

Ser Leu Glu Leu Met Lys Asp Pro Val Ile Val Ser Thr Gly Gln Leu
            260                 265                 270

Asn Phe Ser Thr Leu Gln Thr Tyr Glu Arg Ser Ser Ile Gln Lys Trp
        275                 280                 285

Leu Asp Ala Gly His Lys Thr Cys Pro Lys Ser Gln Glu Thr Leu Leu
    290                 295                 300
```

```
His Ala Gly Leu Thr Pro Asn Tyr Val Leu Lys Ser Leu Ile Ala Leu
305                 310                 315                 320

Trp Cys Glu Ser Asn Gly Ile Glu Leu Pro Gln Asn Gln Gly Ser Cys
            325                 330                 335

Arg Thr Thr Lys Ile Gly Gly Ser Ser Ser Asp Cys Asp Arg Thr
        340                 345                 350

Phe Val Leu Ser Leu Leu Glu Lys Leu Ala Asn Gly Thr Thr Glu Gln
        355                 360                 365

Gln Arg Ala Ala Ala Gly Glu Leu Arg Leu Leu Ala Lys Arg Asn Val
370                 375                 380

Asp Asn Arg Val Cys Ile Ala Glu Ala Gly Ala Ile Pro Leu Leu Val
385                 390                 395                 400

Glu Leu Leu Ser Ser Pro Asp Pro Arg Thr Gln Glu His Ser Val Thr
            405                 410                 415

Ala Leu Leu Asn Leu Ser Ile Asn Glu Gly Asn Lys Gly Ala Ile Val
            420                 425                 430

Asp Ala Gly Ala Ile Thr Asp Ile Val Glu Val Leu Lys Asn Gly Ser
        435                 440                 445

Met Glu Ala Arg Glu Asn Ala Ala Thr Leu Phe Ser Leu Ser Val
450                 455                 460

Ile Asp Glu Asn Lys Val Ala Ile Gly Ala Ala Gly Ala Ile Gln Ala
465                 470                 475                 480

Leu Ile Ser Leu Leu Glu Glu Gly Thr Arg Arg Gly Lys Lys Asp Ala
            485                 490                 495

Ala Thr Ala Ile Phe Asn Leu Cys Ile Tyr Gln Gly Asn Lys Ser Arg
        500                 505                 510

Ala Val Lys Gly Gly Ile Val Asp Pro Leu Thr Arg Leu Leu Lys Asp
        515                 520                 525

Ala Gly Gly Gly Met Val Asp Glu Ala Leu Ala Ile Leu Ala Ile Leu
530                 535                 540

Ser Thr Asn Gln Glu Gly Lys Thr Ala Ile Ala Glu Ala Glu Ser Ile
545                 550                 555                 560

Pro Val Leu Val Glu Ile Ile Arg Thr Gly Ser Pro Arg Asn Arg Glu
            565                 570                 575

Asn Ala Ala Ala Ile Leu Trp Tyr Leu Cys Ile Gly Asn Ile Glu Arg
            580                 585                 590

Leu Asn Val Ala Arg Glu Val Gly Ala Asp Val Ala Leu Lys Glu Leu
        595                 600                 605

Thr Glu Asn Gly Thr Asp Arg Ala Lys Arg Lys Ala Ala Ser Leu Leu
610                 615                 620

Glu Leu Ile Gln Gln Thr Glu Gly Val Ala Val Thr Thr Val Pro
625                 630                 635

<210> SEQ ID NO 41
<211> LENGTH: 1899
<212> TYPE: DNA
<213> ORGANISM: Arabidopsis thaliana
<220> FEATURE:
<221> NAME/KEY: CDS
<222> LOCATION: (1)..(1899)

<400> SEQUENCE: 41 atg gga tta acg aat tgt tgt tcc cac gag gag cta atg agt cga ctc      48
Met Gly Leu Thr Asn Cys Cys Ser His Glu Glu Leu Met Ser Arg Leu
1               5                   10                  15 gtt gac tcc gtt aaa gaa ata tca ggg ttt tca tct tca agg ggt ttt     96
```

-continued

```
                Val Asp Ser Val Lys Glu Ile Ser Gly Phe Ser Ser Arg Gly Phe
                         20              25                  30 att ggg aag atc caa ggc gat ctt gtt cgt agg atc acg ctt ctc agc      144
Ile Gly Lys Ile Gln Gly Asp Leu Val Arg Arg Ile Thr Leu Leu Ser
         35              40                  45 cct ttc ttc gag gaa ttg att gac gtc aat gtt gaa ttg aaa aag gat      192
Pro Phe Phe Glu Glu Leu Ile Asp Val Asn Val Glu Leu Lys Lys Asp
 50              55                  60 cag att aca ggg ttt gag gct atg aga atc gct ctt gat tca agt ctt      240
Gln Ile Thr Gly Phe Glu Ala Met Arg Ile Ala Leu Asp Ser Ser Leu
 65              70                  75              80 gag ctt ttt cga tcg gtt aat gga gga agc aag ctt ttt cag ctt ttc      288
Glu Leu Phe Arg Ser Val Asn Gly Gly Ser Lys Leu Phe Gln Leu Phe
                 85                  90                  95 gat aga gat tct ctt gtg gag aag ttc cgt gac atg aca gtg gag ata      336
Asp Arg Asp Ser Leu Val Glu Lys Phe Arg Asp Met Thr Val Glu Ile
             100                 105                 110 gaa gca gcg tta agt cag att cct tat gag aag att gag gta tca gag      384
Glu Ala Ala Leu Ser Gln Ile Pro Tyr Glu Lys Ile Glu Val Ser Glu
         115                 120                 125 gaa gtc aga gaa cag gtt cag ctt ctg cat ttt cag ttc aag aga gca      432
Glu Val Arg Glu Gln Val Gln Leu Leu His Phe Gln Phe Lys Arg Ala
     130                 135                 140 aaa gaa aga tgg gag gag tct gat cta cag ctt agc cat gat cta gct      480
Lys Glu Arg Trp Glu Glu Ser Asp Leu Gln Leu Ser His Asp Leu Ala
145                 150                 155                 160 atg gca gag aat gtg atg gat cct gac cct ata atc ctc aaa aga ctt      528
Met Ala Glu Asn Val Met Asp Pro Asp Pro Ile Ile Leu Lys Arg Leu
                 165                 170                 175 tca caa gag ctc caa ctt act acc att gat gag ctg aag aaa gaa tcg      576
Ser Gln Glu Leu Gln Leu Thr Thr Ile Asp Glu Leu Lys Lys Glu Ser
             180                 185                 190 cat gcg ata cat gag tat ttt ctt tca tat gat gga gat cct gat gac      624
His Ala Ile His Glu Tyr Phe Leu Ser Tyr Asp Gly Asp Pro Asp Asp
         195                 200                 205 tgt ttc gag agg atg tct tca ctt ctt aaa aac ctg gta gac ttt gta      672
Cys Phe Glu Arg Met Ser Ser Leu Leu Lys Asn Leu Val Asp Phe Val
     210                 215                 220 aca atg gaa agt tca gac cct gat cca tcc act ggc agc aga atc gtt      720
Thr Met Glu Ser Ser Asp Pro Asp Pro Ser Thr Gly Ser Arg Ile Val
225                 230                 235                 240 tcg aga cat cgt tct cct gtt ata cca gag tat ttt cgg tgt ccg ata      768
Ser Arg His Arg Ser Pro Val Ile Pro Glu Tyr Phe Arg Cys Pro Ile
                 245                 250                 255 tca ctt gaa ctg atg aag gat cct gtt atc gtc tcc act gga cag aca      816
Ser Leu Glu Leu Met Lys Asp Pro Val Ile Val Ser Thr Gly Gln Thr
             260                 265                 270 tat gaa aga tca tca att cag aag tgg ctt gat gct ggt cat aaa aca      864
Tyr Glu Arg Ser Ser Ile Gln Lys Trp Leu Asp Ala Gly His Lys Thr
         275                 280                 285 tgt ccg aaa tct cag gag aca ctt tta cat gct gga tta acc cct aat      912
Cys Pro Lys Ser Gln Glu Thr Leu Leu His Ala Gly Leu Thr Pro Asn
     290                 295                 300 tat gtg tta aag agt ctc att gct ttg tgg tgt gaa agc aac ggc att      960
Tyr Val Leu Lys Ser Leu Ile Ala Leu Trp Cys Glu Ser Asn Gly Ile
305                 310                 315                 320 gag cta ccg caa aat caa ggg agc tgt aga acc aca aaa ata gga gga     1008
Glu Leu Pro Gln Asn Gln Gly Ser Cys Arg Thr Thr Lys Ile Gly Gly
                 325                 330                 335 agc agc tct tca gat tgt gat cga aca ttt gtc ctt tcc ttg tta gag     1056
```

```
                Ser Ser Ser Ser Asp Cys Asp Arg Thr Phe Val Leu Ser Leu Leu Glu
                            340                 345                 350 aaa ttg gcc aac ggt act aca gaa cag caa aga gct gca gct gga gaa         1104
Lys Leu Ala Asn Gly Thr Thr Glu Gln Gln Arg Ala Ala Ala Gly Glu
            355                 360                 365 tta agg tta cta gcc aag agg aac gtg gat aac aga gtt tgt atc gct         1152
Leu Arg Leu Leu Ala Lys Arg Asn Val Asp Asn Arg Val Cys Ile Ala
    370                 375                 380 gag gct gga gcc ata cca ctc ctt gta gag ctt cta tcc tca cca gat         1200
Glu Ala Gly Ala Ile Pro Leu Leu Val Glu Leu Leu Ser Ser Pro Asp
385                 390                 395                 400 cct cgg act cag gaa cat tct gtg aca gct ctt ctg aat ctt tcc ata         1248
Pro Arg Thr Gln Glu His Ser Val Thr Ala Leu Leu Asn Leu Ser Ile
                405                 410                 415 aat gaa ggg aac aaa gga gcc att gtt gat gca gga gcc ata acg gat         1296
Asn Glu Gly Asn Lys Gly Ala Ile Val Asp Ala Gly Ala Ile Thr Asp
            420                 425                 430 ata gta gaa gtc cta aag aac gga agc atg gaa gct aga gag aac gct         1344
Ile Val Glu Val Leu Lys Asn Gly Ser Met Glu Ala Arg Glu Asn Ala
    435                 440                 445 gct gca acc ctt ttc agt tta tct gtt ata gat gaa aac aaa gtg gca         1392
Ala Ala Thr Leu Phe Ser Leu Ser Val Ile Asp Glu Asn Lys Val Ala
450                 455                 460 ata ggt gct gct gga gct atc caa gca ctt ata agc ttg ctt gag gaa         1440
Ile Gly Ala Ala Gly Ala Ile Gln Ala Leu Ile Ser Leu Leu Glu Glu
465                 470                 475                 480 gga acc cga aga ggc aaa aaa gat gct gct aca gcg att ttc aac tta         1488
Gly Thr Arg Arg Gly Lys Lys Asp Ala Ala Thr Ala Ile Phe Asn Leu
                485                 490                 495 tgc ata tac cag ggg aac aaa tca agg gcg gtt aaa ggc ggt att gtt         1536
Cys Ile Tyr Gln Gly Asn Lys Ser Arg Ala Val Lys Gly Gly Ile Val
            500                 505                 510 gac cct ctg acc aga tta ctg aaa gat gca ggt ggc gga atg gtg gat         1584
Asp Pro Leu Thr Arg Leu Leu Lys Asp Ala Gly Gly Gly Met Val Asp
    515                 520                 525 gag gct ctg gcc att tta gca att ctt tca act aac caa gaa ggg aaa         1632
Glu Ala Leu Ala Ile Leu Ala Ile Leu Ser Thr Asn Gln Glu Gly Lys
530                 535                 540 aca gcg ata gct gaa gca gaa tct atc ccg gtt ttg gtt gag att ata         1680
Thr Ala Ile Ala Glu Ala Glu Ser Ile Pro Val Leu Val Glu Ile Ile
545                 550                 555                 560 agg aca ggg tca cca agg aac cgg gaa aat gct gca gca ata ctt tgg         1728
Arg Thr Gly Ser Pro Arg Asn Arg Glu Asn Ala Ala Ala Ile Leu Trp
                565                 570                 575 tat cta tgt att ggg aat ata gaa agg cta aat gta gca aga gag gtt         1776
Tyr Leu Cys Ile Gly Asn Ile Glu Arg Leu Asn Val Ala Arg Glu Val
            580                 585                 590 ggt gca gat gtg gcc ttg aag gaa ctt act gag aat ggc act gat aga         1824
Gly Ala Asp Val Ala Leu Lys Glu Leu Thr Glu Asn Gly Thr Asp Arg
    595                 600                 605 gca aag agg aaa gct gcg agc ttg ttg gag ctt att cag caa acc gaa         1872
Ala Lys Arg Lys Ala Ala Ser Leu Leu Glu Leu Ile Gln Gln Thr Glu
610                 615                 620 ggt gtt gca gta act act gtt cca tga                                     1899
Gly Val Ala Val Thr Thr Val Pro
625                 630

<210> SEQ ID NO 42
<211> LENGTH: 632
<212> TYPE: PRT
<213> ORGANISM: Arabidopsis thaliana
```

<400> SEQUENCE: 42

```
Met Gly Leu Thr Asn Cys Cys Ser His Glu Glu Met Ser Arg Leu
1               5                   10                  15

Val Asp Ser Val Lys Glu Ile Ser Gly Phe Ser Ser Arg Gly Phe
                20                  25                  30

Ile Gly Lys Ile Gln Gly Asp Leu Val Arg Arg Ile Thr Leu Leu Ser
                35                  40                  45

Pro Phe Phe Glu Glu Leu Ile Asp Val Asn Val Glu Leu Lys Lys Asp
            50                  55                  60

Gln Ile Thr Gly Phe Glu Ala Met Arg Ile Ala Leu Asp Ser Ser Leu
65                  70                  75                  80

Glu Leu Phe Arg Ser Val Asn Gly Gly Ser Lys Leu Phe Gln Leu Phe
                85                  90                  95

Asp Arg Asp Ser Leu Val Glu Lys Phe Arg Asp Met Thr Val Glu Ile
                100                 105                 110

Glu Ala Ala Leu Ser Gln Ile Pro Tyr Glu Lys Ile Glu Val Ser Glu
                115                 120                 125

Glu Val Arg Glu Gln Val Gln Leu Leu His Phe Gln Phe Lys Arg Ala
            130                 135                 140

Lys Glu Arg Trp Glu Glu Ser Asp Leu Gln Leu Ser His Asp Leu Ala
145                 150                 155                 160

Met Ala Glu Asn Val Met Asp Pro Asp Pro Ile Ile Leu Lys Arg Leu
                165                 170                 175

Ser Gln Glu Leu Gln Leu Thr Thr Ile Asp Glu Leu Lys Lys Glu Ser
                180                 185                 190

His Ala Ile His Glu Tyr Phe Leu Ser Tyr Asp Gly Asp Pro Asp Asp
                195                 200                 205

Cys Phe Glu Arg Met Ser Ser Leu Leu Lys Asn Leu Val Asp Phe Val
                210                 215                 220

Thr Met Glu Ser Ser Asp Pro Asp Pro Ser Thr Gly Ser Arg Ile Val
225                 230                 235                 240

Ser Arg His Arg Ser Pro Val Ile Pro Glu Tyr Phe Arg Cys Pro Ile
                245                 250                 255

Ser Leu Glu Leu Met Lys Asp Pro Val Ile Val Ser Thr Gly Gln Thr
                260                 265                 270

Tyr Glu Arg Ser Ser Ile Gln Lys Trp Leu Asp Ala Gly His Lys Thr
                275                 280                 285

Cys Pro Lys Ser Gln Glu Thr Leu Leu His Ala Gly Leu Thr Pro Asn
                290                 295                 300

Tyr Val Leu Lys Ser Leu Ile Ala Leu Trp Cys Glu Ser Asn Gly Ile
305                 310                 315                 320

Glu Leu Pro Gln Asn Gln Gly Ser Cys Arg Thr Thr Lys Ile Gly Gly
                325                 330                 335

Ser Ser Ser Ser Asp Cys Asp Arg Thr Phe Val Leu Ser Leu Leu Glu
                340                 345                 350

Lys Leu Ala Asn Gly Thr Thr Glu Gln Gln Arg Ala Ala Ala Gly Glu
                355                 360                 365

Leu Arg Leu Leu Ala Lys Arg Asn Val Asp Asn Arg Val Cys Ile Ala
                370                 375                 380

Glu Ala Gly Ala Ile Pro Leu Leu Val Glu Leu Leu Ser Ser Pro Asp
385                 390                 395                 400

Pro Arg Thr Gln Glu His Ser Val Thr Ala Leu Leu Asn Leu Ser Ile
                405                 410                 415
```

```
Asn Glu Gly Asn Lys Gly Ala Ile Val Asp Ala Gly Ala Ile Thr Asp
            420                 425                 430

Ile Val Glu Val Leu Lys Asn Gly Ser Met Glu Ala Arg Glu Asn Ala
        435                 440                 445

Ala Ala Thr Leu Phe Ser Leu Ser Val Ile Asp Glu Asn Lys Val Ala
    450                 455                 460

Ile Gly Ala Ala Gly Ala Ile Gln Ala Leu Ile Ser Leu Leu Glu Glu
465                 470                 475                 480

Gly Thr Arg Arg Gly Lys Lys Asp Ala Ala Thr Ala Ile Phe Asn Leu
                485                 490                 495

Cys Ile Tyr Gln Gly Asn Lys Ser Arg Ala Val Lys Gly Gly Ile Val
            500                 505                 510

Asp Pro Leu Thr Arg Leu Leu Lys Asp Ala Gly Gly Gly Met Val Asp
        515                 520                 525

Glu Ala Leu Ala Ile Leu Ala Ile Leu Ser Thr Asn Gln Gly Gly Lys
    530                 535                 540

Thr Ala Ile Ala Glu Ala Glu Ser Ile Pro Val Leu Val Glu Ile Ile
545                 550                 555                 560

Arg Thr Gly Ser Pro Arg Asn Arg Glu Asn Ala Ala Ala Ile Leu Trp
                565                 570                 575

Tyr Leu Cys Ile Gly Asn Ile Glu Arg Leu Asn Val Ala Arg Glu Val
            580                 585                 590

Gly Ala Asp Val Ala Leu Lys Glu Leu Thr Glu Asn Gly Thr Asp Arg
        595                 600                 605

Ala Lys Arg Lys Ala Ala Ser Leu Leu Glu Leu Ile Gln Gln Thr Glu
    610                 615                 620

Gly Val Ala Val Thr Thr Val Pro
625                 630

<210> SEQ ID NO 43
<211> LENGTH: 1419
<212> TYPE: DNA
<213> ORGANISM: Arabidopsis thaliana
<220> FEATURE:
<221> NAME/KEY: CDS
<222> LOCATION: (1)..(1419)

<400> SEQUENCE: 43 atg gta tcg gtg gag gaa cct tta tct cat tcc aat tcc act cgc ttt      48
Met Val Ser Val Glu Glu Pro Leu Ser His Ser Asn Ser Thr Arg Phe
1               5                   10                  15 ccg tta aca acc gat ttc tac ggt tca tca tcg ccg tcg gcg gcg agg      96
Pro Leu Thr Thr Asp Phe Tyr Gly Ser Ser Ser Pro Ser Ala Ala Arg
            20                  25                  30 tta cac cgt caa gct ggc cgg tcg atg aga aca gtg aga tct aac ttc     144
Leu His Arg Gln Ala Gly Arg Ser Met Arg Thr Val Arg Ser Asn Phe
        35                  40                  45 tat caa agc gga gat caa tct tgc tca ttc gtc ggc tca atc ggc gat     192
Tyr Gln Ser Gly Asp Gln Ser Cys Ser Phe Val Gly Ser Ile Gly Asp
    50                  55                  60 aaa tca gag tat gcg tcg gag ttt ctc tcg gat tcc gtc atc gac atg     240
Lys Ser Glu Tyr Ala Ser Glu Phe Leu Ser Asp Ser Val Ile Asp Met
65                  70                  75                  80 aga ctc ggc gag ctt gct ttg aaa aac agt aat tct ctc aat tca aac     288
Arg Leu Gly Glu Leu Ala Leu Lys Asn Ser Asn Ser Leu Asn Ser Asn
                85                  90                  95 gct tcc tca atg aaa gag gaa gcg ttt ctc gac att tct cag gcg ttt     336
Ala Ser Ser Met Lys Glu Glu Ala Phe Leu Asp Ile Ser Gln Ala Phe
```

-continued

```
                    100                 105                 110
agt gat ttt tcc gct tgt agt agt gat atc tcc ggc gag tta cag cgt    384
Ser Asp Phe Ser Ala Cys Ser Ser Asp Ile Ser Gly Glu Leu Gln Arg
            115                 120                 125 ctt gct tgc ttg ccg tcg ccg gag gct gat aga aat gag agc ggc gga    432
Leu Ala Cys Leu Pro Ser Pro Glu Ala Asp Arg Asn Glu Ser Gly Gly
        130                 135                 140 gat aac gaa gcg gag cat gat cca gag tta gag aga gag cct tgt cta    480
Asp Asn Glu Ala Glu His Asp Pro Glu Leu Glu Arg Glu Pro Cys Leu
145                 150                 155                 160 ggg ttt cta cag aga gaa aac ttc tct aca gag att atc gag tgt att    528
Gly Phe Leu Gln Arg Glu Asn Phe Ser Thr Glu Ile Ile Glu Cys Ile
                165                 170                 175 tcg ccg gaa gat ctg cag cca act gtg aaa cta tgc atc gac gga ctt    576
Ser Pro Glu Asp Leu Gln Pro Thr Val Lys Leu Cys Ile Asp Gly Leu
            180                 185                 190 cgt tcc tct tcg gtg gcg ata aag cga tct gct gcg gcg aag cta cgg    624
Arg Ser Ser Ser Val Ala Ile Lys Arg Ser Ala Ala Ala Lys Leu Arg
        195                 200                 205 cta ttg gcg aag aat cga gcg gat aat cgt gtg ttg att ggg gaa tct    672
Leu Leu Ala Lys Asn Arg Ala Asp Asn Arg Val Leu Ile Gly Glu Ser
210                 215                 220 gga gct att caa gct ttg att cca ctt ctt cgt tgt aac gat cca tgg    720
Gly Ala Ile Gln Ala Leu Ile Pro Leu Leu Arg Cys Asn Asp Pro Trp
225                 230                 235                 240 acg caa gag cgc gca gtt aca gct ctg tta aac ctc tcg tta cac gac    768
Thr Gln Glu Arg Ala Val Thr Ala Leu Leu Asn Leu Ser Leu His Asp
                245                 250                 255 cag aac aaa gct gta atc gcc gca gga gga gcg att aaa tca cta gtg    816
Gln Asn Lys Ala Val Ile Ala Ala Gly Gly Ala Ile Lys Ser Leu Val
            260                 265                 270 tgg gta ctc aaa acg ggg acg gag act tca aag cag aac gct gca tgt    864
Trp Val Leu Lys Thr Gly Thr Glu Thr Ser Lys Gln Asn Ala Ala Cys
        275                 280                 285 gct ttg ctt agt ttg gcg cta ttg gag gag aac aaa ggc tca atc gga    912
Ala Leu Leu Ser Leu Ala Leu Leu Glu Glu Asn Lys Gly Ser Ile Gly
290                 295                 300 gct tgc ggt gct att ccg ccg ctg gtt tct ctt ctg ttg aac gga tct    960
Ala Cys Gly Ala Ile Pro Pro Leu Val Ser Leu Leu Leu Asn Gly Ser
305                 310                 315                 320 tgc agg gga aag aag gat gcg ttg acg gcg ctc tac aag ctg tgt acg   1008
Cys Arg Gly Lys Lys Asp Ala Leu Thr Ala Leu Tyr Lys Leu Cys Thr
                325                 330                 335 ctt cag caa aac aag gag aga gcg gtc act gct gga gcg gtg aag ccg   1056
Leu Gln Gln Asn Lys Glu Arg Ala Val Thr Ala Gly Ala Val Lys Pro
            340                 345                 350 ttg gtg gac ctt gtg gct gag gaa ggg act ggt atg gcg gag aaa gct   1104
Leu Val Asp Leu Val Ala Glu Glu Gly Thr Gly Met Ala Glu Lys Ala
        355                 360                 365 atg gtg gtt ctg agt agc ctt gca gcg ata gat gat ggc aaa gag gct   1152
Met Val Val Leu Ser Ser Leu Ala Ala Ile Asp Asp Gly Lys Glu Ala
370                 375                 380 att gtc gag gaa gga ggg atc gca gcg ctt gtt gag gcc atc gag gat   1200
Ile Val Glu Glu Gly Gly Ile Ala Ala Leu Val Glu Ala Ile Glu Asp
385                 390                 395                 400 gga tct gtg aaa ggg aaa gaa ttt gcg atc ttg acg ctg ttg cag ctt   1248
Gly Ser Val Lys Gly Lys Glu Phe Ala Ile Leu Thr Leu Leu Gln Leu
                405                 410                 415 tgt tct gat agc gtt aga aac cgt ggg ttg ctt gtg agg gaa ggc gcg   1296
Cys Ser Asp Ser Val Arg Asn Arg Gly Leu Leu Val Arg Glu Gly Ala
```

```
                        420               425                430
att cct ccg ctt gtg ggc ctc tct cag agc ggc tcc gtc agt gtt aga        1344
Ile Pro Pro Leu Val Gly Leu Ser Gln Ser Gly Ser Val Ser Val Arg
        435                 440                445 gct aag cgc aag gca gaa aga ctt ctg ggg tat ctt cgg gag cca agg        1392
Ala Lys Arg Lys Ala Glu Arg Leu Leu Gly Tyr Leu Arg Glu Pro Arg
    450                 455                 460 aag gag gca agt tca tca agc cca tga                                    1419
Lys Glu Ala Ser Ser Ser Ser Pro
465                 470

<210> SEQ ID NO 44
<211> LENGTH: 472
<212> TYPE: PRT
<213> ORGANISM: Arabidopsis thaliana

<400> SEQUENCE: 44

Met Val Ser Val Glu Glu Pro Leu Ser His Ser Asn Ser Thr Arg Phe
1               5                   10                  15

Pro Leu Thr Thr Asp Phe Tyr Gly Ser Ser Pro Ser Ala Ala Arg
            20                  25                  30

Leu His Arg Gln Ala Gly Arg Ser Met Arg Thr Val Arg Ser Asn Phe
        35                  40                  45

Tyr Gln Ser Gly Asp Gln Ser Cys Ser Phe Val Gly Ser Ile Gly Asp
    50                  55                  60

Lys Ser Glu Tyr Ala Ser Glu Phe Leu Ser Asp Ser Val Ile Asp Met
65                  70                  75                  80

Arg Leu Gly Glu Leu Ala Leu Lys Asn Ser Asn Ser Leu Asn Ser Asn
                85                  90                  95

Ala Ser Ser Met Lys Glu Glu Ala Phe Leu Asp Ile Ser Gln Ala Phe
            100                 105                 110

Ser Asp Phe Ser Ala Cys Ser Ser Asp Ile Ser Gly Glu Leu Gln Arg
        115                 120                 125

Leu Ala Cys Leu Pro Ser Pro Glu Ala Asp Arg Asn Glu Ser Gly Gly
    130                 135                 140

Asp Asn Glu Ala Glu His Asp Pro Glu Leu Glu Arg Glu Pro Cys Leu
145                 150                 155                 160

Gly Phe Leu Gln Arg Glu Asn Phe Ser Thr Glu Ile Ile Glu Cys Ile
                165                 170                 175

Ser Pro Glu Asp Leu Gln Pro Thr Val Lys Leu Cys Ile Asp Gly Leu
            180                 185                 190

Arg Ser Ser Ser Val Ala Ile Lys Arg Ser Ala Ala Lys Leu Arg
        195                 200                 205

Leu Leu Ala Lys Asn Arg Ala Asp Asn Arg Val Leu Ile Gly Glu Ser
    210                 215                 220

Gly Ala Ile Gln Ala Leu Ile Pro Leu Arg Cys Asn Asp Pro Trp
225                 230                 235                 240

Thr Gln Glu Arg Ala Val Thr Ala Leu Leu Asn Leu Ser Leu His Asp
                245                 250                 255

Gln Asn Lys Ala Val Ile Ala Ala Gly Gly Ala Ile Lys Ser Leu Val
            260                 265                 270

Trp Val Leu Lys Thr Gly Thr Glu Thr Ser Lys Gln Asn Ala Ala Cys
        275                 280                 285

Ala Leu Leu Ser Leu Ala Leu Leu Glu Glu Asn Lys Gly Ser Ile Gly
    290                 295                 300

Ala Cys Gly Ala Ile Pro Pro Leu Val Ser Leu Leu Leu Asn Gly Ser
```

```
            305                 310                 315                 320
Cys Arg Gly Lys Lys Asp Ala Leu Thr Ala Leu Tyr Lys Leu Cys Thr
                325                 330                 335

Leu Gln Gln Asn Lys Glu Arg Ala Val Thr Ala Gly Ala Val Lys Pro
            340                 345                 350

Leu Val Asp Leu Val Ala Glu Glu Gly Thr Gly Met Ala Glu Lys Ala
        355                 360                 365

Met Val Val Leu Ser Ser Leu Ala Ala Ile Asp Gly Lys Glu Ala
    370                 375                 380

Ile Val Glu Glu Gly Gly Ile Ala Ala Leu Val Glu Ala Ile Glu Asp
385                 390                 395                 400

Gly Ser Val Lys Gly Lys Glu Phe Ala Ile Leu Thr Leu Leu Gln Leu
                405                 410                 415

Cys Ser Asp Ser Val Arg Asn Arg Gly Leu Leu Val Arg Glu Gly Ala
            420                 425                 430

Ile Pro Pro Leu Val Gly Leu Ser Gln Ser Gly Ser Val Ser Val Arg
        435                 440                 445

Ala Lys Arg Lys Ala Glu Arg Leu Leu Gly Tyr Leu Arg Glu Pro Arg
    450                 455                 460

Lys Glu Ala Ser Ser Ser Ser Pro
465                 470
```

<210> SEQ ID NO 45
<211> LENGTH: 54
<212> TYPE: DNA
<213> ORGANISM: Artificial sequence
<220> FEATURE:
<223> OTHER INFORMATION: GeneRacer Oligo dT primer

<400> SEQUENCE: 45
gctgtcaacg atacgctacg taacggcatg acagtgtttt ttttttttt tttt         54

<210> SEQ ID NO 46
<211> LENGTH: 25
<212> TYPE: DNA
<213> ORGANISM: Artificial sequence
<220> FEATURE:
<223> OTHER INFORMATION: Primer MWG 1

<400> SEQUENCE: 46
gcagacatga cccaatcttg gcagg                                        25

<210> SEQ ID NO 47
<211> LENGTH: 23
<212> TYPE: DNA
<213> ORGANISM: Artificial sequence
<220> FEATURE:
<223> OTHER INFORMATION: GeneRacer 5' primer (Invitrogen)

<400> SEQUENCE: 47
cgactggagc acgaggacac tga                                          23

<210> SEQ ID NO 48
<211> LENGTH: 25
<212> TYPE: DNA
<213> ORGANISM: Artificial sequence
<220> FEATURE:
<223> OTHER INFORMATION: Primer MWG 2

<400> SEQUENCE: 48
ccacggtcag caacctctcc agacg                                        25

<210> SEQ ID NO 49
<211> LENGTH: 26
<212> TYPE: DNA
<213> ORGANISM: Artificial sequence
<220> FEATURE:
<223> OTHER INFORMATION: GeneRacer 5'nested primer (Invitrogen)

<400> SEQUENCE: 49
ggacactgac atggactgaa ggagta                                  26

<210> SEQ ID NO 50
<211> LENGTH: 27
<212> TYPE: DNA
<213> ORGANISM: Artificial sequence
<220> FEATURE:
<223> OTHER INFORMATION: Primer MWG 3

<400> SEQUENCE: 50
cagatgatag ttattgttgt tgactgg                                 27

<210> SEQ ID NO 51
<211> LENGTH: 25
<212> TYPE: DNA
<213> ORGANISM: Artificial sequence
<220> FEATURE:
<223> OTHER INFORMATION: GeneRacer 3' primer (Invitrogen)

<400> SEQUENCE: 51
gctgtcaacg atacgctacg taacg                                   25

<210> SEQ ID NO 52
<211> LENGTH: 24
<212> TYPE: DNA
<213> ORGANISM: Artificial sequence
<220> FEATURE:
<223> OTHER INFORMATION: Primer MWG 4

<400> SEQUENCE: 52
ctcatcttct caagctactg gtgg                                    24

<210> SEQ ID NO 53
<211> LENGTH: 23
<212> TYPE: DNA
<213> ORGANISM: Artificial sequence
<220> FEATURE:
<223> OTHER INFORMATION: GeneRacer 3'nested primer (Invitrogen)

<400> SEQUENCE: 53
cgctacgtaa cggcatgaca gtg                                     23

<210> SEQ ID NO 54
<211> LENGTH: 21
<212> TYPE: DNA
<213> ORGANISM: Artificial sequence
<220> FEATURE:
<223> OTHER INFORMATION: Primer MWG 29

<400> SEQUENCE: 54
atatgcaaat ggctctgcta g                                       21

<210> SEQ ID NO 55
<211> LENGTH: 21
<212> TYPE: DNA
<213> ORGANISM: Artificial sequence
<220> FEATURE:
<223> OTHER INFORMATION: Primer MWG 30

<400> SEQUENCE: 55
tatcatctcc ttcccgagtt c                                              21

<210> SEQ ID NO 56
<211> LENGTH: 27
<212> TYPE: DNA
<213> ORGANISM: Artificial sequence
<220> FEATURE:
<223> OTHER INFORMATION: Primer MWG 31

<400> SEQUENCE: 56
cccgggatga ttttgcggtt ttggcgg                                        27

<210> SEQ ID NO 57
<211> LENGTH: 31
<212> TYPE: DNA
<213> ORGANISM: Artificial sequence
<220> FEATURE:
<223> OTHER INFORMATION: Primer MWG 32

<400> SEQUENCE: 57
cccgggtcac aagacaaaac ataaaaatag g                                   31

<210> SEQ ID NO 58
<211> LENGTH: 21
<212> TYPE: DNA
<213> ORGANISM: Artificial sequence
<220> FEATURE:
<223> OTHER INFORMATION: Primer MWG 32b

<400> SEQUENCE: 58
gactcacact actctaatac c                                              21

<210> SEQ ID NO 59
<211> LENGTH: 20
<212> TYPE: DNA
<213> ORGANISM: Artificial sequence
<220> FEATURE:
<223> OTHER INFORMATION: Primer MWG 33

<400> SEQUENCE: 59
gacatcgttt gtctcacacc                                                20

<210> SEQ ID NO 60
<211> LENGTH: 249
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:

```
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(34)
<223> OTHER INFORMATION: Xaa can be any naturally occurring amino acid
<220> FEATURE:
<221> NAME/KEY: misc_feature
<222> LOCATION: (36)..(38)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (47)..(50)
<223> OTHER INFORMATION: Xaa can be any naturally occurring amino acid
<220> FEATURE:
<221> NAME/KEY: misc_feature
<222> LOCATION: (52)..(54)
<223> OTHER INFORMATION: Xaa can be any naturally occurring amino acid
<220> FEATURE:
<221> NAME/KEY: misc_feature
<222> LOCATION: (56)..(59)
<223> OTHER INFORMATION: Xaa can be any naturally occurring amino acid
<220> FEATURE:
<221> NAME/KEY: misc_feature
<222> LOCATION: (62)..(67)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: MISC_FEATURE
<222> LOCATION: (72)..(72)
<223> OTHER INFORMATION: Xaa can be no or any amino acid
<220> FEATURE:
<221> NAME/KEY: misc_feature
<222> LOCATION: (73)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (85)..(86)
<223> OTHER INFORMATION: Xaa can be any naturally occurring amino acid
<220> FEATURE:
<221> NAME/KEY: misc_feature
<222> LOCATION: (88)..(96)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: MISC_FEATURE
<222> LOCATION: (101)..(101)
<223> OTHER INFORMATION: Xaa can be no or any amino acid
<220> FEATURE:
<221> NAME/KEY: misc_feature
<222> LOCATION: (102)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
```

```
<221> NAME/KEY: misc_feature
<222> LOCATION: (115)..(118)
<223> OTHER INFORMATION: Xaa can be any naturally occurring amino acid
<220> FEATURE:
<221> NAME/KEY: misc_feature
<222> LOCATION: (123)..(128)
<223> OTHER INFORMATION: Xaa can be any naturally occurring amino acid
<220> FEATURE:
<221> NAME/KEY: misc_feature
<222> LOCATION: (130)..(135)
<223> OTHER INFORMATION: Xaa can be any naturally occurring amino acid
<220> FEATURE:
<221> NAME/KEY: misc_feature
<222> LOCATION: (137)..(147)
<223> OTHER INFORMATION: Xaa can be any naturally occurring amino acid
<220> FEATURE:
<221> NAME/KEY: misc_feature
<222> LOCATION: (149)..(150)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: MISC_FEATURE
<222> LOCATION: (153)..(153)
<223> OTHER INFORMATION: Xaa can be no or any amino acid
<220> FEATURE:
<221> NAME/KEY: misc_feature
<222> LOCATION: (154)..(169)
<223> OTHER INFORMATION: Xaa can be any naturally occurring amino acid
<220> FEATURE:
<221> NAME/KEY: misc_feature
<222> LOCATION: (171)..(188)
<223> OTHER INFORMATION: Xaa can be any naturally occurring amino acid
<220> FEATURE:
<221> NAME/KEY: misc_feature
<222> LOCATION: (192)..(195)
<223> OTHER INFORMATION: Xaa can be any naturally occurring amino acid
<220> FEATURE:
<221> NAME/KEY: misc_feature
<222> LOCATION: (197)..(201)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (205)..(207)
<223> OTHER INFORMATION: Xaa can be any naturally occurring amino acid
<220> FEATURE:
<221> NAME/KEY: misc_feature
<222> LOCATION: (209)..(210)
<223> OTHER INFORMATION: Xaa can be any naturally occurring amino acid
<220> FEATURE:
<221> NAME/KEY: misc_feature
<222> LOCATION: (212)..(230)
<223> OTHER INFORMATION: Xaa can be any naturally occurring amino acid
<220> FEATURE:
<221> NAME/KEY: misc_feature
<222> LOCATION: (232)..(237)
<223> OTHER INFORMATION: Xaa can be any naturally occurring amino acid
<220> FEATURE:
<221> NAME/KEY: MISC_FEATURE
<222> LOCATION: (239)..(239)
<223> OTHER INFORMATION: Xaa can be no or any amino acid
<220> FEATURE:
<221> NAME/KEY: MISC_FEATURE
<222> LOCATION: (240)..(240)
<223> OTHER INFORMATION: Xaa can be no or any amino acid
<220> FEATURE:
<221> NAME/KEY: misc_feature
<222> LOCATION: (241)..(242)
<223> OTHER INFORMATION: Xaa can be any naturally occurring amino acid
<220> FEATURE:
<221> NAME/KEY: misc_feature
<222> LOCATION: (244)..(246)
<223> OTHER INFORMATION: Xaa can be any naturally occurring amino acid
<220> FEATURE:
```

<221> NAME/KEY: misc_feature
<222> LOCATION: (248)..(249)
<223> OTHER INFORMATION: Xaa can be any naturally occurring amino acid

<400> SEQUENCE: 60

```
Arg Xaa Leu Xaa Xaa Xaa Xaa Xaa Xaa Arg Xaa Xaa Ile Xaa Xaa
1               5                   10                  15

Xaa Xaa Ala Ile Xaa Xaa Leu Xaa Xaa Leu Xaa Xaa Xaa Xaa Xaa
            20                  25                  30

Xaa Xaa Gln Xaa Xaa Xaa Val Thr Xaa Xaa Leu Asn Leu Ser Xaa
        35                  40                  45

Xaa Xaa Asn Xaa Xaa Xaa Ile Xaa Xaa Xaa Xaa Ala Ile Xaa Xaa Xaa
    50                  55                  60

Xaa Xaa Xaa Leu Xaa Xaa Gly Xaa Xaa Xaa Xaa Xaa Xaa Asn Xaa
65              70                  75                  80

Ala Xaa Xaa Leu Xaa Xaa Leu Xaa Xaa Xaa Xaa Xaa Xaa Xaa Xaa
            85                  90                  95

Ile Gly Xaa Xaa Xaa Xaa Xaa Xaa Xaa Leu Xaa Xaa Xaa Leu Leu Xaa
            100                 105                 110

Xaa Gly Xaa Xaa Xaa Xaa Lys Lys Asp Ala Xaa Xaa Xaa Xaa Xaa
        115                 120                 125

Leu Xaa Xaa Xaa Xaa Xaa Xaa Lys Xaa Xaa Xaa Xaa Xaa Xaa Xaa
    130                 135                 140

Xaa Xaa Xaa Leu Xaa Xaa Leu Xaa Xaa Xaa Xaa Xaa Xaa Xaa Xaa
145                 150                 155                 160

Xaa Xaa Xaa Xaa Xaa Xaa Xaa Xaa Xaa Leu Xaa Xaa Xaa Xaa Xaa
                165                 170                 175

Xaa Xaa Xaa Xaa Xaa Xaa Xaa Xaa Xaa Xaa Xaa Leu Val Glu Xaa
            180                 185                 190

Xaa Xaa Xaa Gly Xaa Xaa Xaa Xaa Xaa Glu Xaa Ala Xaa Xaa Xaa Leu
        195                 200                 205

Xaa Xaa Leu Xaa Xaa Xaa Xaa Xaa Xaa Xaa Xaa Xaa Xaa Xaa Xaa
    210                 215                 220

Xaa Xaa Xaa Xaa Xaa Xaa Leu Xaa Xaa Xaa Xaa Xaa Xaa Gly Xaa Xaa
225                 230                 235                 240

Xaa Xaa Arg Xaa Xaa Xaa Lys Xaa Xaa
                245
```

<210> SEQ ID NO 61
<211> LENGTH: 249
<212> TYPE: PRT
<213> ORGANISM: Artificial
<220> FEATURE:
<223> OTHER INFORMATION: Consensus sequence
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (25)..(25)

```
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (65)..(66)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: MISC_FEATURE
<222> LOCATION: (72)..(72)
<223> OTHER INFORMATION: Xaa can be no or any amino acid
<220> FEATURE:
<221> NAME/KEY: misc_feature
<222> LOCATION: (73)..(74)
<223> OTHER INFORMATION: Xaa can be any naturally occurring amino acid
<220> FEATURE:
<221> NAME/KEY: misc_feature
<222> LOCATION: (95)..(96)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: MISC_FEATURE
<222> LOCATION: (101)..(101)
<223> OTHER INFORMATION: Xaa can be no or any amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (132)..(133)
```

```
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (146)..(147)
<223> OTHER INFORMATION: Xaa can be any naturally occurring amino acid
<220> FEATURE:
<221> NAME/KEY: MISC_FEATURE
<222> LOCATION: (153)..(153)
<223> OTHER INFORMATION: Xaa can be no or any amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (181)..(182)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (216)..(217)
<223> OTHER INFORMATION: Xaa can be any naturally occurring amino acid
<220> FEATURE:
<221> NAME/KEY: misc_feature
<222> LOCATION: (220)..(221)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: MISC_FEATURE
<222> LOCATION: (239)..(239)
<223> OTHER INFORMATION: Xaa can be no or any amino acid
<220> FEATURE:
<221> NAME/KEY: MISC_FEATURE
<222> LOCATION: (240)..(240)
<223> OTHER INFORMATION: Xaa can be no or any amino acid
<220> FEATURE:
<221> NAME/KEY: misc_feature
<222> LOCATION: (242)..(242)
```

<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid

<400> SEQUENCE: 61

Arg Leu Leu Ala Lys Xaa Xaa Xaa Glu Asn Arg Ile Xaa Ile Ala Xaa
1               5                   10                  15

Xaa Gly Ala Ile Xaa Xaa Leu Val Xaa Leu Leu Xaa Ser Xaa Asp Xaa
            20                  25                  30

Xaa Thr Gln Glu Xaa Ala Val Thr Ala Leu Leu Asn Leu Ser Ile Xaa
        35                  40                  45

Asp Xaa Asn Lys Xaa Ala Ile Ala Xaa Ala Gly Ala Ile Xaa Pro Leu
    50                  55                  60

Xaa Xaa Val Leu Xaa Xaa Gly Xaa Xaa Xaa Glu Ala Lys Glu Asn Ser
65                  70                  75                  80

Ala Ala Thr Leu Phe Ser Leu Ser Val Ile Glu Glu Asn Lys Xaa Xaa
                85                  90                  95

Ile Gly Xaa Ser Xaa Gly Ala Ile Xaa Pro Leu Val Asp Leu Leu Gly
            100                 105                 110

Xaa Gly Thr Xaa Arg Gly Lys Lys Asp Ala Ala Thr Ala Leu Phe Asn
        115                 120                 125

Leu Ser Ile Xaa Xaa Glu Asn Lys Xaa Arg Xaa Val Gln Ala Gly Ala
130                 135                 140

Val Xaa Xaa Leu Val Glu Leu Met Xaa Asp Pro Xaa Xaa Gly Met Val
145                 150                 155                 160

Asp Lys Ala Val Ala Val Leu Ala Asn Leu Ala Thr Xaa Pro Glu Gly
                165                 170                 175

Arg Xaa Ala Ile Xaa Xaa Glu Gly Gly Ile Pro Xaa Leu Val Glu Xaa
            180                 185                 190

Val Glu Leu Gly Ser Xaa Arg Xaa Lys Glu Asn Ala Ala Ala Xaa Leu
        195                 200                 205

Leu Gln Leu Cys Xaa Asn Ser Xaa Xaa Phe Cys Xaa Xaa Val Leu Gln
    210                 215                 220

Glu Gly Ala Xaa Pro Pro Leu Val Ala Leu Ser Gln Ser Gly Xaa Xaa
225                 230                 235                 240

Thr Xaa Arg Ala Lys Glu Lys Ala Xaa
            245

<210> SEQ ID NO 62
<211> LENGTH: 249
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:

```
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: MISC_FEATURE
<222> LOCATION: (72)..(72)
<223> OTHER INFORMATION: Xaa can be no or any amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: MISC_FEATURE
<222> LOCATION: (101)..(101)
<223> OTHER INFORMATION: Xaa can be no or any amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
```

```
<221> NAME/KEY: MISC_FEATURE
<222> LOCATION: (153)..(153)
<223> OTHER INFORMATION: Xaa can be no or any amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: MISC_FEATURE
<222> LOCATION: (239)..(239)
<223> OTHER INFORMATION: Xaa can be no or any amino acid
<220> FEATURE:
<221> NAME/KEY: MISC_FEATURE
<222> LOCATION: (240)..(240)
<223> OTHER INFORMATION: Xaa can be no or any amino acid
<220> FEATURE:
<221> NAME/KEY: misc_feature
<222> LOCATION: (242)..(242)
<223> OTHER INFORMATION: Xaa can be any naturally occurring amino acid

<400> SEQUENCE: 62

Arg Leu Leu Ala Lys Xaa Xaa Met Glu Asn Arg Ile Xaa Ile Ala Xaa
1               5                   10                  15

Ala Gly Ala Ile Xaa Xaa Leu Val Xaa Leu Leu Tyr Ser Xaa Asp Xaa
            20                  25                  30

Xaa Thr Gln Glu Xaa Ala Val Thr Ala Leu Leu Asn Leu Ser Ile Xaa
        35                  40                  45

Asp Xaa Asn Lys Xaa Ala Ile Ala Xaa Ala Gly Ala Ile Xaa Pro Leu
    50                  55                  60

Ile His Val Leu Xaa Xaa Gly Xaa Ser Xaa Glu Ala Lys Glu Asn Ser
65                  70                  75                  80

Ala Ala Thr Leu Phe Ser Leu Ser Val Ile Glu Glu Asn Lys Val Xaa
                85                  90                  95

Ile Gly Xaa Ser Xaa Gly Ala Ile Xaa Pro Leu Val Asp Leu Leu Gly
            100                 105                 110

Xaa Gly Thr Xaa Arg Gly Lys Lys Asp Ala Ala Thr Ala Leu Phe Asn
        115                 120                 125

Leu Ser Ile Xaa Xaa Glu Asn Lys Xaa Arg Ile Val Gln Ala Gly Ala
    130                 135                 140

Val Lys Tyr Leu Val Glu Leu Met Xaa Asp Pro Ala Ala Gly Met Val
145                 150                 155                 160

Asp Lys Ala Val Ala Val Leu Ala Asn Leu Ala Thr Val Pro Glu Gly
                165                 170                 175

Arg Xaa Ala Ile Gly Xaa Glu Gly Gly Ile Pro Val Leu Val Glu Val
            180                 185                 190

Val Glu Leu Gly Ser Xaa Arg Gly Lys Glu Asn Ala Ala Ala Val Leu
        195                 200                 205

Leu Gln Leu Cys Thr Asn Ser Xaa Arg Phe Cys Xaa Leu Val Leu Gln
    210                 215                 220
```

Glu Gly Ala Ile Pro Pro Leu Val Ala Leu Ser Gln Ser Gly Xaa Xaa
225                 230                 235                 240

Thr Xaa Arg Ala Lys Glu Lys Ala Gln
            245

```
<210> SEQ ID NO 63
<211> LENGTH: 2023
<212> TYPE: DNA
<213> ORGANISM: Hordeum vulgare
<220> FEATURE:
<221> NAME/KEY: Unsure
<222> LOCATION: (1)..(2023)

<400> SEQUENCE: 63
```

| | | | | | |
|---|---|---|---|---|---|
| gaaagtgcat | tccttgttg | cttccccagg | ctgaccgacc | agccacacca | acccaaacca | 60 |
| acgcggcaaa | accttggccc | ccgcctgtct | agcgctgccg | ccgtgccgtg | ccgtgccgtg | 120 |
| ccgtgcctca | gcgccagcga | ccgccgacga | ctcaatcccg | taccacgccc | caccgccgcc | 180 |
| tcccacgccc | ctcgtgccca | tcgccgatcc | cgttcccccct | caccgcagca | tcgcgctccc | 240 |
| gcgtatccgc | cccttccgca | accgtcggcc | attggtttct | gagagcctca | agatttgagc | 300 |
| accacaggca | acagcctcct | acatcctgtg | tcggtacttg | gtagggtaat | cttccctgga | 360 |
| ccccgggagc | tgacatgtat | agagaagctt | gaacagagca | tgtgaaccat | cctgaaatct | 420 |
| gatgccatgt | gaaccatcct | ggtcatgagg | cctcatcgat | cagtctttag | atatgcaaat | 480 |
| ggctctgcta | gcaaggcttt | ctcttgcaag | ttctgaagga | agagagtcta | gtttggaaga | 540 |
| aagcatgct | ggttctgatg | aacaacttca | gaacaatcaa | cgaaggaagc | atttcaagca | 600 |
| tctcattttg | cagtgattca | caggttcgtc | taggcagatc | ttcagttaat | gataatcttc | 660 |
| ctaatacccg | tcagcttgac | gaggagtgtg | acatcaagat | gggatgatac | gagttccagg | 720 |
| tgataggaca | aattatagta | ggatgcgtct | ggagaggttg | ctgaccgtgg | gctttctatc | 780 |
| tcttctgccc | ctcaaaggga | aaatgtaatc | ctgccagatt | gggtcatgtc | tgcatggagg | 840 |
| gaccatttgt | tcagcggcaa | catctgacaa | gggattcccg | agaataattt | cgtcgttatc | 900 |
| catggatgcc | cgggatgatt | tctctgccat | cgagaatcag | gtacgcgagt | aatcaatgat | 960 |
| ttgggaagtg | attccataga | aggtcagaga | tcagcacatc | agagattcgc | cttctagcta | 1020 |
| agcacaacat | ggagaacaga | ttgccattgc | taattgtggg | gctataactt | gctggttggc | 1080 |
| cttcttcatt | cacccgatgc | caaaatccaa | gaaaatgcag | tgacagccct | ccttaatttg | 1140 |
| tcactcagtg | atatcaataa | gattgccatc | gtgaatgcag | atgctattga | tcctctcatc | 1200 |
| atgtcctgga | aacagggaac | cctgaagcta | aagagaattc | agcagtactt | tgttcagtct | 1260 |
| ctcaattatt | gaagaaaaca | gagtgaggat | agggcgatct | ggtgctgtaa | agcctctcgt | 1320 |
| ggacttgctg | ggaatgggag | cccacgagga | agaaagatg | cggttactgc | attgttaatt | 1380 |
| tatccatact | tcatgagaac | aagggtcgaa | ttgtgcaagc | tgatgcattg | aagcacctag | 1440 |
| ttgagcttat | ggaccctgct | gctgaatggt | cgataaagct | gtagctgtct | tggcaaatct | 1500 |
| tgctacgata | cagaaggaag | gactgcgatt | gggcaggcgc | gtggtattcc | ggcccttgtt | 1560 |
| gaagttgtcg | aactgggttc | agcgaaagga | aggaaaatgc | taccgcggca | ttgcttcagc | 1620 |
| tatgcacaaa | cagcacaggt | tttgcaacat | agttcttcaa | gaggatgccg | tgcccccttt | 1680 |
| agtcgcactg | tcacagtcag | gaacaccacg | cgcaagaaa | aaggcgcagg | ttctcctcag | 1740 |
| ctatttccgc | agccaaagac | atgggaactc | ggaaggagag | gaggacgatg | gtcctacgat | 1800 |
| atattttct | agttacgtcg | agtatttccc | tgaattctc | agatgatagt | tattgttgtt | 1860 |
| gactggcgct | gtgtactgct | tatagtcact | gtgagattgt | gccatcttct | caagctactg | 1920 |

```
gtggattagt tgctgtgttt ggactggtcg ttgttgttgt tgagatggtg tattcttcgg   1980
gtttatattt ttttacatct tgtctattgg tatctaaaaa aaa                    2023
```

<210> SEQ ID NO 64
<211> LENGTH: 480
<212> TYPE: DNA
<213> ORGANISM: Hordeum vulgare
<220> FEATURE:
<221> NAME/KEY: 5'UTR
<222> LOCATION: (1)..(480)

<400> SEQUENCE: 64

```
gaaagtgcat tccttgttg cttccccagg ctgaccgacc agccaccacc aacccaaacc    60
aacgcggcaa aaccttggcc cccgcctgtc ctagcgctgc cgccgtgccg tgccgtgccg   120
tgccgtgcct cagcgccagc gaccgccgac gactcaatcc cgtaccacgc ccccaccgcc   180
gcctcccacg cccctcgtgc ccatcgccga tcccgttccc cctcaccgca gcatcgcgct   240
cccgcggtat ccgcccttc cgcaaccgtc ggccattggt ttctgagagc cttcaagatt    300
tgagcaccac aggcaacagc ctcctacatc ctgtgtcggt acttggtagg gtaatcttcc   360
ctggaccccg ggagctgaca tgtatatgag aagcttgaac agagcatgtg aaccatcctg   420
aaatctgatg cacatgtgaa ccatcctggt catgaggcct catcgatcag tctttagatt   480
```

<210> SEQ ID NO 65
<211> LENGTH: 10
<212> TYPE: DNA
<213> ORGANISM: Artificial sequence
<220> FEATURE:
<223> OTHER INFORMATION: Region of promoter sequence found in the
      promoter of the barley beta-1,3-glucanase

<400> SEQUENCE: 65

```
tcatcttctt                                                          10
```

<210> SEQ ID NO 66
<211> LENGTH: 28
<212> TYPE: DNA
<213> ORGANISM: Artificial sequence
<220> FEATURE:
<223> OTHER INFORMATION: Primer

<400> SEQUENCE: 66

```
taatgataat cttcctaata cccgtcag                                      28
```

<210> SEQ ID NO 67
<211> LENGTH: 23
<212> TYPE: DNA
<213> ORGANISM: Artificial sequence
<220> FEATURE:
<223> OTHER INFORMATION: Primer

<400> SEQUENCE: 67

```
cctttgaggg gcagaagaga tag                                           23
```

<210> SEQ ID NO 68
<211> LENGTH: 20
<212> TYPE: DNA
<213> ORGANISM: Artificial sequence
<220> FEATURE:
<223> OTHER INFORMATION: Oligonucleotide

<400> SEQUENCE: 68

```
cagccaccac caacccaaac                                               20
```

<210> SEQ ID NO 69
<211> LENGTH: 22
<212> TYPE: DNA
<213> ORGANISM: Artificial sequence
<220> FEATURE:
<223> OTHER INFORMATION: Oligonucleotide

<400> SEQUENCE: 69
gcccacggtc agcaacctct cc                                              22

<210> SEQ ID NO 70
<211> LENGTH: 27
<212> TYPE: DNA
<213> ORGANISM: Artificial sequence
<220> FEATURE:
<223> OTHER INFORMATION: Primer

<400> SEQUENCE: 70
accgactagt caccaccaac ccaaacc                                         27

<210> SEQ ID NO 71
<211> LENGTH: 31
<212> TYPE: DNA
<213> ORGANISM: Artificial sequence
<220> FEATURE:
<223> OTHER INFORMATION: Primer

<400> SEQUENCE: 71
gcagggccca gcgccagtca acaacaataa c                                    31

<210> SEQ ID NO 72
<211> LENGTH: 2053
<212> TYPE: DNA
<213> ORGANISM: Hordeum vulgare

<400> SEQUENCE: 72
gaaagtgcat ttccttgttg cttccccagg ctgaccgacc agccaccacc aacccaaacc     60
aacgcggcaa aaccttggcc cccgcctgtc ctagcgctgc cgccgtgccg tgccgtgccg    120
tgccgtgcct cagcgccagc gaccgccgac gactcaatcc cgtaccacgc ccccaccgcc    180
gcctcccacg cccctcgtgc ccatcgccga tcccgttccc cctcaccgca gcatcgcgct    240
cccgcggtat ccgccccttc cgcaaccgtc ggccattggt ttctgagagc cttcaagatt    300
tgagcaccac aggcaacagc ctcctacatc ctgtgtcggt acttggtagg gtaatcttcc    360
ctggaccccg ggagctgaca tgtatatgag aagcttgaac agagcatgtg aaccatcctg    420
aaatctgatg cacatgtgaa ccatcctggt catgaggcct catcgatcag tctttagatt    480
atgcaaatgg ctctgctagc aaggctttct cttgcaagtt ctgaaggaag agagtctagt    540
ttggaagaaa gacatgctgg ttctgatgaa caaacttcag aacaatcaac gaaggaagca    600
tttcaagcat ctcattttga cagtgattca caggttcgtc taggcagatc ttcagttaat    660
gataatcttc ctaatacccg tcagcttgac gaggagtgtg acatcaacga tgggatgata    720
cgagttccag gtgataggac aaattatagt agtgatgcgt ctggagaggt tgctgaccgt    780
gggctttcta tctcttctgc ccctcaaagg gaaaatgtaa tcctgccaag attgggtcat    840
gtctgcatga gggaccatt tgttcagcgg caaacatctg caagggatt cccgagaata    900 atttcgtcgt tatccatgga tgcccgggat gatttctctg ccatcgagaa tcaggtacgc    960
gagctaatca atgatttggg aagtgattcc atagaaggtc agagatcagc aacatcagag   1020
attcgccttc tagctaagca caacatggag aacaggattg ccattgctaa ttgtggggct   1080

-continued

```
ataaacttgc tggttggcct tcttcattca cccgatgcca aaatccaaga aaatgcagtg    1140
acagccctcc ttaatttgtc actcagtgat atcaataaga ttgccatcgt gaatgcagat    1200
gctattgatc ctctcatcca tgtcctggaa acagggaacc ctgaagctaa agagaattca    1260
gcagctactt tgttcagtct ctcaattatt gaagaaaaca gagtgaggat agggcgatct    1320
ggtgctgtaa agcctctcgt ggacttgctg ggaaatggga gcccacgagg aaagaaagat    1380
gcggttactg cattgtttaa tttatccata cttcatgaga acaagggtcg aattgtgcaa    1440
gctgatgcat tgaagcacct agttgagctt atggaccctg ctgctggaat ggtcgataaa    1500
gctgtagctg tcttggcaaa tcttgctacg ataccagaag gaaggactgc gattgggcag    1560
gcgcgtggta ttccggccct tgttgaagtt gtcgaactgg gttcagcgaa agcgaaggaa    1620
aatgctaccg cggcattgct tcagctatgc acaaacagca gcaggttttg caacatagtt    1680
cttcaagagg atgccgtgcc cccttttagtc gcactgtcac agtcaggaac accacgcgca    1740
agagaaaagg cgcaggttct cctcagctat ttccgcagcc aaagacatgg gaactcggga    1800
aggagatgag gacgatggtc ctacgatata tttttctagt gtacgtcgag tatttccctg    1860
aatttctcag atgatagtta ttgttgttga ctggcgctgt gtactgctta tagtcactgt    1920
gagattgtgc tcatcttctc aagctactgg tggattagtt gctgtgtttg tgactggtcg    1980
ttgttgttgt tgagatggtg tattcttcgg gtttatattt ttttacatct tgtctattgg    2040
tatctaaaaa aaa                                                       2053
```